(12) United States Patent
Albrecht et al.

(10) Patent No.: US 7,872,009 B2
(45) Date of Patent: *Jan. 18, 2011

(54) BETA-SECRETASE MODULATORS AND METHODS OF USE

(75) Inventors: Brian K. Albrecht, Cambridge, MA (US); Denise Lyn Andersen, Simi Valley, CA (US); Michael Bartberger, Sherman Oaks, CA (US); James Brown, Moorpark, CA (US); Ryan Brown, Belmont, MA (US); Stuart C. Chaffee, Philadelphia, PA (US); Yuan Cheng, Newbury Park, CA (US); Michael Croghan, Thousand Oaks, CA (US); Russell Graceffa, Hampton, NH (US); Scott Harried, Woodland Hills, CA (US); Stephen Hitchcock, Westlake Village, CA (US); Randall Hungate, Camarillo, CA (US); Ted Judd, Simi Valley, CA (US); Matthew Kaller, Ventura, CA (US); Charles Kreiman, Watertown, MA (US); Daniel La, Brookline, MA (US); Patricia Lopez, West Hills, CA (US); Craig Masse, Cambridge, MA (US); Holger Monenschein, Camarillo, CA (US); Thomas Nguyen, Thousand Oaks, CA (US); Thomas Nixey, Newbury Park, CA (US); Vinod F. Patel, Acton, MA (US); Lewis Pennington, Camarillo, CA (US); Matthew Weiss, Boston, MA (US); Qiufen Xue, Newbury Park, CA (US); Bryant Yang, Simi Valley, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 773 days.

This patent is subject to a terminal disclaimer.

(21) Appl. No.: 11/600,264

(22) Filed: Nov. 14, 2006

(65) Prior Publication Data

US 2007/0185103 A1 Aug. 9, 2007

Related U.S. Application Data

(60) Provisional application No. 60/738,767, filed on Nov. 21, 2005.

(51) Int. Cl.
*A61K 31/50* (2006.01)
(52) U.S. Cl. .................. 514/252.01; 544/238; 544/298; 544/408; 546/242; 549/398
(58) Field of Classification Search .................. 549/398
See application file for complete search history.

(56) References Cited

U.S. PATENT DOCUMENTS

| | | | |
|---|---|---|---|
| 5,441,870 A | 8/1995 | Seubert et al. |
| 5,712,130 A | 1/1998 | Hajko et al. |
| 5,942,400 A | 8/1999 | Anderson et al. |
| 6,864,290 B2 | 3/2005 | Schostarez et al. |
| 6,982,264 B2 | 1/2006 | John et al. |
| 6,992,103 B2 | 1/2006 | Faller et al. |
| 7,067,542 B2 | 6/2006 | Schostarez et al. |
| 7,074,799 B2 | 7/2006 | Bakthavatchalam et al. |
| 7,109,217 B2 | 9/2006 | Coburn et al. |
| 7,115,652 B2 | 10/2006 | Yang |
| 7,115,747 B2 | 10/2006 | Reeder et al. |
| 7,132,568 B2 | 11/2006 | Yang et al. |
| 7,176,242 B2 | 2/2007 | John et al. |
| 7,223,774 B2 | 5/2007 | Aquino et al. |
| 7,244,755 B2 | 7/2007 | Fisher et al. |
| 7,253,198 B2 | 8/2007 | Demont et al. |

(Continued)

FOREIGN PATENT DOCUMENTS

WO    00/17369 A2    3/2000

(Continued)

OTHER PUBLICATIONS

West, Anthony R., Solid State Chemistry and its Applications, Wiley, New York, 1988, pp. 358 and 365.*

(Continued)

*Primary Examiner*—James O Wilson
*Assistant Examiner*—Brian McDowell
(74) *Attorney, Agent, or Firm*—G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I

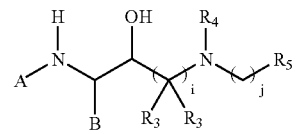

wherein A, B, $R^3$, $R^4$, $R^5$, i and j are defined herein. The invention also comprises pharmaceutical compositions including one or more compounds of Formula I, methods of use for these compounds, including treatment of AD and related diseases, by administering the compound(s) of Formula I, or compositions including them, to a subject. The invention also comprises further embodiments of Formulas II and III, intermediates and processes useful for the preparation of compounds of the invention.

8 Claims, No Drawings

U.S. PATENT DOCUMENTS

| | | |
|---|---|---|
| 7,291,620 B2 | 11/2007 | Coburn et al. |
| 7,312,360 B2 | 12/2007 | TenBrink et al. |
| 7,348,448 B2 | 3/2008 | Nantermet et al. |
| 7,351,738 B2 | 4/2008 | Pulley et al. |
| 7,371,853 B2 | 5/2008 | Coburn et al. |
| 2003/0109559 A1 | 6/2003 | Gailunas et al. |
| 2003/0166580 A1 | 9/2003 | Warpehoski et al. |
| 2004/0180939 A1 | 9/2004 | John et al. |
| 2005/0027007 A1 | 2/2005 | Hom |
| 2005/0038019 A1 | 2/2005 | Beck |
| 2005/0054690 A1 | 3/2005 | Aquino et al. |
| 2005/0267199 A1 | 12/2005 | Hom et al. |
| 2006/0211740 A1 | 9/2006 | Demont et al. |
| 2006/0229302 A1 | 10/2006 | Demont et al. |
| 2006/0241133 A1 | 10/2006 | Shearman et al. |

FOREIGN PATENT DOCUMENTS

| | | |
|---|---|---|
| WO | 01/70671 A2 | 9/2001 |
| WO | 02/02505 A2 | 1/2002 |
| WO | 03/002518 A1 | 1/2003 |
| WO | 2004/099376 A2 | 11/2004 |
| WO | 2005/058915 A2 | 6/2005 |

OTHER PUBLICATIONS

Wolff, Manfred E. "Burger's Medicinal Chemistry, 5ed, Part I", John Wiley & Sons, 1995, pp. 975-977.*

Banker (Modern Pharmaceutics) Banker, G.S. et al, "Modern Pharmaceutics, 3ed.", Marcel Dekker, New York, 1996, pp. 451 and 596.*

Berge, et al., "Pharmaceutical Salts", J. of Pharmaceutical Sciences, 66(1), 1-19 (1977).

Citron, M., "β-Secretase Inhibition for the Treatment of Alzheimer's Disease—Promise and Challenge", Trends in Pharmacological Sciences, 25(2), 92-97 (2004).

Corey, et al., "The Application of a Mechanistic Model Leads to the Extension of the Sharpless Asymmetric Dihydroxylation to Allylic 4-Methoxybenzoates and Conformationally Related Aine and Homoallylic Alcohol Derivatives", J. of Am. Chem. Soc., 117, 10805-10816 (1995).

Joachim, et al., "The Seminal Role of β-Amyloid in the Pathogenesis of Alzheimer Disease", Alzheimer Disease and Associated Disorders, 6(1), 7-34 (1992).

Luo, et al., "Mice deficient in BACE1, the Alzheimer's β-secretase, have normal phenotype and abolished β-amyloid generation", Nature Neuroscience, 4(3), 231-232 (2001).

Reynaud, et al., "New Synthesis of the Thiazole Ring", Bulletin de la Societe chimique de France, 1735-1738 (1962).

Sabbagh, et al.,"β-Amyloid and Treatment Opportunities for Alzheimer's Disease", Alzheimer's Disease Review, 3, 1-19 (1998).

Selkoe, D.M., "The Molecular Pathology of Alzheimer's Disease", Neuron, 6, 487-498 (1991).

Seubert, et al., "Isolation and Quantification of Soluble Alzheimer's β-Peptide from Biological Fluids", Nature, 359, 325-327 (1992).

Sinha, et al., "Purification and Cloning of Amyloid Precursor Protein β-Secretase from Human Brain", Nature, 402, 537-540 (1999).

Strangeland, et al., "Use of Thiazoles in the Halogen Dance Reaction: Application to the Total Synthesis of WS75624 B", J. Org. Chem., 69, 2381-2385 (2004).

Ghosh, et al., "Recent Developments of Structure Based β-Secretase Inhibitors for Alzheimer's Disease", Current Topics in Medicinal Chemistry, 5, 1609-1622 (2005).

Selcoe, D.M., "The Molecular Pathology of Alzheimer's Disease", Neuron, 6, 487-498 (1991).

* cited by examiner

BETA-SECRETASE MODULATORS AND METHODS OF USE

This application claims the benefit of U.S. Provisional Application No. 60/738,767, filed Nov. 21, 2005, which is hereby incorporated herein by reference in its entirety.

FIELD OF THE INVENTION

The invention relates generally to the field of pharmaceutical agents and, more specifically, to pharmaceutically active compounds, pharmaceutical compositions and methods of use thereof, to treat Beta-Secretase mediated disorders, including Alzheimer's disease and plaque formation related conditions. The invention also relates to intermediates and processes useful in the preparation of such compounds.

BACKGROUND OF THE INVENTION

Alzheimer's disease (AD) is a disease that affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is caused by two major physiological factors in the brain. The first factor, beta amyloid plaque formation, supports the "amyloid cascade hyposthesis" which alleges that AD is caused by the formation of characteristic beta amyloid deposits (commonly referred to as beta amyloid "plaques" or "plaque deposits") in the brain and in cerebral blood vessels (beta amyloid angiopathy). The second factor causing AD is intraneuronal tangles, consisting of an aggregate form of the protein tau. Amyloid plaques are thought to be specific for AD, while intraneuronal tangles are also found in other dementia-inducing disorders. Joachim et al., Alz. Dis. Assoc. Dis., 6:7-34 (1992).

Several lines of evidence indicate that progressive cerebral deposition of beta-amyloid peptide (A-beta) plays a seminal role in the pathogenisis of AD and can precede cognitive symptoms by years or even decades. Selkoe, Neuron 6:487 (1991). Release of A-beta from neuronal cells grown in culture and the presence of A-beta in cerebrospinal fluid (CSF) of both normal individuals and AD patients has been demonstrated. Seubert et al., Nature, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-Beta formation is a causative precursor or factor in the development of AD. Deposition of A-beta in areas of the brain responsible for cognitive factors is a major factor in the development of AD. Beta amyloid plaques are primarily composed of amyloid beta peptide (A-beta). A-Beta peptide is derived from the proteolytic cleavage of a large transmembrane amyloid precursor protein (APP), and is a peptide ranging in about 39-42 amino acids. A-Beta 42 (42 amino acids long) is thought to be the major component of these plaque deposits. Citron, Trends in Pharmacological Sciences, 25(2):92-97 (2004).

Several aspartyl proteases are thought to be involved in the processing or cleavage of APP, resulting in the formation of A-beta peptide. Beta secretase (BACE, also commonly referred to as memapsin) is thought to first cleave APP to generate two fragments of the A-beta peptide: (1) a first N-terminus fragment and (2) a second C-99 fragment, which is subsequently cleaved by gamma secretase to generate the C-terminus fragment of the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., Nature, 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., Alz. Dis. Rev. 3:1-19 (1997). Thus, inhibition of the BACE enzyme activity is desirable for the treatment of AD.

Studies have shown that the inhibition of BACE may be linked to the treatment of AD. BACE 1 knockout mice fail to produce A-beta, and present a normal phenotype. When crossed with transgenic mice that over express APP, the progeny show reduced amounts of A-beta in brain extracts as compares with control animals (Luo et al., Nature Neuroscience, 4:231-232 (2001)). This evidence further supports the concept that inhibition of beta secretase activity and a corresponding reduction of A-beta in the brain should provide a therapeutic method for treating AD and other beta amyloid or plaque related disorders.

Several approaches have been taken to treat AD and plaque-related disorders. One approach has been to reduce the formation of plaque on the brain. Particularly, a common approach has been to inhibit the activity of beta secretase. For example, each of the following PCT publications: WO 03/045913, WO 04/043916, WO 03/002122, WO 03/006021, WO 03/002518, WO 04/024081, WO 03/040096, WO 04/050619, WO 04/080376, WO 04/099376, WO 05/004802, WO 04/080459, WO 04/062625, WO 04/042910, WO 05/004803, WO 05/005374, WO 03/106405, WO 03/062209, WO 03/030886, WO 02/002505, WO 01/070671, WO 03/057721, WO 03/006013, WO 03/037325, Wo 04/094384, Wo 04/094413, WO 03/006423, WO 03/050073, WO 03/029169 and WO 04/000821, describe inhibitors of beta secretase, useful for treating AD and other beta-secretase mediated disorders.

BRIEF DESCRIPTION OF THE INVENTION

The present invention provides a new class of compounds useful for the modulation of beta secretase and, to that end, useful for the regulation or reduction of the formation of A-beta peptide and consequently, the reduction of beta amyloid plaque formation on the brain. Accordingly, the compounds of the invention are useful for the treatment of AD and other beta secretase mediated disorders.

The compounds provided by the invention, including stereoisomers, tautomers, solvates, pharmaceutically acceptable salts, derivatives or prodrugs thereof, are defined by general Formula I

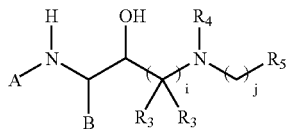

wherein A, B, $R^3$, $R^4$, $R^5$, i and j are as described below. The invention also provides procedures for making compounds of Formula I, as well as intermediates useful in such procedures.

The compounds provided by the invention are capable of modulating beta secretase. To this end, the invention further provides for the use of these compounds for therapeutic, prophylactic, acute and/or chronic treatment of beta secretase mediated diseases, such as those described herein. For example, the compounds are useful for the prophylaxis and treatment of AD and other diseases or conditions involving amyloid plaque formation on the brain.

The invention also provides pharmaceutical compositions, which comprise one or more compounds of the invention, methods for the treatment of beta secretase mediated diseases, such as AD, using the compounds and compositions of the invention, and intermediates and processes useful for the preparation of the compounds of the invention. The invention also provides the preparation of a pharmaceutical composition or of a medicament, containing one or more of the compounds, useful to attenuate, alleviate, or treat disorders through inhibition of beta secretase. For example, and in one embodiment, the invention provides a pharmaceutical composition comprising an effective dosage amount of a compound of Formula I in association with at least one pharmaceutically acceptable carrier.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are defined by

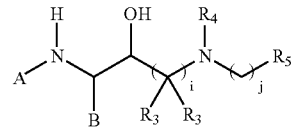

wherein
  A is $R^1$—C(=O)—, $R^1$—OC(=O)—, $R^1$—NHC(=O)—, $R^1$—S(=O)$_b$— or $R^1$—NHS(=O)$_b$—, wherein
  b is 1 or 2; and
  $R^1$ is a partially or fully saturated 3-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2 NR^7R^8$ or $NR^7S(O)_2R^8$;
  B is $R^2$—$(CR^{2a}R^{2a})_h$—, $R^2$—O—$(CR^{2a}R^{2a})_h$—, $R^2$—S—$(CR^{2a}R^{2a})_h$— or $R^2$—$NR^{2a}$—$(CR^{2a}R^{2a})_h$—, wherein
  $R^2$ is $C_1$-$C_{10}$ alkyl, $C_1$-$C_{10}$ haloalkyl, $C_1$-$C_{10}$ alkenyl, $C_1$-$C_{10}$ alkynyl or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said $C_1$-$C_{10}$ alkyl, $C_1$-$C_{10}$ alkenyl, $C_1$-$C_{10}$ alkynyl is optionally substituted independently with one or more substituents of $R^9$, and said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2 NR^7R^8$ or $NR^7S(O)_2R^8$;
  each $R^{2a}$, independently, is H, OH, $NO_2$, CN, $NH_2$, $C_1$-$C_{10}$ alkyl, $C_1$-$C_{10}$ alkoxyl or haloalkyl; and
  h is 0, 1, 2 or 3;
  i is 1, 2 or 3;
  j is 0, 1 or 2;
  each $R^3$, independently, is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^5$ is

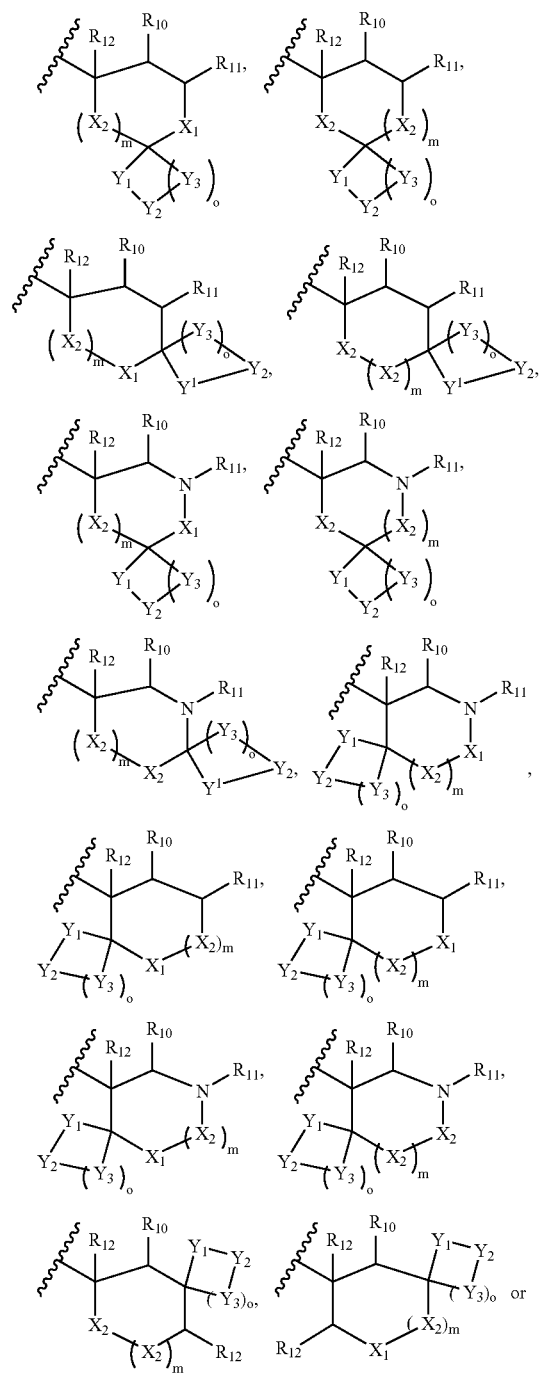

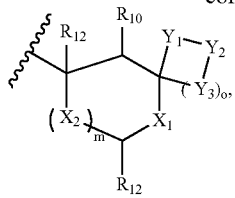

-continued wherein $X^1$ is C(=O), O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;
m is 0, 1 or 2; and
o is 0, 1, 2, 3, 4 or 5;
provided that (a) no more than two of $Y^1$, $Y^2$ and $Y^3$ is O, S or $NR^{12}$ and (b) when
o is 0, then each of $Y^1$ and $Y^2$ is $CR^{12}R^{12}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

alternatively, $R^{10}$ and $R^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substituents of $R^{12}$, $R^{13}$, $R^{14}$ or $R^{15}$ and optionally fused to a 4-7 membered third ring, the third ring formed of carbon atoms optionally including 1-3 heteroatoms selected from O, N, or S, and optionally substituted independently with 1-5 substituents of $R^{12}$, $R^{13}$, $R^{14}$ or $R^{15}$;

$R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$;

$R^{13}$ is $NR^{14}R^{15}$, $NR^{15}R^{15}$, $OR^{14}$, $SR^{14}$, $OR^{15}$, $SR^{15}$, C(O)$R^{14}$, OC(O)$R^{14}$, COOR$^{14}$, C(O)$R^{15}$, OC(O)$R^{15}$, COOR$^{15}$, C(O)NR$^{14}R^{15}$, C(O)NR$^{15}R^{15}$, NR$^{14}$C(O)$R^{14}$, NR$^{15}$C(O)$R^{14}$, NR$^{14}$C(O)$R^{15}$, NR$^{15}$C(O)$R^{15}$, NR$^{15}$C(O)NR$^{14}R^{15}$, NR$^{15}$C(O)NR$^{15}R^{15}$, NR$^{15}$(COOR$^{14}$), NR$^{15}$(COOR$^{15}$), OC(O)NR$^{14}R^{15}$, OC(O)NR$^{15}R^{15}$, $S(O)_2R^{14}$, $S(O)_2R^{15}$, $S(O)_2$ NR$^{14}R^{15}$, $S(O)_2$NR$^{15}R^{15}$, NR$^{14}S(O)_2$NR$^{14}R^{15}$, NR$^{15}S(O)_2$ NR$^{15}R^{15}$, NR$^{14}S(O)_2R^{14}$ or NR$^{15}S(O)_2R^{15}$;

$R^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$; and $R^{15}$ is H, halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, $C_{1-10}$-alkylamino-, $C_{1-10}$-dialkylamino-, $C_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

In another embodiment, the compounds of Formula I include $R^1$—C(=O)— as A, in conjunction with any of the above or below embodiments.

In another embodiment, the compounds of Formula I include $R^1$—OC(=O)— as A, in conjunction with any of the above or below embodiments.

In another embodiment, the compounds of Formula I include $R^1$—NHC(=O)— as A, in conjunction with any of the above or below embodiments.

In another embodiment, the compounds of Formula I include $R^1$—S(=O)$_b$— as A wherein b is 0, 1 or 2, in conjunction with any of the above or below embodiments.

In another embodiment, the compounds of Formula I include or $R^1$—NHS(=O)$_b$— as A wherein b is 0, 1 or 2, in conjunction with any of the above or below embodiments.

In another embodiment, the compounds of Formula I include as $R^1$

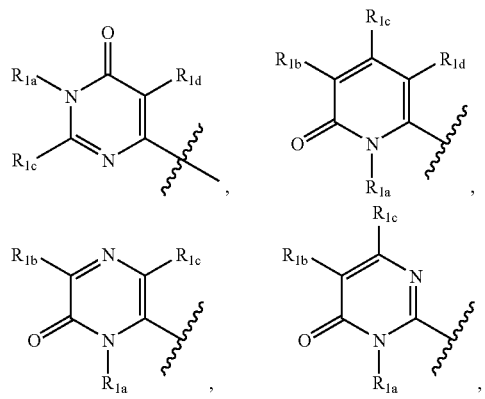

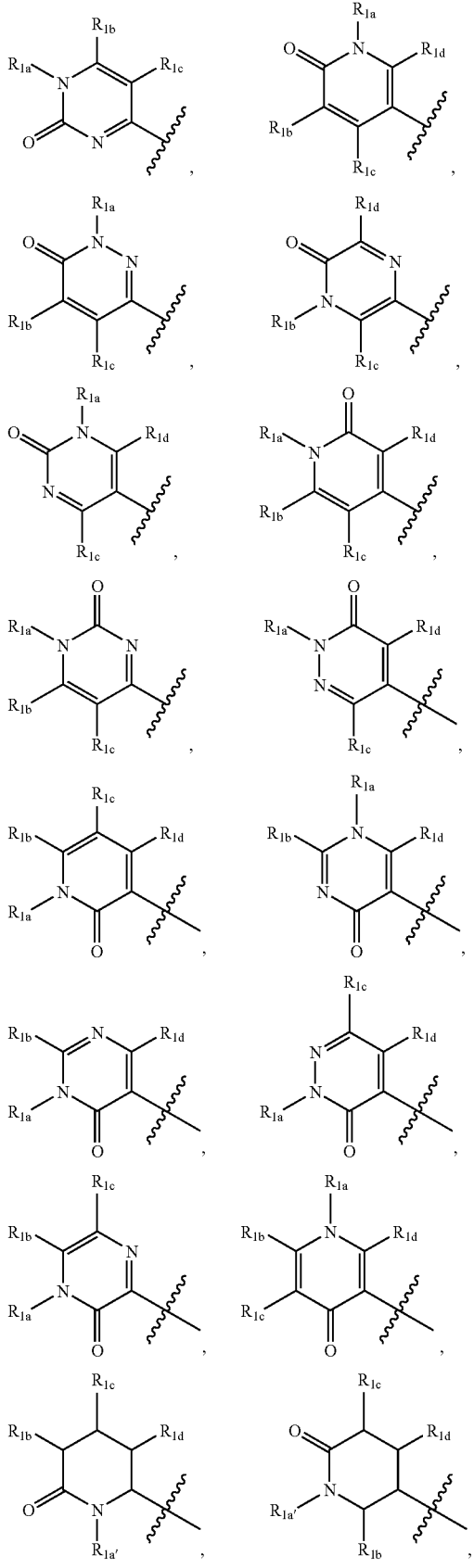
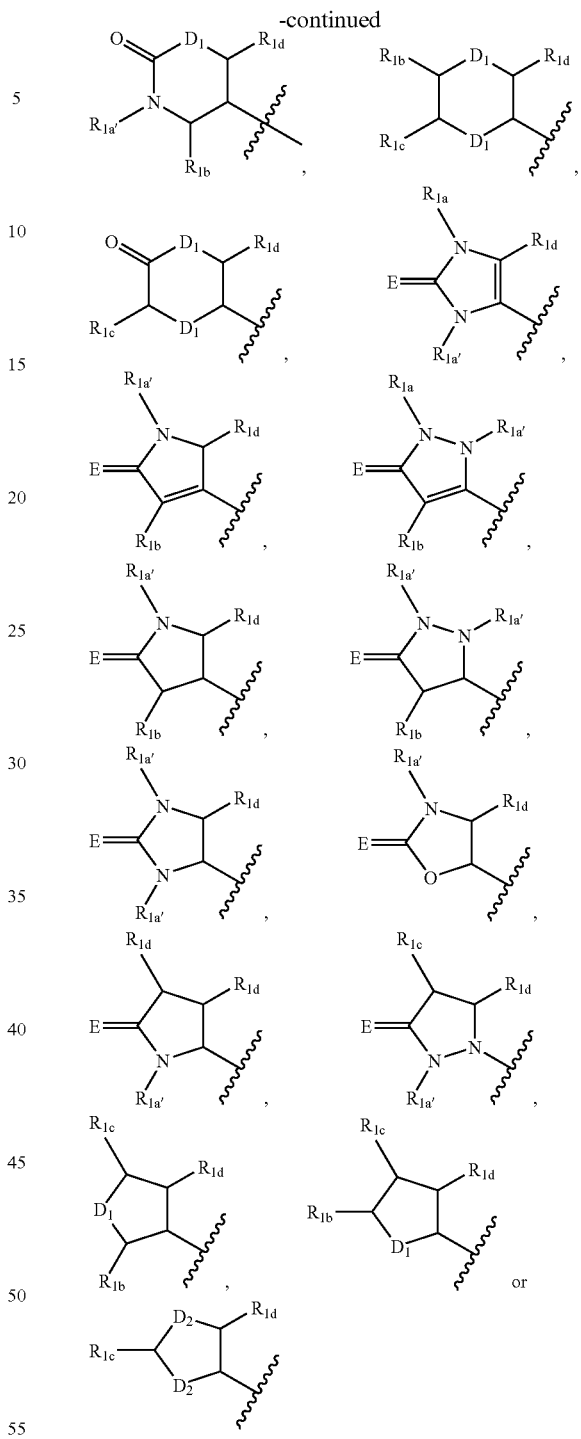

wherein
$D^1$ is $CR^{1a'}R^{1a'}$, $NR^{1a'}$, O or S;
$D^2$ is $NR^{1a'}$, O or S;
E is O or S;
each $R^{1a}$, independently, is $R^7$, $R^8$, $R^9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$, provided that $R^{1a}$ is not H;
each $R^{1a'}$, independently, is $R^7$, $R^8$, $R^9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$; and each $R^{1b}$, $R^{1c}$ and $R^{1d}$, independently, is $R^7$, $R^8$, $R^9$, $NR^7R^7$, $NR^7R^8$, $OR^7$, $SR^7$, $OR^8$, $SR^8$, $C(O)R^7$, $COOR^7$, $C(O)R^8$, $COOR^8$, $C(O)NR^7R^7$, $C(S)NR^7R^7$, $NR^7C(O)R^7$, $NR^7C(S)R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$, in conjunction with any of the above or below embodiments.

The phrase "provided that $R^{1a}$ is not H" is intended to mean that the $R^1$ group (ring) may not be fully unsaturated, such as by tautomerization of the proton, where $R^{1a}$ was H. The present invention excludes compounds where $R^1$ is fully unsaturated or aromatic.

In the immediately preceeding embodiment, the compounds of Formula I include $R^7$, $R^8$ or $R^9$, independently, as each of $R^{1a}$, $R^{1b}$, $R^{1c}$ and $R^{1d}$, independently, in conjunction with any of the above or below embodiments.

In another embodiment, the compounds of Formula I include as $R^1$

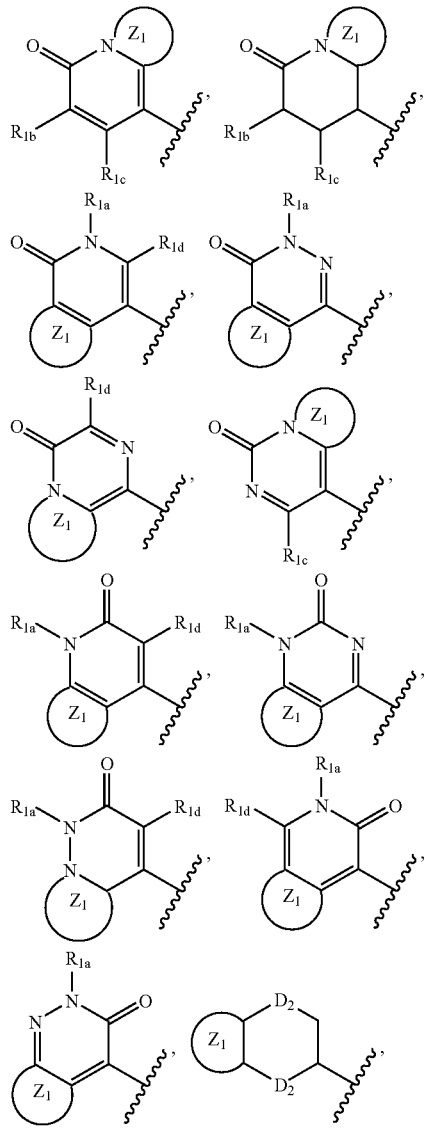

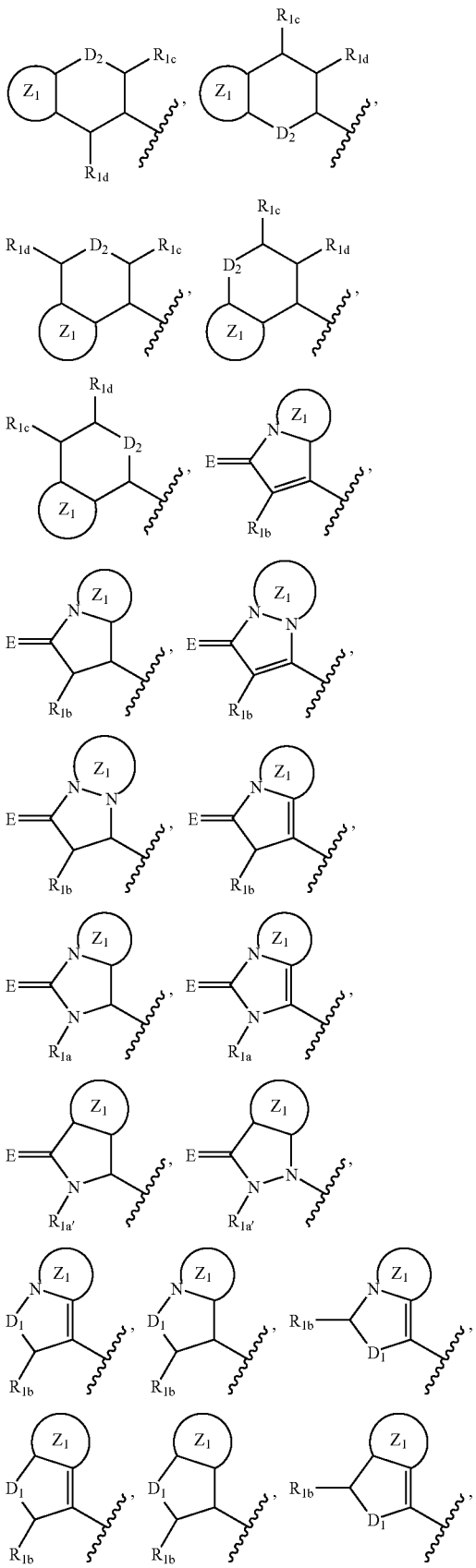

-continued

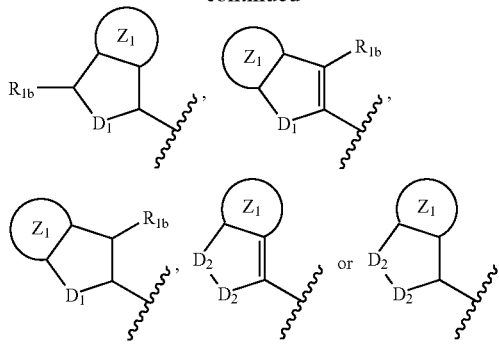

wherein
D¹ is CR^{1a'}R^{1a'}, NR^{1a'}, O or S;
D² is NR^{1a'}, O or S;
E is O or S;
each R^{1a}, independently, is R⁷, R⁸, R⁹, C(O)R⁷, C(O)R⁸, C(O)NR⁷R⁷, C(S)NR⁷R⁷, C(O)NR⁷R⁸, C(S)NR⁷R⁸, S(O)₂NR⁷R⁷, S(O)₂R⁸, or S(O)₂NR⁷R⁸, provided that R^{1a} is not H;
each R^{1a}, independently, is R⁷, R⁸, R⁹, C(O)R⁷, C(O)R⁸, C(O)NR⁷R⁷, C(S)NR⁷R⁷, C(O)NR⁷R⁸, C(S)NR⁷R⁸, S(O)₂NR⁷R⁷, S(O)₂R⁸, or S(O)₂NR⁷R⁸;
each R^{1b}, R^{1c} and R^{1d}, independently, is R⁷, R⁸, R⁹, NR⁷R⁷, NR⁷R⁸, OR⁷, SR⁷, OR⁸, SR⁸, C(O)R⁷, COOR⁷, C(O)R⁸, COOR⁸, C(O)NR⁷R⁷, C(S)NR⁷R⁷, NR⁷C(O)R⁷, NR⁷C(S)R⁷, NR⁷C(O)NR⁷R⁷, NR⁷C(S)NR⁷R⁷, NR⁷(COOR⁷), OC(O)NR⁷R⁷, C(O)NR⁷R⁸, C(S)NR⁷R⁸, NR⁷C(O)R⁸, NR⁷C(S)R⁸, NR⁷C(O)NR⁷R⁸, NR⁷C(S)NR⁷R⁸, NR⁷(COOR⁸), OC(O)NR⁷R⁸, S(O)₂NR⁷R⁷, NR⁷S(O)₂NR⁷R⁷, NR⁷S(O)₂R⁷, S(O)₂R⁸, S(O)₂NR⁷R⁸, NR⁷S(O)₂NR⁷R⁸ or NR⁷S(O)₂R⁸; and
Z¹ is a partially or fully saturated or unsaturated 5-8 membered monocyclic ring, said ring formed of carbon atoms optionally including 1-3 heteroatoms if monocyclic, 1-6 heteroatoms if bicyclic, or 1-9 heteroatoms if tricyclic, said heteroatoms selected from O, N, or S and optionally substituted independently with one or more substituents of oxo, R⁷, R⁸, R⁹, NR⁷R⁷, NR⁷R⁸, OR⁷, SR⁷, OR⁸, SR⁸, C(O)R⁷, OC(O)R⁷, COOR⁷, C(O)R⁸, OC(O)R⁸, COOR⁸, C(O)NR⁷R⁷, C(S)NR⁷R⁷, NR⁷C(O)R⁷, NR⁷C(S)R⁷, NR⁷C(O)NR⁷R⁷, NR⁷C(S)NR⁷R⁷, NR⁷(COOR⁷), OC(O)NR⁷R⁷, C(O)NR⁷R⁸, C(S)NR⁷R⁸, NR⁷C(O)R⁸, NR⁷C(S)R⁸, NR⁷C(O)NR⁷R⁸, NR⁷C(S)NR⁷R⁸, NR⁷(COOR⁸), OC(O)NR⁷R⁸, S(O)₂NR⁷R⁷, NR⁷S(O)₂NR⁷R⁷, NR⁷S(O)₂R⁷, S(O)₂R⁸, S(O)₂NR⁷R⁸, NR⁷S(O)₂NR⁷R⁸ or NR⁷S(O)₂R⁸, in conjunction with any of the above or below embodiments.

In the immediately preceeding embodiment, the compounds of Formula I include R⁷, R⁸ or R⁹, independently, as each of R^{1a}, R^{1b}, R^{1c} and R^{1d}, in conjunction with any of the above or below embodiments.

In the preceeding embodiment, the compounds of Formula I include an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring as Z¹, in conjunction with any of the above or below embodiments.

In the preceeding embodiment, the compounds of Formula I include an optionally substituted pyrrole, imidazole, pyrazole, triazole, thiophene, thiazole, thiadiazole, isothiazole, furan, oxazole, oxadiazole or isoxazole ring as Z¹, in conjunction with any of the above or below embodiments.

In another embodiment, the compounds of Formula I include as R¹

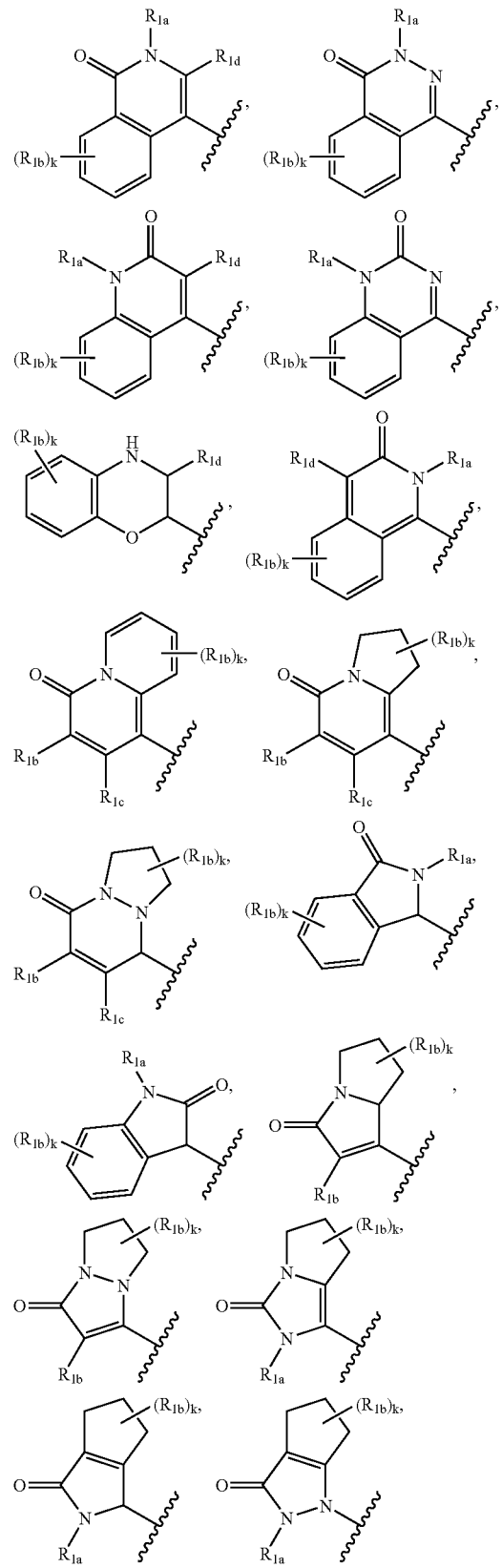

-continued

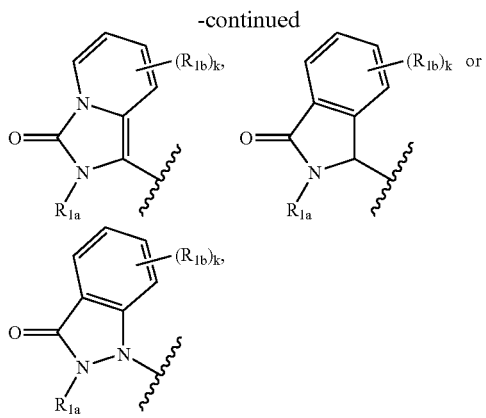

wherein $R^{1a}$ is $R^7$, $R^8$, $R^9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$, provided that provided that $R^{1a}$ is not H;

each $R^{1b}$, $R^{1c}$ and $R^{1d}$, independently, is $R^7$, $R^8$, $R^9$, $NR^7R^7$, $NR^7R^8$, $OR^7$, $SR^7$, $OR^8$, $SR^8$, $C(O)R^7$, $COOR^7$, $C(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$; and k is 0, 1, 2 or 3, in conjunction with any of the above or below embodiments.

In another embodiment, the compounds of Formula I include $R^2$—$(CR^{2a}R^{2a})_h$— as B wherein each $R^{2a}$, independently, is H, OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I include $R^2$—O—$(CR^{2a}R^{2a})_h$— as B wherein each $R^{2a}$a, independently, is H, OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I include $R^2$—S—$(CR^{2a}R^{2a})_h$— as B wherein each $R^{2a}$, independently, is H, OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I include $R^2$—$NR^{2a}$—$(CR^{2a}R^{2a})_h$— as B wherein each $R^{2a}$, independently, is H, OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I include $R^2$—$(CHR^{2a})_h$— as B wherein $R^{2a}$ is OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I include $R^2$—$(CH_2)_h$— as B, in conjunction with any of the above or below embodiments.

In another embodiment, the compounds of Formula I include $R^2$—O—$(CH_2)_h$— as B, in conjunction with any of the above or below embodiments.

In another embodiment, the compounds of Formula I include $R^2$—S—$(CH_2)_h$— as B, in conjunction with any of the above or below embodiments.

In another embodiment, the compounds of Formula I include $R^2$—NH—$(CH_2)_h$— as B, in conjunction with any of the above or below embodiments.

In another embodiment, the compounds of Formula I include an optionally substituted ring system selected from phenyl, naphthyl, pyridyl, pyrimidyl, pyridazinyl, pyrazinyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl as $R^2$, in conjunction with any of the above or below embodiments.

In another embodiment, the compounds of Formula I include an optionally substituted ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl and benzimidazoly as $R^2$, in conjunction with any of the above or below embodiments.

In another embodiment, the compounds of Formula I include $C_1$-$C_{10}$ alkyl, $C_1$-$C_{10}$ alkenyl or $C_1$-$C_{10}$ alkynyl as $R^2$, in conjunction with any of the above or below embodiments.

In another embodiment, the compounds of Formula I include $C_1$-$C_{10}$ haloalkyl as $R^2$, in conjunction with any of the above or below embodiments.

In another embodiment, the compounds of Formula I include H, haloalkyl, CN, $C_{1-10}$-alkyl, $C_{2-10}$-alkenyl or $C_{2-10}$-alkynyl as $R^3$, in conjunction with any of the above or below embodiments.

In another embodiment, the compounds of Formula I include H as $R^3$, in conjunction with any of the above or below embodiments.

In another embodiment, the compounds of Formula I include $C_{1-10}$-alkyl as $R^3$, in conjunction with any of the above or below embodiments.

In another embodiment, the compounds of Formula I include H, haloalkyl, CN, $C_{1-10}$-alkyl, $C_{2-10}$-alkenyl or $C_{2-10}$-alkynyl as $R^4$, in conjunction with any of the above or below embodiments.

In another embodiment, the compounds of Formula I include H as $R^4$, in conjunction with any of the above or below embodiments.

In another embodiment, the compounds of Formula I include haloalkyl or $C_{1-10}$-alkyl as $R^4$, in conjunction with any of the above or below embodiments.

In another embodiment, the compounds of Formula I include h as 0, 1 or 2, in conjunction with any of the above or below embodiments.

In another embodiment, the compounds of Formula I include h as 1, in conjunction with any of the above or below embodiments.

In another embodiment, the compounds of Formula I include i as 1, 2 or 3, in conjunction with any of the above or below embodiments.

In another embodiment, the compounds of Formula I include i as 1, in conjunction with any of the above or below embodiments.

In another embodiment, the compounds of Formula I include j as 0, 1 or 2, in conjunction with any of the above or below embodiments.

In another embodiment, the compounds of Formula I include j as 0, in conjunction with any of the above or below embodiments.

In another embodiment, the compounds of Formula I include as $R^5$

[Chemical structures depicting various ring systems with substituents $R_{12}$, $(R_{12})_p$, $(R_{12})_{p'}$, $Z_2$, $X_1$, $X_2$, $Y_1$, $Y_2$, $Y_3$, with subscripts $m$ and $o$]

wherein m, o, $R^{12}$, $X^1$, $X^2$, $Y^1$, $Y^2$ and $Y^3$ are as defined herein above with respect to compounds of formula I;

$Z^2$ is an optionally substituted, partially saturated or fully unsaturated 5-8 membered monocyclic ring, said ring formed of carbon atoms optionally including 1-3 heteroatoms if monocyclic, 1-6 heteroatoms if bicyclic, or 1-9 heteroatoms if tricyclic, said heteroatoms selected from O, N, or S, provided that (a) no more than two of $Y^1$, $Y^2$ and $Y^3$ is O, S or $NR^{12}$ and (b) when o is 0, then each of $Y^1$ and $Y^2$ is $CR^{12}R^{12}$; and p is 0, 1, 2, 3, 4 or 5, in conjunction with any of the above or below embodiments.

In the immediately preceeding embodiment, the compounds of Formula I include $CR^{12}R^{12}$ as $X^1$, in conjunction with any of the above or below embodiments.

In the preceeding embodiment, the compounds of Formula I include $CHR^{12}$ as $X^1$, in conjunction with any of the above or below embodiments.

In the preceeding embodiment, the compounds of Formula I include $CH_2$ as $X^1$, in conjunction with any of the above or below embodiments.

In the preceeding embodiment, the compounds of Formula I include C(=O) as $X^1$, in conjunction with any of the above or below embodiments.

In the preceeding embodiment, the compounds of Formula I include O as $X^1$, in conjunction with any of the above or below embodiments.

In the preceeding embodiment, the compounds of Formula I include S as $X^1$, in conjunction with any of the above or below embodiments.

In the preceeding embodiment, the compounds of Formula I include $NR^{12}$ as $X^1$, in conjunction with any of the above or below embodiments.

In the preceeding embodiment, the compounds of Formula I include NH as $X^1$, in conjunction with any of the above or below embodiments.

In the preceeding embodiment, the compounds of Formula I include $CR^{12}R^{12}$ as each $X^2$, independently, in conjunction with any of the above or below embodiments.

In the preceeding embodiment, the compounds of Formula I include $CHR^{12}$ as each $X^2$, independently, in conjunction with any of the above or below embodiments.

In the preceeding embodiment, the compounds of Formula I include $CH_2$ as each $X^2$, independently, in conjunction with any of the above or below embodiments.

In the preceeding embodiment, the compounds of Formula I include $CR^{12}R^{12}$ as each of $Y^1$, $Y^2$ and $Y^3$, independently, in conjunction with any of the above or below embodiments.

In the preceeding embodiment, the compounds of Formula I include $CHR^{12}$ as each of $Y^1$, $Y^2$ and $Y^3$, independently, in conjunction with any of the above or below embodiments.

In the preceeding embodiment, the compounds of Formula I include $CH_2$ as each of $Y^1$, $Y^2$ and $Y^3$, independently, in conjunction with any of the above or below embodiments.

In the preceeding embodiment, the compounds of Formula I include O as any one or two of $Y^1$, $Y^2$ and $Y^3$, independently, in conjunction with any of the above or below embodiments.

In the preceeding embodiment, the compounds of Formula I include S as any one or two of $Y^1$, $Y^2$ and $Y^3$, independently, in conjunction with any of the above or below embodiments.

In the preceeding embodiment, the compounds of Formula I include $NR^{12}$ as any one or two of $Y^1$, $Y^2$ and $Y^3$, independently, in conjunction with any of the above or below embodiments.

In the preceeding embodiment, the compounds of Formula I include O as $Y^2$ and $CH_2$ as each of $Y^1$ and $Y^3$, in conjunction with any of the above or below embodiments.

In the preceeding embodiment, the compounds of Formula I include S as $Y^2$ and $CH_2$ as each of $Y^1$ and $Y^3$, in conjunction with any of the above or below embodiments.

In the preceeding embodiment, the compounds of Formula I include $NR^{12}$ as $Y^2$ and $CH_2$ as each of $Y^1$ and $Y^3$, in conjunction with any of the above or below embodiments.

In the preceeding embodiment, the compounds of Formula I include an optionally substituted benzene, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring as $Z^2$, in conjunction with any of the above or below embodiments.

In another embodiment, the compounds of Formula I include compounds wherein $R^5$ is

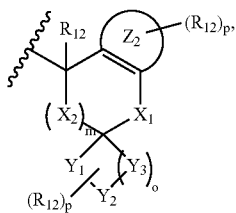

wherein m, o, $X^1$, $X^2$, $Y^1$, $Y^2$ and $Y^3$ are as defined herein with respect to compounds of formula I, $Z^2$ is an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring, each p, independently, is 0, 1, 2, 3, 4 or 5, and $R^{12}$, in each instance, is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$, in conjunction with any of the above or below embodiments.

In another embodiment, the invention provides compounds of Formula I, wherein h is 1 or 2;
i is 1;
j is 0;
$R^1$ is

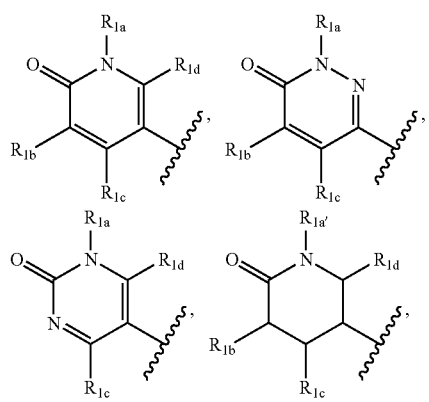

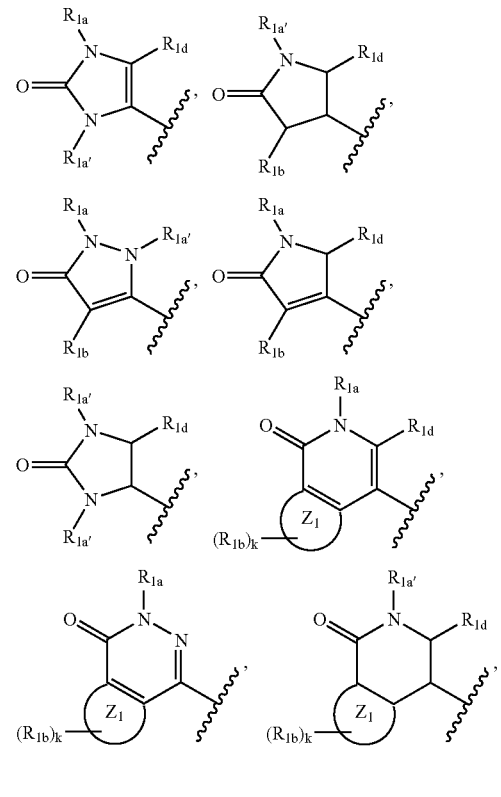

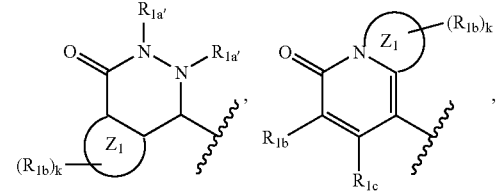

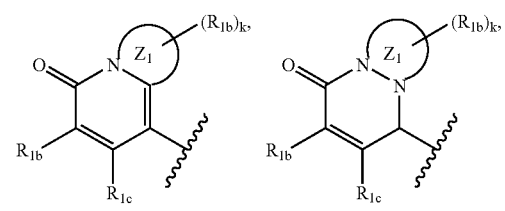

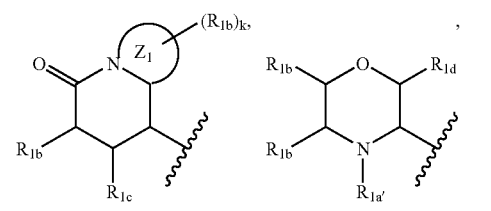

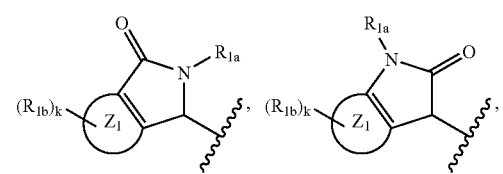

-continued

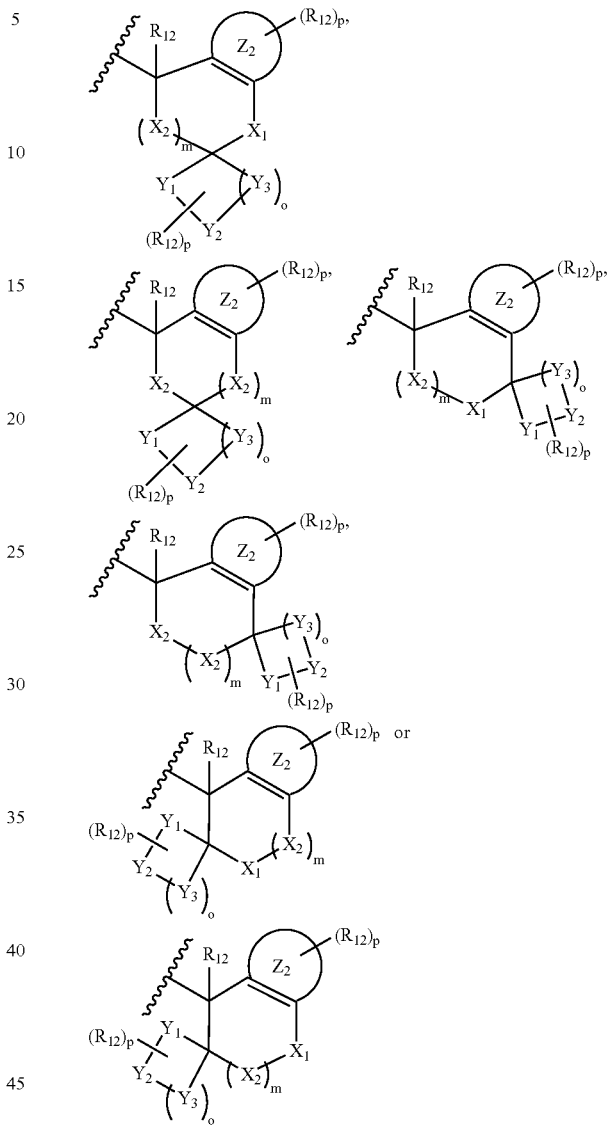

wherein $R^{1a}$ is $R^7$, $R^8$, $R^9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$, provided that $R^{1a}$ is not H;

each $R^{1a'}$, independently, is $R^7$, $R^8$, $R^9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$;

each $R^{1b}$, $R^{1c}$ and $R^{1d}$, independently, is $R^7$, $R^8$, $R^9$, $NR^7R^7$, $NR^7R^8$, $OR^7$, $SR^7$, $OR^8$, $SR^8$, $C(O)R^7$, $COOR^7$, $C(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2 NR^7R^8$, $NR^7S(O)_2NR^7R^8$ or $NR^7S(O)_2R^8$;

$Z^1$ is an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring; and k is 0, 1, 2 or 3;

$R^2$ is an optionally substituted ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzoxazolyl, benzisoxazolyl, benzothiazolyl, benzisothiazolyl, benzotriazolyl and benzimidazolyl;

each $R^3$, independently, is H, haloalkyl, CN, $C_{1-10}$-alkyl, $C_{2-10}$-alkenyl or $C_{2-10}$-alkynyl;

$R^4$ is H, CN or $C_{1-10}$-alkyl;
$R^5$ is wherein m, o, $R^{12}$, $X^2$, $Y^1$, $Y^2$ and $Y^3$ are as defined herein above;

$X^1$ is $C(=O)$, O, S or $NR^{12}$;

$Z^2$ is an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring; and p is 0, 1, 2, 3, 4 or 5.

$R^7$ is H, $C_{1-10}$-alkyl or $C_{2-10}$-alkenyl, each of the $C_{1-10}$-alkyl, or $C_{2-10}$-alkenyl optionally substituted with 1-3 substituents of $R^9$;

$R^8$ is a ring system selected from phenyl, pyridyl, pyrimidinyl, triazinyl, quinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl and cycloheptyl, said ring system optionally substituted independently with 1-3 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, or a ring system selected from phenyl, pyridyl, pyrimidinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl and cycloheptyl, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, tert-butyl, cyclobutyl, $C_{1-10}$-alkylamino-, $C_{1-10}$-dialkylamino-, $C_{1-10}$-thioalkoxyl, benzyl or phenyl; and $R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopently, hexyl, cyclohexyl, $C_{1-10}$-alkylamino-, $C_{1-10}$-dialkylamino-, $C_{1-10}$-thioalkoxyl, benzyl or phenyl.

In another embodiment, the invention provides compounds generally defined by Formula II,

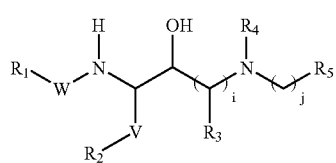

II or stereoisomer, tautomer, solvate, pharmaceutically acceptable salt, derivative or prodrug thereof, wherein W is —C(=O)—, —OC(=O)—, —NHC(=O)—, —S(=O)$_b$— or —NHS(=O)$_b$—, wherein b is 1 or 2;

$R^1$ is

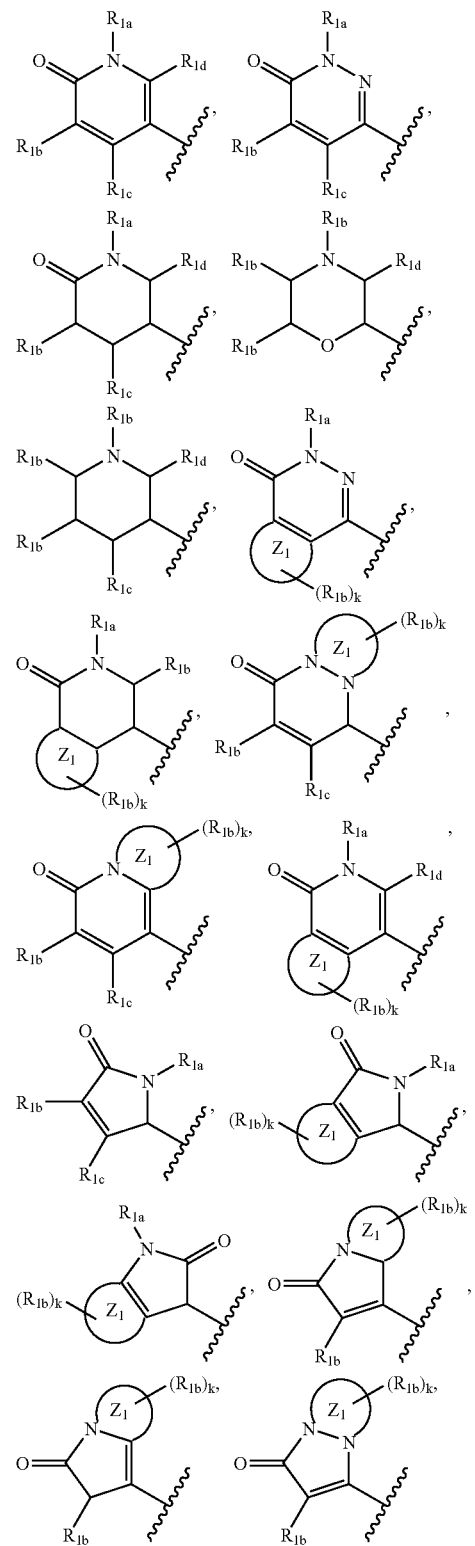

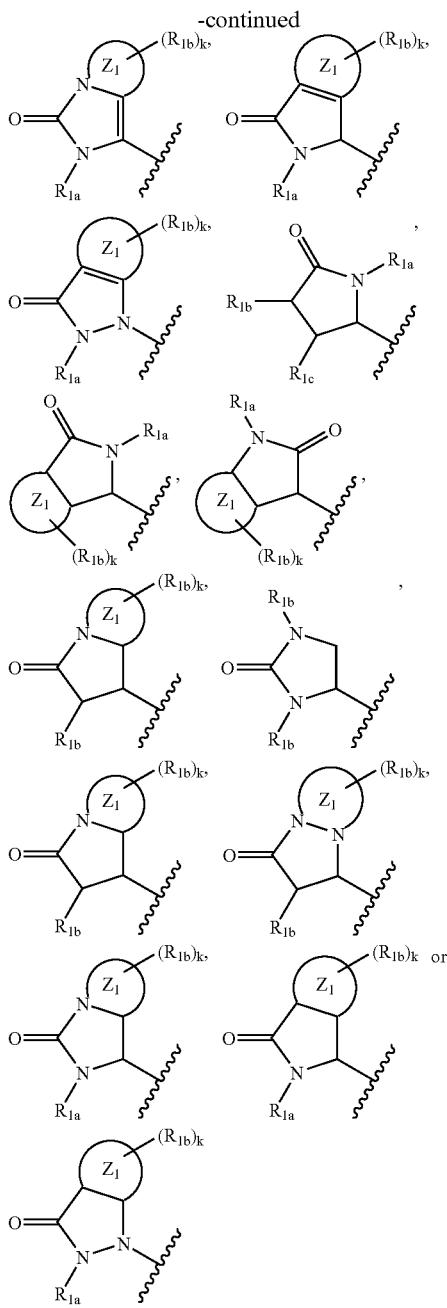

wherein R$^{1a}$ is R$^7$, R$^8$, R$^9$, C(O)R$^7$, C(O)R$^8$, C(O)NR$^7$R$^7$, C(S)NR$^7$R$^7$, C(O)NR$^7$R$^8$, C(S)NR$^7$R$^8$, S(O)$_2$NR$^7$R$^7$, S(O)$_2$R$^8$, or S(O)$_2$NR$^7$R$^8$, provided that R$^{1a}$ is not H;

each R$^{1b}$, R$^{1c}$ and R$^{1d}$, independently, is R$^7$, R$^8$, R$^9$, NR$^7$R$^7$, NR$^7$R$^8$, OR$^7$, SR$^7$, R$^8$, SR$^8$, C(O)R$^7$, COOR$^7$, C(O)R$^8$, COOR$^8$, C(O)NR$^7$R$^7$, C(S)NR$^7$R$^7$, NR$^7$C(O)R$^7$, NR$^7$C(S)R$^7$, NR$^7$C(O)NR$^7$R$^7$, NR$^7$C(S)NR$^7$R$^7$, NR$^7$(COOR$^7$), OC(O)NR$^7$R$^7$, C(O)NR$^7$R$^8$, C(S)NR$^7$R$^8$, NR$^7$C(O)R$^8$, NR$^7$C(S)R$^8$, NR$^7$C(O)NR$^7$R$^8$, NR$^7$C(S)NR$^7$R$^8$, NR$^7$(COOR$^8$), OC(O)NR$^7$R$^8$, S(O)$_2$NR$^7$R$^7$, NR$^7$S(O)$_2$NR$^7$R$^7$, NR$^7$S(O)$_2$R$^7$, S(O)$_2$R$^8$, S(O)$_2$NR$^7$R$^8$, NR$^7$S(O)$_2$NR$^7$R$^8$ or NR$^7$S(O)$_2$R$^8$;

Z$^1$ is a phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring; and k is 0, 1, 2 or 3;

V is —(CR$^{2a}$R$^{2a}$)$_h$—, —O—(CR$^{2a}$R$^{2a}$)$_h$—, —S—(CR$^{2a}$R$^{2a}$)$_h$— or —NR$^{2a}$—(CR$^{2a}$R$^{2a}$)$_h$—, wherein each R$^{2a}$, independently, is H, C$_1$-C$_{10}$ alkyl or haloalkyl, and h is 0, 1 or 2;

R$^2$ is a C$_1$-C$_{10}$ haloalkyl or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substituents of oxo, R$^7$, R$^8$, R$^9$, NR$^7$R$^7$, NR$^7$R$^8$, OR$^7$, SR$^7$, OR$^8$, SR$^8$, C(O)R$^7$, OC(O)R$^7$, COOR$^7$, C(O)R$^8$, OC(O)R$^8$, COOR$^8$, C(O)NR$^7$R$^7$, C(S)NR$^7$R$^7$, NR$^7$C(O)R$^7$, NR$^7$C(S)R$^7$, NR$^7$C(O)NR$^7$R$^7$, NR$^7$C(S)NR$^7$R$^7$, NR$^7$(COOR$^7$), OC(O)NR$^7$R$^7$, C(O)NR$^7$R$^8$, C(S)NR$^7$R$^8$, NR$^7$C(O)R$^8$, NR$^7$C(S)R$^8$, NR$^7$C(O)NR$^7$R$^8$, NR$^7$C(S)NR$^7$R$^8$, NR$^7$(COOR$^8$), OC(O)NR$^7$R$^8$, S(O)$_2$NR$^7$R$^7$, NR$^7$S(O)$_2$NR$^7$R$^7$, NR$^7$S(O)$_2$R$^7$, S(O)$_2$R$^8$, S(O)$_2$NR$^7$R$^8$, NR$^7$S(O)$_2$NR$^7$R$^8$ or NR$^7$S(O)$_2$R$^8$;

R$^3$ is H, haloalkyl, CN, C$_{1-10}$-alkyl, C$_{2-10}$-alkenyl or C$_{2-10}$-alkynyl;

R$^4$ is H, haloalkyl, CN, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with 1-5 substituents of R$^8$ or R$^9$;

R$^5$ is

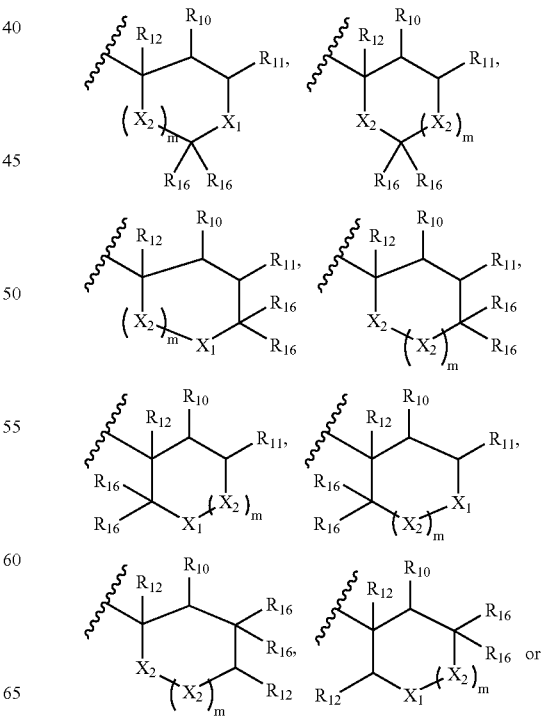

-continued

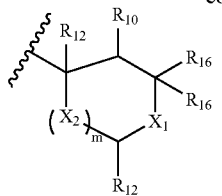

wherein X¹ is C(=O), O, S or NR¹²;
each X², independently, is CR¹²R¹²; and
m is 0, 1 or 2;

R⁷ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of NR⁸R⁹, NR⁹R⁹, OR⁸, SR⁸, OR⁹, SR⁹, C(O)R⁸, OC(O)R⁸, COOR⁸, C(O)R⁹, OC(O)R⁹, COOR⁹, C(O)NR⁸R⁹, C(O)NR⁹R⁹, NR⁹C(O)R⁸, NR⁹C(O)R⁹, NR⁹C(O)NR⁸R⁹, NR⁹C(O)NR⁹R⁹, NR⁹(COOR⁸), NR⁹(COOR⁹), OC(O)NR⁸R⁹, OC(O)NR⁹R⁹, S(O)₂R⁸, S(O)₂NR⁸R⁹, S(O)₂R⁹, S(O)₂NR⁹R⁹, NR⁹S(O)₂NR⁸R⁹, NR⁹S(O)₂NR⁹R⁹, NR⁹S(O)₂R⁸, NR⁹S(O)₂R⁹, R⁸ or R⁹;

R⁸ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R⁹, oxo, NR⁹R⁹, OR⁹; SR⁹, C(O)R⁹ or a partially or fully saturated or unsaturated 5-6 membered ring of carbon atoms optionally including 1-3 heteroatoms selected from O, N, or S, and optionally substituted independently with 1-5 substituents of R⁹;

R⁹ is H, halo, haloalkyl, CN, OH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, NO₂, NH₂, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopentyl, hexyl, cyclohexyl, $C_{1-10}$-alkylamino-, $C_{1-10}$-dialkylamino-, $C_{1-10}$-thioalkoxyl, benzyl or phenyl;

R¹⁰ is H, halo, haloalkyl, CN, OH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, NO₂, NH₂, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopentyl, hexyl, cyclohexyl, $C_{1-10}$-alkylamino-, $C_{1-10}$-dialkylamino-, $C_{1-10}$-thioalkoxyl, benzyl or phenyl;

R¹¹ is H, halo, haloalkyl, CN, OH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, NO₂, NH₂, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopentyl, hexyl, cyclohexyl, $C_{1-10}$-alkylamino-, $C_{1-10}$-dialkylamino-, $C_{1-10}$-thioalkoxyl, benzyl or phenyl;

alternatively, R¹⁰ and R¹¹ taken together with the carbon atoms to which they are attached form a partially or fully saturated or unsaturated 5-6 membered ring of carbon atoms optionally including 1-3 heteroatoms selected from O, N, or S, and the ring optionally substituted independently with 1-5 substituents of R¹², R¹³, R¹⁴ or R¹⁵;

R¹² is H, halo, haloalkyl, CN, OH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, NO₂, NH₂, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopentyl, hexyl, cyclohexyl, $C_{1-10}$-alkylamino-, $C_{1-10}$-dialkylamino-, $C_{1-10}$-thioalkoxyl, benzyl or phenyl;

R¹³ is NR¹⁴R¹⁵, NR¹⁵R¹⁵, OR¹⁴; SR¹⁴, OR¹⁵; SR¹⁵, C(O)R¹⁴, OC(O)R¹⁴, COOR¹⁴, C(O)R¹⁵, OC(O)R¹⁵, COOR¹⁵, C(O)NR¹⁴R¹⁵, C(O)NR¹⁵R¹⁵, NR¹⁴C(O)R¹⁴, NR¹⁵C(O)R¹⁴, NR¹⁴C(O)R¹⁵, NR¹⁵C(O)R¹⁵, NR¹⁵C(O)NR¹⁴R¹⁵, NR¹⁵C(O)NR¹⁵R¹⁵, NR¹⁵(COOR¹⁴), NR¹⁵(COOR¹⁵), OC(O)NR¹⁴R¹⁵, OC(O)NR¹⁵R¹⁵, S(O)₂R¹⁴, S(O)₂R¹⁵, S(O)₂ NR¹⁴R¹⁵, S(O)₂NR¹⁵R¹⁵, NR¹⁴S(O)₂NR¹⁴R¹⁵, NR¹⁵S(O)₂NR¹⁵R¹⁵, NR¹⁴S(O)₂R¹⁴ or NR¹⁵S(O)₂R¹⁵;

R¹⁴ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$;

$R^{15}$ is H, halo, haloalkyl, CN, OH, $NO_2$, $NH_2$, oxo, acetyl, methyl, methoxyl, ethyl, ethoxyl, propyl, propoxyl, isopropyl, cyclopropyl, butyl, isobutyl, tert-butyl, cyclobutyl, $C_{1-10}$-alkylamino-, $C_{1-10}$-dialkylamino-, $C_{1-10}$-thioalkoxyl, benzyl, phenyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, tert-butyl, cyclobutyl, $C_{1-10}$-alkylamino-, $C_{1-10}$-dialkylamino-, $C_{1-10}$-thioalkoxyl, benzyl or phenyl;

each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl;

h is 0, 1 or 2;

i is 1, 2 or 3; and j is 0, 1 or 2.

In another embodiment, the compounds of Formula II include O as $X^1$, in conjunction with any of the above or below embodiments.

In another embodiment, the compounds of Formula II include C(=O) as $X^1$, in conjunction with any of the above or below embodiments.

In another embodiment, the compounds of Formula II include S as $X^1$, in conjunction with any of the above or below embodiments.

In another embodiment, the compounds of Formula II include $NR^{12}$ as $X^1$, in conjunction with any of the above or below embodiments.

In another embodiment, the compounds of Formula II include methyl, ethyl, propyl, isopropyl, butyl, isobutyl or sec-butyl as $R^{16}$, independently, in conjunction with any of the above or below embodiments.

In another embodiment, the compounds of Formula I include compounds wherein A is $R^1$—C(=O)—, $R^1$—OC(=O)—, $R^1$—NHC(=O)—, $R^1$—S(=O)$_b$— or $R^1$—NHS(=O)$_b$—, wherein b is 1 or 2; and $R^1$ is a partially or fully saturated 3-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2 NR^7R^8$ or $NR^7S(O)_2R^8$;

B is $R^2$—O—$(CR^{2a}R^{2a})_h$—, $R^2$—S—$(CR^{2a}R^{2a})_h$— or $R^2$—N($R^{2a}$)—$(CR^{2a}R^{2a})_h$—, wherein $R^2$ is $C_1$-$C_{10}$alkyl, $C_1$-$C_{10}$ alkenyl, $C_1$-$C_{10}$ alkynyl or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said $C_1$-$C_{10}$ alkyl, $C_1$-$C_{10}$ alkenyl, $C_1$-$C_{10}$ alkynyl is optionally substituted independently with one or more substituents of $R^9$, and said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2 NR^7R^8$, $NR^7S(O)_2NR^7R^8$ or $NR^7S(O)_2R^8$;

each $R^{2a}$, independently, is H, OH, $NO_2$, CN, $NH_2$, $C_1$-$C_{10}$ alkyl, $C_1$-$C_{10}$ alkoxyl or haloalkyl; and h is 0, 1 or 2;

i is 1, 2 or 3;

j is 0, 1 or 2;

each $R^3$, independently, is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^5$ is

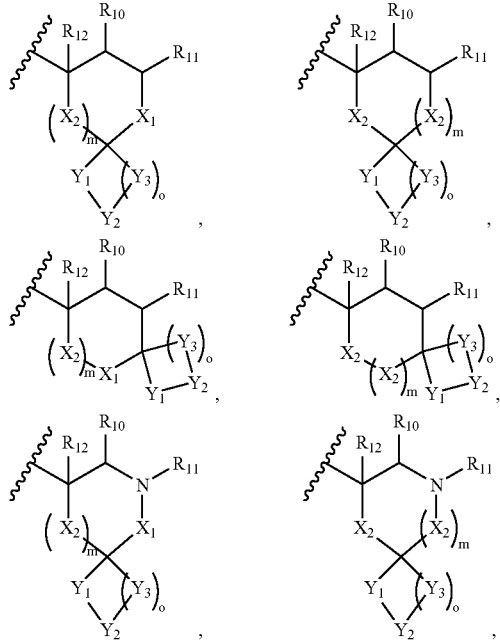

-continued

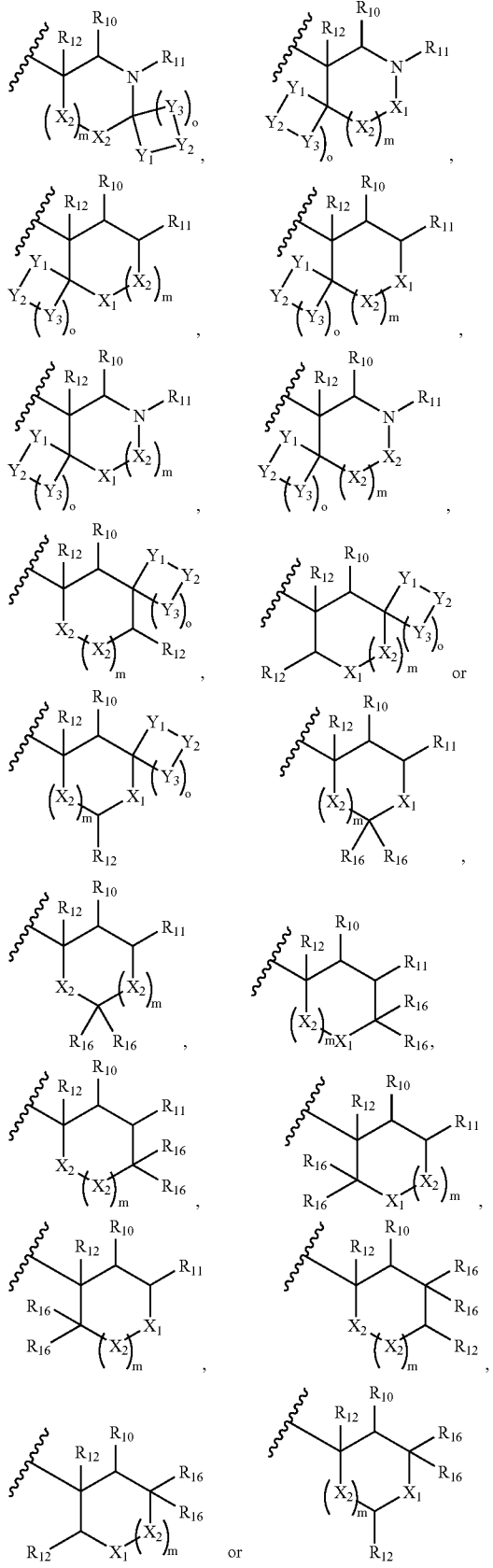

wherein $X^1$ is C(=O), O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;
m is 0, 1 or 2; and
o is 0, 1, 2, 3, 4 or 5;
provided that (a) no more than two of $Y^1$, $Y^2$ and $Y^3$ is O, S or $NR^{12}$ and (b) when
o is 0, then each of $Y^1$ and $Y^2$ is $CR^{12}R^{12}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

alternatively, $R^{10}$ and $R^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substituents of $R^{12}$, $R^{13}$, $R^{14}$ or $R^{15}$ and optionally fused to a 4-7 membered third ring, the third ring formed of carbon atoms optionally including 1-3 heteroatoms selected from O, N, or S, and optionally substituted independently with 1-5 substituents of $R^{12}$, $R^{13}$, $R^{14}$ or $R^{15}$;

$R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2 NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$;

$R^{15}$ is H, halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, $C_{1-10}$-alkylamino-, $C_{1-10}$-dialkylamino-, $C_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl; and each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl, in conjunction with any of the above or below embodiments.

In another embodiment, the compounds of Formula II include each independent embodiment, as described herein for variables A, B, $R^1$, $R^{1a}$, $R^{1b}$, $R^{1c}$, $R^{1d}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, W, V, $X^1$, $X^2$, $Y^1$, $Y^2$, $Y^3$, $Z^1$ and $Z^2$ for compounds of Formula I, independently, in conjunction with any of the above or below embodiments for compounds of Formula II.

In yet another embodiment, the invention provides compounds generally defined by Formula III,

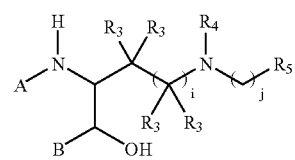

or stereoisomer, tautomer, solvate, pharmaceutically acceptable salt, derivative or prodrug thereof, wherein A is $R^1$—C(=O)—, $R^1$—OC(=O)—, $R^1$—NHC(=O)—, $R^1$—S(=O)$_b$— or $R^1$—NHS(=O)$_b$—, wherein b is 1 or 2; and $R^1$ is a partially or fully saturated 3-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2$ $NR^7R^7$, $NR^7S(O)_2R^7$, $S(O)_2R^8$, $S(O)_2NR^7R^8$, $NR^7S(O)_2 NR^7R^8$ or $NR^7S(O)_2R^8$;

B is $R^2—(CR^{2a}R^{2a})_h—$, $R^2—O—(CR^{2a}R^{2a})_h—$, $R^2—S—(CR^{2a}R^{2a})_h—$ or $R^2—NR^{2a}—(CR^{2a}R^{2a})_h—$, wherein $R^2$ is $C_1$-$C_{10}$ alkyl, $C_1$-$C_{10}$ alkenyl, $C_1$-$C_{10}$ alkynyl or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said $C_1$-$C_{10}$ alkyl, $C_1$-$C_{10}$ alkenyl, $C_1$-$C_{10}$ alkynyl is optionally substituted independently with one or more substituents of $R^9$, and said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2 NR^7R^8$, $NR^7S(O)_2NR^7R^8$ or $NR^7S(O)_2R^8$;

each $R^{2a}$, independently, is H, OH, $NO_2$, CN, $NH_2$, $C_1$-$C_{10}$ alkyl, $C_1$-$C_{10}$ alkoxyl or haloalkyl; and h is 0, 1 or 2;

i is 1, 2 or 3;

j is 0, 1 or 2;

each $R^3$, independently, is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^5$ is

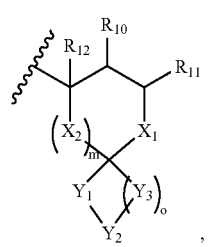, 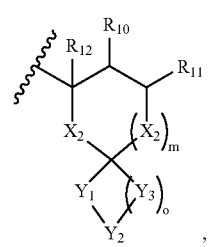,

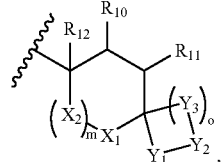, 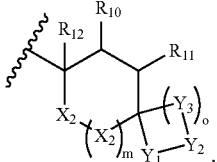,

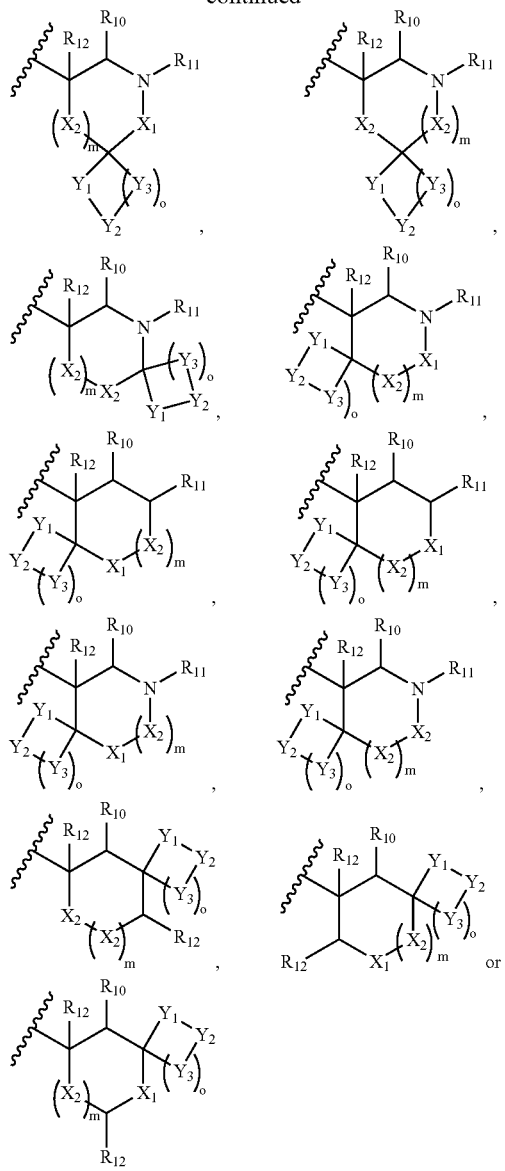

wherein $X^1$ is C(=O), O, S or $NR^{12}$;

each $X^2$, independently, is $CR^{12}R^{12}$;

each of $Y^1$, $Y^2$ and $Y^3$, independently, is $CR^{12}R^{12}$, O, S or $NR^{12}$;

m is 0, 1 or 2; and o is 0, 1, 2, 3, 4 or 5;

provided that (a) no more than two of $Y^1$, $Y^2$ and $Y^3$ is O, S or $NR^{12}$ and (b) when o is 0, then each of $Y^1$ and $Y^2$ is $CR^{12}R^{12}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, OC(O)NR$^9$R$^9$, S(O)$_2$R$^8$, S(O)$_2$NR$^8$R$^9$, S(O)$_2$R$^9$, S(O)$_2$NR$^9$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$, R$^8$ or R$^9$;

R$^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R$^9$, oxo, NR$^9$R$^9$, OR$^9$; SR$^9$, C(O)R$^9$ or a partially or fully saturated or unsaturated 5-6 membered ring of carbon atoms optionally including 1-3 heteroatoms selected from O, N, or S, and optionally substituted independently with 1-5 substituents of R$^9$;

R$^9$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;

R$^{10}$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;

R$^{11}$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;

alternatively, R$^{10}$ and R$^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substituents of R$^{12}$, R$^{13}$, R$^{14}$ or R$^{15}$ and optionally fused to a 4-7 membered third ring, the third ring formed of carbon atoms optionally including 1-3 heteroatoms selected from O, N, or S, and optionally substituted independently with 1-5 substituents of R$^{12}$, R$^{13}$, R$^{14}$ or R$^{15}$;

R$^{12}$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl, phenyl or R$^{14}$;

R$^{13}$ is NR$^{14}$R$^{15}$, NR$^{15}$R$^{15}$, OR$^{14}$; SR$^{14}$, OR$^{15}$; SR$^{15}$, C(O)R$^{14}$, OC(O)R$^{14}$, COOR$^{14}$, C(O)R$^{15}$, OC(O)R$^{15}$, COOR$^{15}$, C(O)NR$^{14}$R$^{15}$, C(O)NR$^{15}$R$^{15}$, NR$^{14}$C(O)R$^{14}$, NR$^{15}$C(O)R$^{14}$, NR$^{14}$C(O)R$^{15}$, NR$^{15}$C(O)R$^{15}$, NR$^{15}$C(O)NR$^{14}$R$^{15}$, NR$^{15}$C(O)NR$^{15}$R$^{15}$, NR$^{15}$(COOR$^{14}$), NR$^{15}$(COOR$^{15}$), OC(O)NR$^{14}$R$^{15}$, OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{14}$S(O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

R$^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R$^{15}$; and R$^{15}$ is H, halo, haloalkyl, CN, OH, NO$_2$, NH$_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, C$_{1-10}$-alkylamino-, C$_{1-10}$-dialkylamino-, C$_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

In another embodiment, the compounds of Formula III include each independent embodiment, as described herein for variables A, B, $R^1$, $R^{1a}$, $R^{1b}$, $R^{1c}$, $R^{1d}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, W, V, $X^1$, $X^2$, $Y^1$, $Y^2$, $Y^3$, $Z^1$ and $Z^2$ for compounds of Formula I, independently, in conjunction with any of the above or below embodiments for compounds of Formula III.

In another embodiment, the invention provides each of the compounds, and stereoisomers, tautomers, solvates, pharmaceutically acceptable salts, derivatives or prodrugs thereof, and intermediates described in each of the examples herein.

Definitions

The following definitions should assist in understanding the invention described herein.

The term "comprising" is meant to be open ended, including the indicated component(s), but not excluding other elements.

The term "H" denotes a single hydrogen atom. This radical may be attached, for example, to an oxygen atom to form a hydroxyl radical.

The term "$C_{\alpha-\beta}$ alkyl", when used either alone or within other terms such as "haloalkyl" and "alkylamino", embraces linear or branched radicals having α to β number of carbon atoms (such as $C_1$-$C_{10}$). One or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$ alkoxyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—$CH_2$—O— or —O—$CH_2$—$CH_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 5-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The terms "carboxy" or "carboxyl", whether used alone or with other terms, such as "carboxyalkyl", denotes —$CO_2$H.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)$NH_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3$S—).

The term "haloalkylthio" embraces radicals containing a haloalkyl radical, of one to ten carbon atoms, attached to a divalent sulfur atom. An example of "haloalkylthio" is trifluoromethylthio.

The term "alkylaminoalkyl" embraces alkyl radicals substituted with alkylamino radicals. Examples of alkylaminoalkyl radicals include "lower alkylaminoalkyl" radicals having alkyl radicals of one to six carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. Examples of alkylaminoalkoxy radicals include "lower alkylaminoalkoxy" radicals having alkoxy radicals of one to six carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "Formula I" includes any sub formulas, such as Formula II. Similarly, the term "Formula II" includes any sub formulas and "Formula III" includes any sub formulas.

The term "pharmaceutically-acceptable" when used with reference to a compound of Formulas I-III is intended to refer to a form of the compound that is safe for administration. For example, a salt form, a solvate, a hydrate or derivative form of a compound of Formula I, II or of Formula III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid.

Suitable pharmaceutically-acceptable base addition salts of compounds of Formulas I, II and III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydrobromic acid, citric acid, sulphuric acid and phosphoric acid and such organic acids as oxalic acid, stearic and, salicylic acid, pamoic acid, gluconic acid, ethanesulfonic acid, methanesulfonic acid, toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-III. A "pharmaceutically-acceptable prodrug" as used herein, denotes a prodrug which is pharmaceutically acceptable. Pharmaceutically acceptable modifications to the compounds of Formula I-III are readily appreciated by those of ordinary skill in the art.

The compound(s) of Formulas I-III may be used to treat a subject by administering the compound(s) as a pharmaceutical composition. To this end, the compound(s) can be combined with one or more carriers, diluents or adjuvants to form a suitable composition, which is described in more detail herein.

The term "carrier", as used herein, denotes any pharmaceutically acceptable additive, excipient, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject.

For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, II and III.

The compounds of Formulas I, II and III can be synthesized according to the procedures described in the following Schemes 1-5, wherein the substituents are as defined for Formulas I, II and III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

| | |
|---|---|
| ACN, MeCN | acetonitrile |
| BOP | benzotriazol-1-yl-oxy hexafluorophosphate |
| $Cs_2CO_3$ | cesium carbonate |
| $CHCl_3$ | chloroform |
| $CH_2Cl_2$, DCM | dichloromethane, methylene chloride |
| CuI | copper iodide |
| DCC | dicyclohexylcarbodiimide |
| DIC | 1,3-diisopropylcarbodiimide |
| DIEA, DIPEA | diisopropylethylamine |
| DME | dimethoxyethane |
| DMF | dimethylformamide |
| DMAP | 4-dimethylaminopyridine |
| DMS | dimethylsulfide |
| DMSO | dimethylsulfoxide |
| EDC, EDCI | 1-(3-dimethylaminopropyl)-3-ethylcarbodiimide |
| $Et_2O$ | diethyl ether |
| EtOAc | ethyl acetate |
| FBS | fetal bovine serum |
| G, gm | gram |
| h, hr | hour |
| $H_2$ | hydrogen |
| $H_2O$ | water |
| HATU | O-(7-azabenzotriazol-1-yl)-N,N,N',N'-tetramethyluroniumhexafluorophosphate |
| HBr | hydrobromic acid |
| HCl | hydrochloric acid |
| HOBt | 1-hydroxybenzotriazole hydrate |
| HOAc | acetic acid |
| HPLC | high pressure liquid chromatography |
| IPA, IpOH | isopropyl alcohol |
| $K_2CO_3$ | potassium carbonate |
| KI | potassium iodide |
| LG | leaving group |
| LiOH | lithium hydroxide |
| $MgSO_4$ | magnesium sulfate |
| MS | mass spectrum |

-continued

| | |
|---|---|
| MeOH | methanol |
| $N_2$ | nitrogen |
| $NaCNBH_3$ | sodium cyanoborohydride |
| $Na_2CO_3$ | sodium carbonate |
| $NaHCO_3$ | sodium bicarbonate |
| NaH | sodium hydride |
| $NaBH_4$ | sodium borohydride |
| NaOH | sodium hydroxide |
| $Na_2SO_4$ | sodium sulfate |
| $NH_4Cl$ | ammonium chloride |
| $NH_4OH$ | ammonium hydroxide |
| $P(t-bu)_3$ | tri(tert-butyl)phosphine |
| PBS | phospate buffered saline |
| Pd/C | palladium on carbon |
| $Pd(PPh_3)_4$ | palladium(0)triphenylphosphine tetrakis |
| $Pd(dppf)Cl_2$ | palladium(1,1-bisdiphenylphosphinoferrocene) II chloride |
| $Pd(PhCN)_2Cl_2$ | palladium di-cyanophenyl dichloride |
| $Pd(OAc)_2$ | palladium acetate |
| $Pd_2(dba)_3$ | bis(dibenzylideneacetone) palladium |
| PyBop | benzotriazol-1-yl-oxy-tripyrrolidino-phosphonium hexafluorophosphate |
| RT, rt | room temperature |
| RBF, rbf | round bottom flask |
| TBTU | O-benzotriazol-1-yl-N,N,N',N'-tetramethyluronium tetrafluoroborate |
| TEA, $Et_3N$ | triethylamine |
| TFA | trifluoroacetic acid |
| THF | tetrahydrofuran |
| UV | ultraviolet light |

While the synthetic strategy for preparing the compounds of Formulas I, II and III may vary, as appreciated by persons skilled in the art, one strategy for devising a method of making compounds of these formulas is by retro-synthetic disconnection. For example,

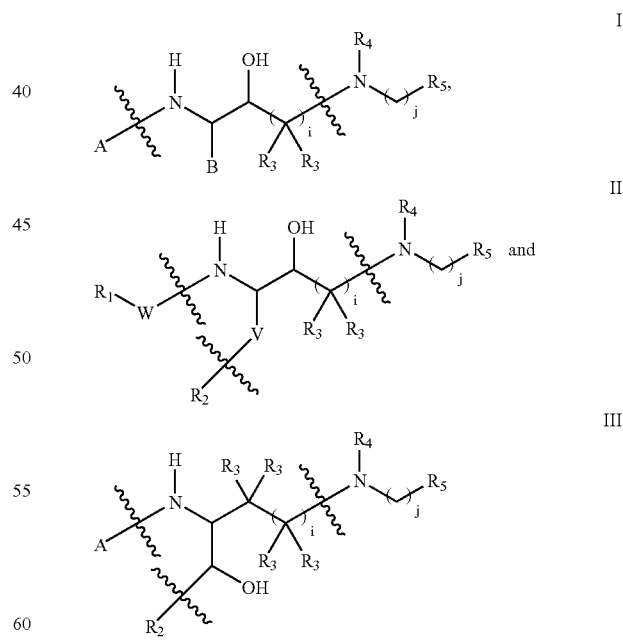

as shown in Formulas I-III above, each squiggly line represents a possible point of bond-construction, whose order is generally dependent upon the particular compound being synthesized. Such bond construction methods are generally described in synthetic schemes 1-5 below.

Scheme 1

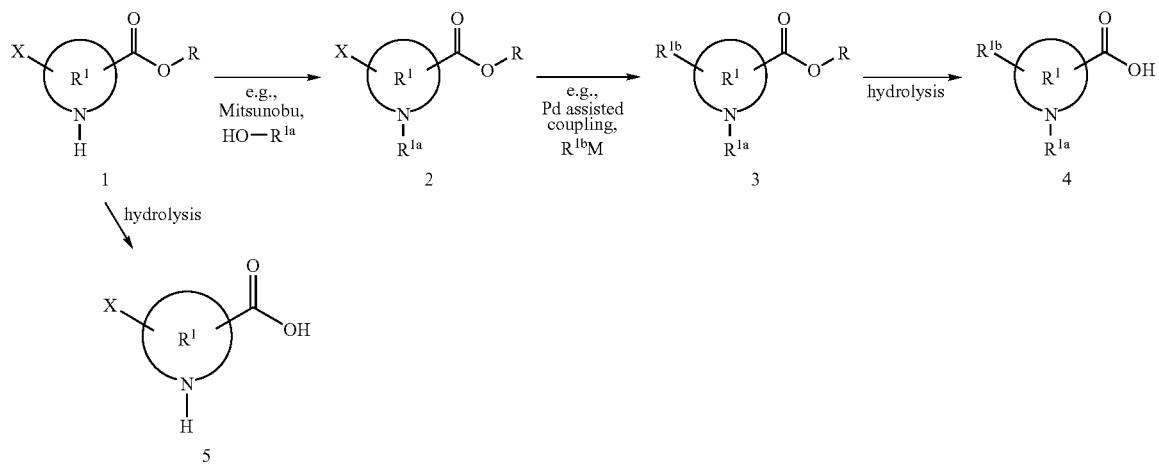

wherein,
R is C1-C4 alkyl, e.g., $CH_3$, $C_2H_5$, etc.
and e.g., X = Br, I, Cl, etc.; $R^{1b} = R^{1b}B(OH)_2$, $R^{1b}SnBu_3$, etc.

Scheme 1 describes one method of preparing an $R^1$-substituted carboxylic acids 4 and 5, which may then be used to couple to an amine to make an $R^1$-amide linked A group, or converted to an isocyanate which can then be coupled to an amine to make an $R^1$-urea linked A group (where W=—C(O)— or —NHC(O)—). An ester-halo (X=halogen such as Br or I) substituted $R^1$ ring compound 4 or 5, both of which include a substitutable nitrogen in the ring, and which are generally referred to herein as the left-hand portion of the compounds of Formulas I, II and III, can be prepared according to the method generally described in Scheme 1. As shown, a methyl ester-halo substituted compound 1 can be reacted in a Mitsunobu-type reaction with a desired hydroxyl-substituted $R^{1a}$ compound under suitable conditions, such as in the presence of tri-phenyl phosphine and diethylazodicarboxylate (commonly referred to as DEAD) for a suitable time period to form the ring N—$R^{1a}$ substituted adduct 2. Intermediate 2 may also be formed using a suitable reductive amination method as well utilizing an aldehyde, for example (not shown in scheme 1). Compound 2 can be reacted in a palladium-catalyzed coupling reaction, such as a suzuki-type reaction, in the presence of suitable solvents and accompanying reagents, such as a base, to form the $R^1$—$R^{1b}$ substituted compound 3. Formation of compound 3 may require heat, up to and including reflux temperatures depending on the particular substrate, solvent and reagent(s) concentration, as appreciated by those skilled in the art. Compound 3 can then be hydrolyzed in the presence of a suitable base and solvent to form the corresponding acid-adduct 4. Acid 4 is then utilized as an intermediate to couple, as described in Scheme 2 below, with desired intermediates or other building blocks to make compounds of Formulas I-III.

Alternatively, compound 1 can be hydrolyzed directly to the corresponding acid 5. Ester-Halo-substituted compound 5 is a useful intermediate for coupling the backbone core compounds with desired B, $R^3$ and $R^4$ substitutions already in place. Compound 5 can then be modified to include desirable $R^1$ substitutions, including $R^{1a}$, $R^7$, $R^8$ and $R^9$ groups. In this fashion, analogs of a variety of desired left-hand pieces of compounds of Formulas I-III may be readily synthesized (see Scheme 3).

Scheme 2

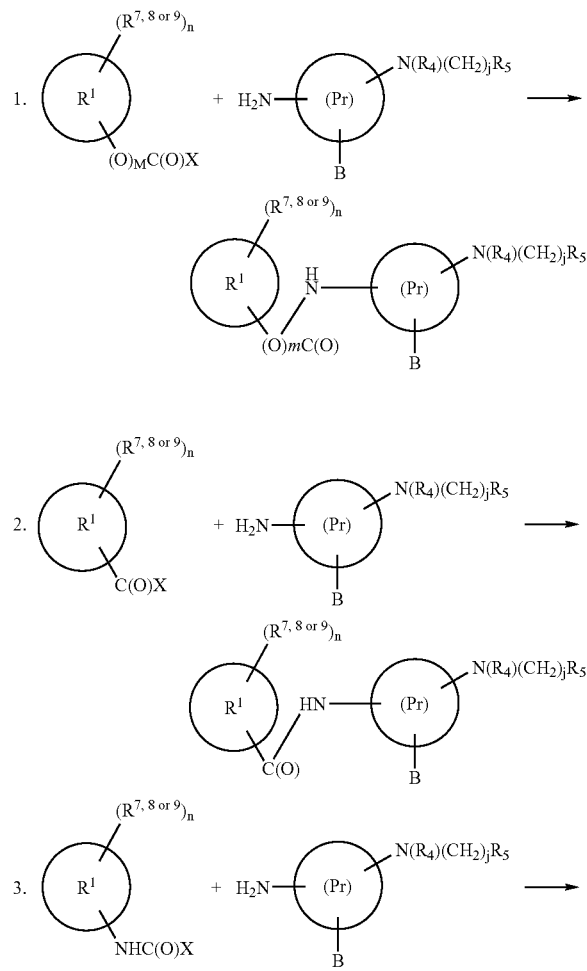

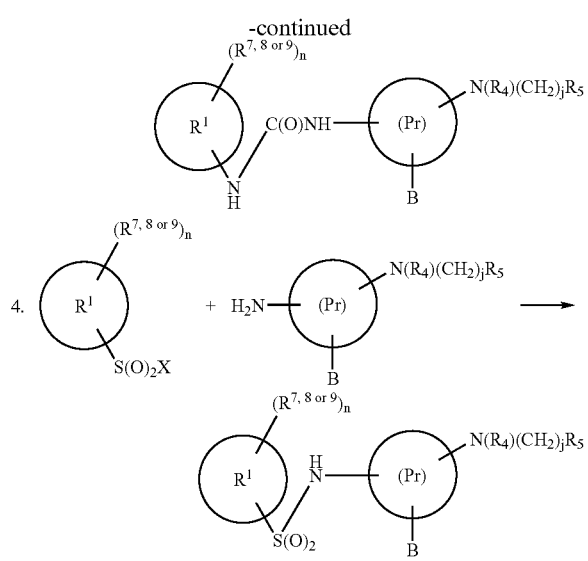

$R^1$ ring systems, which may be substituted with various substitutions including one or more $R^7$, $R^8$ or $R^9$ groups, can be coupled to the core hydroxyl-propyl, hydroxyl-butyl or hydroxyl-pentyl backbone structure, generally designated in Scheme 2 as "Pr" group, by various coupling methods as described in Scheme 2. In each of the 4 sub-schemes, X refers generally to a "leaving group" such as a halide (bromine, chlorine, iodine or fluorine), alkylsulfonate and other known groups (also see definitions herein) which generally forms an electrophilic species ($E^+$) and m is an integer from 0-1. The $NH_2$ group (primary amine) is a nucleophilic species ($Nu^-$), as is secondary amines, hydroxides, alkoxides, an anionic carbon species and the like, which should be sufficiently strong to the attack the $E^+$ species and displace the leaving group X thereby effecting a coupling of ring $R^1$ to the Pr backbone. Examples of suitable electrophilic carbonyl species include, without limitation, acid halides, mixed anhydrides, aldehydes, carbamoyl-chlorides, sulfonyl chlorides, acids activated by coupling with activating reagents such as TBTU, HBTU, HATU, HOBT, BOP, PyBOP and carbodiimides (DCC, EDC and the like), and other electrophilic species including halides, isocyanates, daizonium ions and the like.

The coupled adduct of $R^1$ and Pr, shown as products in sub-schemes 1-4, can be brought about using various conventional methods. For example, an amide or a sulfonamide linkage, as shown in sub-schemes 2 and 4, can be made utilizing an amine on the Pr intermediate and an activated electrophilic species, on the $R^1$ ring such as the acid chloride or sulfonyl chloride as shown. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N, N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates as illustrated in sub-scheme 1 and ureas as illustrated in sub-scheme 3 may be made as shown, wherein X has the same definition as above, using the same coupling methods described above for sub-schemes 2 and 4. While the above methods are so described, they are not exhaustive, and other methods for linking $R^1$ rings and desired Pr groups together may be utilized as appreciated by those skilled in the art.

The coupling methods described in sub-schemes 1-4 of scheme 2 are also applicable for coupling desired $R^1$ rings to desired Pr intermediates not containing desired $R^5$ groups, although sub-schemes 1-4 as illustrated do contain $R^5$ groups.

Scheme 3

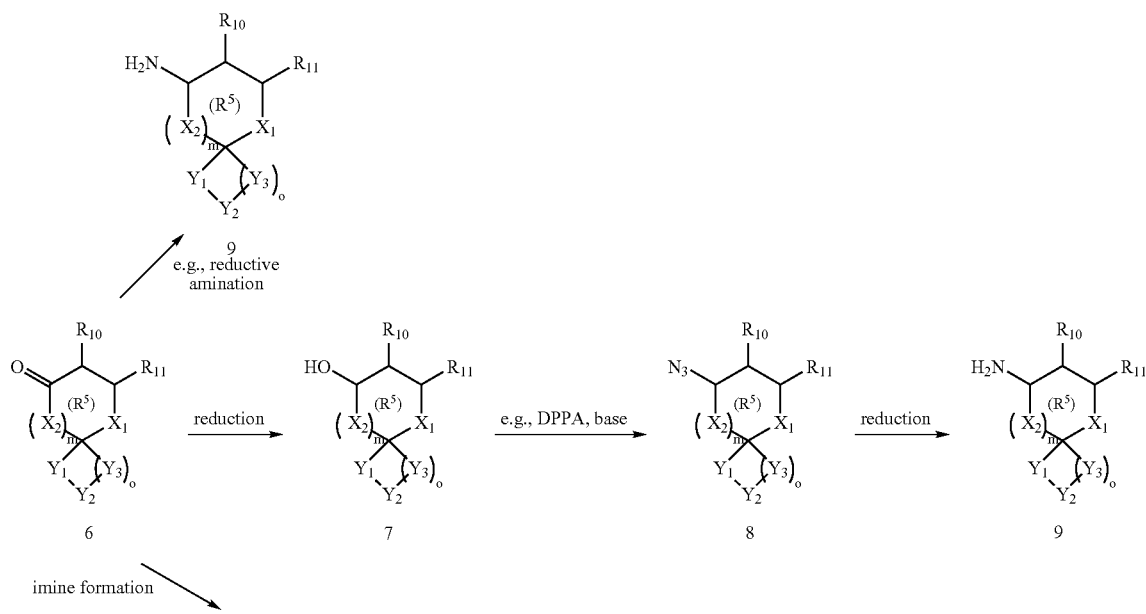

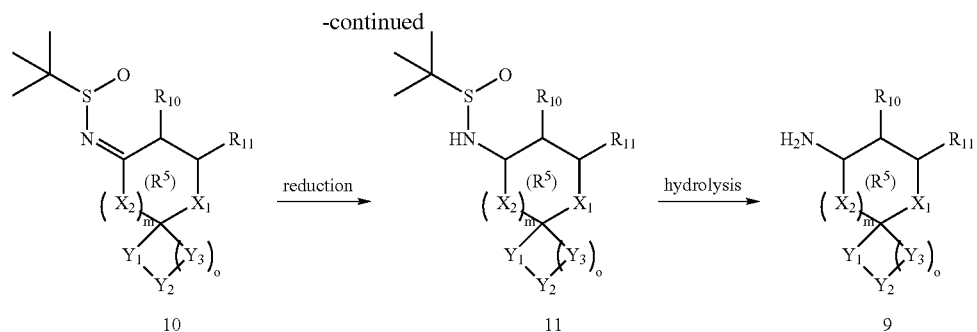

10 → reduction → 11 → hydrolysis → 9

Amine intermediate 9 (j=0) can be prepared according to the method generally described in Scheme 3. As shown, spiro-substituted- or gem-dialky-substituted (not shown) oxo-$R^5$ ring intermediates 6 can be converted directly to the amino-intermediate 9 using known reductive amination methods, such as in the presence of sodium cyanoborohydride and ammonium acetate. Alternatively, the carbonyl of $R^5$ may be reduced to the corresponding alcohol using conventional reducing reagents, and then displaced to form the corresponding azido-intermediate 8 using known reagents, such as DPPA, in the presence of a suitable base as shown. Intermediate 8 may be reduced with a suitable reducing agent or by known methods, including triphenylphosphene, trimethylphosphene or lithium aluminum hydride (LAH), to produce the desired amino adduct 9.

Yet another method of forming the amine adduct 9, can be via an imine formation to form compound 10. The imine double bond of compound 10 may then be successively reduced and hydrolyzed to yield the primary amine product 9. Such steps may be conducted using known, convention methods, as appreciated by those skilled in the art.

Scheme 4

1.

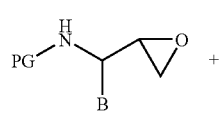

PG = protecting group

12'

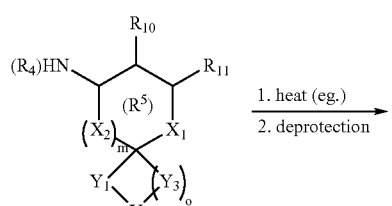

9

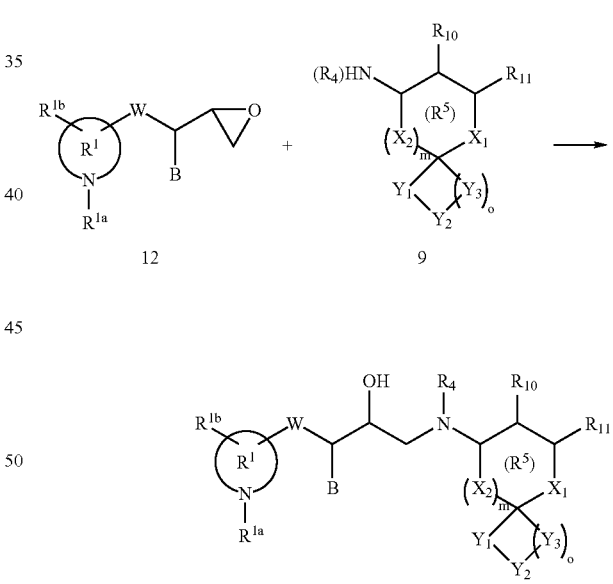

3.

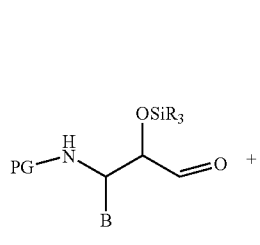

PG = protecting group

13'

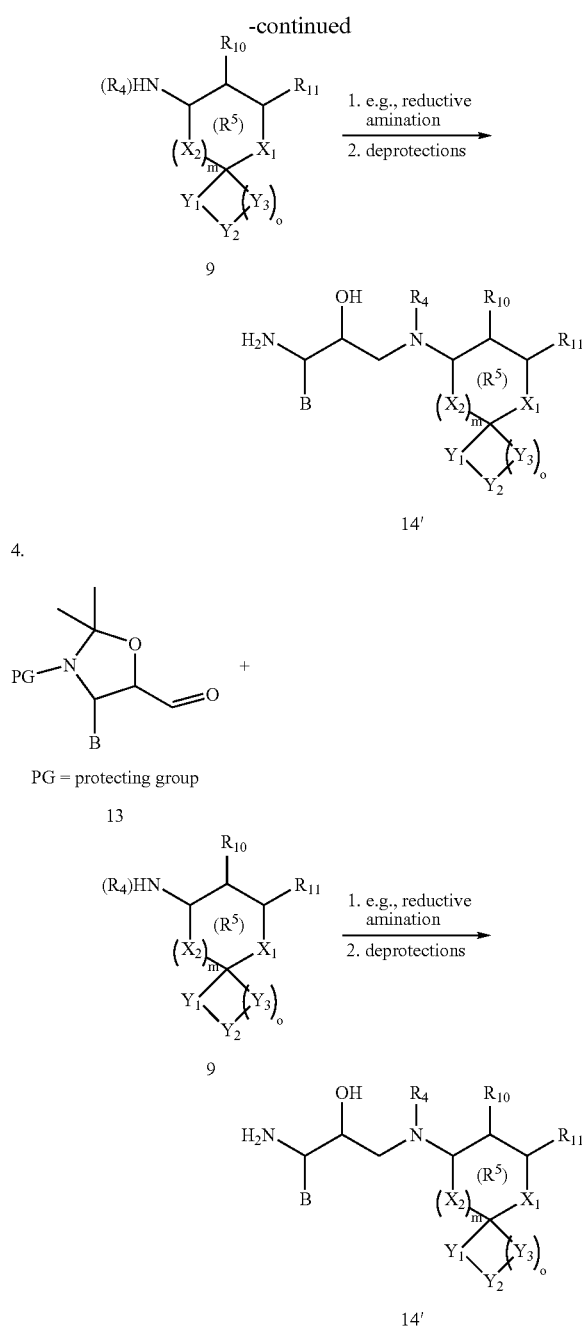

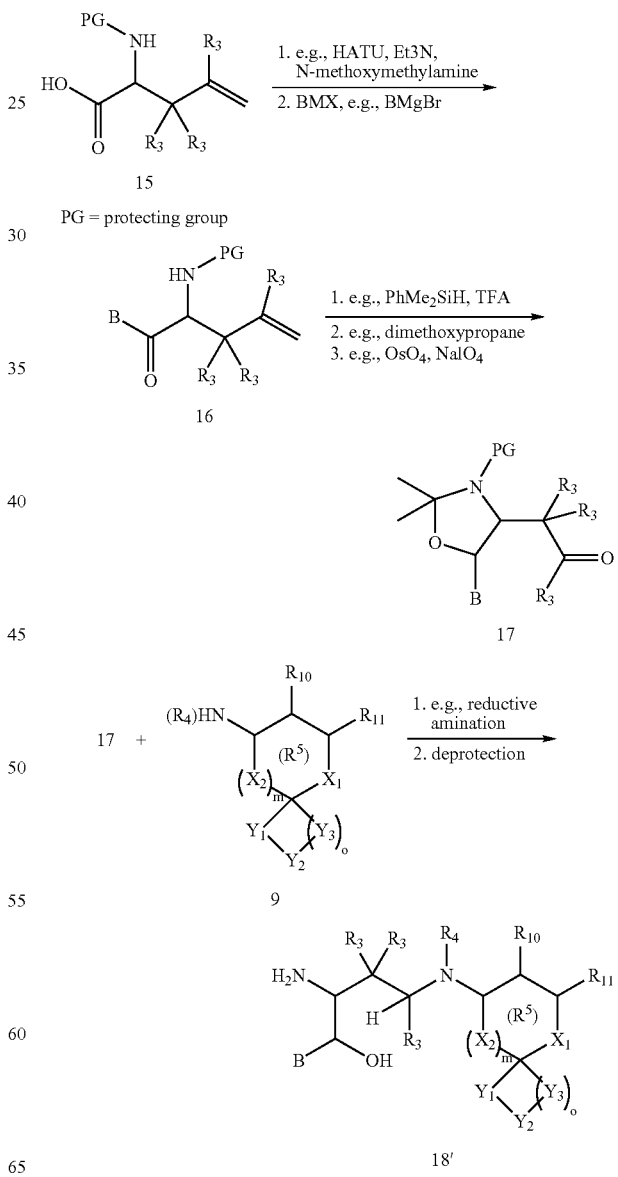

Scheme 4 describes, generally, multiple different methods for constructing the bond between the Pr starting material or intermediate 12' (sub-scheme 1) or 12 (sub-scheme 2) and an $R^5$ ring intermediate 9, thereby synthesizing a desired intermediate 14' or a final compound 14 of Formulas I-III. One method to make this bond is to react an epoxide intermediate 12 or 12' (Note: the epoxide 12 or 12' may be purchased commercially or made via known, published methods such as from the olefin precursor), with an amino-$R^5$ intermediate 9, as shown. The reaction may proceed in the presence of a polar solvent, such as an alcohol or dioxanes, and may require additional reagents, as appreciated by those skilled in the art. Additionally, the reaction may require heat for a period of time. Note that while the scheme described the addition o heat, this is by way of example, and not every reaction would require heat as appreciated by those of ordinary skill in the art. The protecting group may be removed using an acid, such as HCl, such that the bonded adduct 14' is recovered as an HCl salt.

Alternatively, desired intermediates 14' may be synthesized starting with an amine-protected aldehyde intermediate 13' (sub-scheme 3) or 13 (sub-scheme 4) and condensing the aldehyde with a primary or secondary amine 9 to form an imine (not shown, generally formed in-situ and not isolated). The imine can then be reduced using a known reducing agent, such as a hydride or borohydride, the reduced intermediate may be deprotected to provide an intermediate 14' having an amine useful to prepare compounds 14 of Formulas I-III.

Method B:

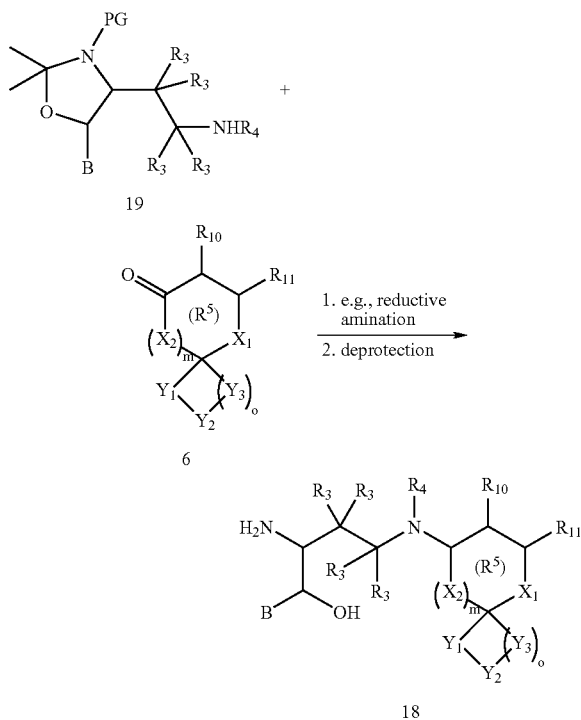

Scheme 5 describes, generally, two different methods (Methods A and B) for constructing intermediates 18' (Method A) or 18 (Method B) which are useful for making compounds of Formula III. As shown in Method A, the acid group of an olefinic amino-acid compound 15 may be modified with a desired B group to form a compound 16, by first activating the acid of 15 with a known activating agent, such as HATU in the presence of a suitable base, and treating activated 15 with a B-substituted grignard reagent or B-ligand metal reagent, which delivers the desired B group to displace the carbonyl activating group and form compound 16. Compound 16 may be oxidized to the corresponding ketone 17 by known methods, such as with sodium periodiate and osmium tetroxide. Ketone 17 may then be reacted with amine 9, via a reductive amination step, to form an amino protected intermediate, which can be deprotected to yield intermediate 18', as shown.

Alternatively, intermediate 18 may be made using a reductive amination step with an amine-protected diamine compound 19 and a ketone 6. Such reductive amination step may be employed with conventional conditions using known reducing reagents in suitable solvents, at suitable temperatures, as appreciated by one of ordinary skill in the art.

To enhance the understanding and appreciation of the present invention, the following specific examples (starting reagents, intermediates and compounds of Formulas I-III) are set forth. The following analytical methods were used to purify and/or characterize the compounds, and intermediates, described in the examples below.

Analytical HPLC and LC-MS Methods:

Unless otherwise indicated, all analytical HPLC analyses were run on an Agilent Model 1100 series system LC/MSD SL using one of the two following Columns: (a) Phenomenex Sernegi (4 micron, C18, 50×2 mm) or (b) a Gemini column (5 micron, C18, 100×2 mm). A typical run through the instrument included: eluting at 1 ml/min with an linear gradient of 10% (v/v) to 100% MeCN (0.1% v/v TFA) in water (0.1% TFA) over 10 minutes; conditions may be varied to achieve optimal separation.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 110% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument.

Compounds having an isotopic atom, such as bromine and the like, are generally reported according to the detected isotopic pattern, as appreciated by those skilled in the art.

Naming Convention

The compounds disclosed and described herein have been named using the naming convention provided with Chem-Draw Ultra 8.0 software, available in Chem Office. In some instances, compounds were named with the term "spirocarbocycle" inserted where appropriate. For example, where the chroman is substituted with 2,2-spirocyclobutyl, "2,2-spirocyclobutyl" is added to the Chem-Draw nomenclature in the appropriate place. Chem-Draw utilizes the ISIS Draw software compound naming convention, as appreciated by those skilled in the art.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I, II and III. It should be appreciated that the general methods above and specific examples below are illustrative only, for purpose of assistance in understanding the invention, and should not be construed as limiting the scope of the present invention in any manner.

Example 1

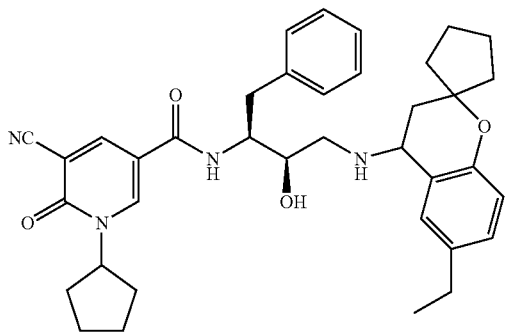

5-cyano-1-cyclopentyl-N-(2S,3R)-4-(6-ethyl-2,2-spirocyclopentylchroman-4-ylamino)-3-hydrodroxy-1-phenylbutan-2-yl)-6-oxo-1,6-dihydropyridine-3-carboxamide

Step 1: Methyl 5-cyano-1-cyclopentyl-6-oxo-1,6-dihydropyridine-3-carboxylate A mixture of methyl 5-bromo-1-cyclopentyl-6-oxo-1,6-dihydropyridine-3-carboxylate (500 mg, 1.67 mmol), tris (dibenzylideneacetone)dipalladium (31 mg, 0.033 mmol), DPPF (37 mg, 0.07 mmol), Zinc (13 mg, 0.20 mmol) and zinc cyanide (120 mg, 1.00 mmol) was purged with nitrogen, followed by the addition of dimetbylacetamide (3.3 mL). The resulting mixture was heated to 120° C. for 2 h. The mixture was brought to room temperature, diluted in ethylacetate and washed with saturated $NH_4Cl$. The organic phase was separated, washed again with saturated $NH_4Cl$, brine, dried and chromatographed on silica gel using 3:1 hexanes:ethylacetate to afford the title compound as a yellow oil. MS m/z: 247 (M+1).

Step 2: 5-Cyano-1-cyclopentyl-6-oxo-1,6-dihydropyridine-3-carboxylic acid

A mixture of Methyl 5-cyano-1-cyclopentyl-6-oxo-1,6-dihydropyridine-3-carboxylate (290 mg, 1.2 mmol) and 1N sodium hydroxide (6 mL, 6.0 mmol) in methanol (12 mL) was heated to reflux for 1 h and brought to RT. The mixture was concentrated and the residue obtained was dissolved in ethylacetate (20 mL), acidified with 1N hydrochloric acid (pH ~5). The organic phase was separated, dried over magnesium sulfate and concentrated to afford the title compound as a light yellow solid. MS m/z: 233 (M+1).

Step 3: 5-cyano-1-cyclopentyl-N-(2S,3R)-4-(6-ethyl-2,2-spirocyclopentylchroman-4-ylamino)-3-hydrodroxy-1-phenylbutan-2-yl)-6-oxo-1,6-dihydropyridine-3-carboxamide To a solution of 5-cyano-1-cyclopentyl-6-oxo-1,6-dihydropyridine-3-carboxylic acid (50 mg, 0.20 mmol) in N—N-dimethylformamine (2 mL) was added N—N -diisopropylethylamine (70 uL, 0.40 mmoL) and stirred at room temperature. After 5 min, 1-[3-dimethylamino)propyl]-3-ethylcarbodiimide (78 mg, 0.40 mmoL), (2S,3R)3-amino-1-(6-ethyl-2,2-spirocyclopentylchroman-4-ylamino)-4-pbenylbutan-2-ol hydrochloride (110 mg, 0.26 mmol) and HBTU (72 mg, 0.20 mmol) were added. The resulting solution was stirred at room temperature for 20 h. The mixture was poured into water (8 mL) and extracted with ethylacetate. The organic extracts were combined, washed with saturated $NH_4Cl$ (3x), brine, dried over magnesium sulfate, concentrated, and purified by HPLC to afford the title compound as an off-white solid. MS m/z: 609 (M+1).

Example 2

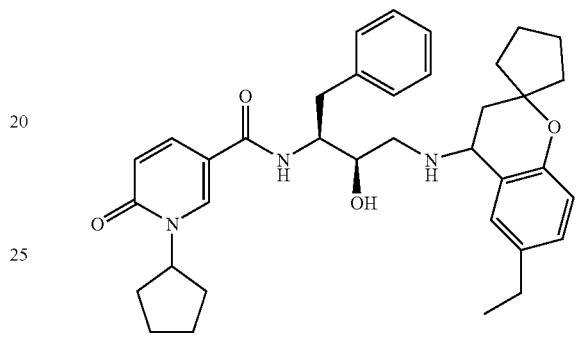

1-cyclopentyl-N-(2S,3R)-4-(6-ethyl-2,2-spirocyclopentylchroman-4-ylamino)-3-hydrodroxy-1-phenylbutan-2-yl)-6-oxo-1,6-dihydropyridine-3-carboxamide

Step 1: Methyl 1-cyclopentyl-6-oxo-1,6-dihydropyridine-3-carboxylate

Through a solution of methyl 5-bromo-1-cyclopentyl-6-oxo-1,6-dihydropyridine-3-carboxylate (300 mg, 1 mmol) and Pd/C (300 mg) in methanol (30 mL) was bubbled $H_2$ through a balloon for 48 h. The mixture was filtered through Celite® and concentrated to afford the title compound. MS m/z: 222 (M+1).

Step 2: 1-Cyclopentyl-6-oxo-1,6-dihydropyridine-3-carboxylic acid

The title compound was obtained using a procedure analogous to that described in Example 1, with methyl 1-cyclopentyl-6-oxo-1,6-dihydropyridine-3-carboxylate. MS m/z: 208 (M+1).

Step 3: 1-cyclopentyl-N-(2S,3R)-4-(6-ethyl-2,2-spirocyclopentylchroman-4-ylamino)-3-hydrodroxy-1-phenylbutan-2-yl)-6-oxo-1,6-dihydropyridine-3-carboxamide The title compound was obtained using a procedure analogous to that described in Example 1, with 1-cyclopentyl-6-oxo-1,6-dihydropyridine-3-carboxylic acid (50 mg, 0.24 mmol) and (2S,3R)3-amino-1-(6-ethyl-2,2-spirocyclopentylchroman-4-ylamino)-4-phenylbutan-2-ol hydrochloride (120 mg, 0.29 mmol). MS m/z: 584 (M+1).

Example 3

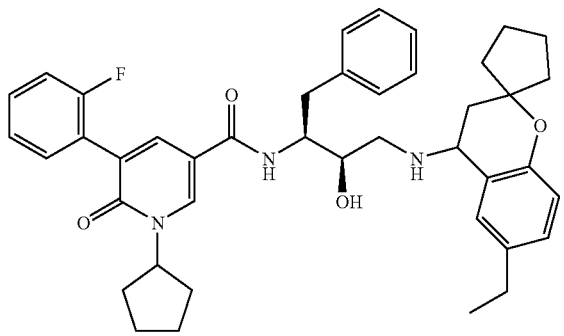

1-cyclopentyl-N-(2S,3R)-4-(6-ethyl-2,2-spirocyclopentylchroman-4-ylamino)-3-hydroxy-1-phenylbutan-2-yl)-5-(2-fluorophenyl)-6-oxo-1,6-dihydropyridine-3-carboxamide A mixture of 2-fluoroboronic acid (50 mg, 0.36 mmol), 5-bromo-1-cyclopentyl-N-(2S,3R)-4-(6-ethyl-2,2-spirocyclopentylchroman-4-ylamino)-3-hydroxy-1-phenylbutan-2-yl)-6-oxo-1,6-dihydropyridine-3-carboxamide (200 mg, 0.30 mmol), tetrakis(triphenylphosphine) palladium (0) (17 mg, 0.015 mmol) and sodium carbonate (160 mg, 1.5 mmol) was purged with nitrogen for 10 min, followed by the addition of dioxane (3 mL). The resulting yellow suspension was heated to reflux for 3 h and brought to room temperature. The mixture was diluted in EtOAc, washed with saturated NaHCO$_3$, brine, dried over MgSO$_4$ and chromatographed by HPLC to afford the title compound as a white-solid. MS m/z: 678 (M+1).

Example 4

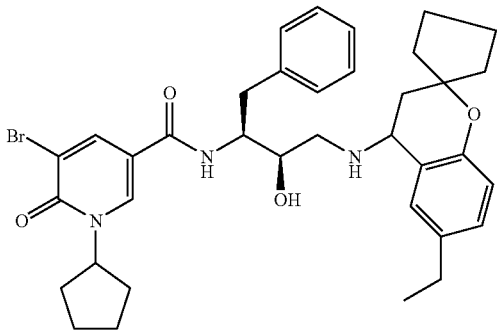

5-Bromo-1-cyclopentyl-N-((2S,3R)-4-(6-ethyl-2,2-spirocyclopentylchroman-4-ylamino)-3-hydroxy-1-phenylbutan-2-yl)-6-oxo-1,6-dihydropyridine-3-carboxamide The title compound was obtained using a procedure analogous to that described in Example 1, with 5-bromo-1-Cyclopentyl-6-oxo-1,6-dihydropyridine -3-carboxylic acid (700 mg, 2.5 mmol) and N-((2S,3R)-4-(6-ethyl-2,2-spirocyclopentylchroman-4-ylamino)-3-hydroxy-1-phenylbutanediamine (1.3 g, 3.0 mmol) to afford the title compound as a light yellow oil. MS m/z: 662 (M+1).

Example 5

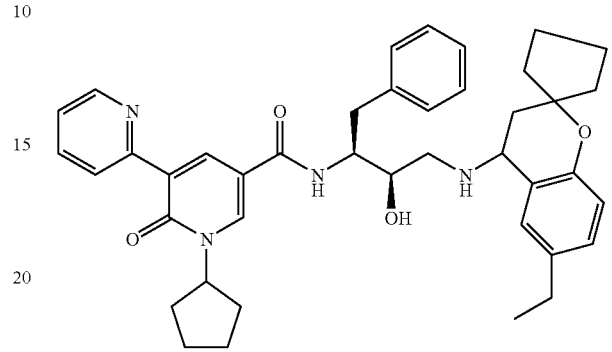

A mixture of 5-Bromo-1-cyclopentyl-N-((2S,3R)-4-(6-ethyl -2,2-spirocyclopentylchroman-4-ylamino)-3-hydroxy-1-phenylbutan-2-yl)-6-oxo-1,6-dihydropyridine-3-carboxamide (200 mg, 0.30 mmol), 2-tri-methylstannylpyridine (87 mg, 0.36 mmol), tris(dibenzylideneacetone)dipalladium (4.1 mg, 0.0045 mmol), tri-tert-butylphosphine (3.6 mg, 0.018 mmol), cesium fluoride (100 mg, 0.66 mmol) in dioxane (2 mL) was heated to 100° C. for 17 h. The mixture was brought to room temperature, diluted with ethylacetate, washed with water, saturated NaHCO$_3$, dried over MgSO$_4$, concentrated and purified by HPLC to afford the title compound as a white solid. MS m/z: 661 (M+1).

Example 6

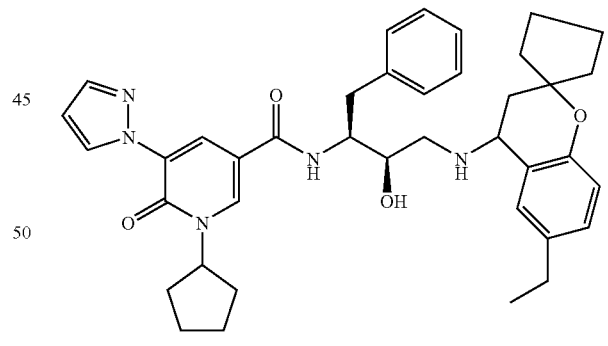

1-cyclopentyl-N-(2S,3R)-4-(6-ethyl-2,2-spirocyclopentylchroman-4-ylamino)-3-hydroxy-1-phenylbutan-2-yl)-6-oxo-5-(1H-pyrazol-1-yl)-1,6-dihydropyridine-3-carboxamide Step 1: Methyl 1-cyclopentyl-6-oxo-5-(1H-pyrazol-1-yl)-1,6-dihydropyridine-3-carboxylate A mixture of methyl 5-bromo-1-cyclopentyl-6-oxo-1,6-dihydropyridine-3-carboxylate (300 mg, 1.00 mmol), pyrazole (23 mg, 0.34 mmol), K$_2$CO$_3$ (99 mg, 0.72 mmol), CuI (9.1 mg, 0.048 mmol), $N^1$—$N^2$-dimethylethane-1,2-diamine (5 uL, 0.048 mmol) in toluene (3 mL) was heated to 100° C. for 17 h. The mixture was brought to RT and quenched with saturated $NH_4Cl$, brine, dried over $MgSO_4$ and chromatographed on silica gel using 3:1 hexanes:ethylacetate to afford the title compound as a white solid. MS m/z: 288 (M+1).

Step 2: 1-cyclopentyl-6-oxo-5-(1H-pyrazol-1-yl)-1,6-dihydropyridine-3-carboxylic acid The title compound was obtained using a procedure analogous to that described in Example 1, with methyl 1-cyclopentyl-6-oxo-5-(1H-pyrazol-1-yl)-1,6-dihydropyridine-3-carboxylate (60 mg, 0.21 mmol). MS m/z: 274(M+1).

Step 3: 1-cyclopentyl-N-(2S,3R)-4-(6-ethyl-2,2-spirocyclopentylchroman-4-ylamino)-3-hydroxy-1-phenylbutan-2-yl)-6-oxo-5-(1H-pyrazol-1-yl)-1,6-dihydropyridine-3-carboxamide A mixture of 5-bromo-1-cyclopentyl-N-(2S,3R)-4-(6-ethyl-2,2-spirocyclopentylchroman-4-ylamino)-3-hydroxy-1-phenylbutan-2-yl)-6-oxo-1,6-dihydropyridine-3-carboxamide (160 mg, 0.24 mmol), pyrazole (23 mg, 0.34 mmol), $K_2CO_3$ (99 mg, 0.72 mmol), CuI (9.1 mg, 0.048 mmol), $N^1$—$N^2$-dimethylethane-1,2-diamine (5 uL, 0.048 mmol) in toluene (3 mL) was heated to 100° C. for 17 h. The mixture was brought to room temperature and quenched with saturated $NH_4Cl$, brine, dried over $MgSO_4$ and chromatographed by HPLC, to afford the title compound. MS m/z: 650 (M+1).

Example 7

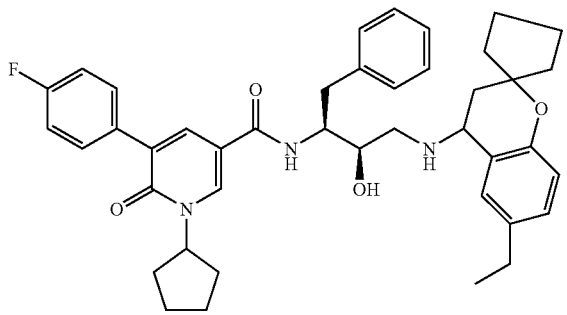

1-cyclopentyl-N-(2S,3R)-4-(6-ethyl-2,2-spirocyclopentylchroman-4-ylamino)-3-hydroxy-1-phenylbutan-2-yl)-5-(2-fluorophenyl)-6-oxo-1,6-dihydropyridine-3-carboxamide A mixture of 4-fluoroboronic acid (32 mg, 0.23 mmol), 5-bromo-1-cyclopentyl-N-(2S,3R)-4-(6-ethyl-2,2-spirocyclopentylchroman-4-ylamino)-3-hydroxy-1-phenylbutan-2-yl)-6-oxo-1,6-dihydropyridine-3-carboxamide (125 mg, 0.19 mmol), tetrakis(triphenylphosphine) palladium (0) (11 mg, 0.010 mmol) and sodium carbonate (100 mg, 0.95 mmol) was purged with nitrogen for 10 min, followed by the addition of dioxane (3 mL). The resulting yellow suspension was heated at reflux for 3 h and brought to room temperature. The mixture was diluted in EtOAc, washed with saturated NaHCO$_3$, brine, dried over $MgSO_4$ and chromatographed by HPLC to afford the title compound as a white solid. MS m/z: 678 (M+1).

Example 8

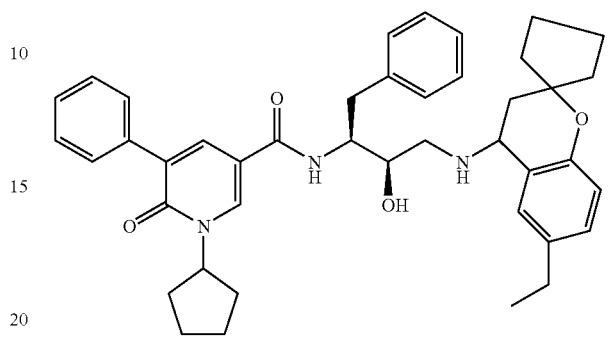

1-cyclopentyl-N-(2S,3R)-4-(6-ethyl-2,2-spirocyclopentylchroman-4-ylamino)-3-hydroxy-1-phenylbutan-2-yl)-6-oxo-5-phenyl-1,6-dihydropyridine-3-carboxamide A mixture of phebnylboronic acid (26 mg, 0.22 mmol), 5-bromo-1-cyclopentyl-N-(2S,3R)-4-(6-ethyl-2,2-spirocyclopentylchroman-4-ylamino)-3-hydroxy-1-phenylbutan-2-yl)-6-oxo-1,6-dihydropyridine-3-carboxamide (116 mg, 0.18 mmol), tetrakis(triphenylphosphine) palladium (0) (10 mg, 0.009 mmol) and sodium carbonate (95 mg, 0.90 mmol) was purged with nitrogen for 10 min followed, by the addition of dioxane (3 mL). The resulting yellow suspension was heated at reflux for 3 h and brought to room temperature. The mixture was diluted in EtOAc, washed with saturated NaHCO$_3$, brine, dried over $MgSO_4$ and chromatographed by HPLC to afford the title compound as a white-solid. MS m/z: 660(M+1).

Example 9

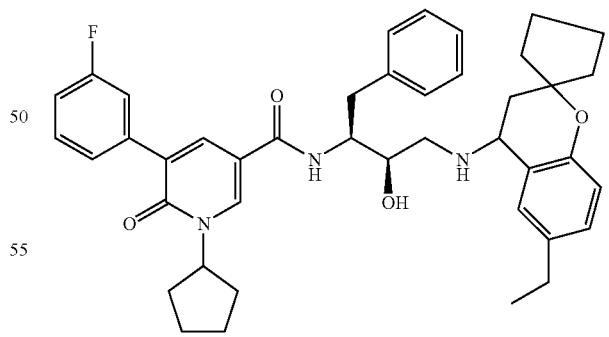

1-cyclopentyl-N-(2S,3R)-4-(6-ethyl-2,2-spirocyclopentylchroman-4-ylamino)-3-hydroxy-1-phenylbutan-2-yl)-5-(3-fluorophenyl)-6-oxo-1,6-dihydropyridine-3-carboxamide A mixture of 3-fluoroboronic acid (41 mg, 0.29 mmol), 5-bromo-1-cyclopentyl-N-(2S,3R)-4-(6-ethyl-2,2-spirocyclopentylchroman-4-ylamino)-3-hydrodroxy-1-phenylbutan-2-yl)-6-oxo-1,6-dihydropyridine-3-carboxamide (160 mg, 0.0.24 mmol), tetrakis(triphenylphosphine) palladium (0) (14 mg, 0.012 mmol) and sodium carbonate (130 mg, 1.2 mmol) was purged with nitrogen for 10 min, followed by the addition of dioxane (3 mL). The resulting yellow suspension was heated at reflux for 3 h and brought to RT. The mixture was diluted in EtOAc, washed with saturated NaHCO₃, brine, dried over MgSO₄ and chromatographed by HPLC to afford the title compound as a white-solid. MS m/z: 678 (M+1).

Example 10

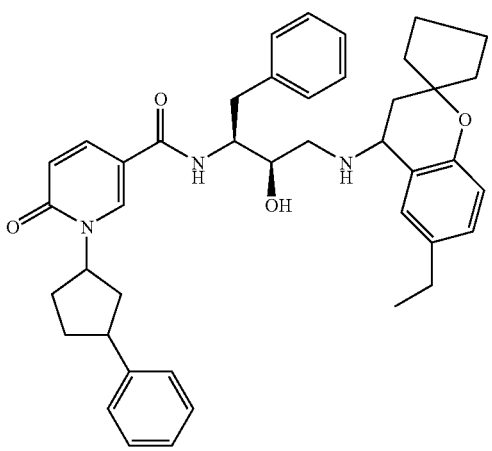

N-(2S,3R)-4-(6-ethyl-2,2-spirocyclopentylchroman-4-ylamino)-3-hydrodroxy-1-phenylbutan-2-yl)-6-oxo-1-(3-phenylcyclopentyl)-1,6-dihydropyridine-3-carboxamide Step 1: 3-Phenylcyclopentanone A mixture of phenylboronic acid (1.63 g, 13.4 mmol), cyclopent-2-enone (1.0 g, 10.4 mmol), and Na₂CO₃ (2.2 g, 20.8 mmol) was purged with nitrogen for 15 min followed by the addition of [Rh(cod)Cl]₂ (100 mg, 0.21 mmol) and water (30 mL). The resulting suspension was heated to 80° C. for 20 min. The mixture was extracted with CH₂Cl₂, washed with brine, dried over MgSO₄ and chromatographed on silica gel using 3:1 hexanes:ethylacetate to afford the title compound as a colorless oil. MS m/z: 161 (M+1).

Step 2: 3-Phenylcyclopentanol

A mixture of 3-phenylcyclopentanone (1.3 g, 8.12 mmol) and NaBH₄ (0.61 g, 16.24 mmol) in methanol (15 mL) was stirred at room temperature for 1 h. The mixture was concentrated, dissolved in CH₂Cl₂, washed with 10% HCl, brine, dried over MgSO₄ and concentrated to afford the title compound as a white solid. MS m/z: 163 (M+1).

Step 3: Methyl 5-bromo-6-oxo-1-(3-phenylcyclopentyl)-1,6-dihydropyridine-3-carboxylate To a suspension of methyl 5-bromo-6-oxo-1,6-dihydropyridine-3-carboxylate (1.6 g, 6.8 mmol), 3-phenylcyclopentanol (1.32 g, 8.15 mmol) and triphenylphosphine (2.7 g, 10.2 mmol) in dry THF (15 mL) was slowly added diethyl azodicarboxylate (1.8 g, 10.2 mmol) at RT. The resulting yellow solution was stirred at room temperature for 17 h. The mixture was diluted in ethylacetate, washed with water, brine, dried over MgSO₄, and chromatographed on silica gel using hexanes to 3:1 hexanes:ethylacetate, to afford the title compound. MS m/z: 376 (M+1).

Step 4: 5-Bromo-6-oxo-1-(3-phenylcyclopentyl)-1,6-dihydropyridine-3-carboxylic acid The title compound was obtained using a procedure analogous to that described in Example 1, with methyl 5-bromo-6-oxo-1-(3-phenylcyclopentyl)-1,6-dihydropyridine-3-carboxylate (390 mg, 1.04 mmol). MS m/z: 361(M+1).

Step 5: 6-oxo-1-(3-phenylcyclopentyl)-1,6-dihydropyridine-3-carboxylic acid

The title compound was obtained using a procedure analogous to that described in Example 2, using 5-bromo-6-oxo-1-(3-phenylcyclopentyl)-1,6-dihydropyridine-3-carboxylic acid (360 mg, 1.0 mmol). MS m/z: 284(M+1).

Step 6: N-(2S,3R)-4-(6-ethyl-2,2-spirocyclopentylchroman-4-ylamino)-3-hydrodroxy-1-phenylbutan-2-yl)-6-oxo-1-(3-phenylcyclopentyl)-1,6-dihydropyridine-3-carboxamide The title compound was obtained using a procedure analogous to that described in Example 1, using 6-oxo-1-(3-phenylcyclopentyl)-1,6-dihydropyridine-3-carboxylic acid (100 mg, 0.35 mmol) and (2S,3R)3-amino-1-(6-ethyl -2,2-spirocyclopentylchroman-4-ylamino)-4-phenylbutan-2-ol hydrochloride (180 mg, 0.42 mmol). MS m/z: 660(M+1).

Example 11

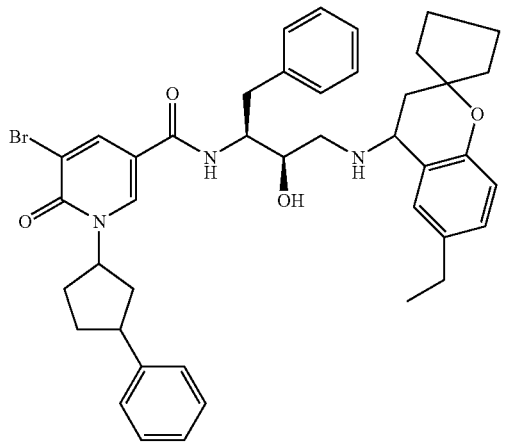

N-(2S,3R)-4-(6-ethyl-2,2-spirocyclopentylchroman-4-ylamino)-3-hydrodroxy-1-phenylbutan-2-yl)-6-oxo-5-bromo-1-(3-phenylcyclopentyl)-1,6-dihydropyridine-3-carboxamide The title compound may be obtained using a procedure analogous to that described in Example 1.

Example 12

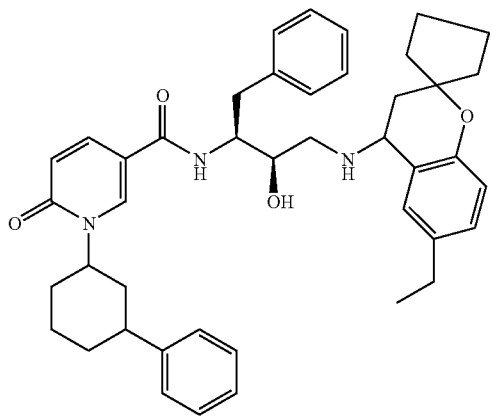

N-(2S,3R)-4-(6-ethyl-2,2-spirocyclopentylchroman-4-ylamino)-3-hydrodroxy-1-phenylbutan-2-yl)-6-oxo-1-(3-phenylcyclohexyl)-1,6-dihydropyridine-3-carboxamide Step 1: 3-Phenylcyclohexanone The title compound was obtained using a procedure analogous to that described in Step 1 of Example 10 using cyclohex-2-enone (1.0 g, 10.4 mmol) and phenylboronic acid (1.3 g, 10.4 mmol) to afford the title compound as a colorless oil. MS m/z: 175(M+1).

Step 2: 3-Phenylcyclohexanol

The title compound was obtained using a procedure analogous to that described in Step 2 of Example 10, using 3-phenylcyclohexanone (100 mg, 0.57 mmol) to afford a white solid. MS m/z: 177(M+1).

Step 3: Methyl 5-bromo-6-oxo-1-(3-phenylcyclohexyl)-1,6-dihydropyridine-3-carboxylate The title compound was obtained using a procedure analogous to that described in Step 3 of Example 10. MS m/z: 390(M+1).

Step 4: 5-Bromo-6-oxo-1-(3-phenylcyclohexyl)-1,6-dihydropyridine-3-carboxylic acid The title compound was obtained using a procedure analogous to that described in Step 4 of Example 10. MS m/z: 376(M+1).

Step 5: 6-oxo-1-(3-phenylcyclohexyl)-1,6-dihydropyridine-3-carboxylic acid

The title compound was obtained using a procedure analogous to that described in Step 5 of Example 10, using 5-bromo-6-oxo-1-(3-phenylcyclohexyl)-1,6-dihydropyridine-3-carboxylic acid (70 mg, 0.19 mmol). MS m/z: 298(M+1).

Step 6: N-(2S,3R)-4-(6-ethyl-2,2-spirocyclopentylchroman-4-ylamino)-3-hydrodroxy-1-phenylbutan-2-yl)-6-oxo-1-(3-phenylcyclohexyl)-1,6-dihydropyridine-3-carboxamide The title compound was obtained using a procedure analogous to that described in Example 1, using 6-oxo-1-(3-phenylcyclohexyl)-1,6-dihydropyridine-3-carboxylic acid (30 mg, 0.10 mmol) and (2S,3R)3-amino-1-(6-ethyl-2,2-spirocyclopentylchroman-4-ylamino)-4-phenylbutan-2-ol hydrochloride (52 mg, 0.12 mmol) to afford the title compound as a white solid. MS m/z: 674(M+1).

Example 13

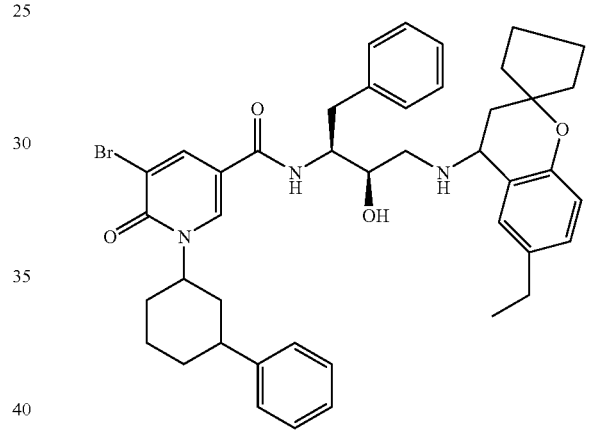

N-(2S,3R)-4-(6-ethyl-2,2-spirocyclopentylchroman-4-ylamino)-3-hydrodroxy-1-phenylbutan-2-yl)-6-oxo-5-bromo-1-(3-phenylcyclohexyl)-1,6-dihydropyridine-3-carboxamide The title compound may be obtained using a procedure analogous to that described in Example 1.

Example 14

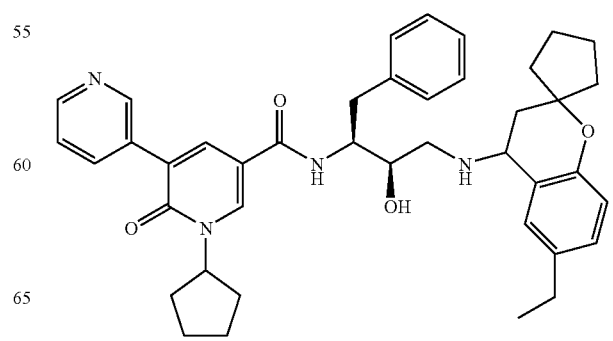

1-cyclopentyl-N-((2S,3R)-4-(6-ethyl-2,2-spirocyclopentylchroman-4-ylamino)-3-hydroxy-1-phenylbutan-2-yl)-6-OXO-5-(pyridine-3-yl)-1,6-dihydropyridine-3-carboxamide Example 15

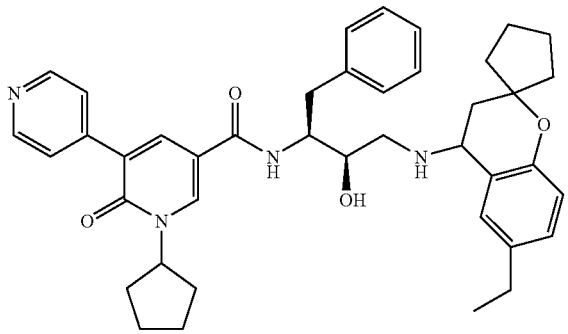

1-cyclopentyl-N-((2S,3R)-4-(6-ethyl-2,2-spirocyclopentylchroman-4-ylamino)-3-hydroxy-1-phenylbutan-2-yl)-6-OXO-5-(pyridin-4-yl)-1,6-dihydropyridine-3-carboxamide Example 16

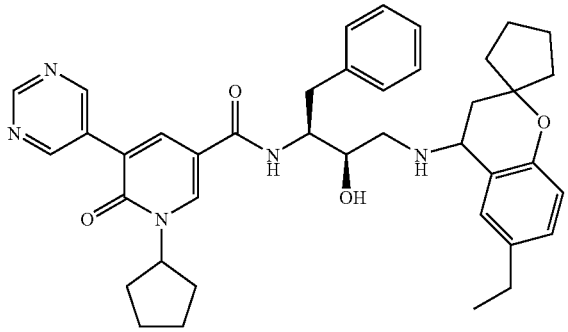

1-cyclopentyl-N-((2S,3R)-4-(6-ethyl-2,2-spirocyclopentylchroman-4-ylamino)-3-hydroxy-1-phenylbutan-2-yl)-6-OXO-5-(pyrimidin-5-yl)-1,6-dihydropyridine-3-carboxamide The title compounds, Example 14, 15 and 16, were obtained using a procedure analogous to that described in Example 8, using pyridine-3-ylboronic acid (24 mg, 0.20 mmol), 5-bromo-1-cyclopentyl-N-(2S,3R)-4-(6-ethyl-2,2-spirocyclopentylchroman-4-ylamino)-3-hydroxy-1-phenylbutan-2-yl)-6-oxo-1,6-dihydropyridine-3-carboxamide (in Ex. 14, 100 mg, 0.15 mmol); pyridine-4-ylboronic acid (26 mg, 0.21 mmol), 5-bromo-1-cyclopentyl-N-(2S,3R)-4-(6-ethyl-2,2-spirocyclopentylchroman-4-ylamino)-3-hydroxy-1-phenylbutan-2-yl)-6-oxo-1,6-dihydropyridine-3-carboxamide (in Ex. 15, 105 mg, 0.16 mmol) and pyrimidin-5-ylboronic acid (13 mg, 0.10 mmol), 5-bromo-1-cyclopentyl-N-(2S,3R)-4-(6-ethyl-2,2-spirocyclopentylchroman-4-ylamino)-3-hydroxy-1-phenylbutan-2-yl)-6-oxo-1,6-dihydropyridine-3-carboxamide (in Ex. 16, 50 mg, 0.08 mmol), respectively, to afford the title compound Example 14 as a light brown solid (MS m/z: 661(M+1); title compound Example 15 as a light yellow solid; and title compound Example 16 (MS m/z: 662 (M+1).

Example 17

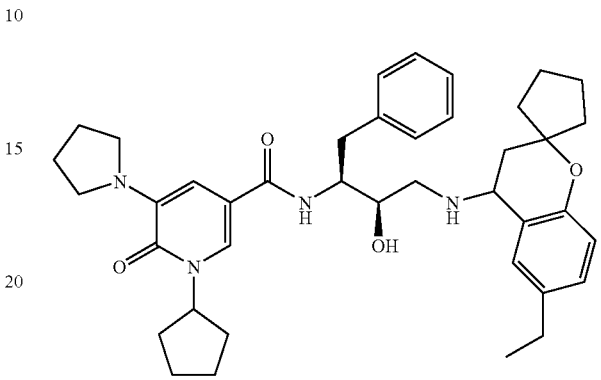

1-cyclopentyl-N-((2S,3R)-4-(6-ethyl-2,2-spirocyclopentylchroman-4-ylamino)-3-hydroxy-1-phenylbutan-2-yl)-6-OXO-5-(pyrrolidin-1-yl)-1,6-dihydropyridine-3-carboxamide Step 1: Methyl 1-cyclopentyl-6-oxo-5-(pyrrolidin-1-yl)-1,6-dihydropyridine-3-carboxylate A mixture of methyl 5-bromo-1-cyclopentyl-6-oxo-1,6-dihydropyridine-3-carboxylate (100 mg, 0.33 mmol), pyrrolidine (33 uL, 0.40 mmol), cesium carbonate (150 mg, 0.46 mmol), tris(dibenzylideneacetone)dipalladium (0) (3 mg, 0.0033 mmol), rac-2-2'-bis(diphenyl-phosphino)-1,1'-binaphthyl (3.1 mg, 0.005 mmol) was purged with nitrogen for 30 min, followed by the addition of anhydrous toluene (1.5 mL). The resulting light-brown solution was heated to 95° C. for 17. The mixture was brought to room temperature and partitioned between ethyl acetate and saturated $NH_4Cl$. The organic phase was separated, washed with saturated $NH_4Cl$, brine, dried over $MgSO_4$ and chromatographed on silica gel using 3:1 hexanes:ethyl acetate to afford the title compound as a yellow oil. MS m/z: 291(M+1).

Step 2: 1-cyclopentyl-6-oxo-5-(pyrrolidin-1-yl)-1,6-dihydropyridine-3-carboxylic acid The title compound was obtained using a procedure analogous to that described in Example 10, as a light green-yellow solid. MS m/z: 277(M+1).

Step 3: 1-cyclopentyl-N-((2S,3R)-4-(6-ethyl-2,2-spirocyclopentylchroman-4-ylamino)-3-hydroxy-1-phenylbutan-2-yl)-6-OXO-5-(pyrrolidin-1-Iy)-1,6-dihydropyridine-3-carboxamide The title compound was obtained using a procedure analogous to that described in Example 1, reacting 1-cyclopentyl-6-oxo-5-(pyrrolidin-1-yl)-1,6-dihydropyridine-3-carboxylic acid (35 mg, 0.13 mmol) and (2S,3R)3-amino-1-(6-ethyl-2, 2-spirocyclopentylchroman-4-ylamino)-4-phenylbutan-2-ol hydrochloride (50 mg, 0.13 mmol) to afford the title compound as a light yellow solid. MS m/z: 653(M+1).

Example 18

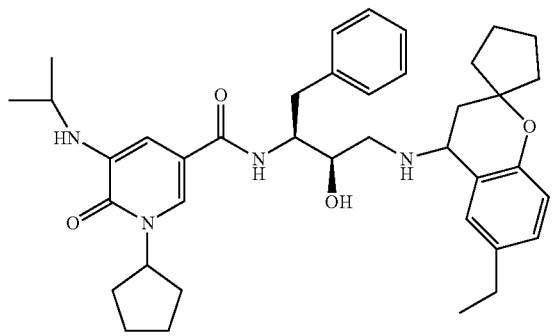

1-cyclopentyl-N-((2S,3R)-4-(6-ethyl-2,2-spirocyclopentylchroman-4-ylamino)-3-hydrodroxy-1-phenylbutan-2-yl)-5-(isopropylamino)-6-oxo-1,6-dihydropyridine-3-carboxamide Step 1: Methyl 1-cyclopentyl-5-(isopropylamino)-6-oxo-1,6-dihydropyridine-3-carboxylate The title compound was obtained using a procedure analogous to that described in Example 17. MS m/z: 279(M+1).

Step 2: 1-cyclopentyl-5-(isopropylamino)-6-oxo-1,6-dihydropyridine-3-carboxylic acid The title compound was obtained using a procedure analogous to that described in Example 10. MS m/z: 265(M+1).

1-cyclopentyl-N-((2S,3R)-4-(6-ethyl-2,2-spirocyclopentylchroman-4-ylamino)-3-hydrodroxy-1-phenylbutan-2-yl)-5-(isopropylamino)-6-oxo-1,6-dihydropyridine-3-carboxamide The title compound was obtained using a procedure analogous to that described in Example 1, reacting 1-cyclopentyl-5-(isopropylamino)-6-oxo-1,6-dihydropyridine-3-carboxylic acid (22.5 mg, 0.085 mmol) and (2S,3R)3-amino-1-(6-ethyl-2,2-spirocyclopentylchroman-4-ylamino)-4-phenylbutan-2-ol (34 mg, 0.085 mmol) to afford the title compound as a light yellow solid. MS m/z: 641(M+1).

Example 19

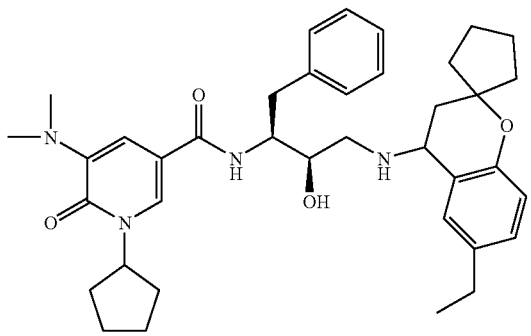

1-cyclopentyl-5-(dimethylamino)-N-((2S,3R)-4-(6-ethyl-2,2-spirocyclopentylchroman-4-ylamino)-3-hydrodroxy-1-phenylbutan-2-yl)-6-oxo-1,6-dihydropyridine-3-carboxamide The title compound was obtained using a procedure analogous to that described in Example 18, using 1-cyclopentyl-5-(dimethylamino)-6-oxo-1,6-dihydropyridine-3-carboxylic acid (25 mg, 0.10 mmol) and (2S,3R)3-amino-1-(6-ethyl-2,2-spirocyclopentylchroman-4-ylamino)-4-phenylbutan-2-ol (39.4 mg, 0.10 mmol) to afford the title compound as a light yellow solid. MS m/z: 627(M+1).

Example 20

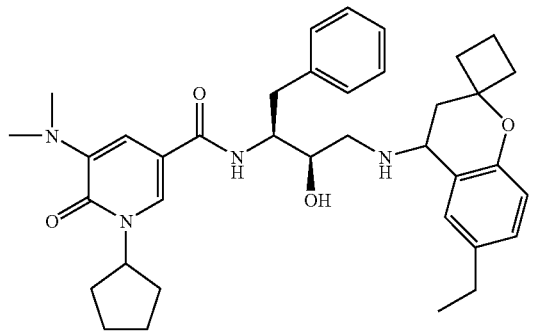

1-cyclopentyl-5-(dimethylamino)-N-((2S,3R)-4-(6-ethyl-2,2-spirocyclobutylchroman-4-ylamino)-3-hydrodroxy-1-phenylbutan-2-yl)-6-oxo-1,6-dihydropyridine-3-carboxamide The title compound, using a procedure analogous to that described in Example 19, was obtained as a light yellow solid. MS m/z: 613 (M+1).

Example 21

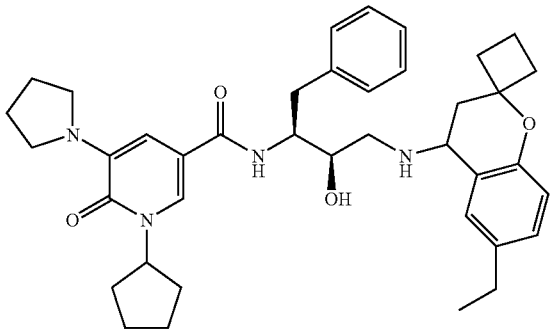

1-cyclopentyl-N-((2S,3R)-4-(6-ethyl-2,2-spirocyclobutylchroman-4-ylamino)-3-hydrodroxy-1-phenylbutan-2-yl)-6-OXO-5-(pyrrolidin-1-yl)-1,6-dihydropyridine-3-carboxamide The title compound was obtained using a procedure analogous to that described in Example 1, as a light yellow solid. MS m/z: 639(M+1).

Example 22

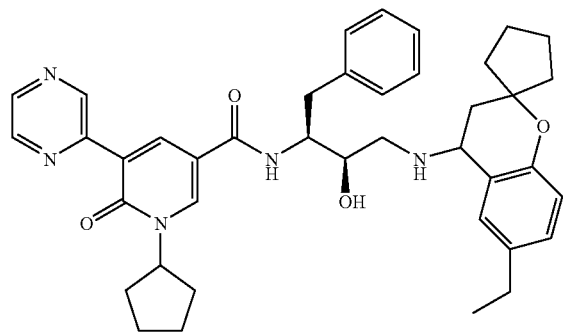

1-cyclopentyl-N-((2S,3R)-4-(6-ethyl-2,2-spirocyclopentylchroman-4-ylamino)-3-hydroxy-1-phenylbutan-2-yl)-6-oxo-5-(pyrazin-2-yl)-1,6-dihydropyridine-3-carboxamide The title compound was obtained using procedures analogous to those described in Example 9 (Step 1; MS m/z: 300 (M+1) and Example 10 (Step 2, acid, MS m/z: 286 (M+1)), and Example 1. MS m/z: 662(M+1).

Example 23

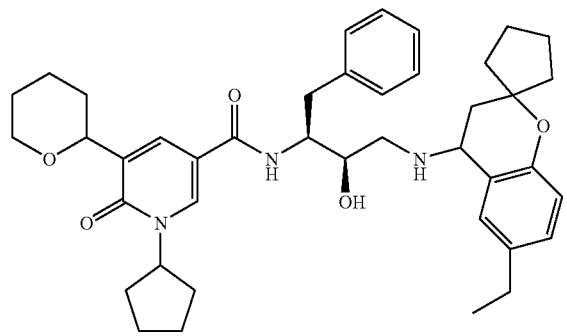

1-cyclopentyl-N-((2S,3R)-4-(6-ethyl-2,2-spirocyclopentylchroman-4-ylamino)-3-hydroxy-1-phenylbutan-2-yl)-6-OXO-5-(tetrahydro-2H-pyran-2-yl)-1,6-dihydropyridine-3-carboxamide Step 1: Tributyl(5,6-dihydro-4H-pyran-2-yl)stannane A mixture of 3,4-dihydro-2H-pyran (500 mg, 5.94 mmol) in THF (10 mL) was brought to −78° C. followed by the addition of tert-butyllithium (12.2 mL, 20.8 mmol, 1.7 M in pentane). The resulting yellow solution was brought to 0° C. and stirred for 15 min. The reaction was then cooled to −78° C. and tributyltin chloride (4.8 mL, 17.8 mmol) was slowly added. The reaction was monitored by TLC. Upon completion by TLC, water was added (20 mL) to the reaction. The organic phase was separated, washed with water, dried over MgSO$_4$, concentrated and chromatographed on silica gel using hexanes (500 ml hexanes and 0.5 mL triethylamine). The title compound was obtained as a colorless oil. MS m/z: 375(M+1).

Step 2: Methyl 1-cyclopentyl-5-(5,6-dihydro-4H-pyran-2-yl)-6-oxo-1,6-dihydropyridine-3-carboxylate The title compound was obtained, as a light yellow oil, using a procedure analogous to that described in Example 5. MS m/z: 304(M+1).

Step 3: Methyl 1-cyclopentyl-6-oxo-5-(tetrahydro-2H-pyran-2-yl)-1,6-dihydropyridine-3-carboxylate The title compound was obtained using a procedure analogous to that described in Example 2. MS m/z: 306 (M+1).

Step 4: 1-cyclopentyl-6-oxo-5-(tetrahydro-2H-pyran-2-yl)-1,6-dihydropyridine-3-carboxylic acid The title compound, a white solid, was obtained using a procedure analogous to that described in Example 10. MS m/z: 292 (M+1).

Step 5: 1-cyclopentyl-N-((2S,3R)-4-(6-ethyl-2,2-spirocyclopentylchroman-4-ylamino)-3-hydroxy-1-phenylbutan-2-yl)-6-OXO-5-(tetrahydro-2H-pyran-2-yl)-1,6-dihydropyridine-3-carboxamide The title compound was obtained using a procedure analogous to that described in Example 1. MS m/z: 668 (M+1).

Example 24

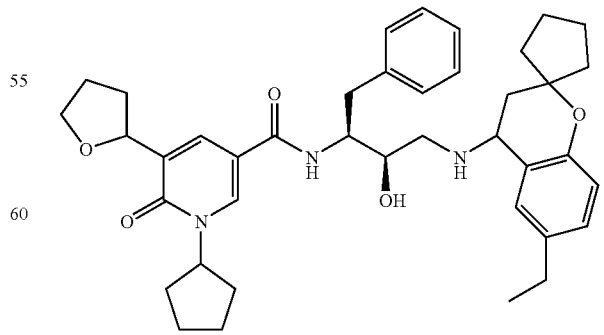

1-cyclopentyl-N-((2S,3R)-4-(6-ethyl-2,2-spirocyclo-
pentylchroman-4-ylamino)-3-hydroxy-1-phe-
nylbutan-2-yl)-6-OXO-5-(tetrahydrofuran-2-yl)-1,6-
dihydropyridine-3-carboxamide The title compound was obtained using a procedure analogous to that described in Example 23. MS m/z: 654 (M+1).

Example 25

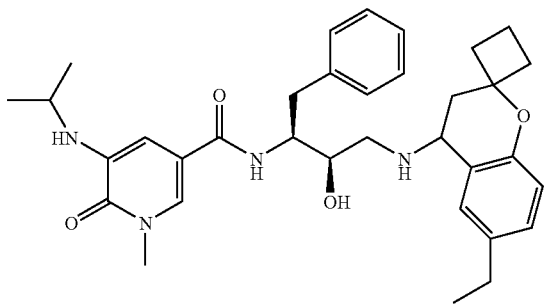

N-((2S,3R)-4-(6-ethyl-2,2-spirocyclobutylchroman-
4-ylamino)-3-hydroxy-1-phenylbutan-2-yl)-5-
(isopropylamino)-1-methyl-6-oxo-1,6-dihydropyri-
dine-3-carboxamide Step 1: Methyl 5-bromo-1-methyl-6-oxo-1,6-dihy-
dropyridine-3-carboxylate A mixture of methyl 5-bromo-6-oxo-1,6-dihydropyridine-3-caboxylate (1.5 g, 6.5 mmol) and potassium carbonate (0.99 g, 7.15 mmol) in DMF (25 mL) was stirred at room temperature for 15 min followed by the addition of methyl iodide (0.42 mL, 6.83 mmol). The resulting suspension was stirred at room temperature for 17 h. The mixture was partitioned between ethylacetate and water. The organic phase was separated and the aqueous phase was extracted with ethylacetate. The organic extracts were combined, washed with brine, dried over $MgSO_4$ and concentrated to afford the title compound as a light yellow solid. MS m/z: 246(M+1).

Step 2: Methyl 5-(isopropylamino)-1-methyl-6-oxo-
1,6-dihydropyridine-3-carboxylate The title compound, a light yellow oil, was obtained using a procedure analogous to that described in Example 17. MS m/z: 225(M+1).

Step 3: 5-(isopropylamino)-1-methyl-6-oxo-1,6-
dihydropyridine-3-carboxylic acid The title compound was obtained as a light yellow oil, using a procedure analogous to that described in Example 10. MS m/z: 211(M+1).

Step 4: N-((2S,3R)-4-(6-ethyl-2,2-spirocyclobutyl-
chroman-4-ylamino)-3-hydroxy-1-phenylbutan-
2-yl)-5-(isopropylamino)-1-methyl-6-oxo-1,6-dihy-
dropyridine-3-carboxamide The title compound was obtained as a yellow solid, using a procedure analogous to that described in Example 1. MS m/z: 573(M+1).

Example 26

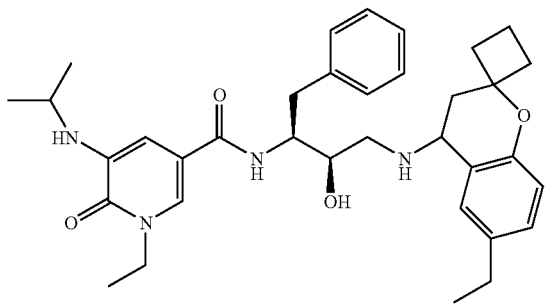

N-((2S,3R)-4-(6-ethyl-2,2-spirocyclobutylchroman-
4-ylamino)-3-hydroxy-1-phenylbutan-2-yl)-5-
(isopropylamino)-1-ethyl-6-oxo-1,6-dihydropyri-
dine-3-carboxamide The title compound was obtained as an off-white solid, using a procedure analogous to that described in Example 25. MS m/z: 587(M+1)

Example 27

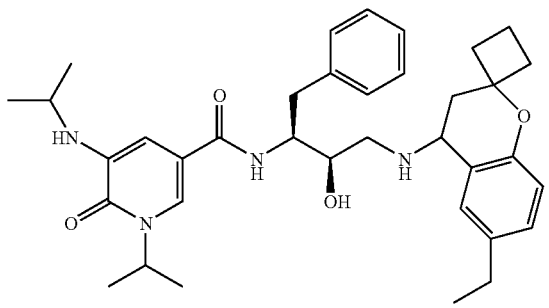

N-((2S,3R)-4-(6-ethyl-2,2-spirocyclobutylchroman-
4-ylamino)-3-hydroxy-1-phenylbutan-2-yl)-1-
isopropyl-5-(isopropylamino)-6-oxo-1,6-dihydropy-
ridine-3-carboxamide The title compound was obtained as a yellow solid, using a procedure analogous to that described in Example 25. MS m/z: 573 (M+1).

Example 28

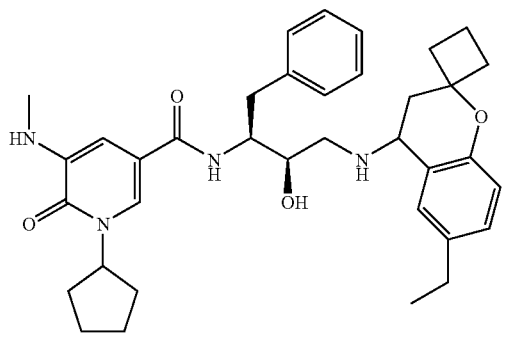

1-cyclopentyl-N-((2S,3R)-4-(6-ethyl-2,2-spirocyclobutylchroman-4-ylamino)-3-hydroxy-1-phenylbutan-2-yl)-5-(methylamino)-6-oxo-1,6-dihydropyridine-3-carboxamide Step 1: Methyl 5-((4-methoxybenzyl)(methyl)amino)-1-cyclopentyl-6-oxo-1,6-dihydropyridine-3-carboxylate The title compound was obtained as a colorless oil, using a procedure analogous to that described in Example 17, with methyl 5-bromo-1-cyclopentyl-6-oxo-1,6-dihydropyridine-3-carboxylate (200 mg, 0.67 mmol) and (4-methoxyphenyl)-N-methylmethanamine (130 mg, 0.87 mmol). MS m/z: 371 (M+1).

Step 2: Methyl-1-cyclopentyl-5-(methylamino)-6-oxo-1,6-dihydropyridine-3-carboxylate The title compound was obtained as a colorless oil, using a procedure analogous to that described in Example 2, with methyl 5-((4-methoxybenzyl)(methyl)amino) -1-cyclopentyl-6-oxo-1,6-dihydropyridine-3-carboxylate (30 mg, 0.081 mmol). MS m/z: 251 (M+1).

Step 3: 1-cyclopentyl-5-(methylamino)-6-oxo-1,6-dihydropyridine-3-carboxylic acid The title compound was obtained as a light yellow solid, using a procedure analogous to that described in Example 10. MS m/z: 237 (M+1).

Step 4: 1-cyclopentyl-N-((2S,3R)-4-(6-ethyl-2,2-spirocyclobutylchroman-4-ylamino)-3-hydrodroxy-1-phenylbutan-2-yl)-5-(methylamino)-6-oxo-1,6-dihydropyridine-3-carboxamide The title compound was obtained as a light yellow solid, using a procedure analogous to that described in Example 1. MS m/z: 599 (M+1).

Example 29

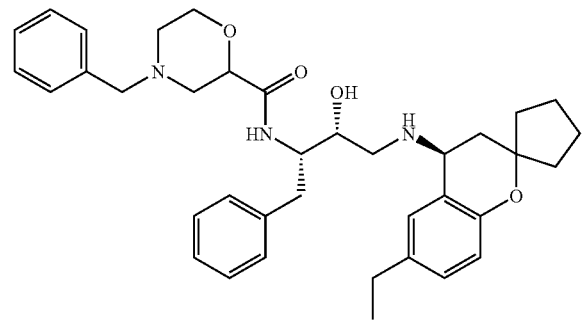

4-Benzyl-N-((2S,3R)-4-((S)-6-ethyl-2,2-spirocyclopentylchroman-4-ylamino)-3-hydroxy-1-phenylbutan-2-yl)morpholine-2-carboxamide Racemic 4-benzylmorpholine-2-carboxylic acid (16 mg) was dissolved in DMF (0.5 mL) in a reaction flask (1) and DIPEA (0.1 mL) and HATU (42 mg, 0.11 mmol) were added. In a separate flask (2) was placed (2R,3S)-3-amino-1-((S)-6-ethyl-2,2-spirocyclopentylchroman-4-ylamino)-4-phenylbutan-2-ol,bis HCl salt (35 mg, 0.075 mmol), DIPEA (0.1 mL) and DMF (0.5 mL) and the reaction was allowed to stir for 10 min before the solution was added to flask (1). The reaction in flask (1) was allowed to stir for 1 h and then diluted with MeOH (2.0 mL), filtered. The filtrate was injected directly onto a reverse phase HPLC purification (80 mL/min on a 30.0×150.0 mm C-18(2)Luna Phenomonex column, 10% CH3CN gradient to 100% over 30 min). The pure fractions were evaporated to give the title compound. MS m/z: 598 (M+1).

Example 30

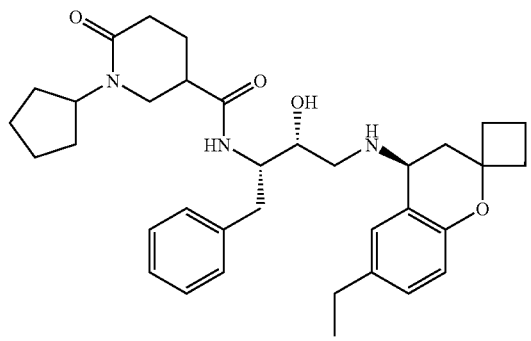

1-cyclopentyl-N-((2S,3R)-4-((S)-6-ethyl-2,2-spirocyclobutylchroman-4-ylamino)-3-hydroxy-1-phenylbutan-2-yl)-6-oxopiperidine-3-carboxamide Methyl 6-oxo-6H-pyran-3-carboxylate (Aldrich, 4.00 g, 26.0 mmol) was placed in a 500 mL rbf before 1,4-dioxane (40.0 mL) was added via syringe. After 5 min, cyclopentyl amine (13.0 mL) was added via syringe and the reaction was allowed to stir for 14 h before the volatiles were removed by rotary evaporation. The solid residue was dissolved in diethyl ether (100 mL) and then washed with HCl (10%, 1×100 mL), NaHCO3 (sat, 1×100 mL), brine (sat 100 mL), and dried with magnesium sulfate. The dried solution was filtered and concentrated to provide 4.95 g of crude oil which was purified by a 120 g normal phase Isco column chromatography (50% EtOAc-100% EtOAc in hexanes) to give 2.38 g of methyl 1-cyclopentyl-6-oxo-1,6-dihydropyridine-3-carboxylate. MS m/z: 222 (M+1). This methyl ester was dissolved in THF (30 mL) and water was added (10 mL) before the addition of LiOH monohydrate (1.20 g) and then reaction was placed in a 70° C. oil bath for 2 h. The reaction was cooled and the bulk of the THF was removed by rotary evaporation. The reaction was then poured into a separatory funnel and HCl (10%, 75 mL) was added before extracting with diethyl ether (3×100 mL). The combined organics were washed with brine (sat, 200 mL) and dried with magnesium sulfate. The solution was filtered and concentrated to provide an off white solid (920 mg). MS m/z: 208 (M+1).

This acid was dissolved in MeOH (25 mL) and HOAc was added (2.0 mL) before the addition of PtO2 (125 mg). A balloon of H2 was bubbled through the reaction and then it was stirred for 12 h under 1 atm of H2. LC/MS analysis showed that about 50% of the material was reduced. An additional portion of PtO2 was added (125 mg) and the reaction was recharged with H2 and stirred for another 12 h and then filtered through a plug of Celite®. LC/MS showed that the reduction had not progressed any further. The filtrate was concentrated and then dissolved in MeOH (10 mL) and loaded directly to Varian reverse phase HPLC. The chromatography did not provide clean separation of material. The fractions were combined in a 500 mL rbf and the $CH_3CN$ was removed by rotary evaporation. The water was frozen and then removed by lyopholization to provide 510 mg of a white solid that was used in the next reaction without further purification.

The crude 1-cyclopentyl-6-oxopiperidine-3-carboxylic acid (35 mg) from the above procedure and (2R,3S)-3-amino-1-((S)-6-ethyl-2,2-spirocyclobutylchroman-4-ylamino)-4-phenylbutan-2-ol bis hydochloride salt (30 mg) were dissolved in DMF (0.7 mL) before the addition of DIPEA (0.2 mL) and HATU (40 mg) in one portion. The reaction was allowed to stir overnight and then diluted with MeOH (3 mL) and loaded directly to reverse phase HPLC. The pure fractions were evaporated to provide the title compound as a mixture of two diastereomers. MS m/z: 574 (M+1).

Example 31

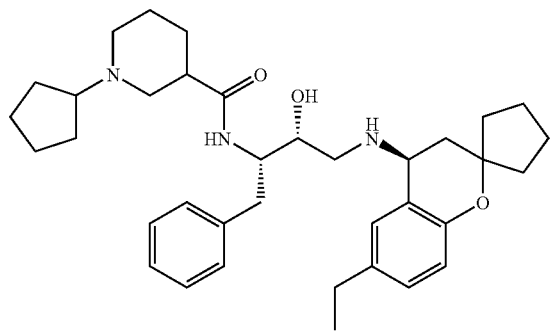

1-cyclopentyl-N-((2S,3R)-4-((S)-6-ethyl-2,2-spiro-cyclopentylchroman-4-ylamino)-3-hydroxy-1-phenylbutan-2-yl)piperidine-3-carboxamide 1-(tert-butoxycarbonyl)piperidine-3-carboxylic acid (Aldrich, 2.20 g, 9.60 mmol) was dissolved in DCM (40 mL) in a round bottom flask (rbf), which was placed in a 0° C. bath. Triethyl amine (1.7 mL) was added to the reaction via syringe and then benzyl chloroformate (1.4 mL) was added dropwise via a syringe. The reaction was allowed to stir for 10 min and then DMAP (117 mg) was added in on portion. The reaction was allowed to stir for 1 h and then quenched by pouring into $NaHCO_3$ (sat, 50 mL). The reaction was extracted with DCM (3×50 mL), washed with brine (sat, 200 mL), and dried with sodium sulfate. The solution was filtered and concentrated to provide the benzyl ester as colorless oil that was taken on to the next step without any further purification. MS m/z: 320 (M+1).

The benzyl ester was dissolved in DCM (10 mL) and the rbf was placed in a 0° C. bath. After stirring for 5 min, TFA (8 mL) was added and the reaction was allowed to stir for 2 h and then concentrated on a rotary evaporator before being placed on high vacuum for 12 h. The crude oil was poured into $Na_2CO_3$ (10%, 100 mL) and extracted with DCM (3×75 mL), washed with brine (sat, 200 mL), dried with sodium sulfate, filtered and concentrated to provide the benzyl piperidine-3-carboxylate as an oil that was taken on to the next step without any further purification. MS m/z: 220 (M+1).

The crude amine from the above step was dissolved in 1,2-dichloroethane (15 mL) and cyclopentanone (1.0 mL) was added via syringe. The reaction was allowed to stir for 5 min before the addition of HOAc (0.6 mL) and $NaBH(OAc)_3$ (2.3 g, 10.9 mmol) in one portion. The reaction was allowed to stir for 48 h and then quenched with $Na_2CO_3$ (10%, 20 mL) and the reaction was allowed to stir for 1 h before being extracted with DCM (3×50 mL). The combined organics were washed with brine (sat, 200 mL), dried with sodium sulfate, filtered, concentrated to provide 1.3 g of crude oil that was purified by a 120 g Isco normal phase column (100% EtOAc) to give benzyl 1-cyclopentylpiperidine-3-carboxylate as a colorless oil. MS m/z: 288 (M+1).

A portion of the benzyl ester from above (164 mg) was dissolved in EtOAc (20 mL) and Pd/C was added (40 mg). One balloon of $H_2$ was bubbled through the reaction and then it was allowed to stir for overnight under 1 atm of $H_2$. The reaction was filtered through a plug of celite and the filtrate was concentrated to provide the acid as an off white solid. MS m/z: 198 (M+1).

The carboxylic acid (20 mg) was dissolved in DMF (0.5 mL) and then DIPEA (0.1 mL) and HATU (42 mg, 0.11 mmol) were added to the reaction flask. In a separate flask was placed (2R,3S)-3-amino-1-((S)-6-ethyl-2,2-spirocyclopentylchroman-4-ylamino)-4-phenylbutan-2-ol,bis HCl salt (40 mg, 0.085 mmol), DIPEA (0.1 mL) and DMF (0.5 mL) and the reaction was allowed to stir for 10 min before the solution was added to the acid/HATU mixture. The reaction was allowed to stir for 1 h and then loaded directly onto a reverse phase HPLC. The pure fractions were concentrated to provide the title compound as a mixture of two diastereomers. MS m/z: 574.8 (M+1).

Example 32

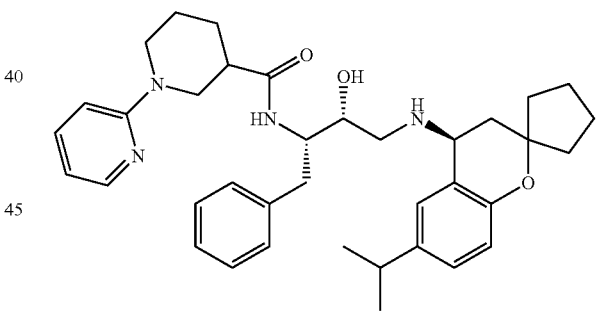

N-((2S,3R)-3-hydroxy-4-((S)-6-isopropyl-2,2-spiro-cyclopentylchroman-4-ylamino)-1-phenylbutan-2-yl)-1-(pyridin-2-yl)piperidine-3-carboxamide Pure benzyl piperidine-3-carboxylate (170 mg, 0.776 mmol; Example 31) was placed in a microwave tube. DIPEA (0.50 mL), tert-BuOH (1.5 mL) and 2-fluoropyridine (Aldrich, 0.40 mL) were added to the tube via syringes before the tube was subjected to microwave irradiation at 180° C. for 20 min. LC/MS showed partial conversion to the desired pyridine derivative. The tube was subjected to further microwave irradiation at 220° C. for 20 min and then it was allowed to cool to room temperature. The volatiles were removed by rotary evaporation to provide 229 mg of crude oil which was dissolved in MeOH (8.0 mL) and then subjected to reverse phase HPLC. The pure fractions were poured into $Na_2CO_3$ (10%, 75 mL) and extracted with EtOAc (3×50 mL), washed with brine (sat, 150 mL), dried with sodium sulfate, filtered and concentrated to provide 90 mg of benzyl 1-(pyridin-2-yl)piperidine-3-carboxylate. MS m/z: 297 (M+1)

The benzyl ester from above was dissolved in EtOAc (30 mL) and 10% Pd/C (20 mg) was added in one portion. A balloon of $H_2$ was bubbled through the reaction before it was allowed to stir under 1 atm of $H_2$ for 48 h. The reaction was filtered through a plug of celite and concentrated to provide 58 mg of clean 1-(pyridin-2-yl)piperidine-3-carboxylic acid. MS m/z: 207 (M+1)

The 1-(pyridin-2-yl)piperidine-3-carboxylic acid was dissolved in DMF (1.0 mL) before DIPEA (0.1 mL), (2R,3S)-3-amino-1-((S)-6-isopropyl-2,2-spirocyclopentylchroman-4-ylamino)-4-phenylbutan-2-ol, bis hydrochloride salt (58 mg), and HATU (50 mg) were added to the reaction. The reaction was allowed to stir for 1 h and then loaded directly to reverse phase HPLC. The pure fractions were poured into $Na_2CO_3$ (10%, 100 mL) and extracted with EtOAc (3×75 mL). The combined organics were washed with brine (sat 100 mL) and dried with sodium sulfate. The solution was filtered and concentrated to provide the title compound. MS m/z: 597.4 (M+1)

Example 33

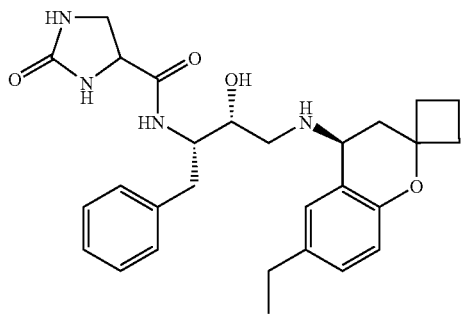

N-((2S,3R)-4-((S)-6-ethyl-2,2-spirocyclobutylchroman-4-ylamino)-3-hydroxy-1-phenylbutan-2-yl)-2-oxoimidazolidine-4-carboxamide To a 25 mL RBF containing (2R,3S)-3-amino-1-((S)-6-ethyl-2,2-spirocyclobutylchroman-4-ylamino)-4-phenylbutan-2-ol bis hydochloride salt (25 mg, 55 µmol) and 2-oxoimidazolidine-4-carboxylic acid (Aldrich, 7.2 mg, 55 µmol) was added DMF (1 mL) and N-ethyl-N-isopropylpropan-2-amine (7.1 mg, 55 µmol) and the mixture was allowed to stir at 23° C. for 5 min. HATU (21 mg, 55 µmol) was added in one portion and the reaction was allowed to stir for 12 h, while monitoring by LC/MS. The crude reaction was quenched with MeOH (2.0 mL) and then loaded directly to reverse phase HPLC, the pure fractions were concentrated in a Gene-vac lyophilizer to provide the TFA salt of the title compound as a white solid. MS m/z: 494 (M+1).

Example 34

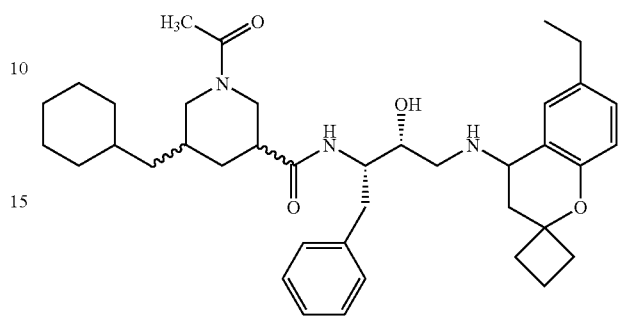

1-acetyl-5-(cyclohexylmethyl)-N-((2S,3R)-4-(2-spirocyclobutyl-6-ethyl-2,2-spirocyclopentylchroman-4-ylamino)-3-hydroxy-1-phenylbutan-2-yl)piperidine The title compound may be obtained using a procedure analogous to that described immediately below, to synthesize 1-acetyl-5-(cyclohexylmethyl)-N-((2S,3R)-4-(6-ethylchroman-4-ylamino)-3-hydroxy-1-phenylbutan-2-yl)piperidine.

Step 1: Ethyl-5-benzylnicotinate

A suspension of Zn (1.0 g, 15 mmol) and $I_2$ (130 mg, 0.5 mmol) in DMA (15 mL) was stirred vigorously until the red color dissipated (3-5 min). Benzyl bromide (1.7 g, 10 mmol) was introduced and the resulting slurry was heated at 80° C. for 2.5 h at which point $Cl_2Pd(PPh_3)_2$ (250 mg, 0.35 mmol) and a solution of ethyl-5-bromonicotinate (1.1 g, 5.0 mmol) in benzene (10 mL) were introduced and the reaction was heated at 80° C. for 1 h. The reaction was allowed to cool to room temperature and was diluted with EtOAc (100 mL). The mixture was poured into $NaHCO_3$ (5% aqueous, 100 mL). The layers were separated and the aqueous layer was extracted with EtOAc (2×50 mL). The combined organic layers were sequentially washed with $H_2O$ (3×100 mL) and brine before being dried over $Na_2SO_4$. Concentration and purification by silica gel chromatography (hexane→50% EtOAc/hexane) provided the title compound as a brown oil. MS m/z: 242.1 (M+1).

Step 2: Ethyl 5-(cyclohexylmethyl)piperidine-3-carboxylate

A suspension of ethyl-5-benzylnicotinate (1.0 g, 4.1 mmol) and $PtO_2$ (800 mg) in EtOH (25 mL) and HCl (conc., 5.0 mL) was mixed in a Parr shaker under 40 psi of $H_2$ for 2 hours. The mixture was filtered through celite and concentrated to about 10% of the original volume. The resulting mixture was extracted with $CH_2Cl_2$ (3×30 mL). The organic layer was concentrated under reduced pressure to furnish the title compound (755 mg, 73% yield) as a white solid. MS m/z: 254.3 (M+1).

Step 3: ethyl 1-acetyl-5-(cyclohexylmethyl)piperidine-3-carboxylate

Triethylamine (410 μL, 2.9 mmol) was added to a solution of ethyl 5-(cyclohexylmethyl)piperidine-3-carboxylate (180 mg, 0.71 mmol) and acetyl chloride (120 mg, 1.4 mmol) in $CH_2Cl_2$ (10 mL). The reaction was maintained at room temperature for 30 min before being diluted with $CH_2Cl_2$ (20 mL) and poured into HCl (1 N, 20 mL). The layers were separated and the aqueous layer was extracted with $CH_2Cl_2$ (3×20 mL). The combined organic layers were sequentially washed with $H_2O$ (10 mL) and brine before being dried over $Na_2SO_4$. Concentration under reduced pressure and purification by silica gel chromatography (hexane→80% EtOAc/hexane) provided the title compound as a yellow oil. MS m/z: 296.1 (M+1).

Step 4: 1-acetyl-5-(cyclohexylmethyl)piperidine-3-carboxylic acid

LiOH (2 N, 500 μL) was added to a solution of ethyl 1-acetyl-5-(cyclohexylmethyl)piperidine-3-carboxylate (180 mL, 0.61 mmol) in MeOH (1 mL) and THF (5 mL). After being maintained for two hours, the reaction was poured into a mixture of $CH_2Cl_2$ (25 mL) and $H_2O$ (10 mL). The layers were separated and the aqueous layer was extracted with $CH_2Cl_2$ (10 mL). The aqueous layer was acidified to pH 1 with 1N HCl and extracted with $CH_2Cl_2$ (3×20 mL). The combined organic layers were sequentially washed with $H_2O$ (10 mL) and brine before being dried over $Na_2SO_4$. Concentration under reduced pressure provided the title compound as a colorless oil. MS m/z: 268.0 (M+1).

Step 5: 1-acetyl-5-(cyclohexylmethyl)-N-((2S,3R)-4-(6-ethyl-2,2-spirocyclopentylchroman-4-ylamino)-3-hydroxy-1-phenylbutan-2-yl)piperidine 1-acetyl-5-(cyclohexylmethyl)piperidine-3-carboxylic acid (25 mg, 0.09 mmol), (2R,3S)-3-amino-1-(6-ethyl-2,2-spirocyclopentylchroman-4-ylamino)-4-phenylbutan-2-ol.2 HCl (40 mg, 0.10 mmol) and HATU (38 mg, 0.10 mmol) were combined in a 5 mL round bottom flask. $CH_2Cl_2$ (1 mL) and DIPEA (65 μL, 0.37 mmol) were introduced and the resulting solution was stirred overnight. The reaction was diluted with EtOAc (10 mL) and poured in 10% aqueous $K_2CO_3$ (10 mL). The layers were separated and the aqueous layer was extracted with $CH_2Cl_2$ (3×30 mL). The combined organic layers were sequentially washed with $H_2O$ (10 mL) and brine before being dried over $Na_2SO_4$. The derived residue was purified by HPLC (Shimadzu, 15-85% MeCN) to provide the title compound as a white solid. MS m/z: 644.3(M+1).

Example 35

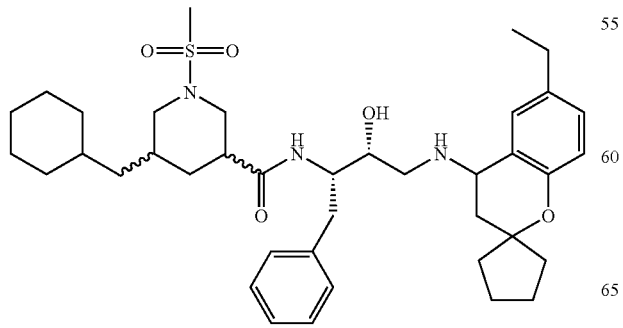

1-methylsulfonyl-5-(cyclohexylmethyl)-N-((2S,3R)-4-(6-ethyl-2,2-spirocyclopentylchroman-4-ylamino)-3-hydroxy-1-phenylbutan-2-yl)piperidine

Step 1: Ethyl 5-(cyclohexylmethyl)-1-(methylsulfonyl)piperidine-3-carboxylate Triethylamine (340 mL, 2.4 mmol) was added to a solution of ethyl 5-(cyclohexylmethyl)piperidine-3-carboxylate (155 mg, 0.60 mmol) and methanesulfonyl chloride (75 mL, 0.90 mmol) in $CH_2Cl_2$ (6 mL) cooled to 0° C. The reaction was maintained at this temperature for 15 min at which point the whole was allowed to warm to RT and stir for an additional 3 h. The reaction was diluted with $CH_2Cl_2$ (20 mL) and poured into HCl (1 N, 20 mL). The layers were separated and the aqueous layer was extracted with $CH_2Cl_2$ (3×20 mL). The combined organic layers were sequentially washed with $H_2O$ (10 mL) and brine before being dried over $Na_2SO_4$. Concentration under reduced pressure provided the title compound. MS m/z: 332.1 (M+1).

Step 2: 5-(cyclohexylmethyl)-1-(methylsulfonyl)piperidine-3-carboxylic acid The title compound was prepared using a procedure analogous to that described in Step 4 of Example 34. MS m/z: 304.0 (M+1).

Step 3: 1-methylsulfonyl-5-(cyclohexylmethyl)-N-((2S,3R)-4-(6-ethyl-2,2-spirocyclopentylchroman-4-ylamino)-3-hydroxy-1-phenylbutan-2-yl)piperidine The title compound was prepared using a procedure analogous to that described in Step 5 of Example 34. MS m/z: 680.3 (M+1).

Example 36

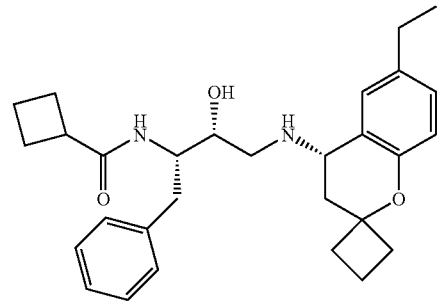

N-((2S,3R)-4-((S)-6-ethyl-2,2-spirocyclobutylchroman-4-ylamino)-3-hydroxy-1-phenylbutan-2-yl) cyclobutanecarboxamide (S)-6-Ethyl-2,2-spirocyclobutylchroman-4-amine-2 HCl (50 mg, 0.11 mmol), cyclobutyl carboxylic acid (11 mg, 0.11 mmol) and HATU (43 mg, 0.11 mmol) were combined in a 1 gram vial. DMF (1.5 mL) was introduced and the resulting solution was treated with DIPEA (100 mL, 0.56 mmol). The reaction was stirred for 1 hour before being quenched with HCl (6 N, ~100 mL). The mixture was purified by HPLC (Shimadzu, 15-85%) to provide the title compound as a white solid. MS m/z: 463.1 (M+1).

Example 37

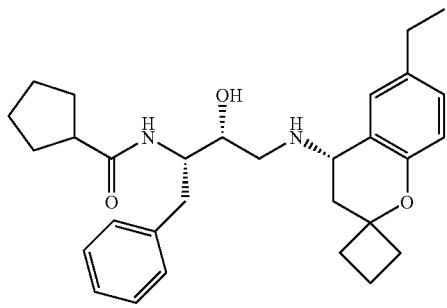

N-((2S,3R)-4-((S)$_{76}$-ethyl-2,2-spirocyclobutylchroman-4-ylamino)-3-hydroxy-1-phenylbutan-2-yl)cyclopentanecarboxamide The title compound was prepared using a procedure analogous to that described in Example 36. MS m/z: 477.2 (M+1).

Example 38

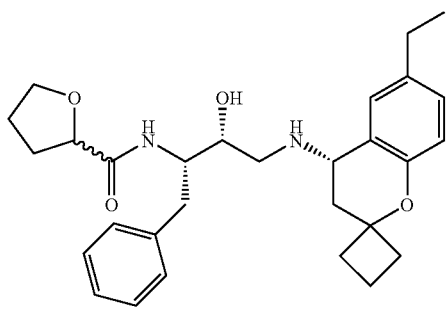

2-ethoxy-N-((2S,3R)-4-((S)-6-ethyl-2,2-spirocyclobutylchroman-4-ylamino)-3-hydroxy-1-phenylbutan-2-yl)butanamide The title compound was prepared using a procedure analogous to that described in Example 36. MS m/z: 495.3 (M+1)

Example 39

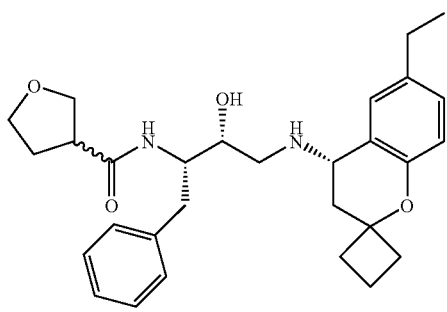

N-((2S,3R)-4-((S)-6-ethyl-2,2-spirocyclobutylchroman-4-ylamino)-3-hydroxy-1-phenylbutan-2-yl)-tetrahydrofuran-3-carboxamide The title compound was prepared using a procedure analogous to that described in Example 36. MS m/z: 495.4 (M+1).

Example 40

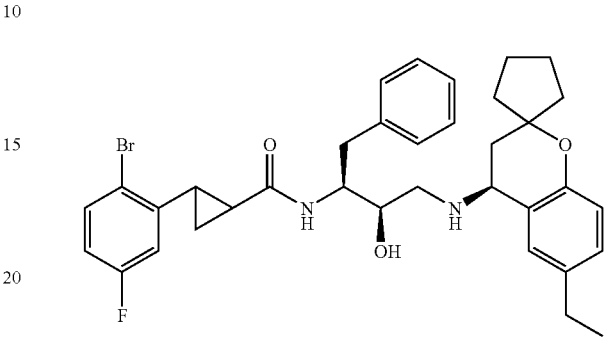

2-(2-Bromo-5-fluorophenyl)-N-((2S,3R)-4-((S)-6-ethyl-2,2-spirocyclopentylchroman-4-ylamino)-3-hydroxy-1-phenylbutan-2-yl)cyclopropanecarboxamide Step 1: (E)-3-(2-Bromo-5-fluorophenyl)-N-methoxy-N-methylacrylamide Oxalyl chloride (2.0 M in dichloromethane, 2.08 mL, 4.16 mmol) was added to a suspension of (E)-3-(2-bromo-5-fluorophenyl)acrylic acid (678 mg, 2.77 mmol) in dichloromethane (8 mL). N,N-dimethylformamide (11 □L, 0.14 mmol) was added, and the resulting mixture was stirred at 25° C. for 1 h. The reaction mixture was concentrated in vacuo, and 4-dimethylaminopyridine (3 mg, 0.025 mmol), N,O-dimethylhydroxylamine hydrochloride (270 mg, 2.77 mmol), Hunig's base (1.44 mL, 8.28 mmol), and dichloromethane (8 ml) were added. The mixture was stirred at 25° C. for 10 h, then transferred to a separatory funnel with dichloromethane (100 mL), and the organic layer was extracted sequentially with water (7 mL), 0.5 M sodium carbonate (7 mL), 1 M hydrochloric acid (7 mL), and half-saturated brine (7 mL), and then dried over sodium sulfate and concentrated. Purification of the concentrate by flash column chromatography (33% to 40% EtOAc/hexane) afforded the title compound as a white solid. MS m/z: 288 & 290 (M+1).

Step 2: 2-(2-Bromo-5-fluorophenyl)-N-methoxy-N-methylcyclopropane-carboxamide

Sodium hydride (60%, 122 mg, 3.05 mmol, Aldrich) was added to a suspension of trimethylsulfoxonium iodide (671 mg, 3.05 mmol, Aldrich) in DMSO (6 mL). The mixture was stirred at 25° C. for 30 min, and (E)-3-(2-bromo-5-fluorophenyl)-N-methoxy-N-methylacrylamide was added as a solution in DMSO (3 mL). The mixture was stirred at 25° C. for 12 h, then transferred to a separatory funnel with H$_2$O (40 mL), and the title compound was extracted using 75% ether/hexane (3×40 mL). The organic layer was dried over sodium sulfate and concentrated. Purification by flash column chromatography (33% EtOAc/hexane) afforded the title compound as a colorless oil. MS m/z: 302 and 304 (M+1).

Step 3: 2-(2-Bromo-5-fluorophenyl)cyclopropanecarboxylic acid

A solution of 2-(2-bromo-5-fluorophenyl)-N-methoxy-N-methylcyclopropane-carboxamide (304 mg, 1.0 mmol), 10 M potassium hydroxide (3.5 mL, 35 mmol), and dioxane (2.5 mL) was heated at 130° C. in a sealed tube for 19 h. Upon cooling to room temperature, the reaction mixture was acidified with 3 M HCl (20 mL), and the product was extracted with 5% methanol/dichloromethane (3×30 mL). The organic fractions were combined, dried over sodium sulfate, and concentrated to afford the title compound as a white solid. MS m/z: 259 & 261 (M+1).

Step 4: Synthesis of 2-(2-Bromo-5-fluorophenyl)-N-((2S,3R)-4-((S)-6-ethyl-2,2-spirocyclopentylchroman-4-ylamino)-3-hydroxy-1-phenylbutan-2-yl)cyclopropanecarboxamide The title compound was prepared using a procedure analogous to that described in Example 35, wherein 2-(2-bromo-5-fluorophenyl)cyclopropanecarboxylic acid (Step 3) was coupled with (2R,3S)-3-amino-1-((S)-6-ethyl-2,2-spirocyclopentylchroman-4-ylamino)-4-phenylbutan-2-ol to afford the desired product (1:1 mixture of cyclopropyl epimers) as a yellow film. MS m/z: 635 & 637 (M+1).

Example 41

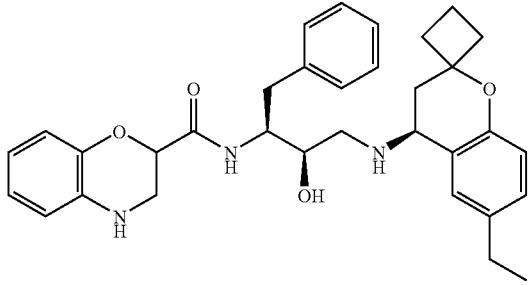

N-((2S,3R)-4-((S)-6-Ethyl-2-spirocyclobutyl-chroman-4-ylamino)-3-hydroxy-1-phenylbutan-2-yl)-3,4-dihydro-2H-benzo[b][1,4]oxazine-2-carboxamide The title compound may be obtained using a procedure analogous to that described immediately below, used to synthesize N-((2S,3R)-4-((S)-6-Ethyl-chroman-4-ylamino)-3-hydroxy-1-phenylbutan-2-yl)-3,4-dihydro-2H-benzo[b][1,4]oxazine-2-carboxamide.

Step 1: (±)-Ethyl 3,4-dihydro-2H-benzo[b][1,4]oxazine-2-carboxylate

To a solution of ethyl 2,3-dibromopropionate (8.05 g, 31.0 mmol, Aldrich) in acetone (35 mL) was added o-aminophenol (3.38 g. 31.0 mmol) and potassium carbonate (5.1 g, 36.9 mmol). The reaction mixture was stirred at reflux under a water condenser for 18 h. Upon cooling to room temperature, the reaction was concentrated in vacuo, and the residue was taken up in water (50 mL) and the product was extracted using EtOAc (3×75 mL). The organic fractions were combined, washed with saturated brine (15 mL), dried over sodium sulfate, and concentrated. Purification of the product by flash column chromatography (30% EtOAc/hexane) afforded the title compound as a yellow oil. MS m/z: 208 (M+1).

Step 2: (±)-Lithium 3,4-dihydro-2H-benzo[b][1,4]oxazine-2-carboxylate

A solution of lithium hydroxide monohydrate (1.43 g, 34.2 mmol) in water (50 mL) was added to a solution of ethyl 3,4-dihydro-2H-benzo[b][1,4]oxazine-2-carboxylate (3.55 g, 17.1 mmol) in dioxane (50 mL), and the mixture was stirred at 25° C. for 21 h. The reaction mixture was concentrated to afford the title compound. MS m/z: 180 (M+1 of acid).

Step 3: N-((2S,3R)-4-((S)-6-Ethylchroman-4-ylamino)-3-hydroxy-1-phenylbutan-2-yl)-3,4-dihydro-2H-benzo[b][1,4]oxazine-2-carboxamide The title compound was prepared using a procedure analogous to that described in Example 35, wherein (±)-lithium 3,4-dihydro-2H-benzo[b][1,4]oxazine-2-carboxylate was coupled with (2R,3S)-3-amino-1-((S)-6-ethylchroman-4-ylamino)-4-phenylbutan-2-ol to afford the title compound (a 1:1 mixture of epimers at the benzooxazine stereocenter) as a white solid. MS m/z: 502 (M+1).

Example 42

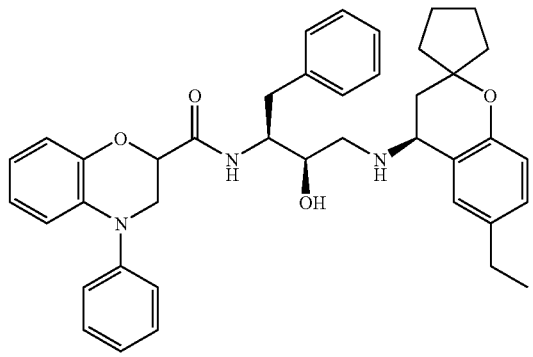

Synthesis of N-((2S,3R)-4-((S)-6-ethyl-2,2-spirocyclopentylchroman-4-ylamino)-3-hydroxy-1-phenylbutan-2-yl)-4-phenyl-3,4-dihydro-2H-benzo[b][1,4]oxazine-2-carboxamide

Step 1: (±)-Ethyl 4-phenyl-3,4-dihydro-2H-benzo[b][1,4]oxazine-2-carboxylate Tris(dibenzylideneacetone)dipalladium (0) (4.3 mg, 0.0046 mmol), xantphos (8.2 mg, 0.014 mmol), and bromobenzene (40 μL, 0.381 mmol) were added to a solution of (±)-ethyl 3,4-dihydro-2H-benzo[b][1,4]oxazine-2-carboxylate (65 mg, 0.31 mmol) in dioxane (2.5 mL). The solids were allowed to dissolve, and cesium carbonate (143 mg, 0.44 mmol) was added, and the suspension was stirred at 100° C. for 24 h. The mixture was cooled to ambient temperature, diluted with water (20 mL), and the product was extracted with 67% EtOAc/hexane (3×25 mL). The organic layers were combined, dried over sodium sulfate, and concentrated. Purification of the crude concentrate by flash column chromatography using 15% EtOAc/hexane afforded the title compound. MS m/z: 284 (M+1).

Step 2: (±)-Lithium 4-phenyl-3,4-dihydro-2H-benzo[b][1,4]oxazine-2-carboxylate (±)-Ethyl 4-phenyl-3,4-dihydro-2H-benzo[b][1,4]oxazine-2-carboxylate was converted to the title compound using the procedure described in Step 2 of Example 41. MS m/z: 256 (M+1 of acid).

Step 3: N-((2S,3R)-4-((S)-6-ethyl-2,2-spirocyclopentylchroman-4-ylamino)-3-hydroxy-1-phenylbutan-2-yl)-4-phenyl-3,4-dihydro-2H-benzo[b][1,4]oxazine-2-carboxamide The title compound was prepared using a procedure analogous to that described in Example 35, wherein (±)-lithium 4-phenyl-3,4-dihydro-2H-benzo[b][1,4]oxazine-2-carboxylate was coupled with (2R,3S)-3-amino-1-((S)-6-ethyl-2,2-spirocyclopentylchroman-4-ylamino)-4-phenylbutan-2-ol to afford the title compound (as a 1:1 mixture of epimers at the benzooxazine stereocenter) as a colorless film. MS m/z: 632 (M+1).

Example 43

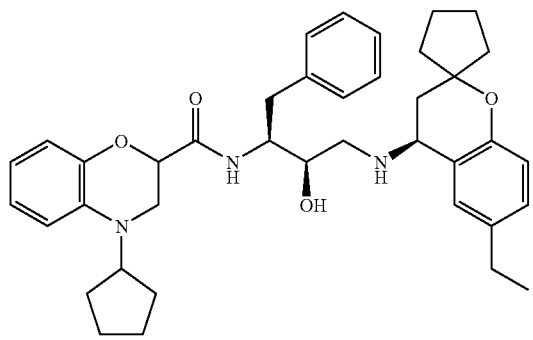

4-Cyclopentyl-N-((2S,3R)-4-((S)-6-ethyl-2,2-spirocyclopentylchroman-4-ylamino)-3-hydroxy-1-phenylbutan-2-yl)-3,4-dihydro-2H-benzo[b][1,4]oxazine-2-carboxamide

Step 1: (±)-Ethyl 4-cyclopentyl-3,4-dihydro-2H-benzo[b][1,4]oxazine-2-carboxylate Cyclopentanone (83 □L, 0.94 mmol), acetic acid (54 □L, 0.94 mmol), and magnesium sulfate (113 mg, 0.94 mmol) were added to a solution of (±)-3,4-dihydro-2H-benzo[b][1,4]oxazine-2-carboxylic acid (Example 3a, 65 mg, 0.31 mmol) in dichloroethane (1.25 mL). Sodium triacetoxyborohydride (100 mg, 0.47 mmol) was added, followed by dichloroethane (1.25 mL), and the suspension was stirred at 25° C. for 48 h. The reaction mixture was quenched with half-saturated sodium bicarbonate, and the product was extracted using 67% EtOAc/hexane (3×25 mL). The combined organic fractions were dried over sodium sulfate and concentrated. Purification of the product by flash column chromatography (10% EtOAc/hexane) afforded the title compound as an oil. MS m/z: 276 (M+1).

Step 2: (±)-Lithium 4-cyclopentyl-3,4-dihydro-2H-benzo[b][1,4]oxazine-2-carboxylate (±)-Ethyl 4-cyclopentyl-3,4-dihydro-2H-benzo[b][1,4]oxazine-2-carboxylate was converted to the title product using the procedure described in step 2 of Example 41. MS m/z: 248 (M+1 of acid).

Step 3: 4-Cyclopentyl-N-((2S,3R)-4-((S)-6-ethyl-2,2-spirocyclopentylchroman-4-ylamino)-3-hydroxy-1-phenylbutan-2-yl)-3,4-dihydro-2H-benzo[b][1,4]oxazine-2-carboxamide The title compound was prepared using a procedure analogous to that described in Example 35, wherein (±)-lithium 4-cyclopentyl-3,4-dihydro-2H-benzo[b][1,4]oxazine-2-carboxylate was coupled with (2R,3S)-3-amino-1-((S)-6-ethyl-2,2-spirocyclopentylchroman-4-ylamino)-4-phenylbutan-2-ol to afford the title compound (as a 1:1 mixture of epimers at the benzooxazine stereocenter) as a white solid. MS m/z: 624 (M+1).

Example 44

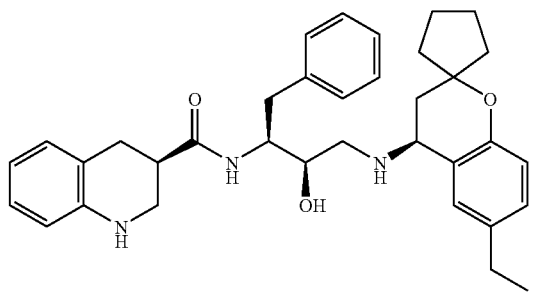

(R)-N-((2S,3R)-4-((S)-6-Ethyl-2,2-spirocyclopentyl-chroman-4-ylamino)-3-hydroxy-1-phenylbutan-2-yl)-1,2,3,4-tetrahydroquinoline-3-carboxamide

Step 1: Potassium quinoline-3-carboxylate

In a sealable tube, quinoline-3-carbonitrile (308 mg, 2.0 mmol) was suspended in 1 M potassium hydroxide (3 mL), and the reaction vessel was sealed and heated at 120° C. for 24 h. The mixture was cooled to ambient temperature, and concentrated. The crude material was used directly in the next step. MS m/z: 174 (M+1 of acid).

Step 2: Ethyl quinoline-3-carboxylate

In a sealable tube, concentrated sulfuric acid (32 □L) was added to a solution of potassium quinoline-3-carboxylate in ethanol (1 mL). The flask was sealed and heated at 85° C. for 24 h. The mixture was cooled to ambient temperature, basified with 1 M sodium carbonate (10 mL), and the product was extracted with dichloromethane (3×15 mL). The organic fractions were dried over sodium sulfate and concentrated. Purification of the product by flash column chromatography (10% to 20% EtOAc/hexane) afforded the title compound (292 mg, 1.45 mmol). MS m/z: 202 (M+1).

Step 3: (±)-Ethyl 1,2,3,4-tetrahydroquinoline-3-carboxylate

Borane-pyridine complex (8 M, 292 mL, 2.34 mmol) was added to a solution of Ethyl quinoline-3-carboxylate (235 mg, 1.17 mmol) in acetic acid (10 mL). The solution was stirred at 25° C. for 20 h. The reaction mixture was concentrated in vacuo, basified with 1 M sodium carbonate (30 mL), and the product was extracted with dichloromethane (3×35 mL). The organic layers were dried over sodium sulfate and concentrated. Purification of the product by flash column chromatography (10% to 20% EtOAc/hexane) afforded the title compound (239 mg, 1.15 mmol). MS m/z: 206 (M+1).

Step 4: (±)-Lithium 1,2,3,4-tetrahydroquinoline-3-carboxylate (±)-Ethyl 1,2,3,4-tetrahydroquinoline-3-carboxylate was converted to the title product using the general procedure described in step 2 of Example 41. MS m/z: 178 (M+1 of acid).

Step 5: (R)-N-((2S,3R)-4-((S)-6-Ethyl-2,2-spirocyclopentylchroman-4-ylamino)-3-hydroxy-1-phenylbutan-2-yl)-1,2,3,4-tetrahydroquinoline-3-carboxamide The title compound, an off-white solid, was prepared using a procedure analogous to that described in Example 35. MS m/z: 554 (M+1).

Example 45

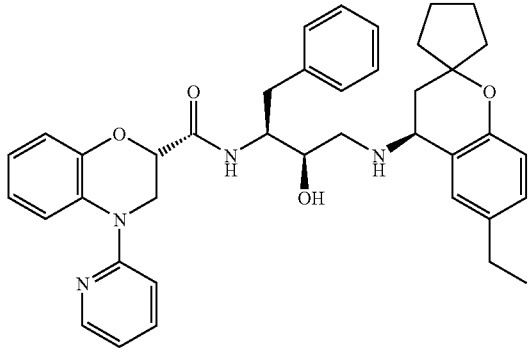

(S)-N-((2S,3R)-4-((S)-6-Ethyl-2,2-spirocyclopentylchroman-4-ylamino)-3-hydroxy-1-phenylbutan-2-yl)-4-(pyridin-2-yl)-3,4-dihydro-2H-benzo[b][1,4]oxazine-2-carboxamide Step 1: (±)-Ethyl 4-(pyridin-2-yl)-3,4-dihydro-2H-benzo[b][1,4]oxazine-2-carboxylate In a sealable tube, tris(dibenzylideneacetone) dipalladium (0) (5.2 mg, 0.0056 mmol), (S)-BINAP (10.7 mg, 0.017 mmol), cesium carbonate (132 mg, 0.41 mmol), 2-bromopyridine (33 □L, 0.35 mmol), and ethyl 3,4-dihydro-2H-benzo[b][1,4]oxazine-2-carboxylate (Example 3a, 60 mg, 0.29 mmol) were dissolved in dioxane (2 mL). The reaction vessel was sealed and the suspension was heated at 100° C. for 20 h. The reaction mixture was cooled to ambient temperature, diluted with water (15 mL), and the product was extracted with dichloromethane (3×20 mL). The organic fractions were dried over sodium sulfate and concentrated. Purification of the product by flash column chromatography (15% to 25% EtOAc/hexane) afforded the title compound (46 mg, 0.16 mmol). MS m/z: 285 (M+1).

Step 2: (±)-Lithium 4-(pyridin-2-yl)-3,4-dihydro-2H-benzo[b][1,4]oxazine-2-carboxylate (±)-Ethyl 4-(pyridin-2-yl)-3,4-dihydro-2H-benzo[b][1,4]oxazine-2-carboxylate was converted to the title compound using the general procedure described in Example 41. MS m/z: 257 (M+1 of acid).

Step 3: (S)-N-((2S,3R)-4-((S)-6-Ethyl-2,2-spirocyclopentylchroman-4-ylamino)-3-hydroxy-1-phenylbutan-2-yl)-4-(pyridin-2-yl)-3,4-dihydro-2H-benzo[b][1,4]oxazine-2-carboxamide The title compound was prepared using a procedure analogous to that described in Example 42, and obtained as a white solid. MS m/z: 633 (M+1).

Example 46

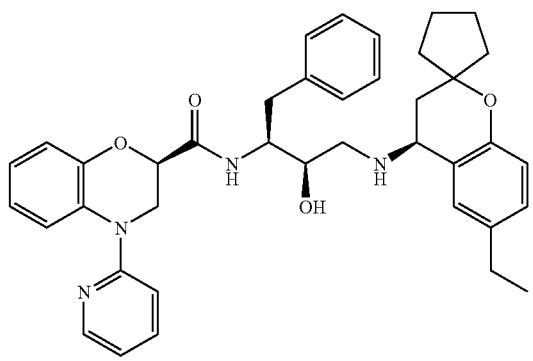

(R)-N-((2S,3R)-4-((S)-6-ethyl-2,2-spirocyclopentylchroman-4-ylamino)-3-hydroxy-1-phenylbutan-2-yl)-4-(pyridin-2-yl)-3,4-dihydro-2H-benzo[b][1,4]oxazine-2-carboxamide The title compound was isolated, from the same crude reaction mixture of Step 3 in Example 45, as a white solid. MS m/z: 633 (M+1).

Example 47

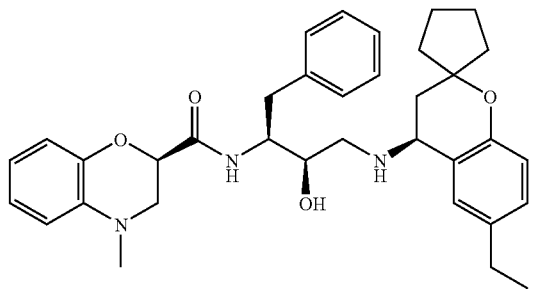

(R)-N-((2S,3R)-4-((S)-6-ethyl-2,2-spirocyclopentyl-chroman-4-ylamino)-3-hydroxy-1-phenylbutan-2-yl)-4-methyl-3,4-dihydro-2H-benzo[b][1,4]oxazine-2-carboxamide Step 1: (±)-Ethyl 4-methyl-3,4-dihydro-2H-benzo[b][1,4]oxazine-2-carboxylate In a sealable vessel, potassium carbonate (56 mg, 0.41 mmol) was added to a solution of (±)-ethyl 3,4-dihydro-2H-benzo[b][1,4]oxazine-2-carboxylate (60 mg, 0.29 mmol) and iodomethane (22 □L, 0.35 mmol) in acetone (2 mL). The vessel was sealed and the reaction mixture was stirred at 60° C. for 24 h. The mixture was cooled to ambient temperature, diluted with dichloromethane (60 mL), and the organic layer was extracted with water (10 mL) and half-saturated brine (10 mL). The organic layer was dried over sodium sulfate and concentrated. Purification of the concentrate by flash column chromatography (5% to 10% EtOAc/hexane) afforded the title compound (43 mg, 0.19 mmol). MS m/z: 222 (M+1).

Step 2: (±)-Lithium 4-methyl-3,4-dihydro-2H-benzo[b][1,4]oxazine-2-carboxylate (±)-Ethyl 4-methyl-3,4-dihydro-2H-benzo[b][1,4]oxazine-2-carboxylate was converted to the title compound using the general procedure described in Example 41. MS m/z: 194 (M+1 of acid).

Step 3: (R)-N-((2S,3R)-4-((S)-6-ethyl-2,2-spirocyclopentylchroman-4-ylamino)-3-hydroxy-1-phenylbutan-2-yl)-4-methyl-3,4-dihydro-2H-benzo[b][1,4]oxazine-2-carboxamide The title compound was prepared using a procedure analogous to that described in Example 42 and obtained as a white solid. MS m/z: 570 (M+1).

Example 48

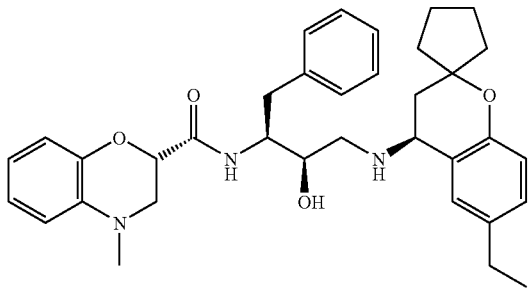

(S)-N-((2S,3R)-4-((S)-6-ethyl-2,2-spirocyclopentyl-chroman-4-ylamino)-3-hydroxy-1-phenylbutan-2-yl)-4-methyl-3,4-dihydro-2H-benzo[b][1,4]oxazine-2-carboxamide The title compound was isolated from the same crude reaction mixture described in Step 3 of Example 47, as a white solid. MS m/z: 570 (M+1).

Example 49

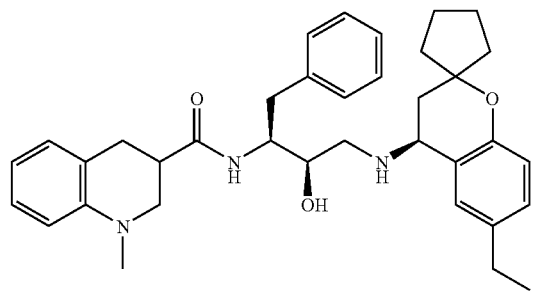

N-((2S,3R)-4-((S)-6-ethyl-2,2-spirocyclopentylchroman-4-ylamino)-3-hydroxy-1-phenylbutan-2-yl)-1-methyl-1,2,3,4-tetrahydroquinoline-3-carboxamide The title compound was obtained, as a 1:1 mixture of epimers at the tetrahydroquinoline stereocenter, as a white solid, in a manner analogous to the general procedure described in Example 47. MS m/z: 568 (M+1).

Example 50

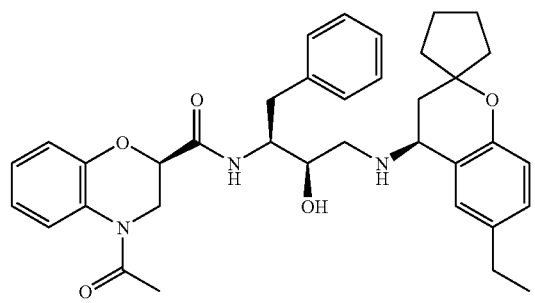

(R)-4-acetyl-N-((2S,3R)-4-((S)-6-ethyl-2,2-spirocyclopentylchroman-4-ylamino)-3-hydroxy-1-phenylbutan-2-yl)-3,4-dihydro-2H-benzo[b][1,4]oxazine-2-carboxamide Step 1: (±)-Ethyl 4-acetyl-3,4-dihydro-2H-benzo[b][1,4]oxazine-2-carboxylate Acetyl chloride (23 □L, 0.33 mmol) was added to a solution of (±)-ethyl 3,4-dihydro-2H-benzo[b][1,4]oxazine-2-carboxylate (Example 3a, 55 mg, 0.27 mmol), DMAP (1.6 mg, 0.013 mmol), and Hunig's base (63 □L, 0.36 mmol) in dichloromethane (2 mL). The solution was stirred at 25° C. for 24 h, then the reaction mixture was diluted with dichloromethane (60 mL) and the mixture was extracted with 0.1 M sodium carbonate (7 mL) and half-saturated brine (7 mL). The organic layer was dried over sodium sulfate and concentrated. Purification of the product by flash column chromatography (40% EtOAc/hexane) afforded the title compound (46 mg, 0.18 mmol). MS m/z: 250 (M+1).

Step 2: (±)-Lithium 4-acetyl-3,4-dihydro-2H-benzo[b][1,4]oxazine-2-carboxylate (±)-Ethyl 4-acetyl-3,4-dihydro-2H-benzo[b][1,4]oxazine-2-carboxylate was converted to the title compound using the general procedure described in Example 41. MS m/z: 222 (M+1 of acid).

Step 3: (R)-4-Acetyl-N-((2S,3R)-4-((S)-6-ethyl-2,2-spirocyclopentylchroman-4-ylamino)-3-hydroxy-1-phenylbutan-2-yl)-3,4-dihydro-2H-benzo[b][1,4]oxazine-2-carboxamide The title compound, a white solid, was prepared using a procedure analogous to that described in Example 42. MS m/z: 598 (M+1).

Example 51

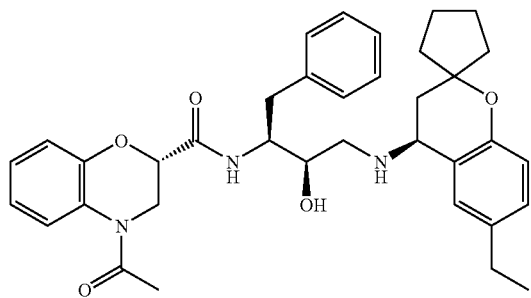

(S)-4-acetyl-N-((2S,3R)-4-((S)-6-ethyl-2,2-spirocyclopentylchroman-4-ylamino)-3-hydroxy-1-phenylbutan-2-yl)-3,4-dihydro-2H-benzo[b][1,4]oxazine-2-carboxamide The title compound was prepared in a manner analogous to that described in Example 50, and obtained as a white solid. MS m/z: 598 (M+1).

Example 52

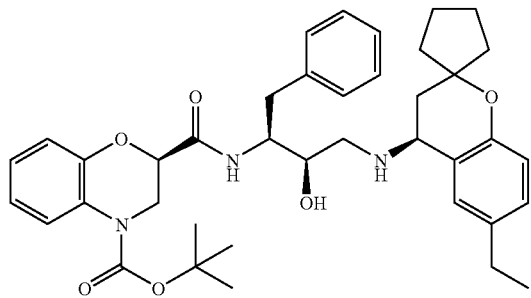

(R)-tert-Butyl 2-(((2S,3R)-4-((S)-6-ethyl-2,2-spirocyclopentylchroman-4-ylamino)-3-hydroxy-1-phenylbutan-2-yl)carbamoyl)-2,3-dihydrobenzo[b][1,4]oxazine-4-carboxylate

Step 1: (±)-4-tert-Butyl 2-ethyl 2,3-dihydrobenzo[b][1,4]oxazine-2,4-dicarboxylate DMAP (3.2 mg, 0.026 mmol), Hunig's base (150 μL, 0.86 mmol), and Boc$_2$O (154 mg, 0.70 mmol) were added to a solution of (±)-Ethyl 3,4-dihydro-2H-benzo[b][1,4]oxazine-2-carboxylate (112 mg, 0.54 mmol) in dichloromethane (4 mL). The solution was stirred at 25° C. for 24 h. The reaction mixture was dissolved in dichloromethane (60 mL), and the organic layer was extracted with 0.5 M sodium carbonate (7 mL) and half-saturated brine (7 mL), dried over sodium sulfate, and concentrated. Purification of the product by flash column chromatography (10% to 20% EtOAc/hexane) afforded the title compound (31 mg, 0.10 mmol). MS m/z: 252 (M+1 of carbamic acid).

Step 2: (±)-Lithium 4-(tert-butoxycarbonyl)-3,4-dihydro-2H-benzo[b][1,4]oxazine-2-carboxylate (±)-4-tert-Butyl 2-ethyl 2,3-dihydrobenzo[b][1,4]oxazine-2,4-dicarboxylate was converted to the title compound using the general procedure described in Example 41. MS m/z: 224 (M+1 of carbamic acid).

Step 3: (R)-tert-butyl 2-(((2S,3R)-4-((S)-6-ethyl-2,2-spirocyclopentylchroman-4-ylamino)-3-hydroxy-1-phenylbutan-2-yl)carbamoyl)-2,3-dihydrobenzo[b][1,4]oxazine-4-carboxylate The title compound, a white solid, was prepared using a procedure analogous to that described in Example 42. MS m/z: 656 (M+1).

Example 53

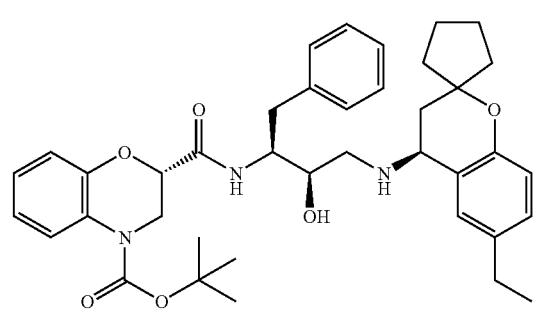

(S)-tert-butyl 2-(((2S,3R)-4-((S)-6-ethyl-2,2-spirocyclopentylchroman-4-ylamino)-3-hydroxy-1-phenylbutan-2-yl)carbamoyl)-2,3-dihydrobenzo[b][1,4]oxazine-4-carboxylate The title compound was isolated from the same reaction mixture described in Example 52, as a white solid. MS m/z: 656 (M+1).

Example 54

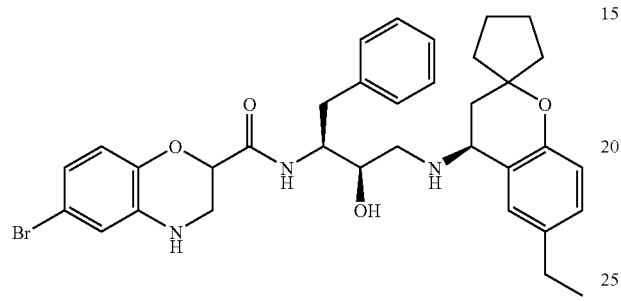

6-bromo-N-((2S,3R)-4-((S)-6-ethyl-2,2-spirocyclopentylchroman-4-ylamino)-3-hydroxy-1-phenylbutan-2-yl)-3,4-dihydro-2H-benzo[b][1,4]oxazine-2-carboxamide The title compound was prepared using a procedure analogous to that described in Example 42, and was obtained as a 1:1 mixture of epimers at the benzooxazine stereocenter, as a white solid. MS m/z: 634 & 636 (M+1).

Example 55

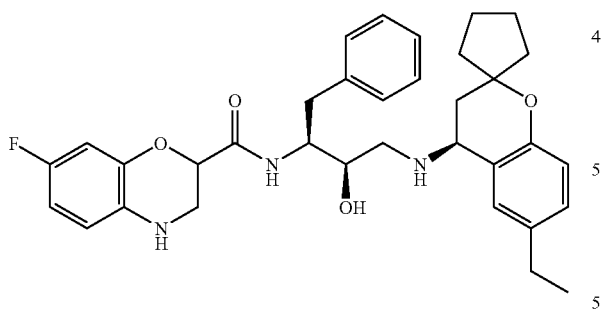

N-((2S,3R)-4-((S)-6-ethyl-2,2-spirocyclopentylchroman-4-ylamino)-3-hydroxy-1-phenylbutan-2-yl)-7-fluoro-3,4-dihydro-2H-benzo[b][1,4]oxazine-2-carboxamide The title compound was prepared using a procedure analogous to that described in Example 42, yielding the title compound as a 1:1 mixture of epimers at the benzooxazine stereocenter, as a white solid. MS m/z: 574 (M+1).

Example 56

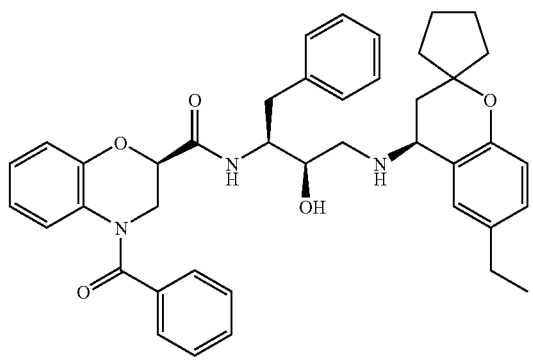

(R)-4-benzoyl-N-((2S,3R)-4-((S)-6-ethyl-2,2-spirocyclopentylchroman-4-ylamino)-3-hydroxy-1-phenylbutan-2-yl)-3,4-dihydro-2H-benzo[b][1,4]oxazine-2-carboxamide The title compound, a white solid, was prepared using a procedure analogous to that described in Example 42. MS m/z: 660 (M+1).

Example 57

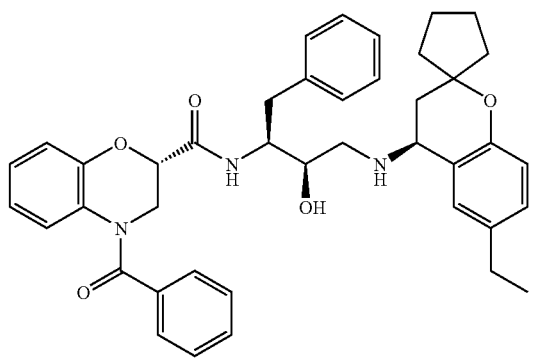

(S)-4-benzoyl-N-((2S,3R)-4-((S)-6-ethyl-2,2-spirocyclopentylchroman-4-ylamino)-3-hydroxy-1-phenylbutan-2-yl)-3,4-dihydro-2H-benzo[b][1,4]oxazine-2-carboxamide The title compound was isolated from the same reaction mixture described in Example 56, as a white solid. MS m/z: 660 (M+1).

Example 58

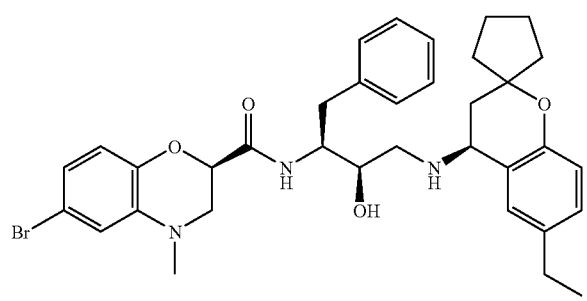

(R)-6-Bromo-N-((2S,3R)-4-((S)-6-ethyl-2,2-spirocyclopentylchroman-4-ylamino)-3-hydroxy-1-phenylbutan-2-yl)-4-methyl-3,4-dihydro-2H-benzo[b][1,4]oxazine-2-carboxamide (1127042)

Step 1: (±)-Ethyl 6-bromo-3,4-dihydro-2H-benzo[b][1,4]oxazine-2-carboxylate

2-Amino-4-bromophenol was converted to the title compound using the procedure described in Example 41. MS m/z: 286 & 288 (M+1).

Step 2: (±)-Ethyl 6-bromo-4-methyl-3,4-dihydro-2H-benzo[b][1,4]oxazine-2-carboxylate (±)-Ethyl 6-bromo-3,4-dihydro-2H-benzo[b][1,4]oxazine-2-carboxylate was converted to the title compound using the general procedure described in Example 41. MS m/z: 300 & 302 (M+1).

Step 3: (±)-Lithium 6-bromo-4-methyl-3,4-dihydro-2H-benzo[b][1,4]oxazine-2-carboxylate (±)-Ethyl 6-bromo-4-methyl-3,4-dihydro-2H-benzo[b][1,4]oxazine-2-carboxylate was converted to the title compound using the general procedure described in Example 41. MS m/z: 272 & 274 (M+1 of acid).

Step 4: (R)-6-Bromo-N-((2S,3R)-4-((S)-6-ethyl-2,2-spirocyclopentylchroman-4-ylamino)-3-hydroxy-1-phenylbutan-2-yl)-4-methyl-3,4-dihydro-2H-benzo[b][1,4]oxazine-2-carboxamide The title compound, a white solid, was prepared using a procedure analogous to that described in Example 35. MS m/z: 648 & 650 (M+1).

Example 59

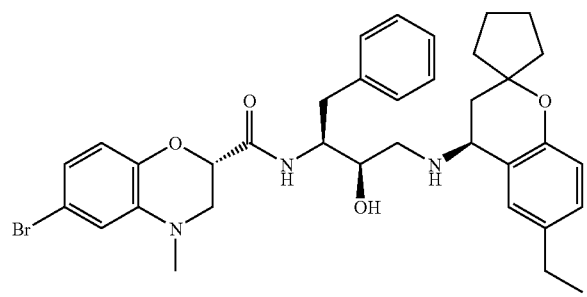

(S)-6-Bromo-N-((2S,3R)-4-((S)-6-ethyl-2,2-spirocyclopentylchroman-4-ylamino)-3-hydroxy-1-phenylbutan-2-yl)-4-methyl-3,4-dihydro-2H-benzo[b][1,4]oxazine-2-carboxamide (1127187)

The title compound was isolated from the same reaction mixture described in Example 58, as a white solid. MS m/z: 648 & 650 (M+1).

Example 60

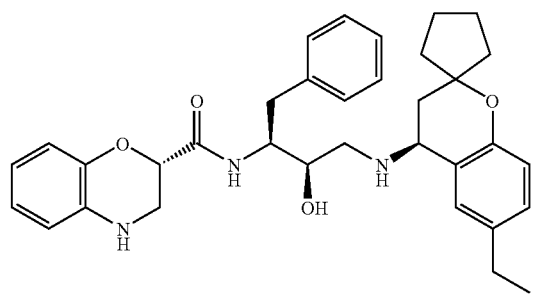

(S)-N-((2S,3R)-4-((S)-6-Ethyl-2,2-spirocyclopentylchroman-4-ylamino)-3-hydroxy-1-phenylbutan-2-yl)-3,4-dihydro-2H-benzo[b][1,4]oxazine-2-carboxamide The title compound was prepared using a procedure analogous to that described in Example 35, and was obtained as a 1:1 mixture of epimers at the benzooxazine stereocenter, as a white solid. MS m/z: 556 (M+1).

Example 61

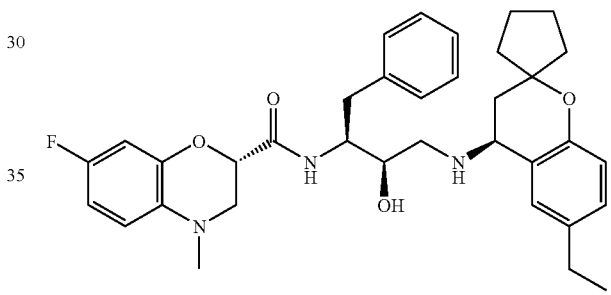

(S)-N-((2S,3R)-4-((S)-6-Ethyl-2,2-spirocyclopentylchroman-4-ylamino)-3-hydroxy-1-phenylbutan-2-yl)-7-fluoro-4-methyl-3,4-dihydro-2H-benzo[b][1,4]oxazine-2-carboxamide The title compound, a white solid, was obtained using the same general procedure described in Examples 41 and 55, as a 1:1 mixture of epimers at the benzooxazine ring. MS m/z: 588 (M+1).

Example 62

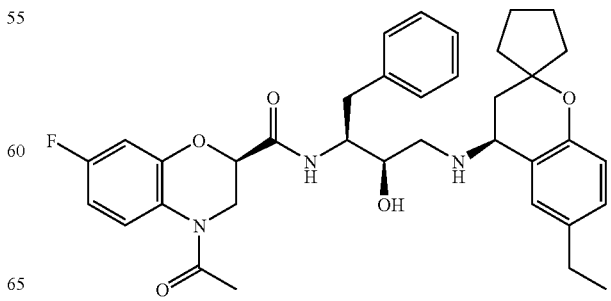

(R)-4-Acetyl-N-((2S,3R)-4-((S)-6-ethyl-2,2-spirocyclopentylchroman-4-ylamino)-3-hydroxy-1-phenylbutan-2-yl)-7-fluoro-3,4-dihydro-2H-benzo[b][1,4]oxazine-2-carboxamide Step 1: (±)-Ethyl 7-fluoro-3,4-dihydro-2H-benzo[b][1,4]oxazine-2-carboxylate 2-Amino-5-fluorophenol was converted to the title compound using the general procedure described in Example 41. MS m/z: 226 (M+1).

Step 2: (±)-Ethyl 4-acetyl-7-fluoro-3,4-dihydro-2H-benzo[b][1,4]oxazine-2-carboxylate (±)-Ethyl 7-fluoro-3,4-dihydro-2H-benzo[b][1,4]oxazine-2-carboxylate was converted to the title compound using the general procedure described in Example 47. MS m/z: 268 (M+1).

Step 3: (±)-Lithium 4-acetyl-7-fluoro-3,4-dihydro-2H-benzo[b][1,4]oxazine-2-carboxylate (±)-Ethyl 4-acetyl-7-fluoro-3,4-dihydro-2H-benzo[b][1,4]oxazine-2-carboxylate was converted to the title compound using the general procedure described in Example 41. MS m/z: 240 (M+1 of acid).

Step 4: (R)-4-acetyl-N-((2S,3R)-4-((S)-6-ethyl-2,2-spirocyclopentylchroman-4-ylamino)-3-hydroxy-1-phenylbutan-2-yl)-7-fluoro-3,4-dihydro-2H-benzo[b][1,4]oxazine-2-carboxamide The title compound was prepared using a procedure analogous to that described in Example 34, and obtained as a white solid. MS m/z: 616 (M+1).

Example 63

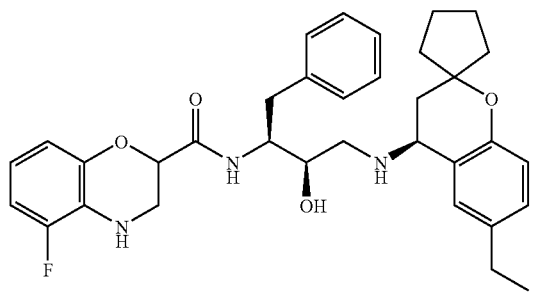

N-((2S,3R)-4-((S)-6-ethyl-2,2-spirocyclopentylchroman-4-ylamino)-3-hydroxy-1-phenylbutan-2-yl)-5-fluoro-3,4-dihydro-2H-benzo[b][1,4]oxazine-2-carboxamide The title compound, a white solid, was prepared using a procedure analogous to that described in Example 62, and obtained as a 1:1 mixture of epimers at the benzooxazine stereocenter. MS m/z: 574 (M+1).

The following compounds in Tables 1 and 2 (Examples 64-104) and the specific Examples described thereafter are additional representative examples of Formulas I-III, as provided by the present invention.

TABLE 1

| Ex. No. | $R^1$ | B | $R^3$ and $R^4$ | $X^1$ | S |
|---|---|---|---|---|---|
| 64 | 1-morpholinyl | phenyl-O—$CH_2$— | H | NH | cyclobutyl |
| 65 | 1-piperazinyl | phenyl-S—$CH_2$— | H | S | cyclobutyl |
| 66 | 1-piperidinyl | phenyl-NH—$CH_2$— | H | O | cyclobutyl |
| 67 | 3-oxo-1-pyrrolidinyl | phenyl-$CH_2$— | H | NH | cyclopentyl |
| 68 | 1-morpholinyl | phenyl-O—$CH_2$— | H | S | cyclopentyl |
| 69 | 1-piperazinyl | phenyl-S—$CH_2$— | H | O | cyclopentyl |
| 70 | oxo-pyrrolidinyl | phenyl-NH—$CH_2$— | H | $SO_2$ | cyclopropyl |
| 71 | oxazolidinyl | phenyl-$CH_2$— | H | NH | cyclopropyl |
| 72 | isoxazolidinyl | phenyl-O—$CH_2$— | H | S | cyclopropyl |
| 73 | indolinyl | phenyl-S—$CH_2$— | H | O | cyclohexyl |
| 74 | 1-morpholinyl | phenyl-NH—$CH_2$— | H | $SO_2$ | cyclohexyl |
| 75 | 1-piperazinyl | phenyl-$CH_2$— | H | NH | cyclohexyl |
| 76 | 1-piperidinyl | phenyl-O—$CH_2$— | H | S | cyclobutyl |
| 77 | 3-oxo-1-pyrrolidinyl | phenyl-S—$CH_2$— | H | O | cyclobutyl |
| 78 | 1-morpholinyl | phenyl-NH—$CH_2$— | H | $SO_2$ | cyclobutyl |
| 79 | 1-piperazinyl | phenyl-$CH_2$— | H | NH | cyclopentyl |
| 80 | oxo-pyrrolidinyl | phenyl-O—$CH_2$— | H | S | cyclopentyl |
| 81 | oxazolidinyl | phenyl-S—$CH_2$— | H | O | cyclopentyl |
| 82 | isoxazolidinyl | phenyl-NH—$CH_2$— | H | $SO_2$ | cyclohexyl |
| 83 | indolinyl | phenyl-$CH_2$— | H | NH | cyclohexyl |
| 84 | 1-morpholinyl | phenyl-O—$CH_2$— | H | S | cyclohexyl |

TABLE 2

| Ex. No. | $R^1$ | B | $R^3$ and $R^4$ | $X^1$ | S |
|---|---|---|---|---|---|
| 85 | 1-morpholinyl | 4-$CH_3$-phenyl | H | NH | cyclobutyl |
| 86 | 1-piperazinyl | 4-$CH_3$-phenyl | H | S | cyclobutyl |
| 87 | 1-piperidinyl | 4-$CH_3$-pyridyl | H | O | cyclobutyl |
| 88 | 3-oxo-1-pyrrolidinyl | 4-$CH_3$-phenyl | H | NH | cyclopentyl |
| 89 | 1-morpholinyl | 3-$CH_3$-phenyl | H | S | cyclopentyl |
| 90 | 1-piperazinyl | 3-$CH_3$-phenyl | H | O | cyclopentyl |
| 91 | oxo-pyrrolidinyl | 3-$CH_3$-phenyl | H | $SO_2$ | cyclopropyl |
| 92 | oxazolidinyl | 3-$CH_3$-phenyl | H | NH | cyclopropyl |
| 93 | isoxazolidinyl | phenyl | H | S | cyclopropyl |
| 94 | indolinyl | phenyl | H | O | cyclohexyl |
| 95 | 1-morpholinyl | phenyl | H | $SO_2$ | cyclohexyl |
| 96 | 1-piperazinyl | pyridyl | H | NH | cyclohexyl |
| 97 | 1-piperidinyl | phenyl | H | S | cyclobutyl |
| 98 | 3-oxo-1-pyrrolidinyl | phenyl | H | O | cyclobutyl |

TABLE 2-continued

![structure]

| Ex. No. | R¹ | B | R³ and R⁴ | X¹ | S |
|---|---|---|---|---|---|
| 99 | 1-morpholinyl | 3-F-phenyl | H | SO₂ | cyclobutyl |
| 100 | 1-piperazinyl | 3-Cl-phenyl | H | NH | cyclopentyl |
| 101 | oxo-pyrrolidinyl | 3-CN-phenyl | H | S | cyclopentyl |
| 102 | oxazolidinyl | 3-NH₂-phenyl | H | O | cyclopentyl |
| 103 | isoxazolidinyl | 2-F-pbenyl | H | SO₂ | cyclobexyl |
| 104 | indolinyl | 4-CH₃-phenyl | H | NH | cyclohexyl |

Example 105

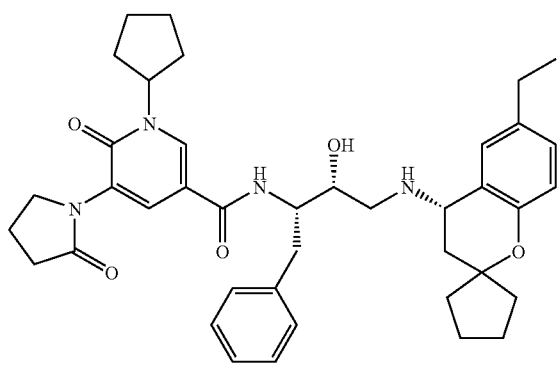

1-Cyclopentyl-N((2S,3R)-4-((S)-6-ethyl-2,2-spirocyclopentylchroman-4-ylamino))-3-hydroxy-1-phenylbutan-2-yl)6-oxo-5-(2-oxopyrrolidin-1-yl)-1,6-dihydropyridne-3-carboxamide.TFA salt Step 1: 6-Ethyl-2,2-spirocyclopentyl-2,3-dihydrochromen-4-one A mixture of 2-hydroxyl-5-ethylacetophenone (5.0 g, 30.47 mmol), cyclopentanone (3.30 g, 39.61 mmol), and pyrrolidine (0.54 g, 7.62 mmol) in toluene (70 mL) was heated at reflux with Dean-Stark trap for 24 h. The mixture was cooled, washed with 5 N HCl, brine, dried over MgSO₄, concentrated and purified by ISCO (5% EtOAc/Hexanes) to give the title compound as a light yellow oil (5.93 g, 84%).

Step 2: (R)-6-Ethyl-2,2-spirocyclopentylchroman-4-ol

To a stirring, cooled (0° C.) solution of(S)-2-methyl-CBS-oxazaborolidine (1.91 mL, 1.92 mmol, 1M solution in toluene) was separately added a solution of 2 M borane-methyl sulfide (9.60 mL, 19.16 mmol) in toluene (30 mL) and a solution of 6-ethyl-2,2-spirocyclopentyl-2,3-dihydrochromen-4-one (4.90 g, 21.29 mmol) in toluene (30 mL), over a period of about 1 h. The reaction mixture was stirred for 15 min., quenched with 5 N HCl (60 mL) and stirred for 1 h. The reaction was extracted with ether (3×), washed with brine, dried over MgSO₄, concentrated and purified by ISCO (20% EtOAc/Hexanes) to give the title compound as a white solid (3.90 g, 80%).

Step 3: (S)-4-Azido-6-ethyl-2,2-spirocyclopentylchroman

To a stirred, cooled (0° C.) solution of (R)-6-ethyl-2,2-spirocyclopentylchroman-4-ol (3.90 g, 16.80 mmol) in toluene (40 mL) was added DPPA (5.10 g, 18.48 mmol) dropwise. After 10 min., DBU (2.82 g, 18.48 mmol) was added in 5 min. The reaction mixture was stirred at RT for 24 h, quenched with H₂O and extracted with ether (3×). The organic extracts were combined, dried over MgSO₄ and concentrated to give the title compound as a crude brown oil (4.30 g, 100%).

Step 4: (S)-6-Ethyl-2,2-spirocyclopentylchroman-4-amine

To a stirring solution of (S)-4-azido-6-ethyl-2,2-spirocyclopentylchroman (5.00 g, 21.44 mmol) in THF (50 mL) was added PPh₃ (5.30 g, 23.58 mmol). After stirring the reaction at RT for 3 h, H₂O was added. The mixture was stirred for 48 h and heated at reflux for 1 h. The mixture was cooled, 2 N HCl was added until the reaction pH=1. The reaction was extracted with toluene (3×, discarded). The aqueous layer was neutralized, extracted with CH₂Cl₂ (3×), dried over Na₂SO₄, and concentrated to give the title compound as a light yellow oil (4.20 g, 93%).

Step 5: (2R,3S)-3-Amino-1-((S)-6-ethyl-2,2-spirocyclopentylchroman-4-ylylamino)-4-phenylbutan-2-ol dihydrochloride salt A mixture of t-butyl(S)-1-((S)-oxiran-2-yl)-2-phenylethylcarbamate (4.85 g, 17.31 mmol) and (S)-6-ethyl-2,2-spirocyclopentyl chroman-4-amine (4.00 g, 17.31 mmol) in EtOH (60 mL) was heated at 70° C. for 24 h. The mixture was cooled, concentrated, purified by chromatography on an ISCO (40% EtOAc/Hexanes) to give an off-white solid. The solid was taken up in p-dioxane (60 mL) to which was added 10 mL of 4 M HCl in p-dioxane and the mixture was stirred at RT overnight. The mixture was concentrated to give the title compound as a light yellow solid (5.30 g, 65%). MS (m/z, M+1): 395.3.

Step 6: 1-Cyclopentyl-N((2S,3R)-4-((S)-6-ethyl-2,2-spirocyclopentylchroman-4-ylamino))-3-hydroxy-1-phenylbutan-2-yl)6-oxo-5-(2-oxopyrrolidin-1-yl)-1,6-dihydropyridne-3-carboxamide.TFA salt A mixture of 1-cyclopentyl-6-oxo-5-(2-oxopyrrolidin-1-yl)-1,6-dihydro pyridine-3-carboxylic acid (0.10 g, 0.33 mmol), (S)-6-ethyl-2,2-spirocyclopentyl chroman-4-amine (0.16 g, 0.40 mmol), HOBt (0.055 g, 0.40 mmol), i-Pr₂Net (0.21 mL, 1.20 mmol), and EDCI (0.08 g, 0.40 mmol) in DMF (2 mL) was stirred at RT for 24 h. The mixture was quenched by H₂O, extracted with CH₂Cl₂ (3×), dried over Na$_2$SO$_4$ and concentrated. The crude concentrate was purified by reverse phase HPLC to give the title compound. MS (m/z, M+1): 667.3.

Example 106

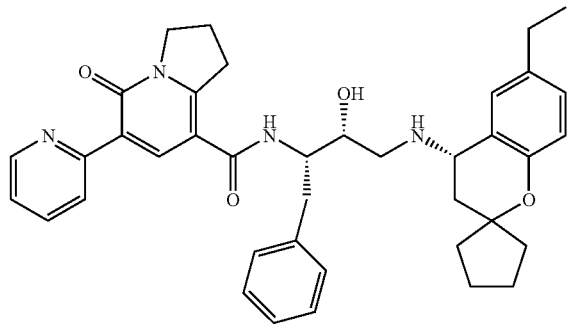

N-((2S,3R)-4-((S)-6-Ethyl-2,2-spirocyclopentylchroman-4-ylamino)3-hyddroxy-1-phenylbutan-2-yl)-5-oxo-6-(pyridin-2-yl)-1,2,3,5-tetrahydroindolizine-8-carboxamide.TFA salt Step 1: 1-(2-Tosylacetyl)pyrrolidin-2-one To a stirred solution of p-toluenesulfonyl acetic acid (8.4 g, 39.21 mmol) in toluene (40 mL) was added oxalyl chloride (58.8 mL, 117.63 mmol) and 4 drops of DMF. The reaction mixture was stirred at RT for 2 h and concentrated. To the concentrate was added 2-pyrrolidinone, and the solution was heated for 12 h. The mixture was cooled, concentrated, taken up in CH$_2$Cl$_2$, washed successively with saturated NaHCO$_3$, brine and dried over MgSO$_4$. The concentrate was purified by chromatography on an ISCO instrument (eluting with 40% EtOAc/Hexanes) to give the title compound as a light yellow solid (6.98 g, 63%).

Step 2: 1-Phenylsulfonyldiazoacetyl)pyrrolidin-2-one

To a stirred, cooled (0° C.) solution of 1-(2-tosylacetyl)pyrrolidin-2-one (6.90 g, 24.83 mmol) in MeCN (70 mL) was added Et$_3$N (8.21 mL, 58.91 mmol). After stirring at 0° C. for 30 min., p-acetamidophenylsulfonyl azide (7.07 g, 29.45 mmol) was added and the mixture was stirred at RT for 24 h. The mixture was concentrated, taken up in CH$_2$Cl$_2$ (3×), and a light brown solid was filtered off. The filtrate was concentrated and purified by ISCO (50% EtOAc/Hexanes) to give the title compound as a yellow solid (2.65 g, 36%).

Step 3: 6-Hydroxy-8-propionyl-2,3-dihydroindolizin-5-(1H)-one

A mixture of the product of step 2 (2.61 g, 8.91 mmol), methyl acrylate (5.9 g, 44.52 mmol), and Rh$_2$(OAc)$_4$ (1 mg, 0.2% mmol) in benzene (40 mL) was heated at reflux in 2 h. The mixture was cooled, concentrated, and purified by ISCO (2% MeOH/CH$_2$Cl$_2$) to give the title compound as an off white solid (1.30 g, 70%).

Step 4: 5-Oxo-8-propionyl-1,2,3,5-tetrahydroindolizin-6-yl trifluoromethanesulfonate To a stirred, cooled (0° C.) solution of 6-hydroxy-8-propionyl-2,3-dihydroindolizin-5-(1H)-one (1.10 g, 4.53 mmol) in CH$_2$Cl$_2$ (10 mL) was added Et$_3$N. After stirring for 20 min., N-phenyltrifluoromethane sulfonamide was added in one portion. The mixture was stirred at RT for 6 h and quenched with H$_2$O. the mixture was extracted with CH$_2$Cl$_2$ (3×) and the combined organic layers were dried over MgSO$_4$, concentrated and purified by ISCO (40% EtOAc/Hexanes) to give the title compound as a white solid (1.50 g, 99%).

Step 5: 5-Oxo-6-(pyridine-2-yl)-1,2,3,5-tetrahydroindolizine-8-carboxylic acid

A mixture of 5-oxo-8-propionyl-1,2,3,5-tetrahydroindolizin-6-yl trifluoromethanesulfonate (0.50 g, 1.46 mmol), 2-trimethylstannyl pyridine (0.46 g, 1.90 mmol), LiCl (0.17 g, 4.38 mmol), and (Ph$_3$P)$_4$Pd (0.12 g, 0.11 mmol) in THF (10 mL) was heated by Microwave Synthesizer at 160° C. for 20 min. The reaction was cooled, diluted with H$_2$O and extracted into EtOAc (3×). The organic layers were combined, dried over MgSO$_4$ and concentrated. The concentrate was triturated in ether to give the salt of the title compound as a light green solid. The solid was dissolved in MeOH (5 mL), to which was added 2 eq. of 1N NaOH and the mixture was stirred for 2 h. The mixture was concentrated, taken up in H$_2$O, neutralized by 10% HCl, extracted with CH$_2$Cl$_2$ (3×), dried over MgSO$_4$, concentrated to give the title compound as a light yellow oil (0.32 g, 85%). MS (m/z, M+1): 257.1.

Step 6: N-((2S,3R)-4-((S)-6-Ethyl-2,2-spirocyclopentylchroman-4-ylamino)3-hyddroxy-1-phenylbutan-2-yl)-5-oxo-6-(pyridin-2-yl)-1,2,3,5-tetrahydroindolizine-8-carboxamide.TFA salt A mixture of 5-oxo-6-(pyridine-2-yl)-1,2,3,5-tetrahydroindolizine-8-carboxylic acid (0.050 g, 0.195 mmol), (2R, 3S)-3-amino-1-((S)-6-ethyl-2,2-spirocyclopentylchroman-4-ylylamino)-4-phenylbutan-2-ol dihydrochloride salt (0.10 g, 0.234 mmol), HOBt (0.032 g, 0.234 mmol), EDCI (0.045 g, 0.234 mmol), and i-Pr$_2$NEt (0.11 g, 0.78 mmol) in DMF (2 mL) was stirred at RT for 24 h. The mixture was concentrated. The concentrate was taken up in H$_2$O, and solids filtered. The filtrate was purified by reverse phase HPLC to give the title compound. MS (m/z, M+1): 633.4.

Example 107

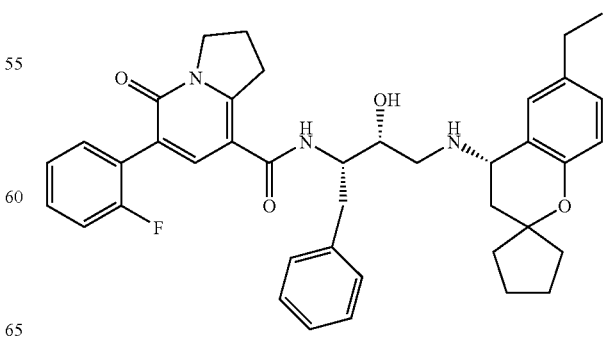

N-((2S,3R)-4-((S)-6-Ethyl-2,2-spirocyclopentylchroman-4-ylamino)3-hyddroxy-1-phenylbutan-2-yl)-6-(2-fluorophenyl)-5-oxo-1,2,3,5-tetrahydroindolizine-8-carboxamide.TFA salt Step 1: 6-(2-Fluorophenyl)-5-oxo-1,2,3,5-tetrahydroindolizine-8-carboxylic acid A mixture of 5-oxo-8-propionyl-1,2,3,5-tetrahydroindolizin-6-yl trifluoromethanesulfonate (0.10 g, 0.292 mmol), 2-fluorophenylboronic acid (0.050 g, 0.38 mmol), and 2M Na$_2$CO$_3$ (0.75 mL, 1.46 mmol) in toluene/EtOH (4 mL, 4:1) was heated at 160° C. for 30 min. in a Microwave Synthesizer. The mixture was cooled, and the layers were separated. The aqueous layer was acidified and the precipitate was filtered and air dried to afford the title compound (0.051 g, 64%). MS (m/z, M+1): 274.1.

Step 2: N-((2S,3R)-4-((S)-6-Ethyl-2,2-spirocyclopentylchroman-4-ylamino)3-hyddroxy-1-phenylbutan-2-yl)-6-(2-fluorophenyl)-5-oxo-1,2,3,5-tetrahydroindolizine-8-carboxamide.TFA salt The title compound was obtained using a procedure analogous to that described in Step 6 of Example 106. MS (m/z, M+1): 650.4.

Example 108

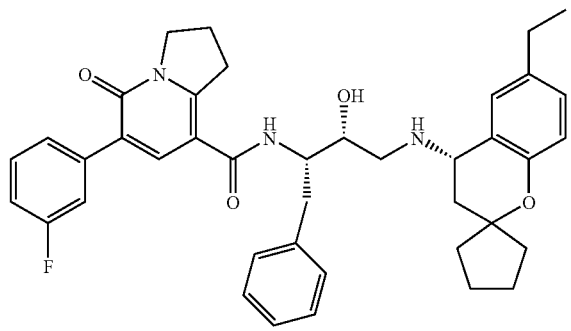

N-((2S,3R)-4-((S)-6-Ethyl-2,2-spirocyclopentylchroman-4-ylamino)3-hyddroxy-1-phenylbutan-2-yl)-6-(3-fluorophenyl)-5-oxo-1,2,3,5-tetrahydroindolizine-8-carboxamide.TFA salt Step 1: 6-(3-Fluorophenyl)-5-oxo-1,2,3,5-tetrahydroindolizine-8-carboxylic acid The title compound was obtained using a procedure analogous to that described in Step 1 of Example 107 (0.055 g, 70%). MS (m/z, M+1): 274.1.

Step 2: N-((2S,3R)-4-((S)-6-Ethyl-2,2-spirocyclopentylchroman-4-ylamino)3-hyddroxy-1-phenylbutan-2-yl)-6-(3-fluorophenyl)-5-oxo-1,2,3,5-tetrahydroindolizine-8-carboxamide.TFA salt The title compound was obtained using a procedure analogous to that described in Step 6 of Example 106. MS (m/z, M+1): 650.4.

Example 109

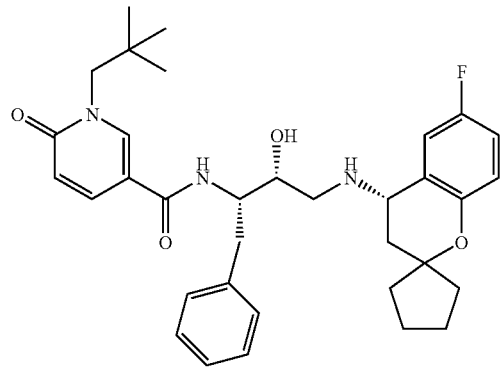

N-((2S,3R)-4-((S)-6-fluoro-2,2-spirocyclopentylchroman-4-ylamino)-3-hyddroxy-1-phenylbutan-2-yl)-1-neopentyl-6-oxo-1,6-dihydropyridine-3-carboxamide.TFA salt Step 1: 6-Fluoro-2,2-spirocyclopentyl-2,3-dihydrochromene-4-one The title compound was obtained using a procedure analogous to that described in Step 1 of Example 105 (12.77 g, 89%).

Step 2: (R)-6-Fluoro-2,2-spirocyclopentylchroman-4-ol

To a stirred solution of (1R,2R)-TsDPEN (0.38 g, 1.05 mmol) in isopropanol (15 mL) was added di-m-chlorobis[(p-cymene)chlororuthenium (II)] (0.36 g, 0.58 mmol) and Et$_3$N (0.21 g, 2.10 mmol). The mixture was heated at 80° C. for 1 h, cooled, then concentrated to dryness. The residue was dissolved in MeCN (10 mL) and added to a solution of 6-fluoro-2,2-spirocyclopentyl-2,3-dihydrochromene-4-one (12.77 g, 58.01 mmol) in MeCN (100 mL). To the mixture was added a solution of HCO$_2$H/Et$_3$N (12 mL, 5:2, Fluka). The reaction mixture was stirred at RT for 24 h, concentrated and purified by chromatography on an ISCO (10% EtOAc/Hexanes) to give the title compound as a white solid (10.50 g, 81%).

Step 3: (S)-4-Azido-6-fluoro-2,2-spirocyclopentylchroman

The title compound was obtained using a procedure analogous to that described in Step 3 of Example 105 (10.50 g, 95%).

Step 4: (S)-6-Fluoro-2,2-spirocyclopentylchroman-4-amine

The title compound was obtained using a procedure analogous to that described in Step 4 of Example 105 (6.66 g, 71%). MS (m/z, M+1): 206.1.

Step 5: (2R,3S)-3-Amino-1-((S)-6-fluoro-2,2-spiro-cyclopentylchroman-4-ylylamino)-4-phenylbutan-2-ol dihydrochloride salt The title compound was obtained using a procedure analogous to that described in Step 5 of Example 105 (9.50 g, 100%). MS (m/z, M+1): 385.3.

Step 6: 1-Neopentyl-6-oxo-1,6-dihydropyridine-3-carboxylic acid

A mixture of methyl coumalate (1.0 g, 6.49 mmol) and neopentylamine was heated at 80° C. for 16 h. The mixture was cooled, taken up in EtOAc, washed with H₂O, dried over MgSO₄, concentrated, and purified by chromatography on an ISCO (30% EtOAC/Hexanes) to give the N-neopentyl-methyl ester intermediate as a light brown oil. The residue was dissolved in THF (3 mL), added LiOH (0.093 g) and 0.2 mL of H₂O, stirred at RT overnight, concentrated, taken up in H₂O, acidified, extracted with CH₂Cl₂ (3×), dried over MgSO₄, concentrated to give the title compound as a light brown solid (0.135 g, 10%). MS (m/z, M+1): 210.2.

Step 7: N-((2S,3R)-4-((S)-6-fluoro-2,2-spirocyclopentylchroman-4-ylamino)-3-hyddroxy-1-phenylbutan-2-yl)-1-neopentyl-6-oxo-1,6-dihydropyridine-3-carboxamide.TFA salt The title compound was obtained using a procedure analogous to that described in Step 6 of Example 106. MS (m/z, M+1): 576.4.

Example 110

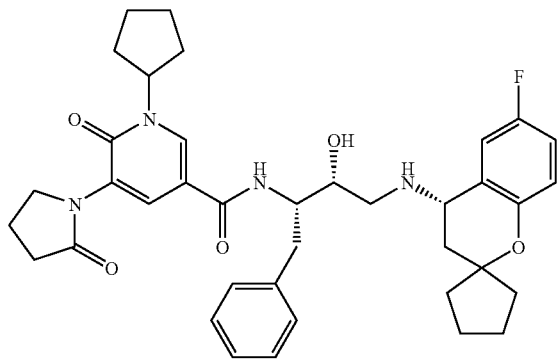

1-Cyclopentyl-N((2S,3R)-4-((S)-6-fluoro-2,2-spiro-cyclopentylchroman-4-ylamino))-3-hydroxy-1-phenylbutan-2-yl)6-oxo-5-(2-oxopyrrolidin-1-yl)-1,6-dihydropyridne-3-carboxamideTFA salt The title compound was obtained using a procedure analogous to that described in Step 6 of Example 105. MS (m/z, M+1): 657.4.

Example 111

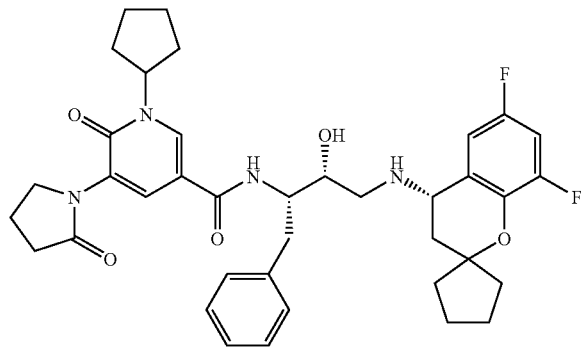

1-Cyclopentyl-N((2S,3R)-4-((S)-6,8-difluoro-2,2-spirocyclopentylchroman-4-ylamino))-3-hydroxy-1-phenylbutan-2-yl)6-oxo-5-(2-oxopyrrolidin-1-yl)-1,6-dihydropyridne-3-carboxamide.TFA salt The title compound was obtained using a procedure analogous to that described in Steps 1-5 of Example 105 and step 6 of Example 106. MS (m/z, M+1): 675.4.

Example 112

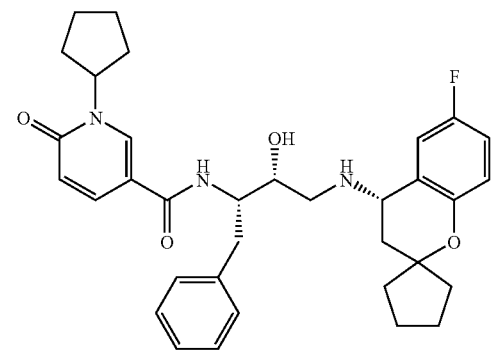

1-Cyclopentyl-N((2S,3R)-4-((S)-6-fluoro-2,2-spiro-cyclopentylchroman-4-ylamino))-3-hydroxy-1-phenylbutan-2-yl)-6-oxo-1,6-dihydropyridne-3-carboxamide.TFA salt Step 1: 1-Cyclopentyl-6-oxo-1,6-dihydropyridine-3-carboxylic acid A mixture of methyl coumalate (3.00 g, 19.46 mmol) and cyclopentylamine (4.97 g, 58.40 mmol) was stirred at RT for 24 h, and purified by chromatography on an ISCO (30% EtOAc/Hexanes) to give the methyl ester as a light yellow oil. The residue was dissolved in THF/H₂O (30 mL, 29:1) to which was added LiOH (0.60 g, 13.56 mmol). The reaction mixture was stirred at RT overnight, concentrated, taken up in H₂O, and acidified with 10% HCl. The off-white precipitated solid, the title compound, was filtered and air dried (1.20 g, 30%). MS (m/z, M+1): 208.2.

Step 2: 1-Cyclopentyl-N((2S,3R)-4-((S)-6-fluoro-2,2-spirocyclopentylchroman-4-ylamino))-3-hydroxy-1-phenylbutan-2-yl)-6-oxo-1,6-dihydropyridne-3-carboxamide.TFA salt The title compound was obtained using a procedure analogous to that described in Step 6 of Example 105. MS (m/z, M+1): 574.3.

Example 113

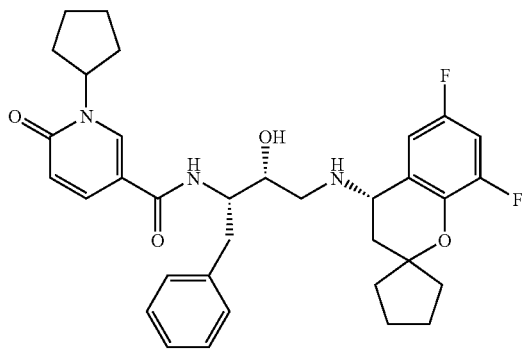

1-Cyclopentyl-N((2S,3R)-4-((S)-6,8-difluoro-2,2-spirocyclopentylchroman-4-ylamino))-3-hydroxy-1-phenylbutan-2-yl)-6-oxo-1,6-dihydropyridne-3-carboxamide.TFA salt The title compound was obtained using a procedure analogous to that described in Step 6 of Example 105. MS (m/z, M+1): 592.3.

Example 114

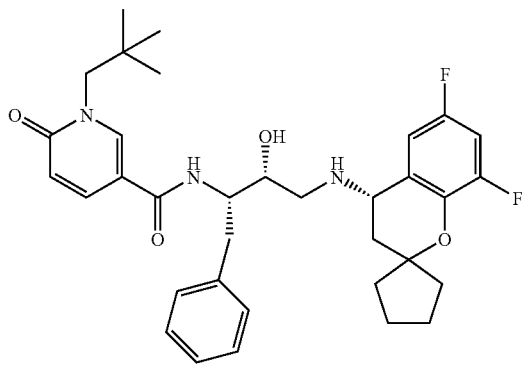

N-((2S,3R)-4-((S)-6,8-difluoro-2,2-spirocyclopentyl-chroman-4-ylamino)-3-hyddroxy-1-phenylbutan-2-yl)-1-neopentyl-6-oxo-1,6-dihydropyridine-3-carboxamide.TFA salt The title compound was obtained using a procedure analogous to that described in Step 6 of Example 105. MS (m/z, M+1): 594.3.

Example 115

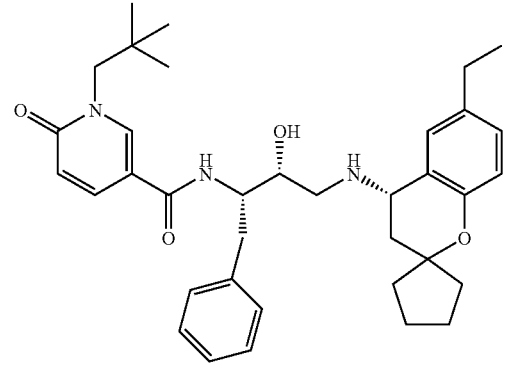

N-((2S,3R)-4-((S)-6-ethyl-2,2-spirocyclopentylchroman-4-ylamino)-3-hyddroxy-1-phenylbutan-2-yl)-1-neopentyl-6-oxo-1,6-dihydropyridine-3-carboxamide.TFA salt The title compound was obtained using a procedure analogous to that described in Step 6 of Example 105. MS (m/z, M+1): 586.4.

Example 116

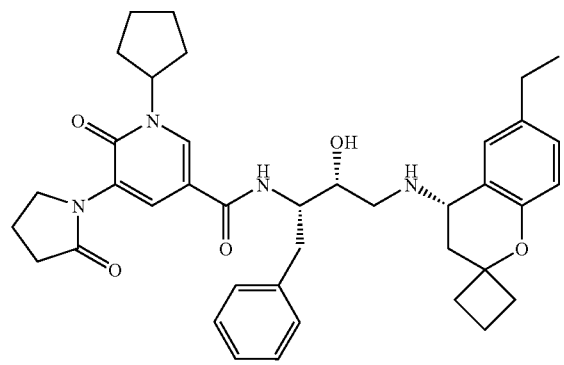

1-Cyclopentyl-N((2S,3R)-4-((S)-6-ethyl-2,2-spirocyclopentylchroman-4-ylamino))-3-hydroxy-1-phenylbutan-2-yl)6-oxo-5-(2-oxopyrrolidin-1-yl)-1,6-dihydropyridne-3-carboxamide.TFA salt The title compound was obtained using a procedure analogous to that described in Example 105. MS (m/z, M+1): 653.4.

Example 117

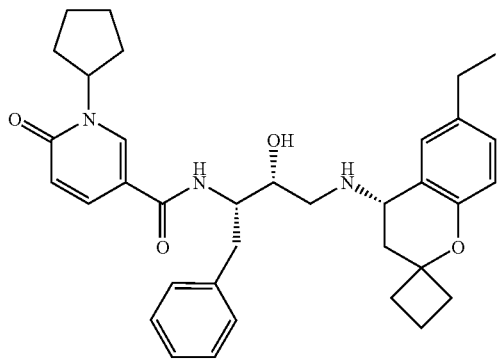

1-Cyclopentyl-N((2S,3R)-4-((S)-6-ethyl-2,2-spirocyclobutylchroman-4-ylamino))-3-hydroxy-1-phenylbutan-2-yl)-6-oxo-1,6-dihydropyridine-3-carboxamide.TFA salt The title compound was obtained using a procedure analogous to that described in Example 105. MS (m/z, M+1): 570.3.

Example 118

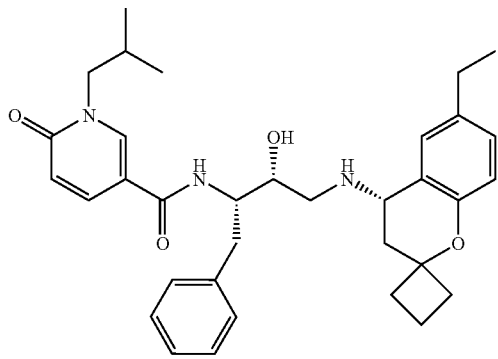

1-Isobutyl-N((2S,3R)-4-((S)-6-ethyl-2,2-spirocyclobutylchroman-4-ylamino))-3-hydroxy-1-phenylbutan-2-yl)-6-oxo-1,6-dihydropyridine-3-carboxamide.TFA salt Step 1:
1-Isobutyl-6-oxo-1,6-dihydropyridine-3-carboxylic acid The title compound was obtained using a procedure analogous to that described in Step 1 of Example 112 (0.20 g, 40%). MS (m/z, M+1): 196.1.

Step 2: 1-Isobutyl-N((2S,3R)-4-((S)-6-ethyl-2,2-spirocyclobutylchroman-4-ylamino))-3-hydroxy-1-phenylbutan-2-yl)-6-oxo-1,6-dihydropyridine-3-carboxamide.TFA salt The title compound was obtained using a procedure analogous to that described in Step 6 of Example 105. MS (m/z, M+1): 558.3.

Example 119

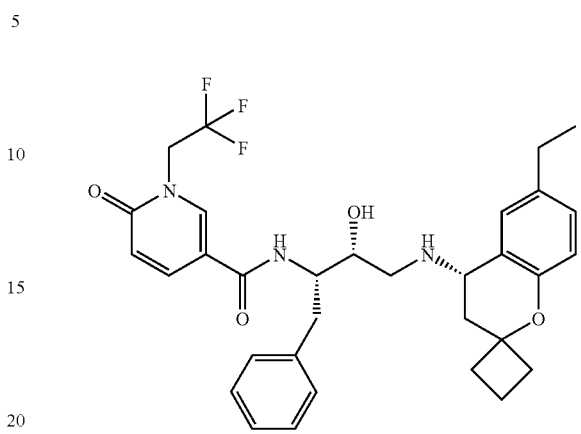

1-(2,2,2-trifluoroethyl)-N-((2S,3R)-4-((S)-6-ethyl-2,2-spirocyclobutylchroman-4-ylamino))-3-hydroxy-1-phenylbutan-2-yl)-6-oxo-1,6-dihydropyridine-3-carboxamide.TFA salt The title compound was obtained using a procedure analogous to that described in Example 118. MS (m/z, M+1): 584.3.

Example 120

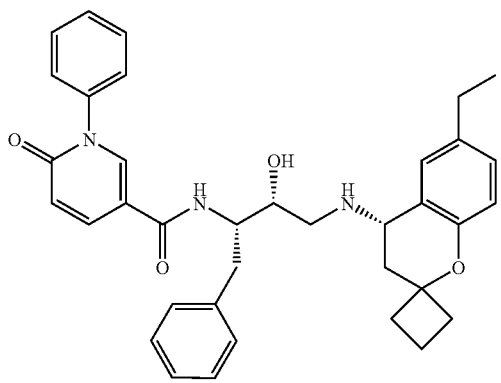

1-(Phenyl)-N((2S,3R)-4-((S)-6-ethyl-2,2-spirocyclobutylchroman-4-ylamino))-3-hydroxy-1-phenylbutan-2-yl)-6-oxo-1,6-dihydropyridine-3-carboxamide.TFA salt The title compound was obtained using a procedure analogous to that described in Example 118. MS (m/z, M+1): 578.3.

Example 121

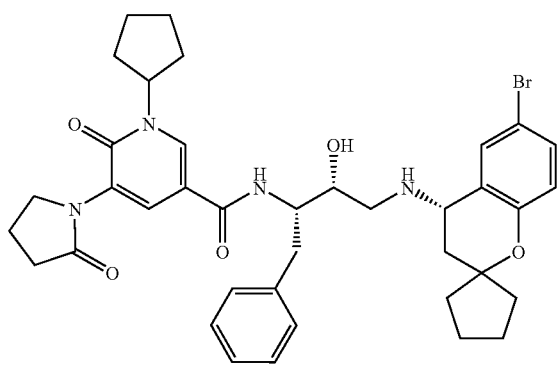

1-Cyclopentyl-N((2S,3R)-4-((S)-6-bromo-2,2-spiro-cyclopentylchroman-4-ylamino))-3-hydroxy-1-phenylbutan-2-yl)-6-oxo-5-(2-oxopyrrolidin-1-yl)-1,6-dihydropyridine-3-carboxamide.TFA salt

Step 1: 6-Bromo-2,2-spirocyclopentyl-2,3-dihydro-chromene-4-one

The title compound was obtained using a procedure analogous to that described in Step I of Example 105. (20.50 g, 97%).

Step 2: (R)-6-Bromo-2,2-spirocyclopentylchroman-4-ol

The title compound was obtained using a procedure analogous to that described in Step 2 of Example 112. (9.0 g, 50%).

Step 3: (S)-4-Azido-6-bromo-2,2-spirocyclopentylchroman

The title compound was obtained using a procedure analogous to that described in Step 3 of Example 105. (8.0 g, 81%).

Step 4: (S)-6-Bromo1-2,2-spirocyclopentylchroman-4-amine

The title compound was obtained using a procedure analogous to that described in Step 4 of Example 105. (4.00 g, 52%). MS (m/z, M+1): 267.1.

Step 5: tert-Butyl (2R,3S)-4-((S)-6-bromo-2,2-spirocyclopentylchroman-4-ylylamino)-3-hydroxyl-1-phenylbutan-2-ylcarbamate A mixture of (S)-6-bromo-2,2-spirocyclopentylchroman-4-amine (4.0 g, 14.18 mmol), t-butyl(S)-1-((S)-oxiran-2-yl)-2-phenylethylarbamate (3.73 g, 14.18 mmol), and LiClO$_4$ (0.15 g, 1.42 mmol) in p-dioxane (60 mL) was heated at 70° C. for 16 h. The mixture was cooled and concentrated. The crude residue was purified by chromatography on an ISCO (40% EtOAc/Hexanes) to give the title compound as a white solid (7.0 g, 91%). MS (m/z, M+2): 430.2.

Step 6: (2R,3S)-4-((S)-6-neopentyl-2,2-spirocyclopentylchroman-4-ylylamino)-3-hydroxyl-1-phenylbutan-2-ol.2TFA salt The title compound was obtained by stirring the product of Step 5 with a solution of TFA in ether or dioxanes. The solution was concentrated and dried under reduced pressure to yield the title compound TFA salt. MS (m/z, M+2): 330.2.

Step 7: 1-Cyclopentyl-N((2S,3R)-4-((S)-6-bromo-2,2-spirocyclopentylchroman-4-ylamino))-3-hydroxy-1-phenylbutan-2-yl)-6-oxo-5-(2-oxopyrrolidin-1-yl)-1,6-dihydropyridine-3-carboxamide.TFA salt The title compound was obtained using a procedure analogous to that described in Step 6 of Example 105. MS (m/z, M+2): 718.3.

Example 122

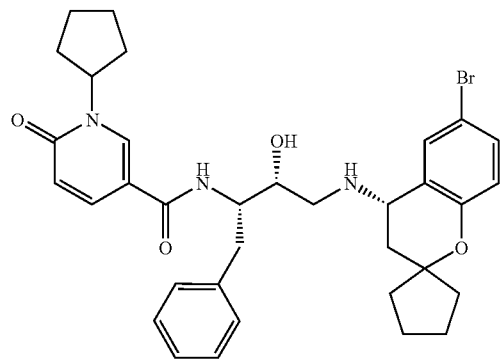

1-Cyclopentyl-N((2S,3R)-4-((S)-6-bromo-2,2-spiro-cyclopentylchroman-4-ylamino))-3-hydroxy-1-phenylbutan-2-yl)-6-oxo-1,6-dihydropyridine-3-carboxamide.TFA salt The title compound was obtained using a procedure analogous to that described in Example 121. MS (m/z, M+2): 635.3.

Example 123

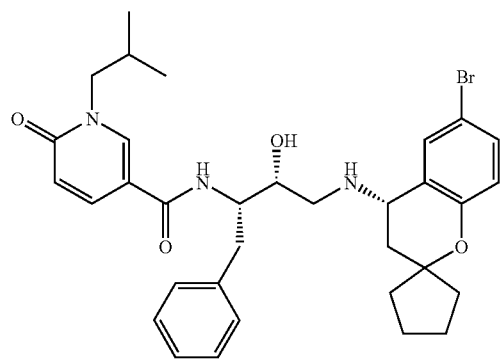

1-Isobutyl-N((2S,3R)-4-((S)-6-bromo-2,2-spirocyclopentylchroman-4-ylamino))-3-hydroxy-1-phenylbutan-2-yl)-6-oxo-1,6-dihydropyridine-3-carboxamide.TFA salt The title compound was obtained using a procedure analogous to that described in Example 121. MS (m/z, M+2): 623.3.

Example 124

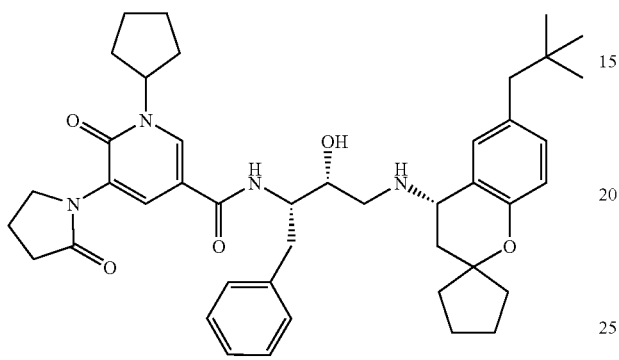

1-Cyclopentyl-N((2S,3R)-4-((S)-6-neopentyl-2,2-spirocyclopentylchroman-4-ylamino))-3-hydroxy-1-phenylbutan-2-yl)-6-oxo-5-(2-oxopyrrolidin-1-yl)-1,6-dihydropyridine-3-carboxamide.TFA salt Step 1:
(1S,5S)-9-Neopentyl-9-bora-bicyclo[3.3.1]nonane To a stirred, cooled (78° C.) solution of 9-methoxy-BBN (20 mL, 20.0 mmol, 1.0M in Hexanes) in THF (40 mL) was added 2,2-dimethylpropyl magnesium chloride (20 ml, 20.0 mmol). After stirring at −78° C. in 3 h, the mixture was quenched by pentane, warmed to RT, filtered the white solid. The filtrate was concentrated to give the light yellow oil (3.98 g, 100%).

Step 2: Tert-Butyl (2R,3S)-4-((S)-6-neopentyl-2,2-spirocyclopentylchroman-4-ylylamino)-3-hydroxyl-1-phenylbutan-2-ylcarbamate. 2TFA salt A mixture of tert-butyl (2R,3S)-4-((S)-6-bromo-2,2-spirocyclopentylchroman-4-ylylamino)-3-hydroxyl-1-phenylbutan-2-ylcarbamate (0.50 g, 0.92 mol), (1S,5S)-9-neopentyl-9-bora-bicyclo[3.3.1]nonane (0.25 g, 1.28 mmol), (Ph$_3$P)$_4$Pd, and 5 N NaOH (0.45 mL, 2.30 mmol) in THF (10 mL) was heated at 80° C. in 24 h. The mixture was concentrated to dryness, dissolved in p-dioxane (10 mL) and added 4 M HCl (1.5 mL, 4.60 mmol) and stirred in 24 h. The mixture was concentrated and purified by reverse phase HPLC to give the white solid (0.276 g, 45%). MS (m/z, M+1): 437.3.

Step 3: 1-Cyclopentyl-N((2S,3R)-4-((S)-6-neopentyl-2,2-spirocyclopentylchroman-4-ylamino))-3-hydroxy-1-phenylbutan-2-yl)-6-oxo-5-(2-oxopyrrolidin-1-yl)-1,6-dihydropyridine-3-carboxamide.TFA salt The title compound was obtained using a procedure analogous to that described in Step 6 of Example 105. MS (m/z, M+1): 709.4.

Example 125

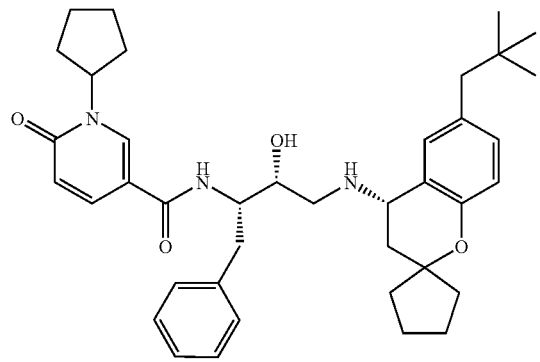

1-Cyclopentyl-N((2S,3R)-4-((S)-6-neopentyl-2,2-spirocyclopentylchroman-4-ylamino))-3-hydroxy-1-phenylbutan-2-yl)-6-oxo-1,6-dihydropyridine-3-carboxamide.TFA salt The title compound was obtained using a procedure analogous to that described in Example 105. MS (m/z, M+1): 626.4.

Example 126

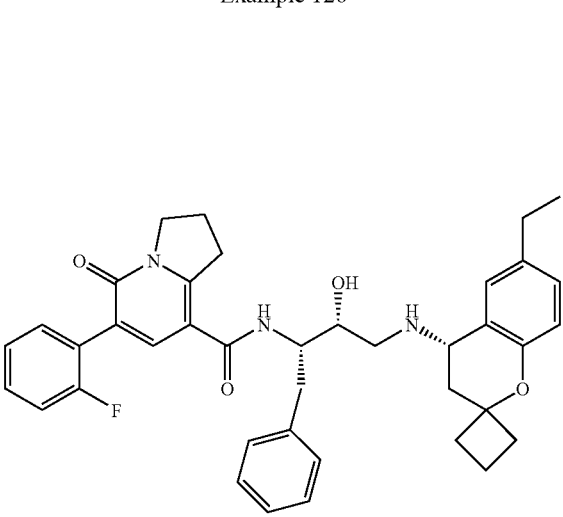

N-((2S,3R)-4-((S)-6-Ethyl-2,2-spirocyclobutylchroman-4-ylamino)3-hyddroxy-1-phenylbutan-2-yl)-6-(2-fluorophenyl)-5-oxo-1,2,3,5-tetrahydroindolizine-8-carboxamide. TFA salt The title compound was obtained using a procedure analogous to that described in Example 106. MS (m/z, M+1): 636.3.

Example 127

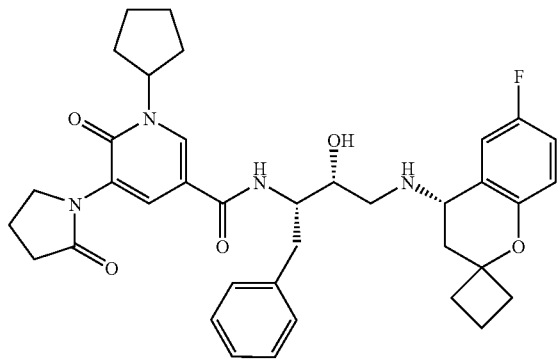

1-Cyclopentyl-N((2S,3R)-4-((S)-6-fluoro-2,2-spiro-cyclobutylchroman-4-ylamino))-3-hydroxy-1-phenylbutan-2-yl)-6-oxo-5-(2-oxopyrrolidin-1-yl) -1,6-dihydropyridine-3-carboxamide. TFA salt The title compound was obtained using a procedure analogous to that described in Example 105. MS (m/z, M+1): 643.3.

Example 128

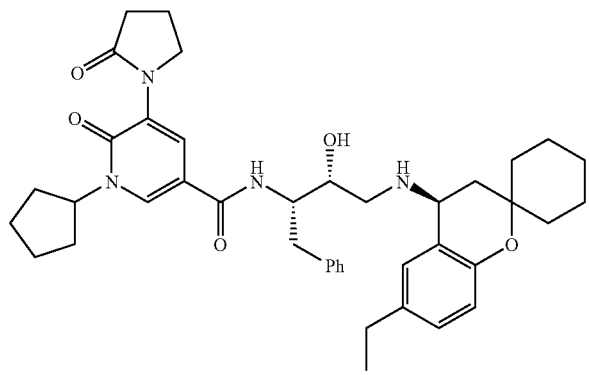

1-cyclopentyl-N-((2S,3R)-4-((S)-6-ethyl-2,2-spiro-cyclohexyl-chroman-4-ylamino)-3-hydroxy-1-phenylbutan-2-yl)-6-oxo-5-(2-oxopyrrolidin-1-yl) -1,6-dihydropyridine-3-carboxamide

Step 1: 6-ethyl-2,2-spirocyclohexylchroman-4-one

A solution of cyclohexyl ketone (8 ml, 78 mmol), 1-(5-ethyl-2-hydroxyphenyl)ethanone (8 g, 48.7 mmol), and pyrrolidine (1.6 ml, 19.5 mmol) were refluxed using a Dean Stark trap for 12 h. The cooled reaction mixture was diluted with 100 ml ether, washed with 30 ml HCl (aq., 5M), dried over MgSO$_4$ and evaporated. Column chromatography (3% EtOAc in Hexanes) gave 6-ethyl-2,2-spirocyclohexylchroman-4-one as a yellow oil 9.4 g (38.5 mmol, 79%). MS m/z: 245 (M+1).

Step 2: (R)-6-ethyl-2,2-spirocyclohexylchroman-4-ol

A solution of(S)-2 Methyl-CBS-oxazaborolidin (1 M, 820 ul, 0.82 mmol) and borane DMS complex (2 ml, 21.3 mmol) in 25 ml toluene was cooled to −20° C. and a solution of 6-ethyl-2,2-spirocyclohexylchroman-4-one (17a, 4 g, 16.4 mmol) in 9 ml THF was added slowly over a period of 2.5 h. The reaction mixture was stirred for 1.5 h at the same temperature and was than carefully hydrolyzed with MeOH. The mixture was washed with HCl (1 M, aq.) and NaHCO$_3$ (sat., aq.) and the organic phase was dried over MgSO$_4$ and evaporated.

The crude material was used without further purification in the next step.

Step 3: (S)-4-azido-6-ethyl-2,2-spirocyclohexylchroman

The crude material from step 2 was dissolved in 30 ml toluene and dppa (4.8 ml, 21.5 mmol) and DBU (3.1 ml, 21.5 mmol) were added, and the mixture was stirred for 12 h. Two phases were observed and the less heavy layer was diluted with ether and washed with HCl (1 M, aq.), then NaHCO$_3$ (sat., aq.), dried over MgSO$_4$ and evaporated under reduced pressure. Column chromatography (3% EtOAc in hexanes) gave 3.3 g (12.2 mmol, 73% (over 2 steps)) of the title compound as a yellow oil MS m/z: 244(60%, M−N$_2$); 229(20%, M−N$_3$).

Step 4: (S)-6-ethyl-2,2-spirocyclohexylchroman-4-amine (S)-4-azido-6-ethyl-2,2-spirocyclohexylchroman (3.3 g, 12.2 mmol) was dissolved in 50 ml THF and cooled to 3° C. LAH (1 M in THF, 12.2 ml, 12.2 mmol) was added and stirring was continued for 2.5 h. The reaction mixture was allowed to warm up to room temperature during this period of time and 50 ml THF and 50 ml CH$_2$Cl$_2$ were added. 15 g NaSO$_4$ 10H$_2$O was added carefully, the mixture was stirred 15 min and was filtered. The filtrate was dried over MgSO4 and evaporated and the crude title compound (MS m/z: 229 (100%, M−NH$_2$)), which was used without purification in the next step.

Step 5: Tert-butyl (2S,3R)-4-((S)-6-ethyl-2,2-spiro-cyclohexyl-chroman-4-ylamino)-3-hydroxy-1-phenylbutan-2-ylcarbamate (S)-6-Ethyl-2,2-spirocyclohexylchroman-4-amine (433 mg, 1.95 mmol) was mixed with 1 ml IPA and tert-butyl(S)-1-((S)-oxiran-2-yl)-2-phenylethylcarbamate (393 mg, 1.5 mmol) and the mixture was heated in a microwave to 125° C. for 15 min. The mixture was diluted with 2 ml DMF and purified on the prep HPLC (Gilson) to give 510 mg of the title compound as its TFA salt (0.82 mmol, 54%, white solid, MS m/z: 509(100%, M+1)).

Step 6: (2R,3S)-3-amino-1-((S)-6-ethyl-2,2-spirocyclohexylchroman-4-ylamino)-4-phenylbutan-2-ol Tert-butyl (2S,3R)-4-((S)-6-ethyl-2,2-spirocyclohexyl-chroman-4-ylamino)-3-hydroxy-1-phenylbutan-2-ylcarbamate TFA (510 mg, 0.82 mmol) was dissolved in 3 ml THF and HCL (4M in dioxane, 5 ml, 20 mmol) was added. The reaction was stirred for 3 h and evaporated. The crude product (white solid, di-HCl salt, MS m/z: 409(100%, M+1)) was used without purification in the next step.

Step 7: 1-cyclopentyl-N-((2S,3R)-4-((S)-6-ethyl-2,2-spirocyclohexyl-chroman-4-ylamino)-3-hydroxy-1-phenylbutan-2-yl)-6-oxo-5-(2-oxopyrrolidin-1-yl)-1,6-dihydropyridine-3-carboxamide (2R,3S)-3-amino-1-((S)-6-ethyl-2,2-spirocyclohexyl-chroman-4-ylamino)-4-phenylbutan-2-ol (48 mg, 0.1 mmol) was dissolved in 1 ml DMF and 1-cyclopentyl-6-oxo-5-(2-oxopyrrolidin-1-yl)-1,6-dihydropyridine-3-carboxylic acid (29 mg, 0.1 mmol), hatu (38 mg, 0.1 mmol) and diisopropyl-ethyl amine (50 ul, 0.3 mmol) were added. The mixture was stirred for 2 h and 5 drops from a Pasteur pipette of HCl (5M, aq.) was added. The mixture was purified, without work up, on a prep HPLC (Gilson) to give the title compound as a white TFA salt. MS m/z: 681 (M+1).

The following Examples 129-142 were obtained using a procedure analogous to that described in Example 128.

Example 129

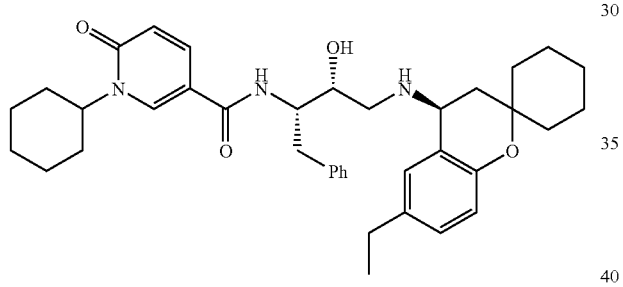

1-cyclohexyl-N-((2S,3R)-4-((S)-6-ethyl-2,2-spirocyclohexyl-chroman-4-ylamino)-3-hydroxy-1-phenylbutan-2-yl)-6-oxo-1,6-dihydropyridine-3-carboxamide (MS m/z: 612(100%, M+1))

Example 130

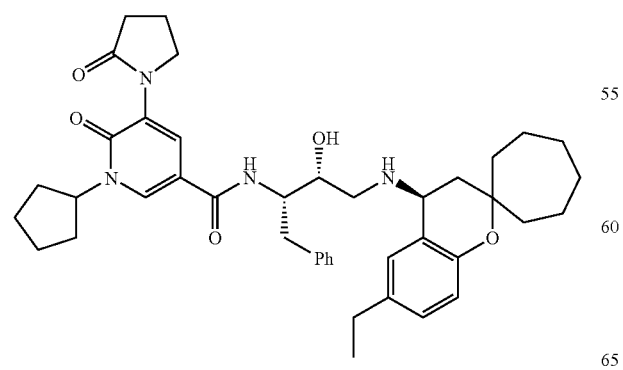

1-cyclopentyl-N-((2S,3R)-4-((S)-6-ethyl-2,2-spirocycloheptyl-chroman-4-ylamino)-3-hydroxy-1-phenylbutan-2-yl)-6-oxo-5-(2-oxopyrrolidin-1-yl)-1,6-dihydropyridine-3-carboxamide (MS m/z: 695(100%, M+1)).

Example 131

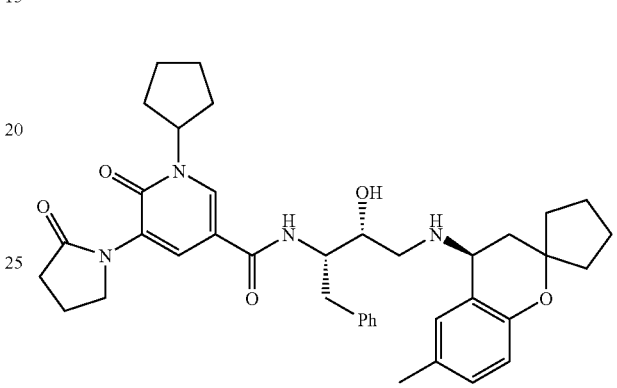

1-cyclopentyl-N-((2S,3R)-4-((S)-2,2-spirocyclopentyl-6-methylchroman-4-ylamino)-3-hydroxy-1-phenylbutan-2-yl)-6-oxo-5-(2-oxopyrrolidin-1-yl)-1,6-dihydropyridine-3-carboxamide (MS m/z: 653(100%, M+1)).

Example 132

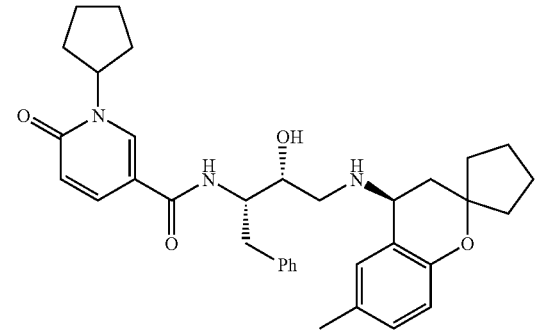

1-cyclopentyl-N-((2S,3R)-4-((S)-2,2-spirocyclopentyl-6-methylchroman-4-ylamino)-3-hydroxy-1-phenylbutan-2-yl)-6-oxo-1,6-dihydropyridine-3-carboxamide (MS m/z: 570(100%, M+1))

1-cyclopentyl-N-((2S,3R)-4-((S)-2,2-spirocyclopentyl-6-(tri-fluoromethoxy)chroman-4-ylamino)-3-hydroxy-1-phenylbutan-2-yl)-6-oxo-1,6-dihydropyridine-3-carboxamide (MS m/z: 640(100%, M+1)).

Example 133

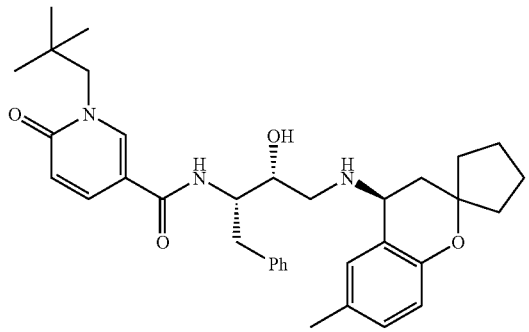

Example 136

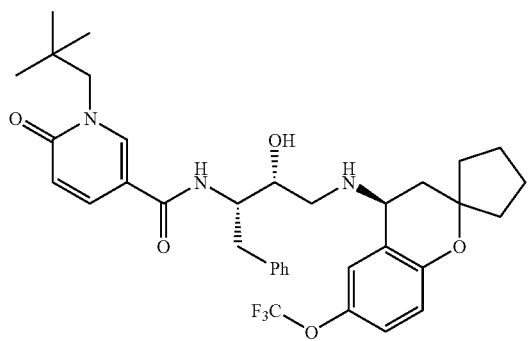

N-((2S,3R)-4-((S)-2,2-spirocyclopentyl-6-methylchroman-4-ylamino)-3-hydroxy-1-phenylbutan-2-yl)-1-neopentyl-6-oxo-1,6-dihydropyridine-3-carboxamide (MS m/z: 572(100%, M+1))

N-((2S,3R)-4-((S)-2,2-spirocyclopentyl-6-(trifluoromethoxy)chroman-4-ylamino)-3-hydroxy-1-phenylbutan-2-yl)-1-neopentyl-6-oxo-1,6-dihydropyridine-3-carboxamide (MS m/z: 642(100%, M+1)).

Example 134

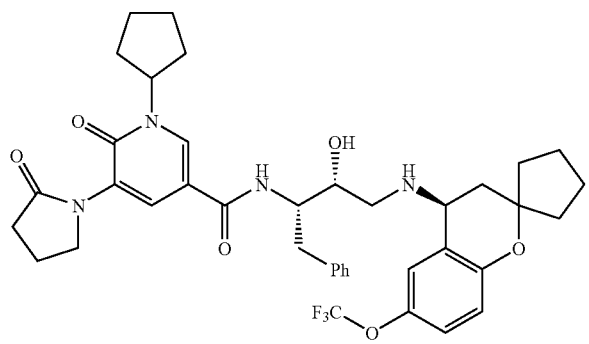

Example 137

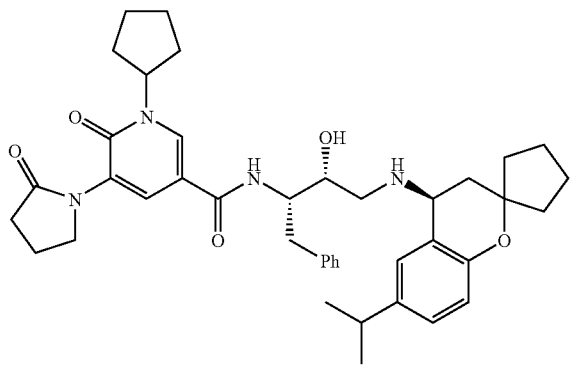

1-cyclopentyl-N-((2S,3R)-4-((S)-2,2-spirocyclopentyl-6-(trifluoromethoxy)chroman-4-ylamino)-3-hydroxy-1-phenylbutan-2-yl)-6-oxo-5-(2-oxopyrrolidin-1-yl)-1,6-dihydropyridine-3-carboxamide (MS m/z: 723(100%, M+1)).

1-cyclopentyl-N-((2S,3R)-4-((S)-2,2-spirocyclopentyl-6-iso-propylchroman-4-ylamino)-3-hydroxy-1-phenylbutan-2-yl)-6-oxo-5-(2-oxopyrrolidin-1-yl)-1,6-dihydropyridine-3-carboxamide (MS m/z: 681 (100%, M+1)).

Example 135

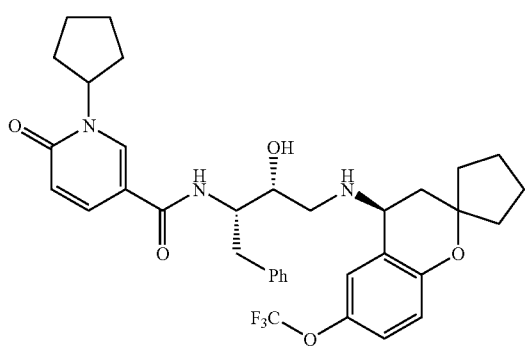

Example 138

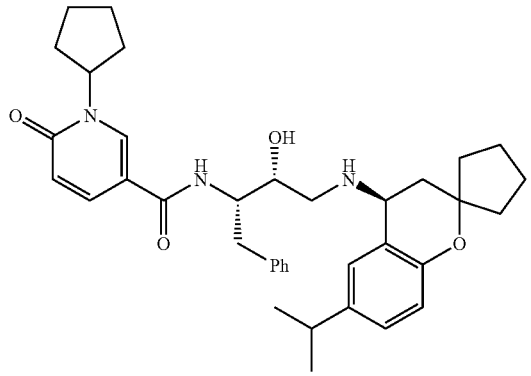

1-cyclopentyl-N-((2S,3R)-4-((S)-2,2-spirocyclopentyl-6-iso-propylchroman-4-ylamino)-3-hydroxy-1-phenylbutan-2-yl)-6-oxo-1,6-dihydropyridine-3-carboxamide (MS m/z: 598(100%, M+1)).

Example 139

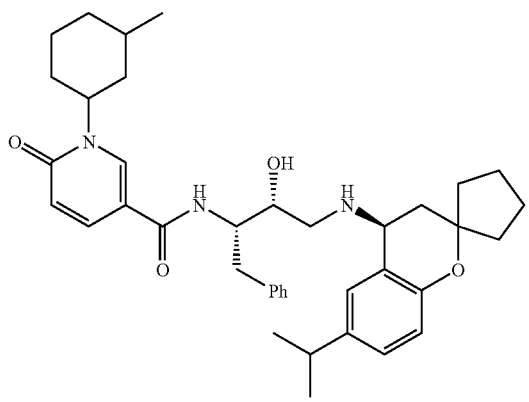

N-((2S,3R)-4-((S)-2,2-spirocyclopentyl-6-isopropyl-chroman-4-ylamino)-3-hydroxy-1-phenylbutan-2-yl)-1-(3-methylcyclohexyl)-6-oxo-1,6-dihydropyridine-3-carboxamide (MS m/z: 626(100%, M+1)).

Example 140

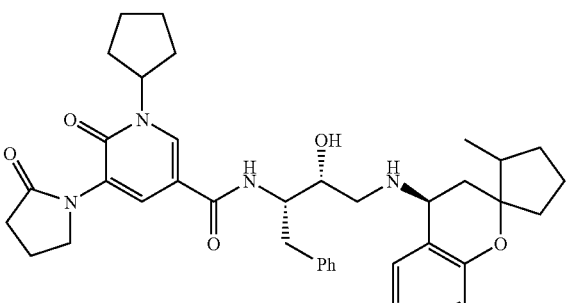

1-cyclopentyl-N-((2S,3R)-4-((S)-6-ethyl-2,2-(□-methyl)-spirocyclopentylchroman-4-ylamino)-3-hydroxy-1-phenylbutan-2-yl)-6-oxo-5-(2-oxopyrrolidin-1-yl)-1,6-dihydropyridine-3-carboxamide The title compound (designated diastereomer was purified by HPLC in Step 5) was obtained as a white TFA salt using a procedure analogous to that described in Example 139 (referring back to Example 128). MS m/z: 681(100%, M+1)). The remaining 3 diastereomers were isolated from the HPLC fractions as a mixture in Step 5, and concentrated to provide a white TFA salt. MS m/z: 681(100%, M+1).

Example 141

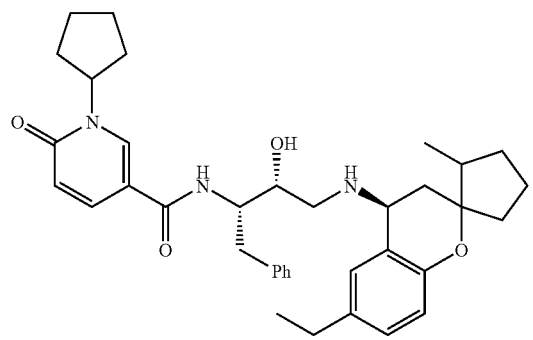

1-cyclopentyl-N-((2S,3R)-4-((S)-6-ethyl-2,2-(□-methyl)-spirocyclopentylchroman-4-ylamino)-3-hydroxy-1-phenylbutan-2-yl)-6-oxo-1,6-dihydropyridine-3-carboxamide The title compound was obtained as a white TFA salt using a procedure analogous to that described in Example 139 (referring back to Example 128). MS m/z: 598(100%, M+1). The remaining 3 diastereomers were isolated from the HPLC fractions as a mixture in Step 5, and concentrated to provide a white TFA salt. MS m/z: 598(100%, M+1)).

Example 142

4-chloro-N-((2S,3R)-4-((S)-6-ethyl-2,2-spirocyclopentylchroman-4-ylamino)-3-hydroxy-1-phenylbutan-2-yl)-6-oxo-1-phenyl-1,6-dihydropyridazine-3-carboxamide The title compound was obtained as a white TFA salt using a procedure analogous to that described in Example 139 (referring back to Example 128). MS m/z: 627(100%, M+1).

Example 143

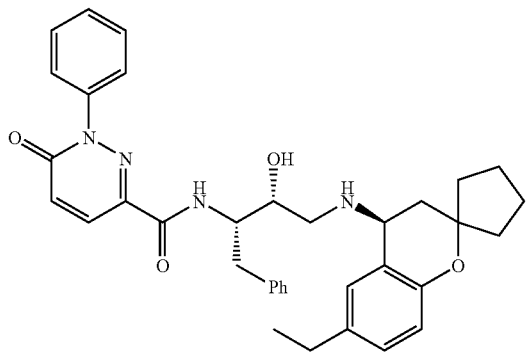

N-((2S,3R)-4-((S)-6-ethyl-2,2-spirocyclopentylchroman-4-ylamino)-3-hydroxy-1-phenylbutan-2-yl)-6-oxo-1-phenyl-1,6-dihydropyridazine-3-carboxamide Step 1:
6-oxo-1-phenyl-1,6-dihydropyridazine-3-carboxylic acid 4-chloro-6-oxo-1-phenyl-1,6-dihydropyridazine-3-carboxylic acid (100 mg, 0.4 mmol) was dissolved in 3 ml EtOH and Pd/C (25 mg) was added. A H₂ balloon was attached to the reaction vessel and the mixture was stirred for 4 h. The reaction was filtered through a pad of Celite®, concentrated and used without further purification in the next reaction. MS m/z: 217(100%, M+1)).

Step 2: N-((2S,3R)-4-((S)-6-ethyl-2,2-spirocyclopentylchroman-4-ylamino)-3-hydroxy-1-phenylbutan-2-yl)-6-oxo-1-phenyl-1,6-dihydropyridazine-3-carboxamide The title compound was obtained as a white TFA salt using a procedure analogous to that described in Example 128. MS m/z: 593(100%, M+1).

Example 144

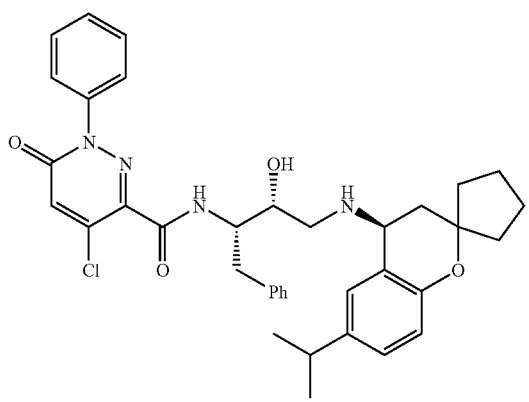

4-chloro-N-((2S,3R)-3-hydroxy-4-((S)-6-isopropyl-2,2-spirocyclopentylchroman-4-ylamino)-1-phenylbutan-2-yl)-6-oxo-1-phenyl-1,6-dihydropyridazine-3-carboxamide MS m/z: 641 (100%, M+1).

Example 145

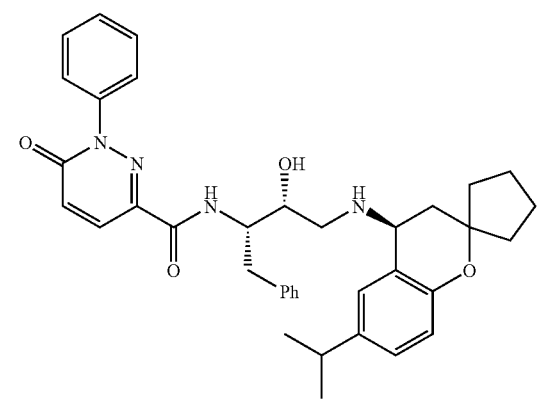

N-((2S,3R)-4-((S)-2,2-spirocyclopentylchroman-6-isopropylchroman-4-ylamino)-3-hydroxy-1-phenylbutan-2-yl)-6-oxo-1-phenyl-1,6-dihydropyridazine-3-carboxamide MS m/z: 607(100%, M+1).

Example 146

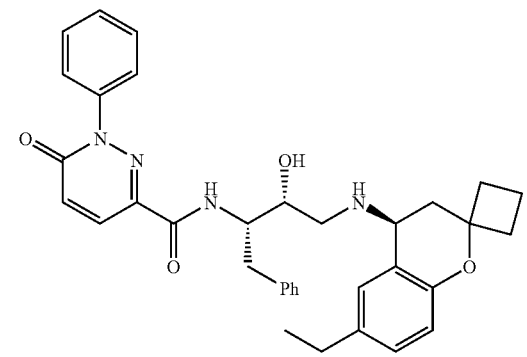

N-((2S,3R)-4-((S)-6-ethyl-2,2-spirocyclobutylchroman-4-ylamino)-3-hydroxy-1-phenylbutan-2-yl)-6-oxo-1-phenyl-1,6-dihydropyridazine-3-carboxamide MS m/z: 579(100%, M+1)

Example 147

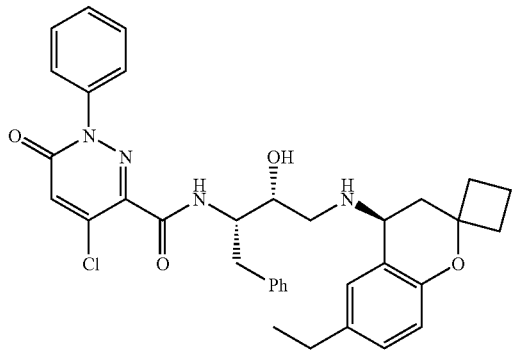

4-chloro-N-((2S,3R)-4-((S)-6-ethyl-2,2-spirocyclobutylchroman-4-ylamino)-3-hydroxy-1-phenylbutan-2-yl)-6-oxo-1-phenyl-1,6-dihydropyridazine-3-carboxamide MS m/z: 613(100%, M+1))

Example 148

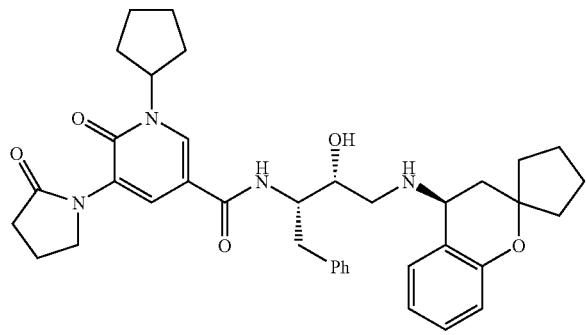

1-cyclopentyl-N-((2S,3R)-4-((S)-2,2-spirocyclopentylchroman-4-ylamino)-3-hydroxy-1-phenylbutan-2-yl)-6-oxo-5-(2-oxopyrrolidin-1-yl)-1,6-dihydropyridine-3-carboxamide (2R,3S)-3-amino-1-((S)-2,2-dimethylchroman-4-ylamino)-4-phenylbutan-2-ol was dissolved in 250 ul DMF and 1-cyclopentyl-6-oxo-5-(2-oxopyrrolidin-1-yl)-1,6-dihydropyridine-3-carboxylic acid (8 mg, 0.027 mmol) HATU (10 mg, 0.027 mmol) and diisopropylethylamine (DIEA, 13 ul, 0.081 mmol) were added. The mixture was stirred for 2 h and 2 drops HCl (5 M, aq.) was added. The mixture was loaded directly, without further work up, onto a prep HPLC (Gilson) system and purified to afford the title compound as a white TFA salt. MS m/z: 639(100%, M+1).

The following Examples 149-150 were synthesized by a method analogous to that described in Example 148.

Example 149

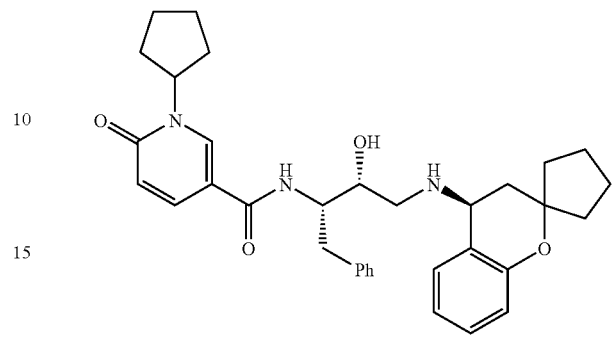

1-cyclopentyl-N-((2S,3R)-4-((S)-2,2-spirocyclopentylchroman-4-ylamino)-3-hydroxy-1-phenylbutan-2-yl)-6-oxo-1,6-dihydropyridine-3-carboxamide MS m/z: 556(100%, M+1)

Example 150

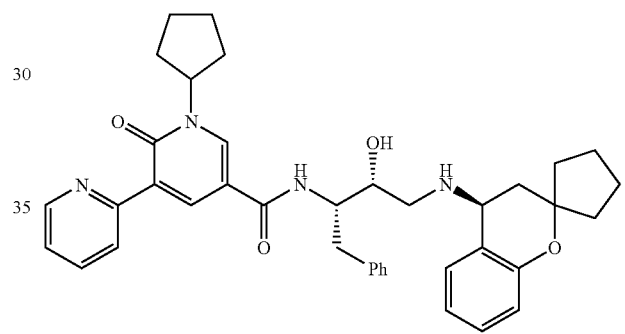

1-cyclopentyl-N-((2S,3R)-4-((S)-2,2-spirocyclopentylchroman-4-ylamino)-3-hydroxy-1-phenylbutan-2-yl)-6-oxo-5-(pyridin-2-yl)-1,6-dihydropyridine-3-carboxamide MS m/z: 633(30%, M+1))

Example 151

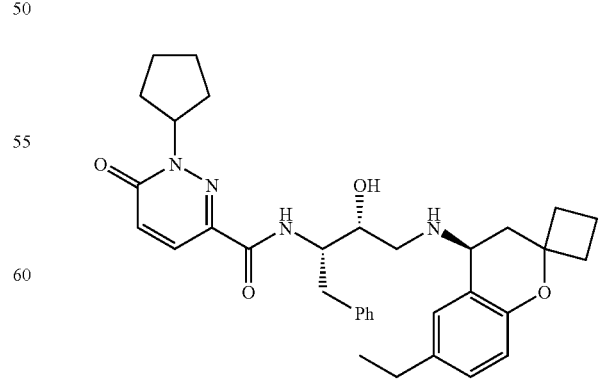

1-cyclopentyl-N-((2S,3R)-4-((S)-6-ethyl-2,2-spiro-cyclo-butylchroman-4-ylamino)-3-hydroxy-1-phenylbutan-2-yl)-6-oxo-1,6-dihydropyridazine-3-carboxamide Step 1: Cyclopentyl-1-cyclopentyl-6-oxo-1,6-dihydropyridazine-3-carboxylate 6-Oxo-1,6-dihydropyridazine-3-carboxylic acid (1 g, 7.14 mmol) was stirred with cyclopentyl iodide (2.05 ml, 17.8 mmol) and potassium carbonate (3 g, 21.4 mmol) in 15 ml DMF for 14 h at room temperature. 50 ml $CH_2Cl_2$ was added and the reaction mixture was filtered. The filtrate was concentrated and the title compound was purified by prep HPLC. Yield: 20 mg (0.072 mmol, 1%, MS m/z: 277(100%, M+1)).

Step 2: 1-cyclopentyl-6-oxo-1,6-dihydropyridazine-3-carboxylic acid

Cyclopentyl-1-cyclopentyl-6-oxo-1,6-dihydropyridazine-3-carboxylate (20 mg, 0.072 mmol) was dissolved in 2 ml THF/water (1/1) and 2 ml NaOH (5M, aq.) was added. The reaction was stirred at 40° C. for 2 h and 5 ml HCl (5M, aq.) was added. The reaction was concentrated and 10 ml of $CH_2Cl_2$/MeOH (1/1) was added and the reaction was sonicated for 10 min and filtered. The filtrate was concentrated and used in the next step without further purification. Yield: 11 mg (0.052 mmol, 73%, film, MS m/z: 209(100%, M+1).

Step 3: 1-cyclopentyl-N-((2S,3R)-4-((S)-6-ethyl-2,2-spirocyclo-butylchroman-4-ylamino)-3-hydroxy-1-phenylbutan-2-yl)-6-oxo-1,6-dihydropyridazine-3-carboxamide The title compound was obtained as a white TFA salt using a procedure analogous to that described in Example 148. MS m/z: 571(100%, M+1).

Example 152

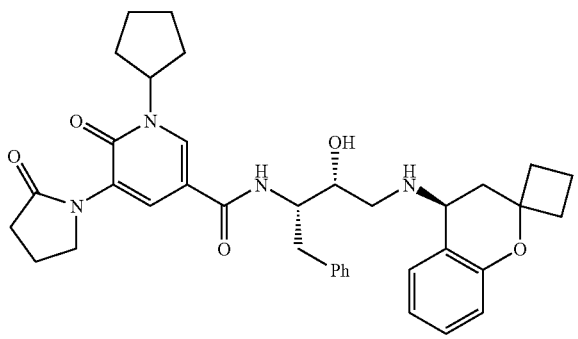

1-cyclopentyl-N-((2S,3R)-4-((S)-2,2-spirocyclobutylchroman-4-ylamino)-3-hydroxy-1-phenylbutan-2-yl)-6-oxo-5-(2-oxopyrrolidin-1-yl)-1,6-dihydropyridine-3-carboxamide The title compound was obtained as a white TFA salt using a procedure analogous to that described in Example 128. MS m/z: 625(100%, M+1)).

Example 153

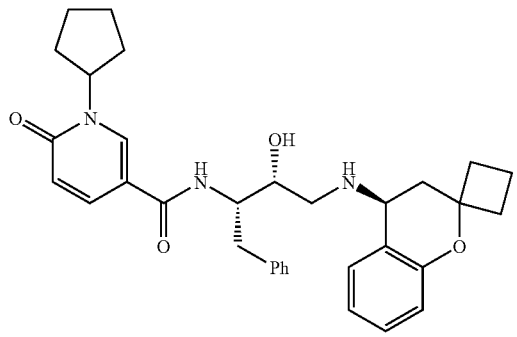

1-cyclopentyl-N-((2S,3R)-4-((S)-2,2-spirocyclobutylchroman-4-ylamino)-3-hydroxy-1-phenylbutan-2-yl)-6-oxo-1,6-dihydropyridine-3-carboxamide The title compound was obtained as a white TFA salt using a procedure analogous to that described in Example 150. MS m/z: 542(100%, M+1)).

Example 154

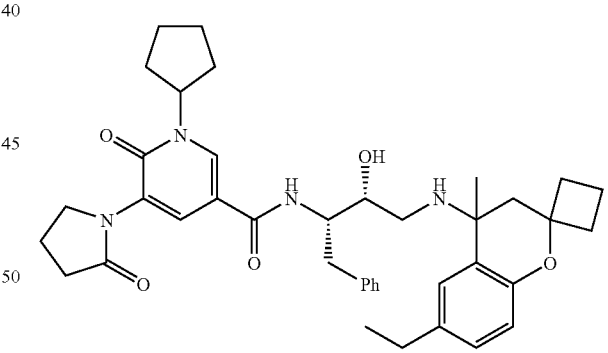

1-cyclopentyl-N-((2S,3R)-4-(6-ethyl-4-methyl-2,2-spiro-cyclobutylchroman-4-ylamino)-3-hydroxy-1-phenylbutan-2-yl)-6-oxo-5-(2-oxopyrrolidin-1-yl)-1,6-dihydropyridine-3-carboxamide Step 1: 6-ethyl-4-methyl-2,2-spirocyclobutylchroman-4-ol 6-ethyl-2,2-spirocyclobutylchroman-4-one (0.32 g, 1.500 mmol) was dissolved in 10 ml THF and cooled to 0° C. While stirring, methyl lithium (1.6 m solution in diethyl ether (4.7 ml, 7.5 mmol)) was added drop wise to the reaction and the cooling bath was removed after the addition. The reaction mixture was stirred for 2 h at RT. 30 ml of Sat. NH4Cl (aq) was added and the mixture was diluted with 100 ml EtOAc. The phases were separated and the aqueous layer was extracted (2x) with EtOAc 50 ml (each). The combined organic layers were dried over MgSO4, filtered and concentrated. Column chromatography gave the title compound (0.267 g, 0.80 mmol, 54% yield) as a yellow oil. MS m/z: 215(100%, M-OH).

Step 2: 4-azido-6-ethyl-4-methyl-2,2-spirocyclobutylchroman

A solution of 6-ethyl-4-methyl-2,2-spirocyclobutylchroman-4-ol (0.276 g, 0.832 mmol) and azidosodium (0.541 g, 8.32 mmol) was dissolved/suspended in 5 ml chloroform and cooled to 0° C. A solution of 2,2,2-trifluoroacetic acid (0.320 ml, 4.16 mmol) in 2 ml chloroform was added over a period of 2 h via syringe pump. After the addition the reaction was warmed up to room temperature and stirring was continued for 2 h. The reaction mixture was diluted with 10 ml of water and extracted 2x with 50 ml dichloromethane. Glass column chromatography gave the title compound (0.2100 g, 0.326 mmol, 39.3% yield, MS m/z: 215(100%, M-N$_3$)).

Step 3: 6-ethyl-4-methyl-2,2-spirocyclobutylchroman-4-amine 4-azido-6-ethyl-4-methyl-2,2-spirocyclobutylchroman (0.210 g, 0.3260 mmol) was dissolved in 2 ml THF and cooled to 0° C. Then, lithium aluminum hydride (1.0M solution in tetrahydrofuran, 3.26 ml, 3.26 mmol) was added drop wise and stirring was continued at 0° C. for 1 h and at RT for 2 h. The reaction mixture was diluted with 10 ml THF and 40 ml dichloromethane and 4 g NaSO$_4$. 10H$_2$O was added carefully. The mixture was filtered, dried over MgSO4 evaporated and the title compound (0.177 g, 0.306 mmol, 93.9% yield, MS m/z: 215(100%, M-NH$_2$)) used in the next reaction without further purification.

Step 4: Tert-butyl (2S,3R)-4-(6-ethyl-4-methyl-2,2-spirocyclo-butylchroman-4-ylamino)-3-hydroxy-1-phenylbutan-2-ylcarbamate 6-ethyl-4-methyl-2,2-spirocyclobutylchroman-4-amine (0.17700 g, 0.3064 mmol) and tert-butyl(S)-1-((S)-oxiran-2-yl)-2-phenylethylcarbamate (0.323 g, 1.23 mmol) were mixed in 1 ml IPA and heated in a microwave to 135° C. for 25 min. The crude product was purified without further workup using a prep HPLC (Gilson), to afford the title compound (0.190 g, 0.259 mmol, 84.6%) as a white TFA salt.

Step 5: (2R,3S)-3-amino-1-(6-ethyl-4-methyl-2,2-spirocyclobutyl-chroman-4-ylamino)-4-phenylbutan-2-ol Tert-butyl (2S,3R)-4-(6-ethyl-4-methyl-2,2-spirocyclo-butylchroman-4-ylamino)-3-hydroxy-1-phenylbutan-2-yl-carbamate (0.190 g, 0.259 mmol) was dissolved in 1 ml dioxane and HCl (4 M in dioxane, 0.648 ml, 2.59 mmol) was added at room temperature. The reaction mixture was stirred for 4 h at RT and evaporated. The crude product was purified on the prep HPLC to give the title compound (0.160 g, 0.257 mmol, 99.2% yield) as a white HCl salt. MS m/z: 395(100%, M+1).

Step 6: 1-cyclopentyl-N-((2S,3R)-4-(6-ethyl-4-methyl-2,2-spiro-cyclobutylchroman-4-ylamino)-3-hydroxy-1-phenylbutan-2-yl)-6-oxo-5-(2-oxopyrrolidin-1-yl)-1,6-dihydropyridine-3-carboxamide (2R,3S)-3-amino-1-(6-ethyl-4-methyl-2,2-spirocyclobutyl-chroman-4-ylamino)-4-phenylbutan-2-ol (0.0311 g, 0.05 mmol) and 1-cyclopentyl-6-oxo-5-(2-oxopyrrolidin-1-yl)-1,6-dihydropyridine-3-carboxylic acid (0.0145 g, 0.05 mmol) were dissolved in 0.5 ml DMF and N-ethyl-N-isopropylpropan-2-amine (0.0348 ml, 0.2 mmol) and HATU (0.0190 g, 0.05 mmol) were added at room temperature. The reaction mixture was stirred at RT for 2 h. 2 drops of HCl (5 M, aq., from a Pasteur pipette) were added. The title compound was purified from the mixture, without further workup, by prep HPLC (Gilson) to give the title compound as a white TFA salt. MS m/z: 667(80%, M+1).

Example 155

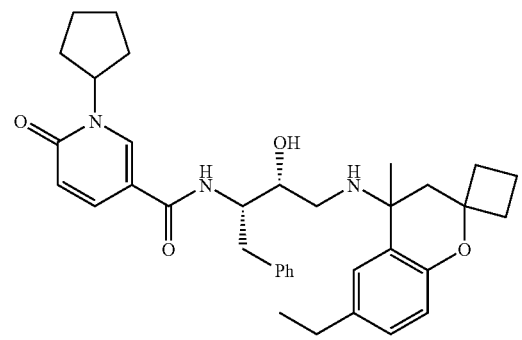

1-cyclopentyl-N-((2S,3R)-4-(6-ethyl-4-methyl-2,2-spiro-cyclobutylchroman-4-ylamino)-3-hydroxy-1-phenylbutan-2-yl)-6-oxo-1,6-dihydropyridine-3-carboxamide The title compound was obtained as a white TFA salt using a procedure analogous to that described in Example 154. MS m/z: 584(100%, M+1)).

Example 156

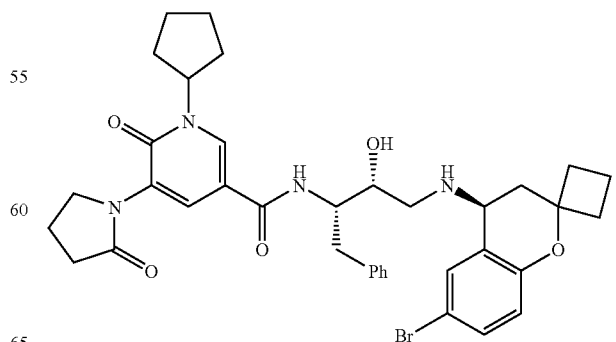

N-((2S,3R)-4-((S)-6-bromo-2,2-spirocyclobutylchroman-4-ylamino)-3-hydroxy-1-phenylbutan-2-yl)-1-cyclopentyl-6-oxo-5-(2-oxopyrrolidin-1-yl)-1,6-dihydropyridine-3-carboxamide Step 1: (2R,3S)-3-amino-1-((S)-6-bromo-2,2-spirocyclobutylchroman-4-ylamino)-4-phenylbutan-2-ol Tert-butyl (2S,3R)-4-((S)-6-bromo-2,2-spirocyclobutylchroman-4-ylamino)-3-hydroxy-1-phenylbutan-2-ylcarbamate (0.132 g, 0.248 mmol) was dissolved in 2 ml of dioxane, and HCl (4 M in dioxane, 3.10 ml, 12.4 mmol) were added at RT. The reaction was stirred for 2 h, then concentrated. The crude title compound (HCl salt) (0.128 g, 0.254 mmol, 102% yield) was used in the next step without further purification. MS m/z: 431(100%, M+1); 433(100%, M+3).

Step 2: N-((2S,3R)-4-((S)-6-bromo-2,2-spirocyclobutylchroman-4-ylamino)-3-hydroxy-1-phenylbutan-2-yl)-1-cyclopentyl-6-oxo-5-(2-oxopyrrolidin-1-yl)-1,6-dihydropyridine-3-carboxamide (2R,3S)-3-amino-1-((S)-6-bromo-2,2-spirocyclobutylchroman-4-ylamino)-4-phenylbutan-2-ol (0.030 g, 0.06 mmol) and 1-cyclopentyl-6-oxo-5-(2-oxopyrrolidin-1-yl)-1,6-dihydropyridine-3-carboxylic acid (0.017 g, 0.06 mmol) were dissolved in 0.5 ml DMF and N-ethyl-N-isopropylpropan-2-amine (0.041 ml, 0.24 mmol) and HATU (0.023 g, 0.060 mmol) were added at room temperature. The reaction mixture was stirred at room temperature for 2 h. 2 drops of HCl (5 M, aq.) were added. The mixture was purified, without further workup, on a prep HPLC (Gilson) to give the title compound as a white TFA salt. MS m/z: 703(100%, M+1); 705(100%, M+3).

Example 157

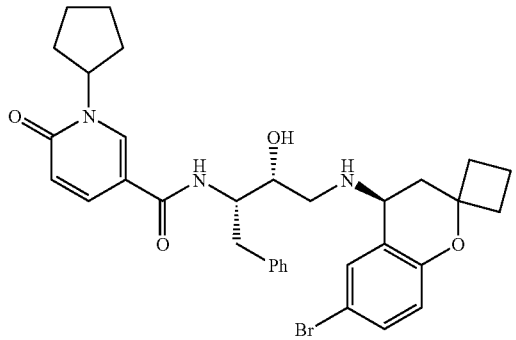

N-((2S,3R)-4-((S)-6-bromo-2,2-spirocyclobutylchroman-4-ylamino)-3-hydroxy-1-phenylbutan-2-yl)-1-cyclopentyl-6-oxo-1,6-dihydropyridine-3-carboxamide The title compound was obtained as a white TFA salt using a procedure analogous to that described in Example 156. MS m/z: 620(100%, M+1); 622(100%, M+3).

Example 158

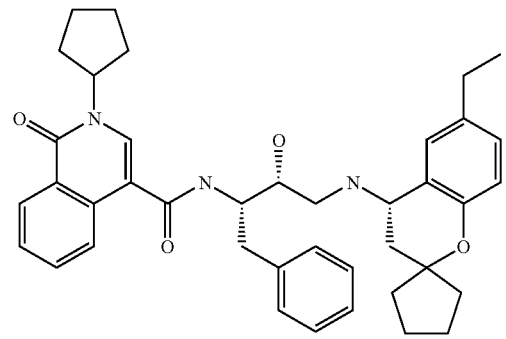

2-cyclopentyl-N-((2S,3R)-4-((S)-6-ethyl-2,2-spirocyclopentylchroman-4-ylamino)-3-hydroxy-1-phenylbutan-2-yl)-1-oxo-1,2-dihydroisoquinoline-4-carboxamide In a 3 mL vial, 2-cyclopentyl-1-oxo-1,2-dihydroisoquinoline-4-carboxylic acid (32.6 mg, 127 mmol) was dissolved in DMF (1 mL). To this was added HATU (48.5 mg, 0.127 mmol), followed by (2R,3S)-3-amino-1-((S)-6-ethyl-2,2-dimethylchroman-4-ylamino)-4-phenylbutan-2-ol dihydrochloride (50 mg, 0.116 mmol) and DIPEA (0.05 ml). Reaction was stirred for 6 h at RT. Reaction was shown to be complete by LCMS and purified by reverse phase LC to give the title compound. MS m/z: 634.3 [M+H]⁺.

Example 159

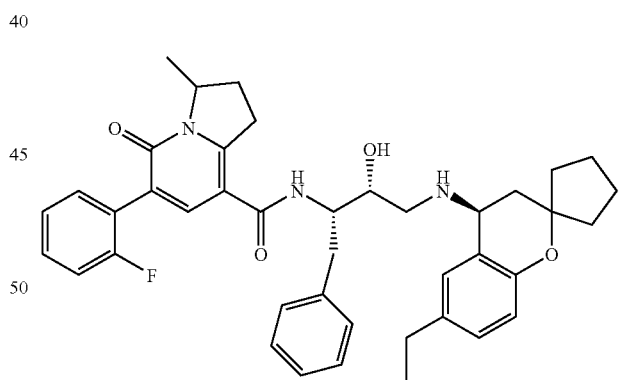

N-((2S,3R)-4((S)-6-ethyl-2,2-spirocyclopentylchroman-4-ylamino)-3-hydroxy-1-phenylbutan-2-yl)-5-oxo-6-(2-fluorophenyl)-1,2,3,5-tetrahydroindolizine-8-carboxamide. TFA salt Step 1: 5-methyl-1-(2-tosylacetyl)pyrrolidin-2-one The title compound was obtained as a golden-colored oil using a procedure analogous to that described in Step 1 of Example 106. MS m/z: 296.4(M+1).

135

Step 2: 5-Methyl-1-(2-tosyl-2-diazoacetyl)pyrrolidin-2-one

The title compound was obtained as a yellow solid using a procedure analogous to that described in Step 2 of Example 106. MS m/z: 294.3(M−N$_2$).

Step 3: Methyl 6-hydroxy-3-methyl-5-oxo-1,2,3,5-tetrahydroindolizine-8-carboxylate The title compound was obtained as a grey solid using a procedure analogous to that described in Step 3 of Example 106. MS m/z: 224.1 (M+1).

Step 4: Methyl 3-methyl-5-oxo-6-(trifluoromethylsulfonyloxy)-1,2,3,5-tetrahydroindolizine-8-carboxylate The title compound was obtained as a golden-colored oil using a procedure analogous to that described in Step 4 of Example 106. MS m/z: 356.1(M+1).

Step 5: 6-(2-Fluorophenyl)-3-methyl-5-oxo-1,2,3,5-tetrahydroindolizine-8-carboxylic acid To a microwave tube was added methyl-3-methyl-5-oxo-6-(trifluoromethylsulfonyloxy)-1,2,3,5-tetrahydroindolizine-8-carboxylate (94 mg, 0.26 mmol), 2-fluorophenylboronic acid (37 mg, 0.26 mmol, Aldrich), and 2 M sodium carbonate (0.65 mL, 1.30 mmol). To this was added 4 mL of toluene, 0.25 mL of EtOH, and Pd(PPh$_3$)$_4$ (20 mg, 0.17 mmol, Aldrich). The tube was sealed and treated in Emry's optimizer for 15 min at 160° C. The aqueous phase was separated and acidified to pH 2 with 2 N HCl and extracted with EtOAc (3×). The combined EtOAc layers were washed with brine, dried over MgSO$_4$, and concentrated in vacuo to give 40 mg (53%) of the title compound as a light brown residue. MS m/z: 288.1(M+1).

Step 6: N-((2S,3R)-4((S)-6-ethyl-2,2-spirocyclopentylchroman-4-ylamino)-3-hydroxy-1-phenylbutan-2-yl)-5-oxo-6-(2-fluorophenyl)-1,2,3,5-tetrahydroindolizine-8-carboxamide.TFA salt To a solution of (2S,3R)-3-amino-1-((S)-6-ethyl-2,2-spirocyclopentylchroman-4-ylamino)-4-phenylbutan-2-ol dihydrochloride salt and 6-(2-fluorophenyl)-3-methyl-5-oxo-1,2,3,5-tetrahydroindolizine-8-carboxylic acid (about 1 eq.) in 1 mL of DMF, was added DIEA (about 3-5 eq.) and HATU (about 1.1 eq.). The solution was stirred at room temperature and monitored by LC-MS for product formation. The reaction mixture was purified by reverse phase HPLC to give the title compound as a colorless residue. MS m/z: 664.3 (M+1).

136

Example 160

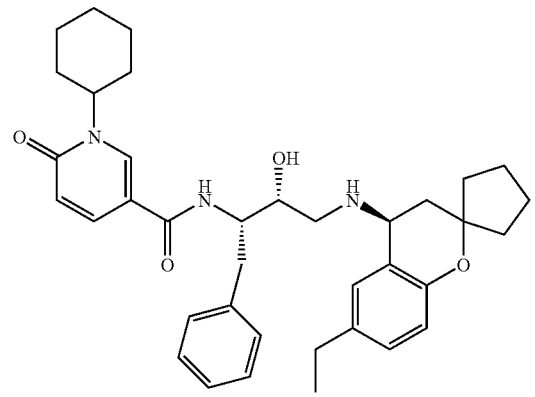

1-cyclohexyl-N-((2S,3R)-4((S)-6-ethyl-2,2-spirocyclopentylchroman4-ylamino))-3-hydroxy-1-phenylbutan-2-yl)-6-oxo-1,6-dihydropyridine-3-carboxamide.TFA salt

Step 1: Methyl 1-cyclohexyl-6-oxo-1,6-dihydropyridine-3-carboxylate

To a solution of 6-oxo-6H-pyran-3-carboxylate (1.14 g, 7.4 mmol, Aldrich) and 20 mL of MeOH was added cyclohexylamine (2.50 mL, 21.9 mmol, Aldrich). The solution was stirred at reflux for 16 hours, then concentrated in vacuo. The crude material was chromatographed through a Redi-Sep® pre-packed silica gel column (12 g), eluting with 5% to 20% EtOAc:hexane to give 460 mg (26%) of the title compound as a dark yellow oil. MS m/z: 236.4(M+1).

Step 2: 1-Cyclohexyl-6-oxo-1,6-dihydropyridine-3-carboxylic acid

To a solution of methyl 1-cyclohexyl-6-oxo-1,6-dihydropyridine-3-carboxylate (100 mg, 0.43 mmol) in 10 mL of THF:MeOH (3:1) was added 1M LiOH (1 mL, 1 mmol). The solution was stirred at room temperature until starting material was consumed as determined by LC-MS. The solution was then concentrated in vacuo, acidified with 2 N HCl to pH 2, and extracted with EtOAc (3×). The combined EtOAc layers were washed with brine, dried over MgSO$_4$, and concentrated in vacuo to give 60 mg (63%) of the title compound as a golden yellow solid. MS m/z: 222.1(M+1).

Step 3: 1-cyclohexyl-N-((2S,3R)-4((S)-6-ethyl-2,2-spirocyclopenlylchroman4-ylamino))-3-hydroxy-1-phenylbutan-2-yl)-6-oxo-1,6-dihydropyridine-3-carboxamide.TFA salt The title compound was obtained as a colorless residue using a procedure analogous to that described in step 6 of Example 161, by reacting (2S,3R)-3-amino-1-((S)-6-ethyl-2,2-spirocyclopentylchroman-4-ylamino)-4-phenylbutan-2-ol dihydrochloride salt and 1-cyclohexyl-6-oxo-1,6-dihydropyridine-3-carboxylic acid. MS m/z: 598.4(M+1).

Example 161

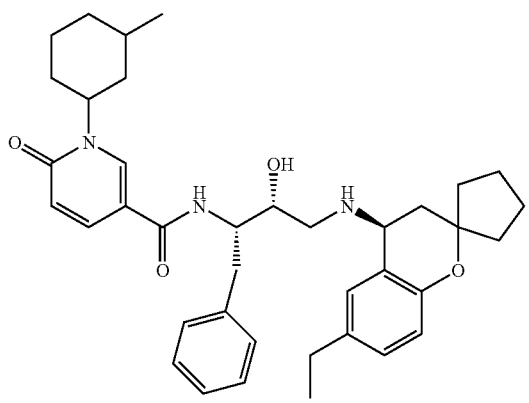

1-(3-Methylcyclohexyl)-N-((2S,3R)-4((S)-6-ethyl-2,2-spirocyclopentylchroman4-ylamino))-3-hydroxy-1-phenylbutan-2-yl)-6-oxo-1,6-dihydropyridine-3-carboxamide.TFA salt Step 1: 1-(3-Methylcyclohexyl)-6-oxo-1,6-dihydropyridine-3-carboxylic acid A solution of methyl 6-oxo-6H-pyran-3-carboxylate (620 mg, 4.0 mmol, Aldrich) and 3-methylcyclohexanamine (900 mg, 8.0 mmol, Pfaltz and Bauer) was heated in the Emry's optimizer microwave at 150° C. for 15 min. The resulting solution was transferred to a 50 mL round bottom flask with THF, then diluted with THF:MeOH to give approximately 40 mL of a 3:1 THF:MeOH solution. Add 1 M LiOH (6 mL, 6 mmol) and stir at RT overnight. The solution was concentrated in vacuo and the residue taken up in H$_2$O. The aqueous solution was extracted with ether (30 mL). 2 N HCl was added to acidify the aqueous solution to pH 2. The aqueous solution was extracted with EtOAc (3×) and the combined EtOAc layers dried over MgSO$_4$, and concentrated in vacuo to give 200 mg (21%) of the desired product as a light brown residue. MS m/z: 612.5(M+1).

Step 2: 1-(3-Methylcyclohexyl)-N-((2S,3R)-4((S)-6-ethyl-2,2-spirocyclopentylchroman4-ylamino))-3-hydroxy-1-phenylbutan-2-yl)-6-oxo-1,6-dihydropyridine-3-carboxamide.TFA salt The title compound was obtained as a colorless residue using a procedure analogous to that described in Step 6 of Example 161, by reacting (2S,3R)-3-amino-1-((S)-6-ethyl-2,2-spirocyclopentylchroman-4-ylamino)-4-phenylbutan-2-ol dihydrochloride salt and 1-(3-methylcyclohexyl)-6-oxo-1,6-dihydropyridine-3-carboxylic acid. MS m/z: 612.5(M+1).

Example 162

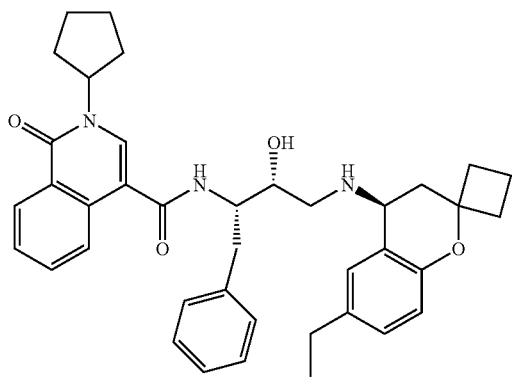

2-cyclopentyl-N-((2S,3R)-4((S)-6-ethyl-2,2-spirocyclobutylchroman4-ylamino))-3-hydroxy-1-phenylbutan-2-yl)-1-oxo-1,2-dihydroisoquinoline-4-carboxamide.TFA salt Step 1: 2-Cyclopentyl-1-oxo-1,2-dihydroisoquinoline-4-carboxylic acid To a solution of methyl-1-oxo-1,2-dihydroisoquinoline-4-carboxylate (780 mg, 3.8 mmol, Bionet), potassium carbonate (650 mg, 4.7 mmol, Aldrich), and 6 mL of DMF was added cyclopentyl iodide (0.52 mL, 4.5 mmol, Aldrich). The solution was stirred at RT for 4 h, then diluted with 50 mL of water. The solids were filtered and washed with CH$_2$Cl$_2$ and EtOAc. The filtrate was concentrated in vacuo and chromatographed through a Redi-Sep® pre-packed silica gel column (12 g), eluting with 0% to 15% EtOAc:hexane to give 240 mg (23%) of methyl 2-cyclopentyl-1-oxo-1,2-dihydroisoquinoline-4-carboxylate as an off-white solid. MS m/z: 272.3(M+1).

The solids were dissolved in 10 ml of THF:MeOH (3:1) and 1M LiOH (2 mL, 2.0 mmol) was added. After stirring at room temperature overnight, the pH was adjusted to 2 with 2N HCl and extracted with EtOAc (3×). The combined organic layers were washed with brine, dried over MgSO$_4$, and concentrated in vacuo to give 230 mg (100%) of the title compound as a white solid. MS m/z: 258.0(M+1).

Step 2: 2-cyclopentyl-N-((2S,3R)-4((S)-6-ethyl-2,2-spirocyclobutylchroman4-ylamino))-3-hydroxy-1-phenylbutan-2-yl)-1-oxo-1,2-dihydroisoquinoline-4-carboxamide.TFA salt The title compound was obtained as an off-white solid using a procedure analogous to that described in Step 6 of Example 161, by reacting (2S,3R)-3-amino-1-((S)-6-ethyl-2,2-spirocyclobutylchroman-4-ylamino)-4-phenylbutan-2-ol

Example 163

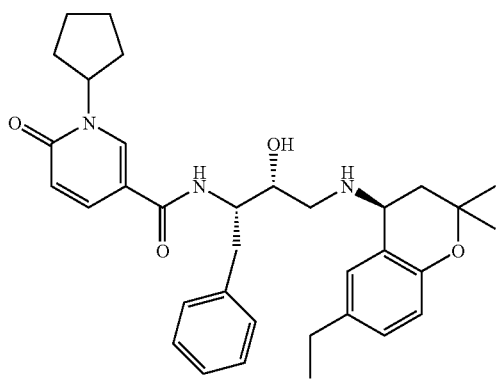

1-cyclopentyl-N-((2S,3R)-4((S)-6-ethyl-2,2-dimethylchroman4-ylamino))-3-hydroxy-1-phenylbutan-2-yl)-6-oxo-1,6-dihydropyridine-3-carboxamide TFA salt The title compound was obtained as a light brown residue using a procedure analogous to that described in Step 6 of Example 159, by reacting (2S,3R)-3-amino-1-((S)-6-ethyl-2, 2-dimethylchroman-4-ylamino)-4-phenylbutan-2-ol dihydrochloride salt and 1-cyclopentyl-6-oxo-1,2-dihydropyridine-3-carboxylic acid. MS m/z: 558.3(M+1).

Example 164

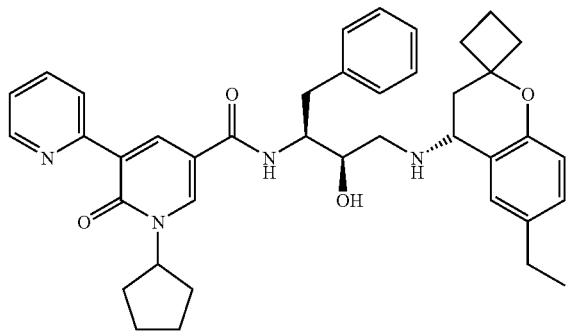

1-Cyclopentyl-N-((2S,3R)-4-((S)-6-ethyl-2,2-spirocyclobutylchroman-4-ylamino)-3-hydroxy-1-phenylbutan-2-yl)-6-oxo-5-(pyridin-2-yl)-1,6-dihydropyridine-3-carboxamide Step 1: methyl 6-(cyclopentyloxy)-5-(pyridin-2-yl)nicotinate A solution of methyl 5-bromo-6-(cyclopentyloxy) nicotinate (4.53 g, 15.1 mmol) and 2-(tributylstannyl) pyridine (5.00 g, 13.6 mmol) was stirred in 100 mL of DMF at 120° C. for 6 h. The resulting solution was cooled and concentrated in vacuo. The crude reaction mixture was then partitioned between EtOAc and water. The layers were separated and the aqueous layer was extracted 1×EtOAc. The organic phases were combined, washed 3×brine, dried over MgSO$_4$, filtered and concentrated under reduced pressure. The residue was taken up in CH$_2$Cl$_2$ and loaded on to a 40 g pre-packed silica gel column. Elution with 0-30% EtOAc:hexanes provided the title compound as an off-white powder (1.71 g, 38%). MS m/z: 299 (M+1).

Step 2: methyl 6-oxo-5-(pyridin-2-yl)-1,6-dihydropyridine-3-carboxylate

A solution of boron tribromide (1.0 M in CH$_2$Cl$_2$, 10.6 mL, 10.6 mmol) was added to a solution of the nicotinate (Step 1, 1.44 g, 4.81 mmol) in 40 mL of CH$_2$Cl$_2$ at −10° C. The cooling bath was removed and stirring was continued at room temperature for 16 h. The reaction mixture was neutralized with saturated NaHCO$_3$ solution and the resultant tan precipitate was filtered and washed with copious amounts of H$_2$O to give 0.77 g (70%) of the title compound. MS m/z: 231 (M+1).

Step 3: methyl 1-cyclopentyl-6-oxo-5-(pyridin-2-yl)-1,6-dihydropyridine-3-carboxylate Methyl 6-oxo-5-(pyridin-2-yl)-1,6-dihydropyridine-3-carboxylate (Step 2, 210 mg, 0.91 mmol), cyclopentyl iodide (196 mg, 1.0 mmol) and potassium carbonate (150 mg, 1.1 mmol) were stirred at room temperature in 2 mL of DMF for 24 h. The reaction mixture was quenched with H$_2$O and extracted 3× with EtOAc. The combined organic extracts were washed 3× with brine, dried over MgSO$_4$, filtered and concentrated in vacuo. The residue was taken up in CH$_2$Cl$_2$ and loaded on to a 5 g pre-packed silica gel column and purified. Elution with 0-30% EtOAc:hexanes gave the title compound as an off-white powder (57 mg, 21%). MS m/z: 299 (M+1).

Step 4: 1-Cyclopentyl-6-oxo-5-(pyridin-2-yl)-1,6-dihydropyridine-3-carboxylic acid The pyridone (Step 3, 57 mg, 0.19 mmol) and lithium hydroxide (16 mg, 0.38 mmol) were stirred at room temperature in a solution of 2 mL of MeOH and 0.3 mL of H$_2$O, for 2 h. The reaction mixture was diluted with water and the pH was adjusted to pH ~2 with concentrated H$_2$SO$_4$. The mixture was extracted 3×20% IPA:CHCl$_3$ and the combined organic fractions were dried over MgSO$_4$ and concentrated. The crude residue was purified to obtain the title compound as a white powder (48 mg, 89%). MS m/z: 285 (M+1).

Step 5: 1-Cyclopentyl-N-((2S,3R)-4-((R)-6-ethyl-2, 2-spirocyclobutylchroman-4-ylamino)-3-hydroxy-1-phenylbutan-2-yl)-6-oxo-5-(pyridin-2-yl)-1,6-dihydropyridine-3-carboxamide The acid (Step 4, 19 mg, 0.066 mmol) was dissolved in 2 mL of DMF and (2R,3S)-3-amino-1-((R)-6-ethyl-2,2-spirocyclobutylchroman-4-ylamino)-4-phenylbutan-2-ol (25 mg, 0.066 mmol), HOBt (10 mg, 0.066 mmol), N, N-diisopropylethylamine (17 mg, 0.13 mmol) and EDCI (13 mg, 0.066 mmol) were added sequentially. The reaction mixture was stirred at room temperature for 10 h before it was quenched with 2 drops of 5 N HCl. The residue was purified directly by reverse phase HPLC (elution 5-95% CH$_3$CN(0.1% TFA):water(0.1% TFA)). The appropriate fractions were combined and concentrated to give the corresponding TFA salt of the title compound as an off-white powder (10 mg, 23%). MS m/z: 647 (M+1).

Example 165

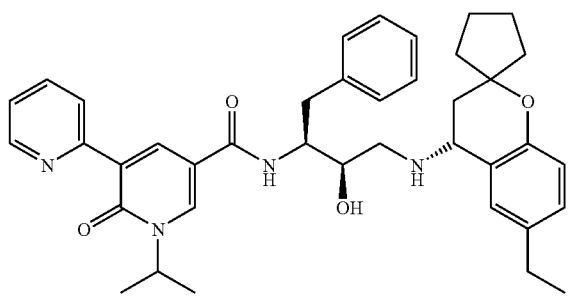

N-((2S,3R)-4-((R)-6-ethyl-2,2-spirocyclopentylchroman-4-ylamino)-3-hydroxy-1-phenylbutan-2-yl)-1-isopropyl-6-oxo-5-(pyridin-2-yl)-1,6-dihydropyridine-3-carboxamide The title compound was obtained, as an off-white solid, by a method analogous to that described in Example 164. MS m/z: 635 (M+1).

Example 166

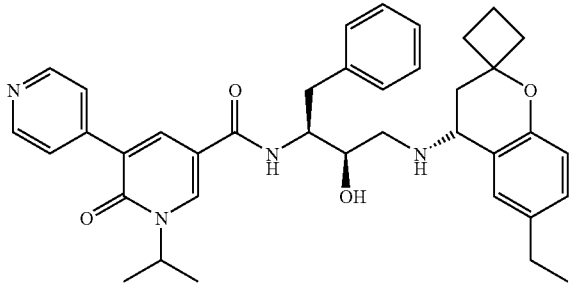

N-((2S,3R)-4-((R)-6-ethyl-2,2-spirocyclobutylchroman-4-ylamino)-3-hydroxy-1-phenylbutan-2-yl)-1-isopropyl-6-oxo-5-(pyridin-4-yl)-1,6-dihydropyridine-3-carboxamide Step 1: Methyl 6-(cyclopentyloxy)-5-(pyridin-4-yl)nicotinate Methyl 5-bromo-6-(cyclopentyloxy)-1,6-dihydropyridine-3-carboxylate (2.50 g, 7.94 mmol) was dissolved in DME (10 mL) and pyridin-4-ylboronic acid (813 mg, 6.61 mmol), DPPF-PdCl$_2$ (108 mg, 0.13 mmol, Strem) and water (0.5 mL, 28 mmol) were added. The mixture was stirred at 40° C. for 4 h. The reaction mixture was cooled to RT, diluted with H$_1$O and extracted 3× with EtOAc. The combined organic extracts were washed 1× with brine, dried (MgSO$_4$), filtered and concentrated in vacuo. The crude residue was purified by silica gel chromatography (40 g pre-packed column, elution 0-30% EtOAc:hexanes) to give the title compound (608 mg, 31%). MS m/z: 299 (M+1).

Step 2: Methyl 6-oxo-5-(pyridin-4-yl)-1,6-dihydropyridine-3-carboxylate

The title compound was obtained, as a brown solid, by a method analogous to that described in Step 2 of Example 164. MS m/z: 231 (M+1).

Step 3: Methyl 1-isopropyl-6-oxo-5-(pyridin-4-yl)-1,6-dihydropyridine-3-carboxylate Methyl 1-isopropyl-6-oxo-5-(pyridin-4-yl)-1,6-dihydropyridine-3-carboxylate was prepared by a method analogous to that described in Step 3 of Example 164. The title compound was obtained as a white solid (77 mg, 33%). MS m/z: 273 (M+1).

Step 4: 1-isopropyl-6-oxo-5-(pyridin-4-yl)-1,6-dihydropyridine-3-carboxylic acid 1-Isopropyl-6-oxo-5-(pyridin-4-yl)-1,6-dihydropyridine-3-carboxylic acid was synthesized by a method analogous to that described in Step 4 of Example 164, and isolated as an off-white solid (60 mg, 82%). MS m/z: 259 (M+1).

Step 5: N-((2S,3R)-4-((R)-6-ethyl-2,2-spirocyclobutylchroman-4-ylamino)-3-hydroxy-1-phenylbutan-2-yl)-1-isopropyl-6-oxo-5-(pyridin-4-yl)-1,6-dihydropyridine-3-carboxamide The title compound was obtained, as a brown solid, by a method analogous to that described in Step 5 of Example 164. The title compound, as a TFA salt, was obtained as an off-white solid. MS m/z: 718 (M+1).

Example 167

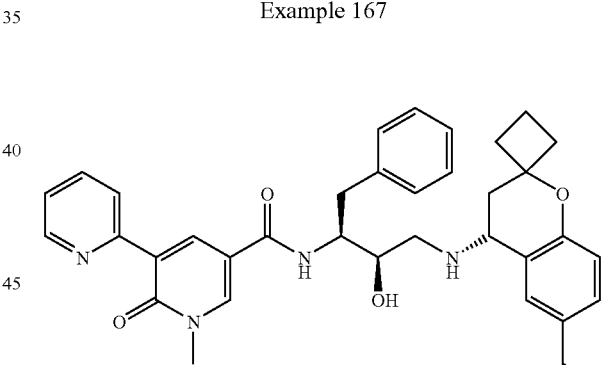

N-((2S,3R)-4-((R)-6-ethyl-2,2-spirocyclobutylchroman-4-ylamino)-3-hydroxy-1-phenylbutan-2-yl)-1-methyl-6-oxo-5-(pyridin-2-yl)-1,6-dihydropyridine-3-carboxamide Step 1: Methyl 1-methyl-6-oxo-5-(pyridin-2-yl)-1,6-dihydropyridine-3-carboxylate Methyl 5-bromo-1-methyl-6-oxo-1,6-dihydropyridine-3-carboxylate (57 mg, 0.23 mmol), 2-(tributylstannyl)pyridine (85 mg, 0.23 mmol) and tetrakis(triphenylphosphine)palladium (13 mg, 0.012 mmol, Strem) were stirred in 1.5 mL of dioxane at 90° C. for 16 h. The reaction mixture was cooled to RT, diluted with H$_2$O and extracted with EtOAc (2×). The combined organic extracts were washed 1× with brine, dried over MgSO$_4$, filtered and concentrated in vacuo. Purification of the crude residue by column chromatography (4 g prepacked column, elution 0-30% EtOAc/Hexanes) gave the title compound (22 mg, 39%) as a light yellow solid. MS m/z: 245 (M+1).

Step 2: N-((2S,3R)-4-((R)-6-ethyl-2,2-spirocyclobutylchroman-4-ylamino)-3-hydroxy-1-phenylbutan-2-yl)-1-methyl-6-oxo-5-(pyridin-2-yl)-1,6-dihydropyridine-3-carboxamide Methyl 1-methyl-6-oxo-5-(pyridin-2-yl)-1,6-dihydropyridine-3-carboxylate (22 mg, 0.090 mmol) and lithium hydroxide monohydrate (4 mg, 0.090 mmol) were stirred in MeOH (5 mL) and $H_2O$ (0.2 mL) for 24 h. The solvent was removed under reduced pressure and the crude acid was used directly in the next step.

The title compound was obtained, as a brown solid, by a method analogous to that described in step 5 of Example 164, using the above acid (20 mg, 0.090 mmol), (2R,3S)-3-amino-1-((R)-6-ethyl-2,2-spirocyclobutylchroman-4-ylamino)-4-phenylbutan-2-ol (33 mg, 0.090 mmol), HOBt (12 mg, 0.090 mmol), N, N-diisopropylethylamine (22 mg, 0.17 mmol) and EDCI (17 mg, 0.090 mmol). The corresponding TFA salt of the title compound was obtained as an off-white solid. MS m/z: 593 (M+1).

Example 168

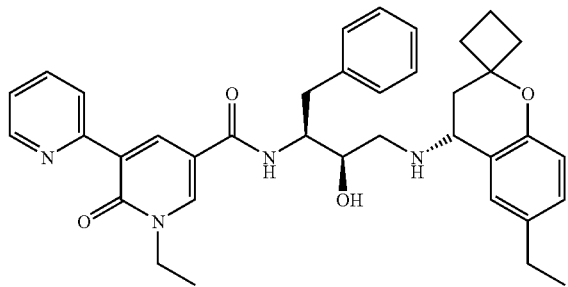

1-ethyl-N-((2S,3R)-4-((R)-6-ethyl-2,2-spirocyclobutylchroman-4-ylamino)-3-hydroxy-1-phenylbutan-2-yl)-6-oxo-5-(pyridin-2-yl)-1,6-dihydropyridine-3-carboxamide The title compound was obtained by a method analogous to that described in Example 167. The title compound was obtained as an off-white solid TFA salt. MS m/z: 607 (M+1).

Example 169

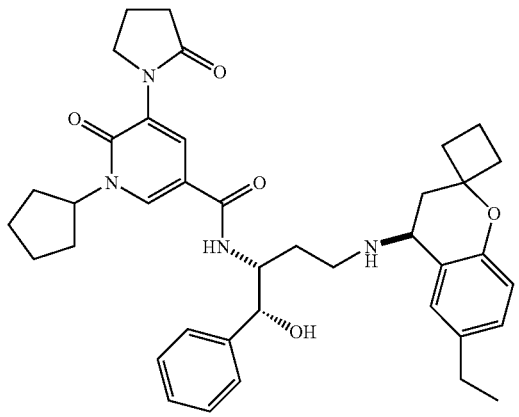

1-cyclopentyl-N-((1R,2R)-4-((S)-6-ethyl-2,2-spirocyclobutyl-3,4-dihydro-2H-chromen-4-ylamino)-1-hydroxy-1-phenylbutan-2-yl)-6-oxo-5-(2-oxopyrrolidin-1-yl)-1,6-dihydropyridine-3-carboxamide Step 1: (R)-2-(benzyloxycarbonylamino)pent-4-enoic acid. (R)-2-(benzyloxycarbonyl)pent-4-enoic acid The title compound was prepared from commercially available D-allylglycine according the method described in Organic Process Research & Development, 6:762-766 (2002).

Step 2: Benzyl (1R,2R)-1-hydroxy-1-phenylpent-4-en-2-ylcarbamate

To a mixture of HATU (0.915 g, 2.41 mmol), (R)-2-(benzyloxycarbonyl)pent-4-enoic acid (0.400 g, 1.60 mmol), N-methoxymethanamine hydrochloride (0.188 g, 1.93 mmol) in $CH_2Cl_2$ (20 mL) at 0° C. was added triethylamine (0.558 ml, 4.01 mmol). The mixture was allowed to stir at 0° C. for 20 min then warmed to RT for 30 min. The reaction was diluted with $CH_2Cl_2$ (20 mL) and washed with 1 M HCl (30 mL), 9% $Na_2CO_3$ (30 mL), brine (30 mL), dried over $Na_2SO_4$, filtered through a small plug of silica gel and washed with ether (10 mL) and concentrated. The crude material was used without further purification. MS m/z=293 [M+1]⁺. Calc'd for $C_{15}H_{20}N_2O_4$: 292.

To a solution of (R)-benzyl 1-(methoxy(methyl)amino)-1-oxopent-4-en-2-ylcarbamate (0.468 g, 1.60 mmol) in THF (10 mL) at 0° C. was added phenylmagnesium bromide (1.0 M in THF, 4.80 ml, 4.80 mmol). The mixture was allowed to warm to room temperature and stir overnight. To the mixture was added saturated aqueous $NH_4Cl$ (10 mL). The volatiles were removed under reduced pressure. The residue was diluted with water and extracted with $Et_2O$ (3×20 mL). The combined organics were washed with HCl (1 M, 20 mL), water (20 mL), brine (20 mL), dried over $Na_2SO_4$, filtered and concentrated. The crude was used without further purification. MS m/z=310 [M+1]⁺. Calc'd for $C_{19}H_{19}NO_3$: 309.

To (R)-benzyl 1-oxo-1-phenylpent-4-en-2-ylcarbamate (2.13 g, 6.89 mmol) in THF (50 mL) at −78° C. under argon was added lithium tri-sec-butylborohydride (20.7 ml, 20.7 mmol). Allowed the mixture to stir for 45 min. Quenched the reaction with saturated aqueous Rochelle's salt (50 mL) and the volatiles were removed in vacuo. The aqueous residue was extracted with ether (3×50 mL). The ether was combined and washed with brine (20 mL), dried over $Na_2SO_4$ and filtered. The filtrate was evaporated onto silica gel and purified via flash chromatography (0% to 20%; EtOAc in hexanes). MS m/z=334 [M+Na]⁺. Calc'd for $C_{19}H_{21}NO_3$: 311.

Step 3: (4R,5R)-benzyl 2,2-dimethyl-4-(2-oxoethyl)-5-phenyloxazolidine-3-carboxylate To a solution of benzyl (1R,2R)-1-hydroxy-1-phenylpent-4-en-2-ylcarbamate (1.14 g, 3.66 mmol) in $CH_2Cl_2$ (50 mL) and 2,2-dimethoxypropane (15.0 ml, 122 mmol) was added p-toluenesulfonic acid monohydrate (0.070 g, 0.366 mmol) and allowed to stir at room temperature overnight. The reaction was diluted with $CH_2Cl_2$ (100 mL), washed with 9% $Na_2CO_3$ (20 mL), brine (20 mL), dried over $Na_2SO_4$, filtered and concentrated. MS m/z=352 [M+1]⁺. Calc'd for $C_{22}H_{25}NO_3$: 351.

To the crude (4R,5R)-benzyl 4-allyl-2,2-dimethyl-5-phenyloxazolidine-3-carboxylate (1.29 g, 3.66 mmol) in THF (50 mL) and water (20 mL) was added osmium tetroxide (0.45 ml, 0.0180 mmol, 4%) solution. The reaction was stirred for 10 min, after which sodium periodate (3.91 g, 18.3 mmol) was added portion wise over 1 hr. Stirring was continued for 2 h. Saturated aqueous $Na_2S_2O_3$ was added and the reaction was stirred for 15 min. The volatiles were removed in vacuo and the aqueous residue extracted with $Et_2O$ (3×50 mL). The combined ether layers were washed with water (20 mL), brine (20 mL), dried over $Na_2SO_4$, filtered and concentrated. The crude residue was evaporated onto silica gel and purified via flash chromatography (0% to 20%; EtOAc in hexanes) to afford (4R,5R)-benzyl 2,2-dimethyl-4-(2-oxoethyl)-5-phenyloxazolidine-3-carboxylate. MS m/z=354 $[M+1]^+$. Calc'd for $C_{21}H_{23}NO_4$: 353.

Step 4: (4R,5R)-benzyl 4-(2-(tert-butoxycarbonyl)ethyl)-2,2-spirocyclobutyl-5-phenyloxazolidine-3-carboxylate A solution of (4R,5R)-benzyl 2,2-dimethyl-4-(2-oxoethyl)-5-phenyloxazolidine-3-carboxylate (0.184 g, 0.521 mmol) and (S)-6-ethyl-2,2-spriocyclobutyl-3,4-dihydro-2H-chromen-4-amine (0.226 g, 1.04 mmol) were allowed to stir for 10 min in THF (5 mL) at RT. Sodium triacetoxyborohydride (0.166 g, 0.781 mmol) was added and the mixture was allowed to stir for an additional 30 min. Di-tert-butyl dicarbonate (0.375 g, 1.72 mmol) was added and the mixture was stirred at RT overnight. The reaction was quenched with 5 mL aqueous Rochelle's salt, and stirred for 10 min. The volatiles were removed in vacuo and the crude aqueous residue was extracted with $CH_2Cl_2$ (3×15 mL). The combined organics were washed with brine (10 mL), dried over $Na_2SO_4$ and filtered. The crude filtrate was evaporated onto silica gel and purified via flash chromatography (0% to 20%; EtOAc in hexanes). MS m/z=643$[M+1]^+$. Calc'd for $C_{39}H_{50}N_2O_6$: 642.

Step 5: Tert-butyl (3R,4R)-3-amino-4-hydroxy-4-phenylbutyl((S)-6-ethyl-2,2-spirocyclobutyl-3,4-dihydro-2H-chromen-4-yl)carbamate To an argon purged solution of (4R,5R)-benzyl 4-(2-(tert-butoxycarbonyl)ethyl)-2,2-spirocyclobutyl-5-phenyloxazolidine-3-carboxylate (0.324 g, 0.495 mmol) in EtOH was added palladium on carbon (10%) (0.0527 g, 0.0495 mmol). Hydrogen was bubbled through the mixture for 45 min and the mixture was then purged with argon. The reaction was filtered through a 0.25 um filter. 3 props of HOAc was added and the reaction was stirred overnight at 0° C. The mixture was concentrated, taken up in $CH_2Cl_2$ and washed with 9% $Na_2CO_3$ (5 mL), brine (10 mL), dried over $Na_2SO_4$, filtered and concentrated. The crude residue was used without further purification. MS m/z=481 $[M+1]^+$. Calc'd for $C_{29}H_{40}N_2O_4$: 480.

Step 6: 1-cyclopentyl-N-((1R,2R)-4-((S)-6-ethyl-2,2-spirocyclobutyl-3,4-dihydro-2H-chromen-4-ylamino)-1-hydroxy-1-phenylbutan-2-yl)-6-oxo-5-(2-oxopyrrolidin-1-yl)-1,6-dihydropyridine-3-carboxamide To 1-cyclopentyl-6-oxo-5-(2-oxopyrrolidin-1-yl)-1,6-dihydropyridine-3-carboxylic acid (0.0683 g, 0.235 mmol), HATU (0.134 g, 0.353 mmol), tert-butyl (3R,4R)-3-amino-4-hydroxy-4-phenylbutyl((S)-6-ethyl-2,2-spirocyclobutyl-3,4-dihydro-2H-chromen-4-yl)carbamate (0.113 g, 0.235 mmol) in $CH_2Cl_2$ (4 mL) was added diisopropylethylamine (0.123 ml, 0.705 mmol). The mixture was stirred at RT for 20 min. Anhydrous HCl in ether (1M, 15 mL) was added and the reaction was allowed to stir for 5 h. The mixture was concentrated, and purified on an RP-HPLC to obtain the title compound. MS m/z=653$[M+1]^+$. Calc'd for $C_{39}H_{48}N_4O_5$: 652

Example 170

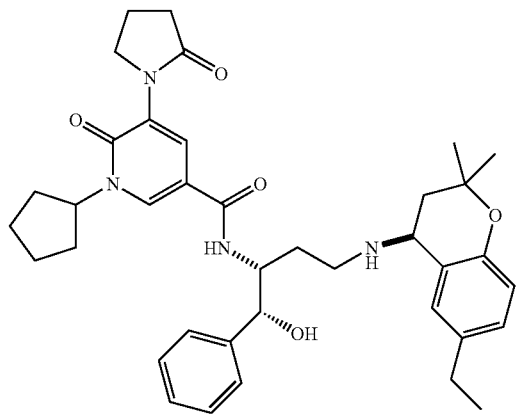

1-cyclopentyl-N-((1R)-3-(((4S)-6-ethyl-2,2-dimethyl-3,4-dihydro-2H-chromen-4-yl)amino)-1-((S)-hydroxy(phenyl)methyl)propyl)-6-oxo-5-(2-oxo-1-pyrrolidinyl)-1,6-dihydro-3-pyridinecarboxamide The title compound was made by a method analogous to that described in Example 169. MS: 642 (M+H$^+$).

Example 171

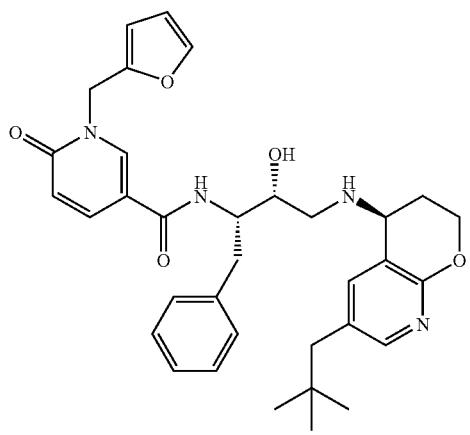

1-(furan-2-ylmethyl)-N-((2S,3R)-3-hydroxy-4-((S)-6-neopentyl-2,2-spirocyclobutyl-3,4-dihydro-2H-pyrano[2,3-b]pyridin-4-ylamino)-1-phenylbutan-2-yl)-6-oxo-1,6-dihydropyridine-3-carboxamide Step 1: 2-Fluoro-5-neopentylpyridine To a stirred, cooled (−78° C.) solution of (1s,5s)-9-methoxy-9-bora-bicyclo[3.3.1]nonane (260 ml, 260 mmol) in THF (200 ml) was added neopentylmagnesium chloride (260 ml, 260 mmol) drop-wise. The mixture slowly warmed to RT and stirred for 3 h. The white solid was filtered off and washed thoroughly with pentane. The filtrate was concentrated to give the light yellow oil. This residue was diluted with p-dioxane (300 ml) and to this was added 5-bromo-2-fluoropyridine (35.20 g, 200 mmol), (Ph$_3$P)$_4$Pd (9.7 g, 8.4 mmol), and 5 N NaOH (168 ml, 838 mmol). The resulting reaction mixture was heated at 95° C. in 16 h. The mixture was cooled and added 5 N HCl (168 ml) and the reaction was stirred for 1 h and extracted with ether (3×). The organic layers were washed with brine, dried over MgSO$_4$, concentrated and purified by ISCO (5% EtOAc/Hexanes) to give the light yellow oil. MS (m+1): 168.2.

Step 2: (1-allylcyclobutoxy)(tert-butyl)dimethylsilane

To a 2 L three-necked round bottom flask was added cyclobutanone (12.47 g, 178 mmol) and THF (1200 mL). The solution was cooled to −78° C. Allylmagnesium bromide, 1 M in ether (196 ml, 196 mmol) was added via an addition funnel over 30 min. The reaction was allowed to stir for 30 min. MeOH (30 mL) was added to the reaction and the cooling bath was removed. The solution was stirred for about 10 min, then HCl (0.5 M, 500 mL) was added. The reaction was transferred to a separatory funnel and extracted with Ether (2×1 L). The organic extracts were dried over MgSO$_4$ and concentrated in vacuo (Note: Volatile Product). The final ~100 mL of concentrate were re-dissolved in 1 L of DCM, dried over MgSO$_4$ and filtered. TEA (61.5 ml, 442 mmol) was added followed by tert-butyldimethylsilyl triflate (66.0 ml, 287 mmol). The reaction was cooled in the warming dry ice bath used earlier in the experiment. After 30 min, the reaction was checked by TLC and found to be complete. HCl (0.5 M, 500 mL) was added to quench the reaction. The reaction layers were separated and the aqueous layer extracted with 600 mL of ether. The combined organic layers were dried over MgSO$_4$ and concentrated in vacuo. The resulting oil was loaded onto a 600 mL Frit almost full of silica gel and purified, eluting with 1400 mL of hexane. The hexane filtrate was carefully concentrated in vacuo to give (1-allylcyclobutoxy)(tert-butyl)dimethylsilane, as a colorless liquid that also contained residual hexane. The crude material was carried on without further purification.

Step 3: 3-(1-(tert-butyldimethylsilyloxy)cyclobutyl)propane-1,2-diol

To a 2 L round bottomed flask was added (1-allylcyclobutoxy) (tert-butyl)dimethylsilane (previous step) and H$_2$O/t-BuOH (1:1, 1 L). NMO (32.68 g, 279 mmol) was added to the mixture. After stirring for 5 min the solution was found to be homogenous. Osmium tetroxide (1.00 g, 3.93 mmol) was added and the reaction was stirred at RT. After 2 h, TLC revealed the reaction to be complete. 500 mL of H$_2$O and sodium sulfite (19.5 g, 155 mmol) were added and the reaction was stirred for another hour. The aqueous solution was extracted with ether (2×1 L). The combined organics were concentrated in vacuo to give 3-(1-(tert-butyldimethylsilyloxy)cyclobutyl)propane-1,2-diol, as a light yellow oil. The oil contained some t-BuOH, but was carried forward without further purification.

Step 4: 2-(1-(tert-butyldimethylsilyloxy)cyclobutyl)acetaldehyde

To a 2 L round bottomed flask was added 3-(1-(tert-butyldimethylsilyloxy)cyclobutyl)propane-1,2-diol (80.0 g, 307 mmol) and THF/t-BuOH/H$_2$O (1:1:2, 2 L). Sodium periodate (120.15 g, 562 mmol) was added and the reaction was stirred at RT. After addition the solution became yellow and thickened. The stirrer was adjusted to maintain stirring. After 1.5 h, the reaction is complete as monitored by TLC (10% EtOAc/Hexane). 300 mL H$_2$O was added to the reaction and the aqueous solution was extracted with ether (3×600 mL). The combined organics were dried over MgSO$_4$ and carefully concentrated in vacuo (Note: volatile product). The oil was re-dissolved in 200 mL of benzene and azeotroped to remove any excess t-BuOH. The crude oil was adsorbed onto a plug of silica gel and chromatographed through a glass column, eluting with 3% EtOAc in hexane, to provide a golden oil after concentrating in vacuo (Note: volatile product). The oil was dissolved in 200 mL of benzene and concentrated in vacuo. The mixture was further concentrated to remove excess benzene to give 2-(1-(tert-butyldimethylsilyloxy)cyclobutyl) acetaldehyde (67.5 g, 296 mmol, 96.2% yield). The title compound yielded contained some benzene and was carried forward without further purification.

Step 5: 2-(1-(tert-butyldimethylsilyloxy)cyclobutyl)-1-(2-fluoro-5-neopentylpyridin-3-yl)ethanol 2,2,6,6-tetramethylpiperidine (13.0 ml, 76.5 mmol) was dissolved in 500 ml THF and cooled to −78° C. Butyllithium (26.8 ml, 67.0 mmol) was added over the period of 10 min and the reaction was allowed to warm up to 0° C. and kept there for 3 min. The mixture was cooled back to −78° C. and a solution of 2-fluoro-5-neopentylpyridine (8.000 g, 47.8 mmol) in 10 ml THF was added over the period of 30 min. The mixture was stirred for 20 min at the same temperature and a solution of 2-(1-(tert-butyldimethylsilyloxy)cyclobutyl) acetaldehyde (19.7 g, 86.1 mmol) in 25 ml THF was added over the period of 20 min. The reaction was stirred for 15 min at the same temperature and hydrolyzed with 200 ml of H$_2$O. The mixture was allowed to warm up to room temp and extracted 2 times with 1 L EtOAc (each). The combined organic extracts were dried over MgSO$_4$ and evaporated. The crude material was used without further purification. MS found 396.2.

Step 6: (R/S)-6-neopentyl-2,2-spirocyclobutyl-3,4-dihydro-2H-pyrano[2,3-b]pyridin-4-ol 2-(1-(tert-butyldimethylsilyloxy)cyclobutyl)-1-(2-fluoro-5-neopentylpyridin-3-yl)ethanol (approx 48 mmol (est.)) was dissolved in 500 ml dry THF and tetrabutylammonium fluoride, 1.0 m in THF (50 ml, 50 mmol) was added at RT. The red solution was stirred for 15 min and filtered through a 600 ml frit, almost filled all the way up with silica. The remaining material was washed of the silica with 1 L dry THF. 300 ml Dry THF was added and sodium hydride (NaH) (4.00 g, 174 mmol) was added portion wise at RT. The mixture was heated to 65° C. for 1 h. The reaction was hydrolyzed with 50 ml H$_2$O at 0° C. and evaporated. The mixture was extracted 3× with 300 ml EtOAc and dried over MgSO$_4$. The material was re-dissolved in 1800 ml THF and treated with NaH (4.00 g, 174 mmol) again. This time no extensive bubbling was observed and the mixture was heated to 65° C. for 2 h. The mixture was cooled to 0° C. and hydrolyzed with 50 ml H$_2$O and evaporated. The mixture was extracted with 300 ml EtOAc (each), dried over MgSO$_4$ and evaporated. The mixture was filtered through a plug of silica and used without further purification.

Step 7: 6-neopentyl-2,2-spirocyclobutyl-2,3-dihydropyrano[2,3-b]pyridin-4-one The product from step 6 (10.000 g, 38.3 mmol) was dissolved in 400 ml DCM and DMP (Dess Martin Reagent) (21.1 g, 49.7 mmol) and monosodium hydrogen carbonate (14.5 g, 172 mmol) were added. The mixture was stirred for 2 h and 50 ml MeOH was added. Stirring was continued for 30 min and the mixture was filtrated and 100 ml NaOH (1 M, aq.) was added to the filtrate. This mixture was extracted 3× with 400 ml EtOAc (each) dried over MgSO4 and evaporated. Glass col. chrom. (30-50% EtOAc in hex.) gave the title compound (9.10 g, 35.1 mmol, 91.7% yield) as a yellow solid.

Step 8: (R)-6-neopentyl-2,2-spirocyclobutyl-3,4-dihydro-2H-pyrano[2,3-b]pyridin-4-ol Borane DMS complex (7.07 ml, 74.5 mmol) and (S)-1-methyl-3,3-diphenyl-hexahydropyrrolo[1,2-c][1,3,2]oxazaborole (5.32 ml, 5.32 mmol) were dissolved in 500 ml of toluene and cooled to 0° C. A solution of the product from Step 7 (13.80 g, 53.2 mmol) in 50 ml toluene was added over the period of 3 h. 50 ml MeOH was added at the same temperature and the mixture was warmed up to RT. After 30 min, 25 ml (1 M) HCl (aq.) was added and stirring was continued for 1 h.

The mixture was neutralized with NaOH (1 M; aq.) and extracted 3 times with 350 ml EtOAc (each).

The combined organic extracts were dried over MgSO$_4$ and evaporated. The crude product was dissolved in 350 ml MeOH and 1.5 g Pd/C was added and stirring was continued under N$_2$ for 2 h. (See Org. Lett., 465-467 (2001)) for borane amine complexes and cleavage with Pd). The mixture was filtered and evaporated and used without further purification. MS found: 262.1.

Step 9: (s)-4-azido-6-neopentyl-2,2-spirocyclobutyl-3,4-dihydro-2H-pyrano[2,3-b]pyridine Product from Step 8 (13.00 g, 49.74 mmol), diphenyl azidophosphate (16.08 ml, 74.61 mmol) and DBU (11.16 ml, 74.61 mmol) were dissolved in 250 ml of toluene and stirred overnight. The mixture was filtered through a pad of silica (600 ml glass sintered frit filled all the way with silica; wash with 15% EtOAc in Hex.) and evaporated. The crude product was dissolved without further purification in the next step.

Step 10: (S)-6-neopentyl-2,2-spirocyclobutyl-3,4-dihydro-2H-pyrano[2,3-b]pyridin-4-amine Product from Step 9 (12.020 g, 42 mmol) was dissolved in 500 ml THF and cooled to −20° C. Lithium aluminum hydride (50 ml, 100 mmol) was added and stirring was continued for 2.5 h at the same temperature. 15 g of Na$_2$SO$_4$ decahydrate was added carefully and stirring of the reaction was continued for 20 min followed by warming the reaction up to RT. The mixture was filtered and purified via glass col. chromatography (10-15% MeOH in DCM): Product 1 (9.800 g, 38 mmol, 90% yield) as a yellow solid. MS found: 261.2.

Step 11: Tert-Butyl (2S,3R)-3-(tert-butyldimethylsilyloxy)-1-phenylpent-4-en-2-ylcarbamate To a 250 mL round bottom flask containing tert-butyl (2S,3R)-3-hydroxy-1-phenylpent-4-en-2-ylcarbamate (3.080 g, 11 mmol) was added DCM (50 mL) and the mixture was allowed to stir at 23° C. for 2 min. At this time, TEA (4.7 ml, 33 mmol) was added via syringe before dropwise addition of tert-butyldimethylsilyl triflate (2.8 ml, 12 mmol). The reaction was allowed to stir for 4 h and then poured into saturated ammonium chloride. The aqueous layer was extracted with DCM (3×75 mL) and the combined organics were washed with brine and dried with sodium sulfate. The solution was filtered and concentrated to provide 4.47 g of a yellow solid. The material was taken on to the next step without any further purification.

Step 12: tert-Butyl (2S,3S)-3-(tert-butyldimethylsilyloxy)-4-oxo-1-phenylbutan-2-ylcarbamate To a 500 mL round bottom flask containing tert-butyl (2S,3R)-3-(tert-butyldimethylsilyloxy)-1-phenylpent-4-en-2-ylcarbamate (1.200 g, 3.06 mmol) was added DCM (30 mL) and the mixture was allowed to stir at −78° C. for 5 min. At this time, ozone was bubble through the reaction until a blue color appeared and then oxygen was bubbled through the reaction until it was clear. DMS (6.80 ml, 91.9 mmol) was added and the reaction was allowed to warm to 23° C. and stirred for 4 h before it was filtered through a plug of silica gel (elute with 10% EtOAc in DCM) and concentrated to afford a colorless oil (1.17 g).

Step 13: tert-Butyl (2S,3R)-3-(tert-butyldimethylsilyloxy)-4-((S)-6-neopentyl-2,2-spirocyclobutyl-3,4-dihydro-2H-pyrano[2,3-b]pyridin-4-ylamino)-1-phenylbutan-2-ylcarbamate.

To a 150 mL round bottom flask containing tert-butyl (2S,3S)-3-(tert-butyldimethylsilyloxy)-4-oxo-1-phenylbutan-2-ylcarbamate (1.9 g, 4.8 mmol) was added DCE (20 mL) and the mixture was allowed to stir at 23° C. for about 2 min. At this time, product from step 10 (800.00 mg, 3.7 mmol) was added and Trimethyl orthoformate (4.1 ml, 37 mmol) was added via a syringe. The reaction was allowed to stir for 20 min. Sodium triacetoxyborohydride (2.3 g, 11 mmol) was added in one portion. The reaction was allowed to stir for 30 min and then sodium carbonate was added (10%, 40 mL). The reaction was allowed to stir for 1 h and then extracted with DCM (4×35 ml), the combined organics were washed with brine and dried with sodium sulfate, filtered and concentrated to give 3.0 g of colorless oil that was purified to a 120 g Isco column (20 to 35% EtOAc in hexanes) to give 1.740 g of a white foamy solid (tlc: Rf=0.50 in 40% EtOAc in hexanes). MS m/z (M+1): 596.

Step 14: (2R,3S)-3-amino-1-((S)-2,2-spirocyclobutyl-6-neopentyl-3,4-dihydro-2H-pyrano[2,3-b]pyridin-4-ylamino)-4-phenylbutan-2-ol tert-Butyl (2S,3R)-3-(tert-butyldimethylsilyloxy)-4-((S)-2,2-spirocyclobutyl-6-neopentyl-3,4-dihydro-2H-pyrano[2,3-b]pyridin-4-ylamino)-1-phenylbutan-2-ylcarbamate (1.52 g, 2.38 mmol) was dissolved in 3 ml dioxane and 4M HCl in dioxane (15.00 ml, 60.0 mmol) was added. The reaction was stirred over the weekend and the BOC group was removed but only approx. 30% deprotection of the silyl group. The reaction was warmed up to 60° C. for 10 h and purified on the HPLC. The material was free based with K$_2$CO$_3$ (10% in water and extracted with EtOAc) and used in the next steps.

Step 15: 1-(furan-2-ylmethyl)-N-((2S,3R)-3-hydroxy-4-((S)-6-neopentyl-2,2-spirocyclobutyl-3,4-dihydro-2H-pyrano[2,3-b]pyridin-4-ylamino)-1-phenylbutan-2-yl)-6-oxo-1,6-dihydropyridine-3-carboxamide (2R,3S)-3-amino-1-((S)-2,2-spirocyclobutyl-6-neopentyl-3,4-dihydro-2H-pyrano[2,3-b]pyridin-4-ylamino)-4- phenylbutan-2-ol (0.020 g, 0.047 mmol), 1-(furan-2-ylmethyl)-6-oxo-1,6-dihydropyridine-3-carboxylic acid (0.010 g, 0.047 mmol), N-ethyl-N-isopropylpropan-2-amine (0.041 ml, 0.24 mmol) and HATU (0.018 g, 0.047 mmol) were dissolved in 1 ml DMF at room temp and the mixture was stirred for 1 h and 5 M HCL (aq) was added until the yellow color disappeared. The mixture was purified on the HPLC without further workup procedure. The title compound was obtained as an off-white solid. MS (M+H$^+$):625.

The following compounds in Table 3 below, synthesized by a method analogous to that described in Example 105, Example 148 or Example 169, provide additional representative examples of Formulas I-III.

| Ex. No. | STRUCTURE | Mass found (M + H+) | MW |
|---|---|---|---|
| 172 | N—((2S,3R)-4-((S)-7-ethyl-3,3-dimethyl-1,3,4,5-tetrahydrobenzo[c]oxepin-5-ylamino)-3-hydroxy-1-phenylbutan-2-yl)-4-oxo-5-(2-oxopyrrolidin-1-yl)-3-(pyrrolidin-1-yl)cyclohexa-1,5-dienecarboxamide | 655.3 | 654.847 |
| 173 | N—((2S,3R)-4-((S)-6-chloro-2,2-spirocyclobutyl-3,4-dihydro-2H-chromen-4-ylamino)-3-hydroxy-1-phenylbutan-2-yl)-1-cyclopentyl-6-oxo-5-(2-oxopyrrolidin-1-yl)-1,6-dihydropyridine-3-carboxamide | 659 | 659.223 |
| 174 | N—((2S,3R)-4-((S)-6-chloro-2,2-spirocyclobutyl-3,4-dihydro-2H-chromen-4-ylamino)-3-hydroxy-1-phenylbutan-2-yl)-1-cyclobutyl-5-oxopyrrolidine-3-carboxamide | 552 | 552.111 |
| 175 | N—((2S,3RS)-1-((S)-6-bromo-2,2-spirocyclobutyl-3,4-dihydro-2H-chromen-4-ylamino)-2-hydroxy-5-methylhexan-3-yl)-1-cyclopentyl-6-oxo-5-(2-oxopyrrolidin-1-yl)-1,6-dihydropyridine-3-carboxamide | 669 | 1339.31 |
| 176 | N—((2S,3RS)-4-((S)-6-bromo-2,2-spirocyclobutyl-3,4-dihydro-2H-chromen-4-ylamino)-3-hydroxy-1-cyclohexylbutan-2-yl)-1-cyclopentyl-6-oxo-5-(2-oxopyrrolidin-1-yl)-1,6-dihydropyridine-3-carboxamide | 711 | 1419.44 |
| 177 | 1-cyclopentyl-N—((2S,3R)-4-((S)-6-ethyl-2,2-spirocyclobutylchroman-4-ylamino)-3-hydroxy-1-(thiophen-3-yl)butan-2-yl)-6-oxo-5-(2-oxopyrrolidin-1-yl)-1,6-dihydropyridine-3-carboxamide | 659 | 658.859 |
| 178 | 1-cyclopentyl-N—((2S,3RS)-4-((S)-6-ethyl-2,2-spirocyclobutylchroman-4-ylamino)-3-hydroxy-1-(thiophen-2-yl)butan-2-yl)-6-oxo-5-(2-oxopyrrolidin-1-yl)-1,6-dihydropyridine-3-carboxamide | 659 | 1317.72 |
| 179 | N—((2S,3RS)-4-((S)-6-bromo-2,2-dimethyl-3,4-dihydro-2H-chromen-4-ylamino)-3-hydroxy-1-(naphthalen-1-yl)butan-2-yl)-1-cyclopentyl-6-oxo-5-(2-oxopyrrolidin-1-yl)-1,6-dihydropyridine-3-carboxamide | 743 | 1483.44 |
| 180 | 1-cyclopentyl-N—((1S,2R)-3-((S)-6-ethyl-2,2-spirocyclobutylchroman-4-ylamino)-2-hydroxy-1-phenylpropyl)-6-oxo-5-(2-oxopyrrolidin-1-yl)-1,6-dihydropyridine-3-carboxamide | 639.4 | 638.804 |
| 181 | 1-cyclobutyl-N—((1S,2R)-3-((S)-6-ethyl-2,2-spirocyclobutylchroman-4-ylamino)-2-hydroxy-1-phenylpropyl)-5-oxopyrrolidine-3-carboxamide | 532.2 | 531.693 |
| 182 | N—((2S,3R)-4-((S)-6-bromo-2,2-dimethylchroman-4-ylamino)-1-(3,5-difluorophenyl)-3-hydroxybutan-2-yl)-1-cyclopentyl-5-(5-methylpyridin-2-yl)-6-oxo-1,6-dihydropyridine-3-carboxamide | 735.3 737.3 | 735.666 |
| 183 | N—((2S,3R)-4-((S)-6-bromo-2,2-dimethylchroman-4-ylamino)-1-(3,5-difluorophenyl)-3-hydroxybutan-2-yl)-1-cyclopentyl-5-(5-methylpyridin-2-yl)-6-oxo-1,6-dihydropyridine-3-carboxamide | 723.1 | 723.45 |
| 184 | N—((2S,3R)-4-((S)-6-bromo-2,2-dimethylchroman-4-ylamino)-1-(3,5-difluorophenyl)-3-hydroxybutan-2-yl)-1-cyclopentyl-5-(5-fluoropyridin-2-yl)-6-oxo-1,6-dihydropyridine-3-carboxamide | 739.3 741.3 | 739.629 |
| 185 | N—((2S,3R)-1-(3-cyanophenyl)-4-((S)-6-ethyl-2,2-spirocyclobutylchroman-4-ylamino)-3-hydroxybutan-2-yl)-tetrahydrofuran-2-carboxamide | 504.3 | 503.639 |
| 186 | N—((2S,3R)-1-(3-cyanophenyl)-4-((S)-6-ethyl-2,2-spirocyclobutylchroman-4-ylamino)-3-hydroxybutan-2-yl)-1-cyclopentyl-6-oxo-5-(2-oxopyrrolidin-1-yl)-1,6-dihydropyridine-3-carboxamide | 678.3 | 677.83 |
| 187 | N—((2S,3R)-1-(3-cyanophenyl)-4-((S)-6-ethyl-2,2-spirocyclobutylchroman-4-ylamino)-3-hydroxybutan-2-yl)-1-cyclopentyl-6-oxo-5-(pyridin-2-yl)-1,6-dihydropyridine-3-carboxamide | 672.4 | 671.838 |
| 188 | (S)—N—((2S,3R)-1-(3-cyanophenyl)-4-((S)-6-ethyl-2,2-spirocyclobutylchroman-4-ylamino)-3-hydroxybutan-2-yl)-1-cyclobutyl-5-oxopyrrolidine-3-carboxamide | 571.4 | 570.73 |
| 189 | N—((2S,3R)-4-((S)-6-bromo-2,2-spirocyclobutylchroman-4-ylamino)-3-hydroxy-1-(3-(trifluoromethyl)phenyl)butan-2-yl)-1-cyclopentyl-6-oxo-5-(2-oxopyrrolidin-1-yl)-1,6-dihydropyridine-3-carboxamide | 771.2 773.1 | 772.659 |

-continued

| Ex. No. | STRUCTURE | Mass found (M + H+) | MW |
|---|---|---|---|
| 190 | (E)-N—((2S,3R)-4-((S)-6-ethyl-2,2-spirocyclopentylchroman-4-ylamino)-3-hydroxy-1-phenylbutan-2-yl)-2,3-dihydro-1H-benzo[b]azepine-4-carboxamide | 594.3 | 565.754 |
| 191 | (RS)—N—((2S,3R)-4-((S)-6-ethyl-2,2-spirocyclopentylchroman-4-ylamino)-3-hydroxy-1-phenylbutan-2-yl)chroman-3-carboxamide | 555.3 | 1109.45 |
| 192 | (S)—N—((2S,3R)-4-((S)-6-ethyl-2,2-spirocyclopentyllchroman-4-ylamino)-3-hydroxy-1-phenylbutan-2-yl)-5-oxopyrrolidine-2-carboxamide | 506.3 | 505.655 |
| 193 | (S)-1-(2-fluorobenzyl)-N—((2S,3R)-4-((S)-6-ethyl-2,2-spirocyclopentylchroman-4-ylamino)-3-hydroxy-1-phenylbutan-2-yl)pyrrolidine-2-carboxamide | 600.4 | 599.786 |
| 194 | N—((2S,3R)-4-((S)-6-ethyl-2,2-spirocyclopentylchroman-4-ylamino)-3-hydroxy-1-phenylbutan-2-yl)-5-oxo-1-phenylpyrrolidine-2-carboxamide | 582.3 | 581.753 |
| 195 | 1-cyclopentyl-N—((2S,3R)-4-((S)-6-ethyl-2,2-spirocyclopentylchroman-4-ylamino)-3-hydroxy-1-phenylbutan-2-yl)-5-oxopyrrolidine-3-carboxamide | 574.3 | 573.773 |
| 196 | N—((2S,3R)-4-((S)-6-ethyl-2,2-spirocyclopentylchroman-4-ylamino)-3-hydroxy-1-phenylbutan-2-yl)-1-methyl-5-oxopyrrolidine-3-carboxamide | 520.2 | 519.682 |
| 197 | 1-cyclobutyl-N—((2S,3R)-4-((S)-6-ethyl-2,2-spirocyclopentylchroman-4-ylamino)-3-hydroxy-1-phenylbutan-2-yl)-5-oxopyrrolidine-3-carboxamide | 560.3 | 559.747 |
| 198 | N—((2S,3R)-4-((S)-6-ethyl-2,2-spirocyclopentylchroman-4-ylamino)-3-hydroxy-1-phenylbutan-2-yl)-1-isobutyl-5-oxopyrrolidine-3-carboxamide | 562.3 | 561.762 |
| 199 | 1-cyclobutyl-N—((2S,3R)-1-(3,5-difluorophenyl)-4-((S)-6-ethyl-2,2-spirocyclobutylchroman-4-ylamino)-3-hydroxybutan-2-yl)-5-oxopyrrolidine-3-carboxamide | 582.2 | 581.7 |
| 200 | (RS)-1-cyclopropyl-N—((2S,3R)-4-((S)-6-ethyl-2,2-spirocyclobutylchroman-4-ylamino)-3-hydroxy-1-phenylbutan-2-yl)-5-oxopyrrolidine-3-carboxamide | 532.3 | 1063.39 |
| 201 | (R/S)-1-cyclobutyl-N—((2S,3R)-4-((S)-6-ethyl-2,2-spirocyclobutylchroman-4-ylamino)-3-hydroxy-1-phenylbutan-2-yl)-5-oxopyrrolidine-3-carboxamide | 546.3 | 1091.44 |
| 202 | (S)-1-cyclopentyl-N—((2S,3R)-4-((S)-6-ethyl-2,2-spirocyclobutylchroman-4-ylamino)-3-hydroxy-1-phenylbutan-2-yl)-5-oxopyrrolidine-3-carboxamide | 560.3 | 1119.49 |
| 203 | 1-cyclopentyl-N—((2S,3R)-4-((S)-2-ethyl-5,5-dimethyl-4,5,6,7-tetrahydrobenzo[d]thiazol-7-ylamino)-3-hydroxy-1-phenylbutan-2-yl)-6-oxo-5-(pyridin-2-yl)-1,6-dihydropyridine-3-carboxamide | 640.3 | 639.86 |
| 204 | (R)-1-cyclobutyl-N—((2S,3R)-4-((S)-6-ethyl-2,2-spirocyclobutylchroman-4-ylamino)-3-hydroxy-1-phenylbutan-2-yl)-5-oxopyrrolidine-3-carboxamide | 546.2 | 545.72 |
| 205 | (S)-1-cyclobutyl-N—((2S,3R)-4-((S)-6-ethyl-2,2-spirocyclobutylchroman-4-ylamino)-3-hydroxy-1-phenylbutan-2-yl)-5-oxopyrrolidine-3-carboxamide | 546.2 | 545.72 |
| 206 | 1-cyclopentyl-N—((2S,3R)-4-((S)-3,3-dimethyl-2,3-dihydro-1H-inden-1-ylamino)-3-hydroxy-1-phenylbutan-2-yl)-6-oxo-5-(2-oxopyrrolidin-1-yl)-1,6-dihydropyridine-3-carboxamide | 597.2 | 596.768 |
| 207 | 1-cyclopentyl-N—((2S,3R)-1-(3,5-difluorophenyl)-4-((S)-6-ethyl-2,2-spiro-(+/−)-tetrahydrofuranchroman-4-ylamino)-3-hydroxybutan-2-yl)-6-oxo-5-(pyridin-2-yl)-1,6-dihydropyridine-3-carboxamide | 669.2 | 1397.61 |
| 208 | 1-cyclopentyl-N—((2S,3R)-4-((S)-6-ethyl-2,2-spirotetrahydrofuranchroman-4-ylamino)-3-hydroxy-1-phenylbutan-2-yl)-6-oxo-5-(pyridin-2-yl)-1,6-dihydropyridine-3-carboxamide | 663.3 | 1325.65 |
| 209 | 1-cyclopentyl-N—((2S,3R)-4-((S)-5,5-dimethyl-2-neopentyl-4,5,6,7-tetrahydrobenzo[d]thiazol-7-ylamino)-3-hydroxy-1-phenylbutan-2-yl)-6-oxo-5-(pyridin-2-yl)-1,6-dihydropyridine-3-carboxamide | 682.3 | 681.941 |
| 210 | (3S,4R)-1-cyclopentyl-N—((2S,3R)-4-((S)-6-ethyl-2,2-spirocyclobutylchroman-4-ylamino)-3-hydroxy-1-phenylbutan-2-yl)-4-phenylpyrrolidine-3-carboxamide | 622.4 | 621.861 |
| 211 | N—((2S,3R)-4-((S)-6-ethyl-2,2-spirotetrahydrofuranchroman-4-ylamino)-3-hydroxy-1-phenylbutan-2-yl)-4-(3-methylbenzoyl)morpholine-2-carboxamide | 628.3 | 1255.56 |
| 212 | N—((2S,3R)-1-(3,5-difluorophenyl)-4-((S)-6-ethyl-2,2-spirotetrahydrofuranchroman-4-ylamino)-3-hydroxybutan-2-yl)-4-(3-methylbenzoyl)morpholine-2-carboxamide | 664.2 | 1327.52 |
| 213 | 1-cyclopentyl-N—((2S,3R)-4-((S)-6-ethyl-2,2-spirotetrahydrofuranchroman-4-ylamino)-3-hydroxy-1-phenylbutan-2-yl)-6-oxo-5-(1H-pyrazol-1-yl)-1,6-dihydropyridine-3-carboxamide | 652.2 | 1303.61 |

| Ex. No. | STRUCTURE | Mass found (M + H+) | MW |
|---|---|---|---|
| 214 | 1-cyclopentyl-N—((2S,3R)-4-((S)-6-ethyl-2,2-spirotetrahydrofuranchroman-4-ylamino)-3-hydroxy-1-phenylbutan-2-yl)-5-(1H-indol-2-yl)-6-oxo-1,6-dihydropyridine-3-carboxamide | 701.2 | 1401.75 |
| 215 | N—((2S,3R)-3-hydroxy-4-((S)-6-neopentyl-2,2-spirocyclobutyl-3,4-dihydro-2H-pyrano[2,3-b]pyridin-4-ylamino)-1-phenylbutan-2-yl)-tetrahydrofuran-2-carboxamide | 522.7 | 521.698 |
| 216 | 1-cyclopentyl-N—((2S,3R)-4-((S)-3,4-dihydro-2H-2,2-spirocyclopentylthiochromen-4-ylamino)-3-hydroxy-1-phenylbutan-2-yl)-6-oxo-5-(2-oxopyrrolidin-1-yl)-1,6-dihydropyridine-3-carboxamide | 655.4 | 654.871 |
| 217 | 1-cyclopentyl-N—((2S,3R)-3-hydroxy-1-phenyl-4-((S)-2,2-spirocyclopentylthiochroman-4-ylamino)butan-2-yl)-6-oxo-1,6-dihydropyridine-3-carboxamide | 572.7 | 571.782 |
| 218 | N—((2S,3R)-4-((R)-6-ethyl-2,2-spirocyclobutylchroman-4-ylamino)-3-hydroxy-1-phenylbutan-2-yl)-1-methyl-6-oxopiperidine-3-carboxamide | 520.2 | 1039.36 |
| 219 | 1,3-dicyclopentyl-N—((2S,3R)-4-((S)-6-ethyl-2,2-spirocyclobutylchroman-4-ylamino)-3-hydroxy-1-phenylbutan-2-yl)-2-oxo-hexahydropyrimidine-5-carboxamide | 643.5 | 642.88 |
| 220 | (S)—N—((2S,3R)-4-((S)-6-ethyl-2,2-spirocyclobutylchroman-4-ylamino)-3-hydroxy-1-phenylbutan-2-yl)-1-methyl-2-oxoimidazolidine-4-carboxamide | 507 | 506.643 |
| 221 | (S)—N—((2S,3R)-4-((S)-6-bromo-2,2-spirocyclobutylchroman-4-ylamino)-3-hydroxy-1-phenylbutan-2-yl)-1-methyl-2-oxoimidazolidine-4-carboxamide | 558, 560 | 557.486 |
| 222 | (S)—N—((2S,3R)-4-((S)-6-ethyl-2,2-spirocyclobutylchroman-4-ylamino)-3-hydroxy-1-phenylbutan-2-yl)-1,3-dimethyl-2-oxoimidazolidine-4-carboxamide | 521 | 520.67 |
| 223 | 1,3-dicyclobutyl-N—((2S,3R)-4-((S)-6-ethyl-2,2-spirocyclobutylchroman-4-ylamino)-3-hydroxy-1-phenylbutan-2-yl)-2-oxo-hexahydropyrimidine-5-carboxamide | 615 | 614.826 |
| 224 | N—((2S,3R)-4-((S)-6-ethyl-2,2spirocyclobutylchroman-4-ylamino)-3-hydroxy-1-phenylbutan-2-yl)-1,3-diisopropyl-2-oxo-hexahydropyrimidine-5-carboxamide | 591.5 | 590.804 |
| 225 | N—((2S,3R)-4-((S)-6-ethyl-2,2-spirocyclobutylchroman-4-ylamino)-3-hydroxy-1-phenylbutan-2-yl)-1-(1-oxoisoindolin-2-yl)cyclopropanecarboxamide | 580 | 579.737 |
| 226 | 1-cyclopentyl-N—((2S,3R)-3-hydroxy-4-((S)-6-neopentyl-3,4-dihydro-(2,2-spirotetrahydrofuranyl)-pyrano[2,3-b]pyridin-4-ylamino)-1-phenylbutan-2-yl)-6-oxo-5-(pyridin-2-yl)-1,6-dihydropyridine-3-carboxamide | 706.3 | 1411.79 |
| 227 | 1-cyclopentyl-N—((2S,3R)-3-hydroxy-1-phenyl-4-((S)-2,2-spirocyclopentylthiochroman-4-ylamino)butan-2-yl)-6-oxo-5-(pyridin-2-yl)-1,6-dihydropyridine-3-carboxamide | 649.2 | 648.868 |
| 228 | N—((3S,4R)-5-((S)-6-bromo-2,2-dimethyl-3,4-dihydro-2H-chromen-4-ylamino)-1,1,1-trifluoro-4-hydroxypentan-3-yl)-1-cyclopentyl-6-oxo-5-(2-oxopyrrolidin-1-yl)-1,6-dihydropyridine-3-carboxamide | 683.1 | 683.562 |
| 229 | 1-Cyclopentyl-6-oxo-5-(pyridin-2-yl)-N—((3S,4R)-1,1,1-trifluoro-4-hydroxy-5-((S)-2,2-spirocyclobutyl-6-neopentyl-3,4-dihydro-2H-pyrano[2,3-b]pyridin-4-ylamino)pentan-3-yl)-1,6-dihydropyridine-3-carboxamide | 682.3 | 681.795 |
| 230 | 1-cyclopentyl-N—((1S,2R)-3-(((4S)-6-ethyl-2,2-dimethyl-1,1-dioxido-3,4-dihydro-2H-1-benzothiopyran-4-yl)amino)-2-hydroxy-1-(phenylmethyl)propyl)-6-oxo-5-(2-oxo-1-pyrrolidinyl)-1,6-dihydro-3-pyridinecarboxamide | 689.3 | 688.885 |
| 231 | 1-cyclopentyl-N—((2S,3R)-4-((S)-6-ethyl-2,2-dimethyl-3,4-dihydro-2H-thiochromen-4-ylamino)-3-hydroxy-1-phenylbutan-2-yl)-6-oxo-5-(2-oxopyrrolidin-1-yl)-1,6-dihydropyridine-3-carboxamide | 657.4 | 656.887 |
| 232 | (E)-N—((2S,3R)-4-((S)-6-ethyl-2,2-spirocyclopentylchroman-4-ylamino)-3-hydroxy-1-phenylbutan-2-yl)-7-fluoro-2,3-dihydro-1H-benzo[b]azepine-4-carboxamide | 584.4 | 583.744 |
| 233 | (E)-N—((2S,3R)-4-((S)-6-ethyl-2,2-spirocyclobutylchroman-4-ylamino)-3-hydroxy-1-phenylbutan-2-yl)-7-fluoro-2,3-dihydro-1H-benzo[b]azepine-4-carboxamide | 570.4 | 569.717 |
| 234 | (E)-N—((2S,3R)-4-((S)-6-ethyl-2,2-spirocyclopentylchroman-4-ylamino)-3-hydroxy-1-phenylbutan-2-yl)-9-fluoro-2,3-dihydro-1H-benzo[b]azepine-4-carboxamide | 584.6 | 583.744 |
| 235 | (E)-N—((2S,3R)-4-((S)-6-ethyl-2,2-spirocyclobutylchroman-4-ylamino)-3-hydroxy-1-phenylbutan-2-yl)-9-fluoro-2,3-dihydro-1H-benzo[b]azepine-4-carboxamide | 570.3 | 569.717 |
| 236 | (E)-N—((2S,3R)-4-((S)-6-ethyl-2,2-dimethylchroman-4-ylamino)-3-hydroxy-1-phenylbutan-2-yl)-9-fluoro-2,3-dihydro-1H benzo[b]azepine-4-carboxamide | 558.3 | 557.706 |

-continued

| Ex. No. | STRUCTURE | Mass found (M + H+) | MW |
|---|---|---|---|
| 237 | (E)-N—((2S,3R)-1-(3,5-difluorophenyl)-4-((S)-6-ethyl-2,2-dimethylchroman-4-ylamino)-3-hydroxybutan-2-yl)-9-fluoro-2,3-dihydro-1H-benzo[b]azepine-4-carboxamide | 594.4 | 593.686 |
| 238 | (E)-7-bromo-N—((2S,3R)-4-((S)-6-ethyl-2,2-spirocyclobutylchroman-4-ylamino)-3-bydroxy-1-phenylbutan-2-yl)-2,3-dihydro-1H-benzo[b]azepine-4-carboxamide | 632.5 | 630.623 |
| 239 | (E)-7-bromo-N—((2S,3R)-4-((S)-6-ethyl-2,2-spirocyclobutylchroman-4-ylamino)-3-hydroxy-1-phenylbutan-2-yl)-1-methyl-2,3-dihydro-1H-benzo[b]azepine-4-carboxamide | 646.6 | 644.65 |
| 240 | 1-cyclopentyl-N—((2S,3R)-3-hydroxy-1-phenyl-4-((S)-2,6,6-trimethyl-4,5,6,7-tetrahydrobenzofuran-4-ylamino)butan-2-yl)-6-oxo-5-(2-oxopyrrolidin-1-yl)-1,6-dihydropyridine-3-carboxamide | 615.6 | 614.782 |
| 241 | (E)-7-fluoro-N—((2S,3R)-3-hydroxy-1-phenyl-4-((S)-2,6,6-trimethyl-4,5,6,7-tetrahydrobenzofuran-4-ylamino)butan-2-yl)-2,3-dihydro-1H-benzo[b]azepine-4-carboxamide | 532.2 | 531.668 |
| 242 | 1-cyclopentyl-N—((2S,3R)-3-hydroxy-1-phenyl-4-((S)-2,6,6-trimethyl-4,5,6,7-tetrahydrobenzo[b]thiophen-4-ylamino)butan-2-yl)-6-oxo-5-(2-oxopyrrolidin-1-yl)-1,6-dihydropyridine-3-carboxamide | 631.6 | 630.849 |
| 243 | 1-cyclopentyl-N—((2S,3R)-3-hydroxy-1-phenyl-4-((S)-2,6,6-trimethyl-4,5,6,7-tetrahydrobenzo[b]thiophen-4-ylamino)butan-2-yl)-6-oxo-1,6-dihydropyridine-3-carboxamide | 548.2 | 547.76 |
| 244 | 1-cyclopentyl-N—((2S,3R)-3-hydroxy-1-phenyl-4-((S)-2,6,6-trimethyl-4,5,6,7-tetrahydrobenzofuran-4-ylamino)butan-2-yl)-6-oxo-1,6-dihydropyridine-3-carboxamide | 532.2 | 531.693 |
| 245 | (E)-7-fluoro-N—((2S,3R)-3-hydroxy-1-phenyl-4-((S)-2,6,6-trimethyl-4,5,6,7-tetrahydrobenzo[b]thiophen-4-ylamino)butan-2-yl)-2,3-dihydro-1H-benzo[b]azepine-4-carboxamide | 548.3 | 547.735 |
| 246 | 1-cyclobutyl-N—((2S,3R)-3-hydroxy-1-phenyl-4-((S)-2,6,6-trimethyl-4,5,6,7-tetrahydrobenzo[b]thiophen-4-ylamino)butan-2-yl)-5-oxopyrrolidine-3-carboxamide | 524.2 | 1047.48 |
| 247 | 1-cyclopentyl-N—((2S,3R)-3-hydroxy-1-phenyl-4-((S)-2,6,6-trimethyl-4,5,6,7-tetrahydrobenzo[b]thiophen-4-ylamino)butan-2-yl)-6-oxo-5-(pyridin-2-yl)-1,6-dihydropyridine-3-carboxamide | 625.3 | 624.846 |
| 248 | (E)-N—((2S,3R)-4-((S)-6-ethyl-2,2-spirocyclobutylchroman-4-ylamino)-3-hydroxy-1-phenylbutan-2-yl)-8,9-dihydro-7H-pyrido[2,3-b]azepine-6-carboxamide | 553.2 | 552.715 |
| 249 | (E)-N—((2S,3R)-3-hydroxy-1-phenyl-4-((S)-2,6,6-trimethyl-4,5,6,7-tetrahydrobenzo[b]thiophen-4-ylamino)butan-2-yl)-8,9-dihydro-7H-pyrido[2,3-b]azepine-6-carboxamide | 531.3 | 530.733 |
| 250 | 1-cyclopentyl-N—((2S,3R)-4-((S)-2-ethyl-6,6-dimethyl-4,5,6,7-tetrahydrobenzo[b]thiophen-4-ylamino)-3-hydroxy-1-phenylbutan-2-yl)-6-oxo-5-(2-oxopyrrolidin-1-yl)-1,6-dihydropyridine-3-carboxamide | 645.6 | 644.876 |
| 251 | 1-cyclopentyl-N—((2S,3R)-4-((S)-2-ethyl-6,6-dimethyl-4,5,6,7-tetrahydrobenzo[b]thiophen-4-ylamino)-3-hydroxy-1-phenylbutan-2-yl)-6-oxo-5-(pyridin-2-yl)-1,6-dihydropyridine-3-carboxamide | 639.5 | 638.872 |
| 252 | N—((2S,3R)-1-(3-cyanophenyl)-3-hydroxy-4-((S)-2,6,6-trimethyl-4,5,6,7-tetrahydrobenzo[b]thiophen-4-ylamino)butan-2-yl)-1-cyclopentyl-6-oxo-5-(pyridin-2-yl)-1,6-dihydropyridine-3-carboxamide | 650.2 | 649.856 |
| 253 | 1-cyclopentyl-N—((2S,3S)-4-((S)-6-ethyl-2,2-spirocyclobutylchroman-4-ylamino)-3-hydroxy-4-oxo-1-phenylbutan-2-yl)-6-oxo-5-(pyridin-2-yl)-1,6-dihydropyridine-3-carboxamide | 661.2 | 660.811 |
| 254 | 1-cyclopentyl-N—((2S,3R)-1-(3,5-difluorophenyl)-3-hydroxy-4-((S)-2,6,6-trimethyl-4,5,6,7-tetrahydrobenzo[b]thiophen-4-ylamino)butan-2-yl)-6-oxo-5-(pyridin-2-yl)-1,6-dihydropyridine-3-carboxamide | 661.2 | 660.826 |
| 255 | N—((2S,3R)-4-((S)-6-ethyl-2,2-spirocyclobutylchroman-4-ylamino)-3-hydroxy-1-phenylbutan-2-yl)-1-isopropyl-6-oxo-5-(pyridin-2-yl)-1,6-dihydropyridine-3-carboxamide | 621.3 | 620.79 |
| 256 | 5-(2-cyanophenyl)-1-cyclopentyl-N—((2S,3R)-3-hydroxy-4-((S)-6-neopentyl-3,4-dihydro-2,2-spirocyclobutyl-pyrano[2,3-b]pyridin-4-ylamino)-1-phenylbutan-2-yl)-6-oxo-1,6-dihydropyridine-3-carboxamide | 714.2 | 713.918 |
| 257 | 1-cyclopentyl-5-(2-fluorophenyl)-N—((2S,3R)-3-hydroxy-4-((S)-6-neopentyl-3,4-dihydro-2,2-spirocyclobutyl-pyrano[2,3-b]pyridin-4-ylamino)-1-phenylbutan-2-yl)-6-oxo-1,6-dihydropyridine-3-carboxamide | 707.2 | 706.898 |
| 258 | 1-cyclopentyl-N—((2S,3R)-3-hydroxy-4-((S)-6-neopentyl-3,4-dihydro-2,2-spirocyclobutyl-pyrano[2,3-b]pyridin-4-ylamino)-1-phenylbutan-2-yl)-6-oxo-5-(1H-pyrrol-2-yl)-1,6-dihydropyridine-3-carboxamide | 678.3 | 677.885 |
| 259 | 1-cyclopentyl-5-(furan-3-yl)-N—((2S,3R)-3-hydroxy-4-((S)-6-neopentyl-3,4-dihydro-2,2-spirocyclobutyl-pyrano[2,3-b]pyridin- | 679.2 | 678.869 |

| Ex. No. | STRUCTURE | Mass found (M + H+) | MW |
|---|---|---|---|
| | 4-ylamino)-1-phenylbutan-2-yl)-6-oxo-1,6-dihydropyridine-3-carboxamide | | |
| 260 | 1-cyclopentyl-N—((2S,3R)-3-hydroxy-4-((S)-6-neopentyl-3,4-dihydro-2,2-spirocyclobutyl-pyrano[2,3-b]pyridin-4-ylamino)-1-phenylbutan-2-yl)-6-oxo-5-(thiazol-2-yl)-1,6-dihydropyridine-3-carboxamide | 696.3 | 695.924 |
| 261 | 1-cyclopentyl-N—((2S,3R)-3-hydroxy-4-((S)-6-neopentyl-3,4-dihydro-2,2-spirocyclobutyl-pyrano[2,3-b]pyridin-4-ylamino)-1-phenylbutan-2-yl)-6-oxo-5-(pyrazin-2-yl)-1,6-dihydropyridine-3-carboxamide | 691.3 | 690.884 |
| 262 | N—((2S,3R)-4-((S)-6-ethyl-2,2-spirocyclobutylchroman-4-ylamino)-3-hydroxy-1-phenylbutan-2-yl)cyclopropanecarboxamide | 449.2 | 448.603 |
| 263 | 1-cyclopentyl-N—((2S,3R)-3-hydroxy-1-phenyl-4-((S)-6-(trifluoromethoxy)-2,2-spirocyclobutylchroman-4-ylamino)butan-2-yl)-6-oxo-5-(2-oxopyrrolidin-1-yl)-1,6-dihydropyridine-3-carboxamide | 709.3 | 708.774 |
| 264 | 1-cyclopentyl-N—((2S,3R)-3-hydroxy-1-phenyl-4-((S)-6-(trifluoromethoxy)-2,2-spirocyclobutylchroman-4-ylamino)butan-2-yl)-6-oxo-1,6-dihydropyridine-3-carboxamide | 626.3 | 625.684 |
| 265 | N—((2S,3R)-4-((S)-6-ethyl-2,2spirocyclobutylchroman-4-ylamino)-3-hydroxy-1-phenylbutan-2-yl)pyrrolidine-1-carboxamide | 478.3 | 477.645 |
| 266 | 1-cyclopentyl-N—((2S,3R)-4-((S)-6-ethyl-7-fluoro-3,4-dihydro-2,2-spirocyclobutylchromen-4-ylamino)-3-hydroxy-1-phenylbutan-2-yl)-6-oxo-5-(2-oxopyrrolidin-1-yl)-1,6-dihydropyridine-3-carboxamide | 671.3 | 670.821 |
| 267 | 1-cyclopentyl-N—((2S,3R)-4-((S)-6-ethyl-7-fluoro-3,4-dihydro-2,2spirocyclobutyl-chromen-4-ylamino)-3-hydroxy-1-phenylbutan-2-yl)-6-oxo-1,6-dihydropyridine-3-carboxamide | 588.3 | 587.732 |
| 268 | N—((2S,3R)-4-((S)-6-ethyl-7-fluoro-3,4-dihydro-2,2-spirocyclobutylchromen-4-ylamino)-3-hydroxy-1-phenylbutan-2-yl)-4-fluoro-3-(2-oxopyrrolidin-1-yl)benzamide | 604.3 | 603.706 |
| 269 | N—((2S,3R)-4-((S)-6-acetyl-3,4-dihydro-2,2-spriocyclobutyl-chromen-4-ylamino)-3-hydroxy-1-phenylbutan-2-yl)-1-cyclopentyl-6-oxo-5-(2-oxopyrrolidin-1-yl)-1,6-dihydropyridine-3-carboxamide | 667.2 | 666.814 |
| 270 | N—((2S,3R)-4-((S)-6-acetyl-2,2-spirocyclobutylchroman-4-ylamino)-3-hydroxy-1-phenylbutan-2-yl)-1-cyclopentyl-6-oxo-5-(pyridin-2-yl)-1,6-dihydropyridine-3-carboxamide | 661.2 | 660.811 |
| 271 | N—((2S,3S)-4-((S)-6-bromo-3,4-dihydro-2,2-spirocyclobutylpyrano[2,3-b]pyridin-4-ylamino)-3-hydroxy-1-phenylbutan-2-yl)-1-cyclopentyl-6-oxo-5-(2-oxopyrrolidin-1-yl)1,6-dihydropyridine-3-carboxamide | 705.2 | 704.662 |
| 272 | 1-cyclopentyl-N—((2S,3S)-3-hydroxy-4-((S)-6-neopentyl-3,4-dihydro-2,2-spirocyclobutyl-pyrano[2,3-b]pyridin-4-ylamino)-1-phenylbutan-2-yl)-6-oxo-5-(pyridin-2-yl)-1,6-dihydropyridine-3-carboxamide | 690.2 | 689.896 |
| 273 | 1-cyclopentyl-N—((2S,3S)-3-hydroxy-4-((S)-6-neopentyl-3,4-dihydro-2,2-spirocyclobutyl-pyrano[2,3-b]pyridin-4-ylamino)-1-phenylbutan-2-yl)-6-oxo-5-(2-oxopyrrolidin-1-yl)-1,6-dihydropyridine-3-carboxamide | 696.2 | 695.9 |
| 274 | N—((2S,3R)-4-((R)-6-bromo-3,4-dihydro-2,2-spirocyclobutyl-pyrano[2,3-b]pyridin-4-ylamino)-3-hydroxy-1-phenylbutan-2-yl)-1-cyclopentyl-6-oxo-5-(2-oxopyrrolidin-1-yl)-1,6-dihydropyridine-3-carboxamide | 706 | 704.662 |
| 275 | N—((2S,3R)-4-((S)-6-bromo-3,4-dihydro-2,2-spirocyclobutyl-pyrano[2,3-b]pyridin-4-ylamino)-3-hydroxy-1-phenylbutan-2-yl)-1-cyclopentyl-6-oxo-5-(2-oxopyrrolidin-1-yl)-1,6-dihydropyridine-3-carboxamide | 704.1 | 704.662 |
| 276 | (S)—N—((2S,3S)-3-hydroxy-4-((S)-6-neopentyl-3,4-dihydro-2,2-spirocyclobutyl-pyrano[2,3-b]pyridin-4-ylamino)-1-phenylbutan-2-yl)-4-(3-methylbenzoyl)morpholine-2-carboxamide and (R)—N—((2S,3S)-3-hydroxy-4-((S)-6-neopentyl-3,4-dihydro-2,2-spirocyclobutyl-pyrano[2,3-b]pyridin-4-ylamino)-1-phenylbutan-2-yl)-4-(3-methylbenzoyl)morpholine-2-carboxamide | 655.3 | 1309.69 |
| 277 | N—((2S,3R)-4-((3R,4S)-6-bromo-3-hydroxy-2,2-spirocyclobutylchroman-4-ylamino)-3-hydroxy-1-phenylbutan-2-yl)-1-cyclopentyl-6-oxo-5-(2-oxopyrrolidin-1-yl)-1,6-dihydropyridine-3-carboxamide and N—((2S,3R)-4-((3S,4R)-6-bromo-3-hydroxy-2,2-spirocyclobutylchroman-4-ylamino)-3-hydroxy-1-phenylbutan-2-yl)-1-cyclopentyl-6-oxo-5-(2-oxopyrrolidin-1-yl)-1,6-dihydropyridine-3-carboxamide | 709 | 1311.58 |
| 278 | N—((2S,3R)-1-(3-cyanophenyl)-3-hydroxy-4-((S)-6-morpholino-2,2-spirocyclobutylchroman-4-ylamino)butan-2-yl)-1-cyclopentyl-6-oxo-5-(2-oxopyrrolidin-1-yl)-1,6-dihydropyridine-3-carboxamide | 735.3 | 734.893 |

-continued

| Ex. No. | STRUCTURE | Mass found (M + H+) | MW |
|---|---|---|---|
| 279 | N—((2S,3R)-1-(3-cyanophenyl)-3-hydroxy-4-((S)-6-morpholino-2,2-spirocyclobutylchroman-4-ylamino)butan-2-yl)-1-cyclopentyl-6-oxo-5-(pyridin-2-yl)-1,6-dihydropyridine-3-carboxamide | 729.3 | 728.889 |
| 280 | N—((2R,3S)-1-((S)-6-bromo-2,2-dimethylchroman-4-ylamino)-2-hydroxyhex-5-yn-3-yl)-1-cyclopentyl-6-oxo-5-(2-oxopyrrolidin-1-yl)-1,6-dihydropyridine-3-carboxamide | 639 | 639.587 |
| 281 | N—((2S,3R)-1-(1-benzyl-1H-1,2,3-triazol-4-yl)-4-((S)-6-ethyl-2,2-spirocyclobutylchroman-4-ylamino)-3-hydroxybutan-2-yl)-1-cyclopentyl-6-oxo-5-(2-oxopyrrolidin-1-yl)-1,6-dihydropyridine-3-carboxamide | 734 | 733.909 |
| 282 | N—((2R,3S)-1-((S)-6-bromo-2,2-dimethylchroman-4-ylamino)-2-hydroxy-5-phenylpentan-3-yl)-1-cyclopentyl-6-oxo-5-(2-oxopyrrolidin-1-yl)-1,6-dihydropyridine-3-carboxamide | 705 | 705.69 |
| 283 | N—((2S,3R)-1-(1-tert-butyl-1H-1,2,3-triazol-4-yl)-4-((S)-6-ethyl-2,2-spirocyclobutylchroman-4-ylamino)-3-hydroxybutan-2-yl)-1-cyclopentyl-6-oxo-5-(2-oxopyrrolidin-1-yl)-1,6-dihydropyridine-3-carboxamide | 700 | 699.892 |
| 284 | N—((2R,3S)-1-((S)-6-bromo-2,2-dimethylchroman-4-ylamino)-2-hydroxyhex-5-en-3-yl)-1-cyclopentyl-6-oxo-5-(2-oxopyrrolidin-1-yl)-1,6-dihydropyridine-3-carboxamide | 641 | 641.603 |
| 285 | N—((2S,3R)-4-((S)-6-cyano-2,2-dimethylchroman-4-ylamino)-1-(3,5-difluorophenyl)-3-hydroxybutan-2-yl)-1-cyclopentyl-6-oxo-5-(pyridin-2-yl)-1,6-dihydropyridine-3-carboxamide | 668 | 667.753 |
| 286 | 1-cyclopentyl-N—((2S,3R)-4-((S)-6-ethyl-2,2-spirocyclobutylchroman-4-ylamino)-3-hydroxy-1-phenylbutan-2-yl)-6-oxo-5-(1H-pyrazol-1-yl)-1,6-dihydropyridine-3-carboxamide | 636 | 635.805 |
| 287 | N—((2S,3R)-1-(3-cyanophenyl)-4-((S)-2,2-spirocyclobutyl-6-neopentyl-3,4-dihydro-2H-pyrano[2,3-b]pyridin-4-ylamino)-3-hydroxybutan-2-yl)-1-cyclopentyl-6-oxo-5-(1H-pyrazol-1-yl)-1,6-dihydropyridine-3-carboxamide | 704 | 703.883 |
| 288 | N—((2R,3S)-1-((S)-6-bromo-2,2-dimethylchroman-4-ylamino)-2-hydroxyhex-5-yn-3-yl)-1-cyclopentyl-6-oxo-5-(pyridin-2-yl)-1,6-dihydropyridine-3-carboxamide | 633 | 633.583 |
| 289 | (S)-methyl 4-((2R,3S)-3-(1-cyclopentyl-2-oxo-3-(2-oxopyrrolidin-1-yl)-1,2-dihydropyridine-5-carboxamido)-4-(3,5-difluorophenyl)-2-hydroxybutylamino)-2,2-spirocyclobutyl-3,4-dihydro-2H-chromene-6-carboxylate | 719 | 718.794 |
| 290 | 1-cyclopentyl-N—((2S,3R)-4-((S)-2,2-spirocyclobutyl-3,4-dihydro-2H-pyrano[2,3-b]pyridin-4-ylamino)-3-hydroxy-1-phenylbutan-2-yl)-6-oxo-5-(2-oxopyrrolidin-1-yl)-1,6-dihydropyridine-3-carboxamide | 626.3 | 625.766 |
| 291 | 1-cyclopentyl-N—((2S,3R)-4-((R)-2,2-spirocyclobutyl-3,4-dihydro-2H-pyrano[2,3-c]pyridin-4-ylamino)-3-hydroxy-1-phenylbutan-2-yl)-6-oxo-5-(2-oxopyrrolidin-1-yl)-1,6-dihydropyridine-3-carboxamide | 626.3 | 625.766 |
| 292 | 1-cyclobutyl-N—((2S,3R)-4-((R)-2,2-spirocyclobutyl-3,4-dihydro-2H-pyrano[2,3-c]pyridin-4-ylamino)-3-hydroxy-1-phenylbutan-2-yl)-5-oxopyrrolidine-3-carboxamide | 519.2 | 1037.31 |
| 293 | 1-cyclopentyl-N—((2S,3R)-4-((S)-2,2-spirocyclobutyl-3,4-dihydro-2H-pyrano[2,3-c]pyridin-4-ylamino)-3-hydroxy-1-phenylbutan-2-yl)-6-oxo-5-(2-oxopyrrolidin-1-yl)-1,6-dihydropyridine-3-carboxamide | 626.3 | 625.766 |
| 294 | (S)-1-cyclobutyl-N—((2S,3R)-4-((S)-2,2-spirocyclobutyl-3,4-dihydro-2H-pyrano[2,3-c]pyridin-4-ylamino)-3-hydroxy-1-phenylbutan-2-yl)-5-oxopyrrolidine-3-carboxamide | 519.2 | 518.654 |
| 295 | (R)-1-cyclobutyl-N—((2S,3R)-4-((S)-2,2-spirocyclobutyl-3,4-dihydro-2H-pyrano[2,3-c]pyridin-4-ylamino)-3-hydroxy-1-phenylbutan-2-yl)-5-oxopyrrolidine-3-carboxamide | 519.3 | 518.654 |
| 296 | 1-cyclopentyl-N—((2S,3R)-4-((R)-2,2-spirocyclobutyl-6-(trifluoromethyl)-3,4-dihydro-2H-pyrano[2,3-b]pyridin-4-ylamino)-3-hydroxy-1-phenylbutan-2-yl)-6-oxo-5-(pyridin-2-yl)-1,6-dihydropyridine-3-carboxamide | 688.3 | 687.759 |
| 297 | 1-cyclopentyl-N—((2S,3R)-4-((S)-2,2-spirocyclobutyl-6-(trifluoromethyl)-3,4-dihydro-2H-pyrano[2,3-b]pyridin-4-ylamino)-3-hydroxy-1-phenylbutan-2-yl)-6-oxo-5-(pyridin-2-yl)-1,6-dihydropyridine-3-carboxamide | 688.3 | 687.759 |
| 298 | 1-cyclopentyl-N—((2S,3R)-4-((S)-2,2-spirocyclobutyl-6-(trifluoromethyl)-3,4-dihydro-2H-pyrano[2,3-b]pyridin-4-ylamino)-3-hydroxy-1-phenylbutan-2-yl)-6-oxo-5-(2-oxopyrrolidin-1-yl)-1,6-dihydropyridine-3-carboxamide | 694.2 | 693.763 |
| 299 | N—((2S,3R)-4-((S)-6-chloro-2,2-spirocyclobutyl-3,4-dihydro-2H-pyrano[2,3-b]pyridin-4-ylamino)-3-hydroxy-1-phenylbutan-2-yl)-1-cyclopentyl-6-oxo-5-(2-oxopyrrolidin-1-yl)-1,6-dihydropyridine-3-carboxamide | 660.2 | 660.211 |
| 300 | N—((2S,3R)-4-((S)-6-chloro-2,2-spirocyclobutyl-3,4-dihydro-2H-pyrano[2,3-b]pyridin-4-ylamino)-3-hydroxy-1-phenylbutan-2-yl)- | 654.2 | 654.207 |

-continued

| Ex. No. | STRUCTURE | Mass found (M + H+) | MW |
|---|---|---|---|
| | 1-cyclopentyl-6-oxo-5-(pyridin-2-yl)-1,6-dihydropyridine-3-carboxamide | | |
| 301 | N—((2S,3R)-4-((S)-6-chloro-2,2-spirocyclobutyl-3,4-dihydro-2H-pyrano[2,3-b]pyridin-4-ylamino)-3-hydroxy-1-phenylbutan-2-yl)-1-cyclopentyl-5-((S)-3-fluoropyrrolidin-1-yl)-6-oxo-1,6-dihydropyridine-3-carboxamide | 664.2 | 664.218 |
| 302 | (S)—N—((2S,3R)-4-((S)-6-chloro-2,2-spirocyclobutyl-3,4-dihydro-2H-pyrano[2,3-b]pyridin-4-ylamino)-3-hydroxy-1-phenylbutan-2-yl)-1-cyclobutyl-5-oxopyrrolidine-3-carboxamide | 553.2 | 553.099 |
| 303 | N—((2S,3R)-4-((R)-6-chloro-2,2-spirocyclobutyl-3,4-dihydro-2H-pyrano[2,3-b]pyridin-4-ylamino)-3-hydroxy-1-phenylbutan-2-yl)-1-cyclopentyl-6-oxo-5-(2-oxopyrrolidin-1-yl)-1,6-dihydropyridine-3-carboxamide | 660.2 | 660.211 |
| 304 | N—((2S,3R)-4-((S)-6-chloro-2,2-spirocyclobutyl-3,4-dihydro-2H-pyrano[2,3-b]pyridin-4-ylamino)-3-hydroxy-1-(thiophen-3-yl)butan-2-yl)-1-cyclopentyl-6-oxo-5-(2-oxopyrrolidin-1-yl)-1,6-dihydropyridine-3-carboxamide | 666.2 | 666.239 |
| 305 | 1-cyclopentyl-N—((2S,3R)-4-((S)-2,2-spirocyclobutyl-6-neopentyl-3,4-dihydro-2H-pyrano[2,3-b]pyridin-4-ylamino)-3-hydroxy-1-phenylbutan-2-yl)-6-oxo-5-(pyridin-2-yl)-1,6-dihydropyridine-3-carboxamide | 690.3 | 689.896 |
| 306 | 1-cyclopentyl-N—((2S,3R)-4-(2,2-spirocyclobutylchroman-4-ylamino)-3-hydroxy-1-phenylbutan-2-yl)-6-oxo-5-(2-oxopyrrolidin-1-yl)-1,6-dihydropyridine-3-carboxamide | 625 | 624.778 |
| 307 | 1-cyclopentyl-N—((2S,3R)-4-((S)-6-ethyl-2,2-spirocyclobutyl-3,4-dihydro-2H-pyrano[2,3-b]pyridin-4-ylamino)-3-hydroxy-1-phenylbutan-2-yl)-6-oxo-5-(2-oxopyrrolidin-1-yl)-1,6-dihydropyridine-3-carboxamide | 654.3 | 653.819 |
| 308 | 1-cyclopentyl-N—((2S,3R)-4-((S)-6-ethyl-2,2-spirocyclobutyl-3,4-dihydro-2H-pyrano[2,3-b]pyridin-4-ylamino)-3-hydroxy-1-phenylbutan-2-yl)-6-oxo-5-(pyridin-2-yl)-1,6-dihydropyridine-3-carboxamide | 648.3 | 647.815 |
| 309 | 1,3-dicyclobutyl-N—((2S,3R)-4-((S)-6-ethyl-2,2-spirocyclobutyl-3,4-dihydro-2H-pyrano[2,3-b]pyridin-4-ylamino)-3-hydroxy-1-phenylbutan-2-yl)-2-oxo-hexahydropyrimidine-5-carboxamide | 616.3 | 615.814 |
| 310 | N—((2S,3R)-4-((S)-2,2-spirocyclobutyl-6-neopentyl-3,4-dihydro-2H-pyrano[2,3-b]pyridin-4-ylamino)-3-hydroxy-1-phenylbutan-2-yl)-6-oxo-1-((R)-tetrahydrofuran-3-yl)-1,6-dihydropyridine-3-carboxamide | 615.3 | 614.782 |
| 311 | 1-cyclopentyl-5-(3,3-difluorocyclopentyl)-N—((2S,3R)-4-((S)-2,2-spirocyclobutyl-6-neopentyl-3,4-dihydro-2H-pyrano[2,3-b]pyridin-4-ylamino)-3-hydroxy-1-phenylbutan-2-yl)-6-oxo-1,6-dihydropyridine-3-carboxamide | 718.3 | 1433.82 |
| 312 | N—((2S,3R)-4-((S)-2,2-spirocyclobutyl-6-neopentyl-3,4-dihydro-2H-pyrano[2,3-b]pyridin-4-ylamino)-3-hydroxy-1-phenylbutan-2-yl)-6-oxo-1-(thiophen-2-ylmethyl)-1,6-dihydropyridine-3-carboxamide | 641.2 | 640.845 |
| 313 | 1-cyclopentyl-N—((2S,3R)-4-((S)-2,2-spirocyclobutyl-6-neopentyl-3,4-dihydro-2H-pyrano[2,3-b]pyridin-4-ylamino)-3-hydroxy-1-phenylbutan-2-yl)-6-oxo-1,6-dihydropyridine-3-carboxamide | 613.3 | 612.81 |
| 314 | 1-cyclopentyl-5-(3,3-difluorocyclopentyl)-N—((2S,3R)-4-((S)-6-ethyl-2,2-spirocyclobutyl-3,4-dihydro-2H-pyrano[2,3-b]pyridin-4-ylamino)-3-hydroxy-1-phenylbutan-2-yl)-6-oxo-1,6-dihydropyridine-3-carboxamide | 718.3 | 1349.66 |
| 315 | N—((2S,3R)-4-((S)-6-ethyl-2,2-spirocyclobutyl-3,4-dihydro-2H-pyrano[2,3-b]pyridin-4-ylamino)-3-hydroxy-1-phenylbutan-2-yl)-6-oxo-1-((R)-tetrahydrofuran-3-yl)-1,6-dihydropyridine-3-carboxamide | 573.2 | 572.702 |
| 316 | N—((2S,3R)-4-((S)-6-ethyl-2,2-spirocyclobutyl-3,4-dihydro-2H-pyrano[2,3-b]pyridin-4-ylamino)-3-hydroxy-1-phenylbutan-2-yl)-1-(furan-2-ylmethyl)-6-oxo-1,6-dihydropyridine-3-carboxamide | 583.2 | 582.697 |
| 317 | N—((2S,3R)-4-((S)-6-ethyl-2,2-spirocyclobutyl-3,4-dihydro-2H-pyrano[2,3-b]pyridin-4-ylamino)-3-hydroxy-1-phenylbutan-2-yl)-6-oxo-1-(thiophen-2-ylmethyl)-1,6-dihydropyridine-3-carboxamide | 599.2 | 598.764 |
| 318 | (S)—N—((2S,3R)-4-((S)-2,2-spirocyclobutyl-6-neopentyl-3,4-dihydro-2H-pyrano[2,3-b]pyridin-4-ylamino)-3-hydroxy-1-phenylbutan-2-yl)-5-oxo-tetrahydrofuran-2-carboxamide | 536.2 | 535.681 |
| 319 | 1-cyclopentyl-N—((2S,3R)-3-hydroxy-4-((S)-6-isopentyl-2,2-spirocyclobutyl-3,4-dihydro-2H-pyrano[2,3-b]pyridin-4-ylamino)-1-phenylbutan-2-yl)-6-oxo-5-(pyridin-2-yl)-1,6-dihydropyridine-3-carboxamide | 690.3 | 689.896 |
| 320 | 1-cyclopentyl-N—((2S,3R)-4-((S)-2,2-spirocyclobutyl-6-neopentylchroman-4-ylamino)-3-hydroxy-1-phenylbutan-2-yl)-6-oxo-5-(2-oxopyrrolidin-1-yl)-1,6-dihydropyridine-3-carboxamide | 695.4 | 694.912 |

-continued

| Ex. No. | STRUCTURE | Mass found (M + H+) | MW |
|---|---|---|---|
| 321 | 1-cyclopentyl-N—((2S,3R)-4-((S)-2,2-spirocyclobutyl-6-neopentylchroman-4-ylamino)-3-hydroxy-1-phenylbutan-2-yl)-6-oxo-1,6-dihydropyridine-3-carboxamide | 612.4 | 611.822 |
| 322 | 1-cyclopentyl-N—((2S,3R)-4-((S)-2,2-spirocyclobutyl-6-(trifluoromethyl)chroman-4-ylamino)-3-hydroxy-1-phenylbutan-2-yl)-6-oxo-5-(2-oxopyrrolidin-1-yl)-1,6-dihydropyridine-3-carboxamide | 693.3 | 692.775 |
| 323 | 1-cyclopentyl-N—((2S,3R)-4-((S)-2,2-spirocyclobutyl-6-(trifluoromethyl)chroman-4-ylamino)-3-hydroxy-1-phenylbutan-2-yl)-6-oxo-1,6-dihydropyridine-3-carboxamide | 598.3 | 609.685 |
| 324 | (S)—N—((2S,3R)-4-((S)-2,2-spirocyclobutyl-6-(trifluoromethyl)chroman-4-ylamino)-3-hydroxy-1-phenylbutan-2-yl)-6-oxopiperidine-2-carboxamide | 546.3 | 545.599 |
| 325 | (S)—N—((2S,3R)-4-((S)-2,2-spirocyclobutyl-6-neopentylchroman-4-ylamino)-3-hydroxy-1-phenylbutan-2-yl)-6-oxopiperidine-2-carboxamide | 548.3 | 547.735 |
| 326 | 1-cyclopentyl-N—((2S,3R)-4-((S)-2,2-spirocyclobutyl-6-(trifluoromethyl)chroman-4-ylamino)-3-hydroxy-1-phenylbutan-2-yl)-6-oxo-5-(pyridin-2-yl)-1,6-dihydropyridine-3-carboxamide | 687.3 | 686.771 |
| 327 | 1-cyclopentyl-N—((2S,3R)-1-(3,5-difluorophenyl)-4-((S)-2,2-spirocyclobutyl-6-neopentyl-3,4-dihydro-2H-pyrano[2,3-b]pyridin-4-ylamino)-3-hydroxybutan-2-yl)-6-oxo-5-(pyridin-2-yl)-1,6-dihydropyridine-3-carboxamide | 726.4 | 725.876 |
| 328 | N—((2S,3R)-1-(3-cyanophenyl)-4-((S)-2,2-spirocyclobutyl-6-neopentyl-3,4-dihydro-2H-pyrano[2,3-b]pyridin-4-ylamino)-3-hydroxybutan-2-yl)-1-cyclopentyl-6-oxo-5-(pyridin-2-yl)-1,6-dihydropyridine-3-carboxamide | 715.4 | 714.906 |
| 329 | N—((2S,3R)-4-((S)-6-chloro-2,2-spirocyclobutyl-7-(morpholinomethyl)chroman-4-ylamino)-3-hydroxy-1-phenylbutan-2-yl)-1-cyclopentyl-6-oxo-5-(pyridin-2-yl)-1,6-dihydropyridine-3-carboxamide | 752.3 | 752.351 |
| 330 | N—((2S,3R)-4-((S)-6-chloro-2,2-spirocyclobutyl-7-(piperidinomethyl)chroman-4-ylamino)-3-hydroxy-1-phenylbutan-2-yl)-1-cyclopentyl-6-oxo-5-(pyridin-2-yl)-1,6-dihydropyridine-3-carboxamide | 750.3 | 750.379 |
| 331 | N—((2S,3R)-4-((S)-6-chloro-2,2-spirocyclobutyl-7-morpholinochroman-4-ylamino)-3-hydroxy-1-phenylbutan-2-yl)-1-cyclopentyl-6-oxo-5-(pyridin-2-yl)-1,6-dihydropyridine-3-carboxamide | 738.3 | 738.324 |
| 332 | (S)—N—((2S,3R)-1-(3-cyanophenyl)-4-((S)-2,2-spirocyclobutyl-6-neopentyl-3,4-dihydro-2H-pyrano[2,3-b]pyridin-4-ylamino)-3-hydroxybutan-2-yl)-1-oxo-1,2,3,4-tetrahydroisoquinoline-3-carboxamide | 622.3 | 621.778 |
| 333 | N—((2S,3R)-4-((S)-6-ethyl-2,2-spirocyclopentylchroman-4-ylamino)-3-hydroxy-1-phenylbutan-2-yl)cyclopent-1-enecarboxamide | 489 | 488.668 |
| 334 | N—((2S,3R)-4-((S)-6-ethyl-2,2-spirocyclopentylchroman-4-ylamino)-3-hydroxy-1-phenylbutan-2-yl)-2-oxo-2H-chromene-3-carboxamide | 567 | 566.694 |
| 335 | 1-cyclopentyl-N—((2S,3R)-4-((2S,4S)-6-ethyl-2-(methoxymethyl)-2-methylchroman-4-ylamino)-3-hydroxy-1-phenylbutan-2-yl)-6-oxo-5-(2-oxopyrrolidin-1-yl)-1,6-dihydropyridine-3-carboxamide and 1-cyclopentyl-N—((2S,3R)-4-((2R,4S)-6-ethyl-2-(methoxymethyl)-2-methylchroman-4-ylamino)-3-hydroxy-1-phenylbutan-2-yl)-6-oxo-5-(2-oxopyrrolidin-1-yl)-1,6-dihydropyridine-3-carboxamide | 671 | 1341.69 |
| 336 | 1-cyclopentyl-N—((2S,3R)-4-((2R,4S)-6-ethyl-2-(methoxymethyl)-2-methylchroman-4-ylamino)-3-hydroxy-1-phenylbutan-2-yl)-6-oxo-5-(pyridin-2-yl)-1,6-dihydropyridine-3-carboxamide and 1-cyclopentyl-N—((2S,3R)-4-((2S,4S)-6-ethyl-2-(methoxymethyl)-2-methylchroman-4-ylamino)-3-hydroxy-1-phenylbutan-2-yl)-6-oxo-5-(pyridin-2-yl)-1,6-dihydropyridine-3-carboxamide | 665 | 1329.68 |
| 337 | 1-cyclopentyl-N—((2S,3R)-4-((2R,4S)-6-ethyl-2-(methoxymethyl)-2-methylchroman-4-ylamino)-3-hydroxy-1-phenylbutan-2-yl)-6-oxo-5-(2-oxopyrrolidin-1-yl)-1,6-dihydropyridine-3-carboxamide | 671 | 670.846 |
| 338 | 1-cyclopentyl-N—((2S,3R)-4-((2S,4S)-6-ethyl-2-(methoxymethyl)-2-methylchroman-4-ylamino)-3-hydroxy-1-phenylbutan-2-yl)-6-oxo-5-(2-oxopyrrolidin-1-yl)-1,6-dihydropyridine-3-carboxamide | 671 | 670.846 |
| 339 | 1-cyclopentyl-N—((2S,3R)-4-((2R,4S)-6-ethyl-2-(methoxymethyl)-2-methylchroman-4-ylamino)-3-hydroxy-1-phenylbutan-2-yl)-6-oxo-5-(pyridin-2-yl)-1,6-dihydropyridine-3-carboxamide | 665 | 664.842 |
| 340 | 1-cyclopentyl-N—((2S,3R)-4-((2S,4S)-6-ethyl-2-(methoxymethyl)-2-methylchroman-4-ylamino)-3-hydroxy-1-phenylbutan-2-yl)-6-oxo-5-(pyridin-2-yl)-1,6-dihydropyridine-3-carboxamide | 665 | 664.842 |

-continued

| Ex. No. | STRUCTURE | Mass found (M + H+) | MW |
|---|---|---|---|
| 341 | 1-cyclopentyl-N—((2S,3R)-4-((S)-6-ethyl-2,2-dimethylchroman-4-ylamino)-3-hydroxy-1-phenylbutan-2-yl)-6-oxo-5-(pyridin-2-yl)-1,6-dihydropyridine-3-carboxamide | 635 | 634.816 |
| 342 | 1-cyclopentyl-N—((2S,3R)-4-((S)-6-ethyl-2,2-spirotetrahydrofuranylchroman-4-ylamino)-3-hydroxy-1-phenylbutan-2-yl)-6-oxo-5-(2-oxopyrrolidin-1-yl)-1,6-dihydropyridine-3-carboxamide | 669.3 | 1337.66 |
| 343 | 1-cyclopentyl-N—((2S,3R)-4-((S)-2-cyclopropyl-6,6-dimetbyl-4,5,6,7-tetrahydrobenzo[d]oxazol-4-ylamino)-3-hydroxy-1-phenylbutan-2-yl)-6-oxo-5-(2-oxopyrrolidin-1-yl)-1,6-dihydropyridine-3-carboxamide | 642.3 | 641.808 |
| 344 | 1-cyclopentyl-N—((2S,3R)-3-hydroxy-1-phenyl-4-((S)-3,7,7-trimethyl-5,6,7,8-tetrahydroquinolin-5-ylamino)butan-2-yl)-6-oxo-5-(2-oxopyrrolidin-1-yl)-1,6-dihydropyridine-3-carboxamide | 626.3 | 625.809 |
| 345 | 1-cyclopentyl-N—((2S,3R)-4-((S)-6-ethyl-2,2-spirotetrahydropyran-4-ylchroman-4-ylamino)-3-hydroxy-1-phenylbutan-2-yl)-6-oxo-5-(pyridin-2-yl)-1,6-dihydropyridine-3-carboxamide | 677.3 | 676.853 |
| 346 | 1-cyclopentyl-N—((2S,3R)-4-((S)-6-ethyl-(R)-2,2-spirotetrahydrofuranylchroman-4-ylamino)-3-hydroxy-1-phenylbutan-2-yl)-6-oxo-5-(2-oxopyrrolidin-1-yl)-1,6-dihydropyridine-3-carboxamide | 669.3 | 668.83 |
| 347 | 1-cyclopentyl-N—((2S,3R)-4-((S)-6-ethyl-(S)-2,2-spirotetrahydrofuranylchroman-4-ylamino)-3-hydroxy-1-phenylbutan-2-yl)-6-oxo-5-(2-oxopyrrolidin-1-yl)-1,6-dihydropyridine-3-carboxamide | 669.3 | 668.83 |
| 348 | 1-cyclopentyl-N—((2S,3R)-3-hydroxy-4-((S)-3-methyl-7,7-spirocyclobutyl-5,6,7,8-tetrahydroquinolin-5-ylamino)-1-phenylbutan-2-yl)-6-oxo-5-(pyridin-2-yl)-1,6-dihydropyridine-3-carboxamide | 632.3 | 631.817 |
| 349 | 1-cyclopentyl-N—((2S,3R)-1-(3,5-difluorophenyl)-3-hydroxy-4-((S)-3-methyl-7,7-spirocyclobutyl-5,6,7,8-tetrahydroquinolin-5-ylamino)butan-2-yl)-6-oxo-5-(pyridin-2-yl)-1,6-dihydropyridine-3-carboxamide | 668.3 | 667.797 |
| 350 | 1-allyl-N—((2S,3R)-1-(3-allylphenyl)-4-((S)-6-ethyl-2,2-spirocyclobutylchroman-4-ylamino)-3-hydroxybutan-2-yl)-6-oxo-5-(pyridin-2-yl)-1,6-dihydropyridine-3-carboxamide | 659.3 | 658.838 |
| 351 | 1-allyl-N—((2S,3R)-1-(3-allylphenyl)-4-((S)-6-ethyl-2,2-spirocyclobutylchroman-4-ylamino)-3-hydroxybutan-2-yl)-5-bromo-6-oxo-1,6-dihydropyridine-3-carboxamide | 660.2; 662.2 | 660.649 |
| 352 | 1-cyclopentyl-N—((2S,3R)-4-((S)-6-ethyl-2,2-spirocyclobutylchroman-4-ylamino)-3-hydroxy-1-phenylbutan-2-yl)-5-(1H-indol-2-yl)-6-oxo-1,6-dihydropyridine-3-carboxamide | 685.3 | 684.876 |
| 353 | 1-acetyl-5-(cyclohexylmethyl)-N—((2S,3R)-4-((S)-6-ethyl-2,2-spirocyclopentylchroman-4-ylamino)-3-hydroxy-1-phenylbutan-2-yl)piperidine-3-carboxamide | 644.3 | 2575.63 |
| 354 | 5-(cyclohexylmethyl)-N—((2S,3R)-4-((S)-6-ethyl-2,2-spirocyclopentylchroman-4-ylamino)-3-hydroxy-1-phenylbutan-2-yl)-1-(methylsulfonyl)piperidine-3-carboxamide | 680.3 | 2719.85 |
| 355 | N—((2S,3R)-4-((S)-6-ethyl-2,2-spirocyclobutylchroman-4-ylamino)-3-hydroxy-1-phenylbutan-2-yl)cyclohexanecarboxamide | 491.3 | 490.684 |
| 356 | N—((2S,3R)-4-((S)-6-ethyl-2,2-spirocyclobutylchroman-4-ylamino)-3-hydroxy-1-phenylbutan-2-yl)-2-phenylcyclopropanecarboxamide | 525.3 | 1049.4 |
| 357 | N—((2S,3R)-1-(1-acetylpiperidin-3-yl)-4-((S)-6-ethyl-2,2-spirocyclobutylchroman-4-ylamino)-3-hydroxybutan-2-yl)-1-cyclopentyl-6-oxo-5-(2-oxopyrrolidin-1-yl)-1,6-dihydropyridine-3-carboxamide | 702.3 | 701.904 |
| 358 | N—((2S,3R)-4-((S)-6-bromo-2,2-spirocyclobutylchroman-4-ylamino)-3-hydroxy-1-(pyridin-3-yl)butan-2-yl)-1-cyclopentyl-6-oxo-5-(2-oxopyrrolidin-1-yl)-1,6-dihydropyridine-3-carboxamide | 704 | 704.662 |
| 359 | 1-cyano-N—((2S,3R)-4-((S)-6-ethyl-2,2-spirocyclobutylchroman-4-ylamino)-3-hydroxy-1-phenylbutan-2-yl)cyclopropanecarboxamide | 474.2 | 473.613 |
| 360 | (S)-1-(cyclopentanecarbonyl)-N—((2S,3R)-4-((S)-6-ethyl-2,2-dimethylchroman-4-ylamino)-3-hydroxy-1-phenylbutan-2-yl)pyrrolidine-3-carboxamide | 562.3 | 561.762 |
| 361 | 1-cyclopentyl-N—((2S,3R)-3-hydroxy-1-phenyl-4-(-2,6,6-trimethyl-3-oxo-2,3,5,6,7,8-hexahydroisoquinolin-8-ylamino)butan-2-yl)-6-oxo-5-(2-oxopyrrolidin-1-yl)-1,6-dihydropyridine-3-carboxamide | 642.2 | 1283.62 |
| 362 | 1-cyclopentyl-N—((2S,3R)-3-hydroxy-1-phenyl-4-((S)-2,6,6-trimethyl-3-oxo-2,3,5,6,7,8-hexahydroisoquinolin-8-ylamino)butan-2-yl)-6-oxo-5-(2-oxopyrrolidin-1-yl)-1,6-dihydropyridine-3-carboxamide | 642.3 | 641.808 |

-continued

| Ex. No. | STRUCTURE | Mass found (M + H+) | MW |
|---|---|---|---|
| 363 | 1-cyclopentyl-N—((2S,3R)-3-hydroxy-1-phenyl-4-((R)-2,6,6-trimethyl-3-oxo-2,3,5,6,7,8-hexahydroisoquinolin-8-ylamino)butan-2-yl)-6-oxo-5-(2-oxopyrrolidin-1-yl)-1,6-dihydropyridine-3-carboxamide | 642.3 | 641.808 |
| 364 | (R)-3-acetyl-N—((2S,3S)-3-hydroxy-4-((S)-6-neopentyl-3,4-dihydro-2,2-spirocyclobutyl-pyrano[2,3-b]pyridin-4-ylamino)-1-phenylbutan-2-yl)thiazolidine-2-carboxamide | 581.2 | 580.79 |
| 365 | (S)-3-acetyl-N—((2S,3S)-3-bydroxy-4-((S)-6-neopentyl-3,4-dihydro-2,2-spirocyclobutyl-pyrano[2,3-b]pyridin-4-ylamino)-1-phenylbutan-2-yl)thiazolidine-2-carboxamide | 581.2 | 580.79 |
| 366 | N—((2S,3R)-1-(3-cyanophenyl)-4-((S)-6-ethyl-2,2-spirocyclobutylchroman-4-ylamino)-3-hydroxybutan-2-yl)-5-oxo-1-(pyridin-2-yl)pyrrolidine-3-carboxamide | 594.3 | 1187.45 |
| 367 | 1-cyclopentyl-N—((2S,3R)-4-((S)-6-ethyl-2,2-spirocyclobutylchroman-4-ylamino)-3-hydroxy-1-phenylbutan-2-yl)-5-morpholino-6-oxo-1,6-dihydropyridine-3-carboxamide | 655.4 | 654.847 |
| 368 | 1-cyclopentyl-N—((2S,3R)-4-((S)-6-ethyl-2,2-spirocyclobutylchroman-4-ylamino)-3-hydroxy-1-phenylbutan-2-yl)-5-((S)-3-fluoropyrrolidin-1-yl)-6-oxo-1,6-dihydropyridine-3-carboxamide | 657.4 | 656.838 |
| 369 | N—((2S,3R)-4-((S)-6-chloro-2,2-spirocyclobutylchroman-4-ylamino)-3-hydroxy-1-phenylbutan-2-yl)-1-cyclopentyl-5-((S)-3-fluoropyrrolidin-1-yl)-6-oxo-1,6-dihydropyridine-3-carboxamide | 663.3 | 663.23 |
| 370 | N—((2S,3R)-4-((S)-2,2-spirocyclobutylchroman-4-ylamino)-3-hydroxy-1-phenylbutan-2-yl)-1-cyclopentyl-5-((S)-3-fluoropyrrolidin-1-yl)-6-oxo-1,6-dihydropyridine-3-carboxamide | 629.3 | 628.784 |
| 371 | 1-cyclopentyl-5-((S)-3-fluoropyrrolidin-1-yl)-N—((2S,3R)-3-hydroxy-1-phenyl-4-((S)-6-(trifluoromethyl)-2,2-spirocyclobutylchroman-4-ylamino)butan-2-yl)-6-oxo-1,6-dihydropyridine-3-carboxamide | 697.3 | 696.782 |
| 372 | 1-cyclopentyl-5-((S)-3-fluoropyrrolidin-1-yl)-N-(-4-(2,7,7-trimethyl-5,6,7,8-tetrahydroquinazolin-5-ylamino)butan-2-yl)-6-oxo-1,6-dihydropyridine-3-carboxamide | 631.4 | 1261.64 |
| 373 | 1-cyclopentyl-N—((2S,3R)-3-hydroxy-1-phenyl-4-(2,7,7-trimethyl-5,6,7,8-tetrahydroquinazolin-5-ylamino)butan-2-yl)-6-oxo-5-(2-oxopyrrolidin-1-yl)-1,6-dihydropyridine-3-carboxamide | 627.4 | 1253.59 |
| 374 | 1-cyclopentyl-N—((2S,3R)-3-hydroxy-1-phenyl-4-(2,7,7-trimethyl-5,6,7,8-tetrahydroquinazolin-5-ylamino)butan-2-yl)-6-oxo-5-(pyridin-2-yl)-1,6-dihydropyridine-3-carboxamide | 621.3 | 1241.59 |
| 375 | (S)-1-cyclobutyl-N—((2S,3R)-3-hydroxy-1-phenyl-4-(2,7,7-trimethyl-5,6,7,8-tetrahydroquinazolin-5-ylamino)butan-2-yl)-5-oxopyrrolidine-3-carboxamide | 520.3 | 1039.37 |
| 376 | 1-cyclopentyl-5-(3,3-difluoropyrrolidin-1-yl)-N—((2S,3R)-4-((S)-6-ethyl-2,2-spirocyclobutylchroman-4-ylamino)-3-hydroxy-1-phenylbutan-2-yl)-6-oxo-1,6-dihydropyridine-3-carboxamide | 675.3 | 674.828 |
| 377 | N—((2S,3R)-1-(3-cyanophenyl)-4-((S)-6-ethyl-2,2-spirocyclobutylchroman-4-ylamino)-3-hydroxybutan-2-yl)-1-cyclopentyl-5-(3,3-difluoropyrrolidin-1-yl)-6-oxo-1,6-dihydropyridine-3-carboxamide | 700.3 | 699.838 |
| 378 | N—((2S,3R)-4-((S)-6-ethyl-2,2-spirocyclobutylchroman-4-ylamino)-3-hydroxy-1-phenylbutan-2-yl)-6-oxo-1-(tetrahydro-2H-pyran-4-yl)-1,6-dihydropyridine-3-carboxamide | 586.3 | 585.741 |
| 379 | N—((2S,3R)-4-((S)-6-ethyl-2,2-spirocyclobutylchroman-4-ylamino)-3-hydroxy-1-phenylbutan-2-yl)-6-oxo-1-((R)-tetrahydrofuran-3-yl)-1,6-dihydropyridine-3-carboxamide | 572.3 | 571.714 |
| 380 | 5-bromo-N—((2S,3R)-4-((S)-6-ethyl-2,2-spirocyclobutylchroman-4-ylamino)-3-hydroxy-1-phenylbutan-2-yl)-6-oxo-1-((R)-tetrahydrofuran-3-yl)-1,6-dibydropyridine-3-carboxamide | 652.2 | 650.61 |
| 381 | N—((2S,3R)-4-((S)-6-ethyl-2,2-spirocyclobutylchroman-4-ylamino)-3-hydroxy-1-phenylbutan-2-yl)-1-(furan-2-ylmethyl)-6-oxo-1,6-dihydropyridine-3-carboxamide | 582.3 | 581.709 |
| 382 | N—((2S,3R)-4-((S)-6-ethyl-2,2-spirocyclobutylchroman-4-ylamino)-3-hydroxy-1-phenylbutan-2-yl)-6-oxo-1-(thiophen-2-ylmethyl)-1,6-dihydropyridine-3-carboxamide | 598.3 | 597.776 |
| 383 | N—((2S,3R)-4-((S)-6-ethyl-2,2-spirocyclobutylchroman-4-ylamino)-3-hydroxy-1-phenylbutan-2-yl)-6-oxo-5-(pyridin-2-yl)-1-((R)-tetrahydrofuran-3-yl)-1,6-dihydropyridine-3-carboxamide | 649.3 | 648.8 |
| 384 | N—((2S,3R)-4-((S)-6-ethyl-2,2-spirocyclobutylchroman-4-ylamino)-3-hydroxy-1-phenylbutan-2-yl)-5-((S)-3-fluoropyrrolidin-1-yl)-6-oxo-1-((R)-tetrahydrofuran-3-yl)-1,6-dihydropyridine-3-carboxamide | 659.3 | 658.81 |
| 385 | N—((2S,3R)-4-((S)-6-cyano-2,2-(spirotetrahydrofuran-3-yl)chroman-4-ylamino)-3-hydroxy-1-phenylbutan-2-yl)-1-cyclopentyl-6-oxo-5-(pyridin-2-yl)-1,6-dihydropyridine-3-carboxamide | 660.2 | 1319.57 |

| Ex. No. | STRUCTURE | Mass found (M + H+) | MW |
|---|---|---|---|
| 386 | N—((2S,3R)-4-((S)-6-cyano-2,2-(spirotetrahydrofuran-3-yl)chroman-4-ylamino)-3-hydroxy-1-phenylbutan-2-yl)-6-oxo-5-(pyridin-2-yl)-1-((R)-tetrahydrofuran-3-yl)-1,6-dihydropyridine-3-carboxamide | 662.2 | 1323.51 |
| 387 | N—((2S,3R)-4-((S)-6-cyano-2,2-(spirotetrahydrofuran-3-yl)chroman-4-ylamino)-3-hydroxy-1-phenylbutan-2-yl)-6-oxo-1-((R)-tetrahydrofuran-3-yl)-1,6-dihydropyridine-3-carboxamide | 585.2 | 1169.34 |
| 388 | N—((2S,3R)-4-((S)-2,2-(spirotetrahydrofuran-3-yl)chroman-4-ylamino)-3-hydroxy-1-phenylbutan-2-yl)-1-cyclopentyl-6-oxo-5-(pyridin-2-yl)-1,6-dihydropyridine-3-carboxamide | 635.2 | 1269.55 |
| 389 | N—((2S,3R)-4-((S)-6-bromo-2,2-spirotetrahydrofuranylchroman-4-ylamino)-3-hydroxy-1-phenylbutan-2-yl)-1-cyclopentyl-6-oxo-5-(pyridin-2-yl)-1,6-dihydropyridine-3-carboxamide | 713 | 1415.32 |
| 390 | (R)—N—((2S,3R)-4-((S)-6-ethyl-2,2-spirocyclopentylchroman-4-ylamino)-3-hydroxy-1-phenylbutan-2-yl)-1,2,3,4-tetrahydroquinoline-3-carboxamide | 554 | 553.743 |
| 391 | (S)—N—((2S,3R)-4-(6-ethyl-2,2-spirocyclopentylchroman-4-ylamino)-3-hydroxy-1-phenylbutan-2-yl)-1,2,3,4-tetrahydroquinoline-3-carboxamide | 554 | 553.743 |
| 392 | N—((2S,3R)-4-((S)-6-ethyl-2,2-spirocyclopentylchroman-4-ylamino)-3-hydroxy-1-phenylbutan-2-yl)-1-methyl-1,2,3,4-tetrahydroquinoline-3-carboxamide | 568 | 1135.54 |
| 393 | 4-acetyl-N—((2S,3R)-4-((S)-6-ethyl-2,2-spirocyclopentylchroman-4-ylamino)-3-hydroxy-1-phenylbutan-2-yl)-4H-benzo[b][1,4]oxazine-2-carboxamide | 596 | 595.736 |
| 394 | (R)-4-benzoyl-N—((2S,3R)-4-((S)-6-ethyl-2,2-spirocyclopentylchroman-4-ylamino)-3-hydroxy-1-phenylbutan-2-yl)-7-fluoro-3,4-dihydro-2H-benzo[b][1,4]oxazine-2-carboxamide | 678 | 677.813 |
| 395 | N—((2S,3R)-4-((S)-6-ethyl-2,2-spirocyclopentylchroman-4-ylamino)-3-hydroxy-1-phenylbutan-2-yl)-5-fluoro-3,4-dihydro-2H-benzo[b][1,4]oxazine-2-carboxamide | 574 | 1147.41 |
| 396 | (R)-4-acetyl-N—((2S,3R)-4-((S)-6-ethyl-2,2-spirocyclopentylchroman-4-ylamino)-3-hydroxy-1-phenylbutan-2-yl)-5-fluoro-3,4-dihydro-2H-benzo[b][1,4]oxazine-2-carboxamide | 616 | 615.742 |
| 397 | (S)-4-acetyl-N—((2S,3R)-4-((S)-6-ethyl-2,2-spirocyclopentylchroman-4-ylamino)-3-hydroxy-1-phenylbutan-2-yl)-5-fluoro-3,4-dihydro-2H-benzo[b][1,4]oxazine-2-carboxamide | 616 | 615.742 |
| 398 | (R)-4-benzoyl-N—((2S,3R)-4-((S)-6-ethyl-2,2-spirocyclopentylchroman-4-ylamino)-3-hydroxy-1-phenylbutan-2-yl)-5-fluoro-3,4-dihydro-2H-benzo[b][1,4]oxazine-2-carboxamide | 678 | 677.813 |
| 399 | (S)-4-benzoyl-N—((2S,3R)-4-((S)-6-ethyl-2,2-spirocyclopentylchroman-4-ylamino)-3-hydroxy-1-phenylbutan-2-yl)-5-fluoro-3,4-dihydro-2H-benzo[b][1,4]oxazine-2-carboxamide | 678 | 677.813 |
| 400 | (R)—N—((2S,3R)-4-((S)-6-ethyl-2,2-spirocyclopentylchroman-4-ylamino)-3-hydroxy-1-phenylbutan-2-yl)-7-fluoro-4-isobutyryl-3,4-dihydro-2H-benzo[b][1,4]oxazine-2-carboxamide | 644 | 643.795 |
| 401 | (S)—N—((2S,3R)-4-((S)-6-ethyl-2,2-spirocyclopentylchroman-4-ylamino)-3-hydroxy-1-phenylbutan-2-yl)-7-fluoro-4-isobutyryl-3,4-dihydro-2H-benzo[b][1,4]oxazine-2-carboxamide | 644 | 643.795 |
| 402 | (R)—N—((2S,3R)-4-((S)-6-ethyl-2,2-spirocyclopentylchroman-4-ylamino)-3-hydroxy-1-phenylbutan-2-yl)-5-fluoro-4-isobutyryl-3,4-dihydro-2H-benzo[b][1,4]oxazine-2-carboxamide | 644 | 643.795 |
| 403 | (S)—N—((2S,3R)-4-((S)-6-ethyl-2,2-spirocyclopentylchroman-4-ylamino)-3-hydroxy-1-phenylbutan-2-yl)-5-fluoro-4-isobutyryl-3,4-dihydro-2H-benzo[b][1,4]oxazine-2-carboxamide | 644 | 643.795 |
| 404 | N—((2S,3R)-4-((S)-6-ethyl-2,2-spirocyclopentylchroman-4-ylamino)-3-hydroxy-1-phenylbutan-2-yl)morpholine-2-carboxamide | 508 | 1015.34 |
| 405 | 4-benzoyl-N—((2S,3R)-4-((S)-6-ethyl-2,2-spirocyclopentylchroman-4-ylamino)-3-hydroxy-1-phenylbutan-2-yl)morpholine-2-carboxamide | 612 | 1223.56 |
| 406 | 4-acetyl-N—((2S,3R)-4-((S)-6-ethyl-2,2-spirocyclopentylchroman-4-ylamino)-3-hydroxy-1-phenylbutan-2-yl)morpholine-2-carboxamide | 550 | 1099.42 |
| 407 | (R)—N—((2S,3R)-4-((S)-6-ethyl-2,2-spirocyclopentylchroman-4-ylamino)-3-hydroxy-1-phenylbutan-2-yl)-4-methylmorpholine-2-carboxamide | 522 | 521.698 |
| 408 | (S)—N—((2S,3R)-4-((S)-6-ethyl-2,2-spirocyclopentylchroman-4-ylamino)-3-hydroxy-1-phenylbutan-2-yl)-4-methylmorpholine-2-carboxamide | 522 | 521.698 |
| 409 | (R)-4-cyclopentyl-N—((2S,3R)-4-((S)-6-ethyl-2,2-spirocyclopentylchroman-4-ylamino)-3-hydroxy-1-phenylbutan-2-yl)morpholine-2-carboxamide | 576 | 575.789 |
| 410 | (S)-4-cyclopentyl-N—((2S,3R)-4-((S)-6-ethyl-2,2-spirocyclopentylchroman-4-ylamino)-3-hydroxy-1-phenylbutan-2-yl)morpholine-2-carboxamide | 576 | 575.789 |

| Ex. No. | STRUCTURE | Mass found (M + H+) | MW |
|---|---|---|---|
| 411 | (R)—N—((2S,3R)-4-((S)-6-ethyl-2,2-spirocyclobutylchroman-4-ylamino)-3-hydroxy-1-phenylbutan-2-yl)-7-fluoro-4-isobutyryl-3,4-dihydro-2H-benzo[b][1,4]oxazine-2-carboxamide | 630 | 629.769 |
| 412 | (S)—N—((2S,3R)-4-((S)-6-ethyl-2,2-spirocyclobutylchroman-4-ylamino)-3-hydroxy-1-phenylbutan-2-yl)-7-fluoro-4-isobutyryl-3,4-dihydro-2H-benzo[b][1,4]oxazine-2-carboxamide | 630 | 629.769 |
| 413 | (R)-4-benzoyl-N—((2S,3R)-4-((S)-6-ethyl-2,2-spirocyclobutylchroman-4-ylamino)-3-hydroxy-1-phenylbutan-2-yl)-5-fluoro-3,4-dihydro-2H-benzo[b][1,4]oxazine-2-carboxamide | 664 | 663.786 |
| 414 | (S)-4-benzoyl-N—((2S,3R)-4-((S)-6-ethyl-2,2-spirocyclobutylchroman-4-ylamino)-3-hydroxy-1-phenylbutan-2-yl)-5-fluoro-3,4-dihydro-2H-benzo[b][1,4]oxazine-2-carboxamide | 664 | 663.786 |
| 415 | N—((2S,3R)-4-((S)-6-ethyl-2,2-spirocyclobutylchroman-4-ylamino)-3-hydroxy-1-phenylbutan-2-yl)-7-fluoro-4-methyl-3,4-dihydro-2H-benzo[b][1,4]oxazine-2-carboxamide | 574 | 1147.41 |
| 416 | (R)—N—((2S,3R)-4-((S)-6-ethyl-2,2-spirocyclobutylchroman-4-ylamino)-3-hydroxy-1-phenylbutan-2-yl)-5-fluoro-4-isobutyryl-3,4-dihydro-2H-benzo[b][1,4]oxazine-2-carboxamide | 630 | 629.769 |
| 417 | (S)—N—((2S,3R)-4-((S)-6-ethyl-2,2-spirocyclobutylchroman-4-ylamino)-3-hydroxy-1-phenylbutan-2-yl)-5-fluoro-4-isobutyryl-3,4-dihydro-2H-benzo[b][1,4]oxazine-2-carboxamide | 630 | 629.769 |
| 418 | (R)-4-benzoyl-N—((2S,3R)-4-((S)-6-ethyl-2,2-spirocyclobutylchroman-4-ylamino)-3-hydroxy-1-phenylbutan-2-yl)-7-fluoro-3,4-dihydro-2H-benzo[b][1,4]oxazine-2-carboxamide | 664 | 663.786 |
| 419 | (R)-4-acetyl-N—((2S,3R)-4-((S)-6-ethyl-2,2-spirocyclobutylchroman-4-ylamino)-3-hydroxy-1-phenylbutan-2-yl)-7-fluoro-3,4-dihydro-2H-benzo[b][1,4]oxazine-2-carboxamide | 602 | 601.715 |
| 420 | tert-butyl 3-(((2S,3R)-4-((S)-6-ethyl-2,2-spirocyclopentylchroman-4-ylamino)-3-hydroxy-1-phenylbutan-2-yl)carbamoyl)morpholine-4-carboxylate | 608 | 1215.57 |
| 421 | (S)-4-acetyl-N—((2S,3R)-4-((S)-6-ethyl-2,2-spirocyclobutylchroman-4-ylamino)-3-hydroxy-1-phenylbutan-2-yl)-7-fluoro-3,4-dihydro-2H-benzo[b][1,4]oxazine-2-carboxamide | 602 | 601.715 |
| 422 | (R)—N—((2S,3R)-4-((S)-6-ethyl-2,2-spirocyclopentylchroman-4-ylamino)-3-hydroxy-1-phenylbutan-2-yl)morpholine-3-carboxamide | 508 | 507.671 |
| 423 | (S)—N—((2S,3R)-4-((S)-6-ethyl-2,2-spirocyclopentylchroman-4-ylamino)-3-hydroxy-1-phenylbutan-2-yl)morpholine-3-carboxamide | 508 | 507.671 |
| 424 | (S)-4-(cyclopentanecarbonyl)-N—((2S,3R)-4-((S)-6-ethyl-2,2-spirocyclobutylchroman-4-ylamino)-3-hydroxy-1-phenylbutan-2-yl)morpholine-2-carboxamide | 590 | 589.772 |
| 425 | N—((2S,3R)-4-((S)-6-ethyl-2,2-spirocyclobutylchroman-4-ylamino)-3-hydroxy-1-phenylbutan-2-yl)-4-(4-methylbenzoyl)morpholine-2-carboxamide | 612 | 1223.56 |
| 426 | N—((2S,3R)-4-((S)-6-ethyl-2,2-spirocyclobutylchroman-4-ylamino)-3-hydroxy-1-phenylbutan-2-yl)-4-(3-methylbenzoyl)morpholine-2-carboxamide | 612 | 1223.56 |
| 427 | 4-(cyclohexanecarbonyl)-N—((2S,3R)-4-((S)-6-ethyl-2,2-spirocyclobutylchroman-4-ylamino)-3-hydroxy-1-phenylbutan-2-yl)morpholine-2-carboxamide | 604 | 1207.6 |
| 428 | 4-(3-chlorobenzoyl)-N—((2S,3R)-4-((S)-6-ethyl-2,2-spirocyclobutylchroman-4-ylamino)-3-hydroxy-1-phenylbutan-2-yl)morpholine-2-carboxamide | 632 | 1264.39 |
| 429 | N—((2S,3R)-4-((S)-6-ethyl-2,2-spirocyclobutylchroman-4-ylamino)-3-hydroxy-1-phenylbutan-2-yl)-4-(2-methylbenzoyl)morpholine-2-carboxamide | 612 | 1223.56 |
| 430 | 4-(4-chlorobenzoyl)-N—((2S,3R)-4-((S)-6-ethyl-2,2-spirocyclobutylchroman-4-ylamino)-3-hydroxy-1-phenylbutan-2-yl)morpholine-2-carboxamide | 632 | 1264.39 |
| 431 | (R)—N—((2S,3R)-4-((S)-6-ethyl-2,2-spirocyclobutylchroman-4-ylamino)-3-hydroxy-1-phenylbutan-2-yl)-7-fluoro-4-(3-methylbenzoyl)-3,4-dihydro-2H-benzo[b][1,4]oxazine-2-carboxamide | 678 | 677.813 |
| 432 | (S)—N—((2S,3R)-4-((S)-6-ethyl-2,2-spirocyclobutylchroman-4-ylamino)-3-hydroxy-1-phenylbutan-2-yl)-7-fluoro-4-(3-methylbenzoyl)-3,4-dihydro-2H-benzo[b][1,4]oxazine-2-carboxamide | 678 | 677.813 |
| 433 | N—((2S,3R)-1-(3-cyanophenyl)-4-((S)-6-ethyl-2,2-spirocyclobutylchroman-4-ylamino)-3-hydroxybutan-2-yl)-4-(3-methylbenzoyl)morpholine-2-carboxamide | 637 | 1273.58 |
| 434 | (R)—N—((2S,3R)-4-((S)-6-ethyl-2,2-spirocyclobutylchroman-4-ylamino)-3-hydroxy-1-phenylbutan-2-yl)-1-(3-methylbenzoyl)piperidine-3-carboxamide | 610 | 609.806 |

-continued

| Ex. No. | STRUCTURE | Mass found (M + H+) | MW |
|---|---|---|---|
| 435 | (S)—N—((2S,3R)-4-((S)-6-ethyl-2,2-spirocyclobutylchroman-4-ylamino)-3-hydroxy-1-phenylbutan-2-yl)-1-(3-methylbenzoyl)piperidine-3-carboxamide | 610 | 609.806 |
| 436 | 4-(3,5-dimethylbenzoyl)-N—((2S,3R)-4-((S)-6-ethyl-2,2-spirocyclobutylchroman-4-ylamino)-3-hydroxy-1-phenylbutan-2-yl)morpholine-2-carboxamide | 626 | 1251.61 |
| 437 | N—((2S,3R)-1-(3-allylphenyl)-4-((S)-6-ethyl-2,2-spirocyclobutylchroman-4-ylamino)-3-hydroxybutan-2-yl)-4-(3-vinylbenzoyl)morpholine-2-carboxamide | 664 | 1327.71 |
| 438 | 4-(cycloheptanecarbonyl)-N—((2S,3R)-4-((S)-6-ethyl-2,2-spirocyclobutylchroman-4-ylamino)-3-hydroxy-1-phenylbutan-2-yl)morpholine-2-carboxamide | 618 | 1235.65 |
| 439 | N—((2S,3R)-4-((S)-6-ethyl-2,2-spirocyclobutylchroman-4-ylamino)-3-hydroxy-1-phenylbutan-2-yl)-4-(tetrahydro-2H-pyran-4-carbonyl)morpholine-2-carboxamide | 606 | 1211.54 |
| 440 | N—((2S,3R)-4-((S)-6-ethyl-2,2-spirocyclobutylchroman-4-ylamino)-3-hydroxy-1-phenylbutan-2-yl)-4-(2-methylpicolinoyl)morpholine-2-carboxamide | 613 | 1225.53 |
| 441 | N—((2S,3R)-4-((S)-6-ethyl-2,2-spirocyclobutylchroman-4-ylamino)-3-hydroxy-1-phenylbutan-2-yl)-4-(3-methylnicotinoyl)morpholine-2-carboxamide | 613 | 1225.53 |
| 442 | N—((2S,3R)-3-hydroxy-4-((S)-6-neopentyl-2,2-spirocyclobutyl-3,4-dihydro-2H-pyrano[2,3-b]pyridin-4-ylamino)-1-phenylbutan-2-yl)-4-(3-methylbenzoyl)morpholine-2-carboxamide | 655 | 1309.69 |
| 443 | N—((2S,3R)-4-((S)-6-ethyl-2,2-spirocyclobutylchroman-4-ylamino)-3-hydroxy-1-(3-vinylphenyl)butan-2-yl)-4-(4-iodobenzoyl) morpholine-2-carboxamide | 750 | 1499.36 |
| 444 | 4-(3-bromobenzoyl)-N—((2S,3R)-4-((S)-6-ethyl-2,2-spirocyclobutylchroman-4-ylamino)-3-hydroxy-1-phenylbutan-2-yl)morpholine-2-carboxamide | 678 | 1353.3 |
| 445 | (S)—N—((2S,3R)-4-((S)-6-ethyl-2,2-spirocyclobutylchroman-4-ylamino)-3-hydroxy-1-phenylbutan-2-yl)-4-(3-iodobenzoyl)morpholine-2-carboxamide | 724 | 1447.29 |
| 446 | 4-(3-phenylbenzoyl)-N—((2S,3R)-4-((S)-6-ethyl-2,2-spirocyclobutylchroman-4-ylamino)-3-hydroxy-1-phenylbutan-2-yl)morpholine-2-carboxamide | 674 | 1347.7 |
| 447 | $N^4$-benzyl-$N^2$—((2S,3R)-4-((S)-6-ethyl-2,2-spirocyclobutylchroman-4-ylamino)-3-hydroxy-1-phenylbutan-2-yl)morpholine-2,4-dicarboxamide | 627 | 1253.59 |
| 448 | N—((2S,3R)-4-(3-(trifluoromethyl)benzylamino)-3-hydroxy-1-phenylbutan-2-yl)-4-(3-methylbenzoyl)morpholine-2-carboxamide | 570 | 1139.24 |
| 449 | $N^2$—((2S,3R)-4-((S)-6-ethyl-2,2-spirocyclobutylchroman-4-ylamino)-3-hydroxy-1-phenylbutan-2-yl)-$N^4$—((S)-1-phenylethyl)morpholine-2,4-dicarboxamide | 641 | 1281.64 |
| 450 | $N^2$—((2S,3R)-4-((S)-6-ethyl-2,2-spirocyclobutylchroman-4-ylamino)-3-hydroxy-1-phenylbutan-2-yl)-$N^4$—((R)-1-phenylethyl)morpholine-2,4-dicarboxamide | 641 | 1281.64 |
| 451 | (S)—N—((2S,3R)-4-((S)-6-ethyl-2,2-spirocyclobutylchroman-4-ylamino)-3-hydroxy-1-phenylbutan-2-yl)-4-(morpholine-4-carbonyl)morpholine-2-carboxamide | 607 | 1213.52 |
| 452 | methyl 3-(2-(((2S,3R)-4-((S)-6-ethyl-2,2-spirocyclobutylchroman-4-ylamino)-3-hydroxy-1-phenylbutan-2-yl)carbamoyl)morpholine-4-carbonyl)benzoate | 656 | 488.668 |
| 453 | 1,1-dimethylethyl 2-(((((1S,2R)-3-(((4S)-6-ethyl-3,4-dihydrospiro[chromene-2,1'-cyclobutan]-4-yl)amino)-2-hydroxy-1-(phenylmethyl)propyl)amino)carbonyl)-4-thiomorpholinecarboxylate | 610 | 609.827 |
| 454 | N—((2S,3R)-4-((S)-6-ethyl-2,2-spirocyclobutylchroman-4-ylamino)-3-hydroxy-1-phenylbutan-2-yl)morpholine-4-carboxamide | 494 | 493.644 |
| 455 | 1'-cyclopentyl-N—((1S,2R)-2-hydroxy-1-(phenylmethyl)-3-(((4S)-6-((trifluoromethyl)oxy)-3,4-dihydrospiro[chromene-2,1'-cyclobutan]-4-yl)amino)propyl)-2'-oxo-1',2'-dihydro-2,3'-bipyridine-5'-carboxamide | 703 | 702.77 |
| 456 | 1'-cyclopentyl-N—((1S,2R)-3-(((4S)-6-ethyl-7-fluoro-3,4-dihydrospiro[chromene-2,1'-cyclobutan]-4-yl)amino)-2-hydroxy-1-(phenylmethyl)propyl)-2'-oxo-1',2'-dihydro-2,3'-bipyridine-5'-carboxamide | 665 | 664.818 |
| 457 | 1'-cyclopentyl-N—((1S,2R)-2-hydroxy-3-(((4S)-6-(4-morpholinyl)-3,4-dihydrospiro[chromene-2,1'-cyclobutan]-4-yl)amino)-1-(phenylmethyl)propyl)-2'-oxo-1',2'-dihydro-2,3'-bipyridine-5'-carboxamide | 704 | 703.879 |

Example 458

(2S)-N-((1S,2R)-3-(((4S)-6-bromo-3,4-dihydrospiro [chromene-2,1'-cyclobutan]-4-yl)amino)-2-hydroxy-1-(phenylmethyl)propyl)-4-((4-propyl-1H-1,2,3-triazol-1-yl)acetyl)-2-morpholinecarboxamide and (2R)-N-((1S,2R)-3-(((4S)-6-bromo-3,4-dihydrospiro [chromene-2,1'-cyclobutan]-4-yl)amino)-2-hydroxy-1-(phenylmethyl)propyl)-4-((4-propyl-1H-1,2,3-triazol-1-yl) acetyl)-2-morpholinecarboxamide

Step 1: 2-Benzyl 4-tert-butyl morpholine-2,4-dicarboxylate

In a 500-mL round-bottom flask, the 4-(tert-butoxycarbonyl)morpholine-2-carboxylic acid (5.0 g, 22 mmol) was dissolved in DMF (75 mL). Benzyl bromide (3.6 ml, 30 mmol) was added via syringe, followed by potassium carbonate (4.8 g, 35 mmol). The sides of the glass were rinsed down with dmf (25 mL), and an air condenser was affixed, and the reaction mixture was heated at 80° C. in an oil bath for 14 h. The reaction was cooled to ambient temperature and concentrated. The residue was transferred to a separatory funnel with 60% ether-hexane (300 mL), and the organic layer was extracted with water (75 mL), half-saturated brine (30 mL), and saturated brine (30 mL), then was dried over sodium sulfate and concentrated. The residue was purified through silica gel (500 mL) using 20% to 30% EtOAc-hexane to afford the title compound (6.81 g, 21 mmol). MS m/z 266 (M+1-isobutylene).

Step 2: Benzyl morpholine-2-carboxylate

In a 500-mL round-bottom flask, 2-benzyl 4-tert-butyl morpholine-2,4-dicarboxylate (7.94 g, 25 mmol) was dissolved in DCM (200 mL). It was then cooled to 0° C. TFA (15 ml, 198 mmol) was added via pipet, and the solution was allowed to warm naturally to ambient temperature in the ice bath, whereupon it was stirred for 14 h. The mixture was concentrated to afford the title compound (50% by weight with the remainder assumed to be TFA, 10.86 g, 24 mmol). MS m/z 222 (M+1).

Step 3: Benzyl 4-(2-chloroacetyl)morpholine-2-carboxylate

In a 100-mL round-bottom flask, the benzyl morpholine-2-carboxylate (50%, 1.00 g, 2.3 mmol) as the crude tfa salt was taken up in dichloromethane (8 mL), resulting in a white suspension. N-Ethyl-N-isopropylpropan-2-amine (1.4 ml, 7.9 mmol) was added, and the solid dissolved. The solution was cooled to 0 deg, and 2-chloroacetyl chloride (0.20 ml, 2.5 mmol) was added. The reaction mixture was allowed to warm naturally to ambient temperature where it was stirred for 14 h. The reaction mixture was diluted with DCM (75 mL), and the organic layer was extracted with dilute sodium bicarbonate (2×7 mL) then with half-saturated brine (7 mL), then was dried over sodium sulfate. The residue was purified through silica gel (100 mL) which had been deactivated with TEA (10 mL) using 90% EtOAc-hexane, affording the title compound (474 mg, 1.6 mmol). MS m/z 298 (M+1).

Step 4: Benzyl 4-(2-azidoacetyl)morpholine-2-carboxylate

In a 25-mL round-bottom flask, the benzyl 4-(2-chloroacetyl)morpholine-2-carboxylate (0.262 g, 0.88 mmol) was dissolved in dmf (4 mL). Sodium azide (0.066 g, 1.0 mmol) was added, and the flask was placed in a 60 deg oil bath overnight. The reaction was concentrated, and the residue was taken up in 80% ether-hexane (60 mL) and the organic layer was extracted with dilute sodium bicarbonate (2×7 mL) then with saturated brine (7 mL), then was dried over magnesium sulfate, filtered, and concentrated. The residue was purified through silica gel (50 mL) which had been deactivated with TEA (5 mL) using 60% EtOAc-hexane to afford the title compound (230 mg, 0.76 mmol). MS m/z 305 (M+1).

Step 5: Benzyl 4-(2-(4-propyl-1H-1,2,3-triazol-1-yl)acetyl)morpholine-2-carboxylate In a sealable vessel, benzyl 4-(2-azidoacetyl)morpholine-2-carboxylate (0.096 g, 0.32 mmol) was suspended in t-BuOH (1 mL) and water (1 mL) was added. An aqueous solution of sodium ascorbate (1.0 M, 0.032 ml, 0.032 mmol) and an aqueous solution of copper(II) sulfate pentahydrate (0.30 M, 0.079 ml, 0.024 mmol) were added, followed by pent-1-yne (0.040 ml, 0.41 mmol). The vessel was sealed and placed in a 65 deg oil bath, whereupon the mixture was stirred for 14 h. The reaction mixture was cooled to RT, taken up in EtOAc (60 mL), and the organic layer was extracted with dilute sodium bicarbonate (5 mL), dilute brine (5 mL), and saturated brine (5 mL), then was dried over sodium sulfate and concentrated. The residue was purified through silica gel (25 mL) eluting with EtOAc, affording the title compound (105 mg, 0.28 mmol). MS m/z 373 (M+1).

Step 6: 4-(2-(4-propyl-1H-1,2,3-triazol-1-yl)acetyl) morpholine-2-carboxylic acid In a 25-mL RBF, benzyl 4-(2-(4-propyl-1H-1,2,3-triazol-1-yl)acetyl)morpholine-2-carboxylate (0.105 g, 0.282 mmol) was taken up in MeOH (1.0 mL). Lithium hydroxide hydrate (0.0130 g, 0.310 mmol) was added as a solution in water (1.0 mL). The mixture was stirred at ambient temperature for 14 h, then concentrated, and used crude in the subsequent step. MS m/z 283 (M+1).

Step 7: (2S)-N-((1S,2R)-3-(((4S)-6-Bromo-3,4-dihydrospiro[chromene-2,1'-cyclobutan]-4-yl)amino)-2-hydroxy-1-(phenylmethyl)propyl)-4-((4-propyl-1H-1,2,3-triazol-1-yl)acetyl)-2-morpholinecarboxamide: and (2R)-N-((1S,2R)-3-(((4S)-6-bromo-3,4-dihydrospiro [chromene-2,1'-cyclobutan]-4-yl)amino)-2-hydroxy-1-(phenylmethyl)propyl)-4-((4-propyl-1H-1,2,3-triazol-1-yl)acetyl)-2-morpholinecarboxamide In a 15-mL RBF, the 4-(2-(4-propyl-1H-1,2,3-triazol-1-yl) acetyl)morpholine-2-carboxylic acid (0.034 g, 0.11 mmol) as the crude lithium salt and (2R,3S)-3-amino-1-((S)-6-bromo-2,2-dimethylchroman-4-ylamino)-4-phenylbutan-2-ol (0.046 g, 0.11 mmol) were taken up in DMF (1.5 mL). When the solids had dissolved, HATU (0.041 g, 0.11 mmol) was added. After 14 h, the reaction was concentrated, and the residue was taken up in EtOAc (60 mL) and the organic layer was extracted with water (5 mL), dried over sodium sulfate and concentrated. The residue was purified through silica gel (15 mL) which had been deactivated with TEA (2.0 mL)

eluting with 4% MeOH-EtOAc, to afford the title compound as a 1:1 mixture of diastereomers. MS m/z 695/697 (M+1).

Example 459

(2R)-4-(Azidoacetyl)-N-((1S,2R)-3-(((4S)-6-bromo-3,4-dihydrospiro[chromene-2,1'-cyclobutan]-4-yl) amino)-2-hydroxy-1-(phenylmethyl)propyl)-2-morpholinecarboxamide; and (2S)-4-(azidoacetyl)-N-((1S,2R)-3-(((4S)-6-bromo-3,4-dihydrospiro [chromene-2,1'-cyclobutan]-4-yl)amino)-2-hydroxy-1-(phenylmethyl)propyl)-2-morpholinecarboxamide

Step 1: 4-(2-Azidoacetyl)morpholine-2-carboxylic acid

Benzyl 4-(2-azidoacetyl)morpholine-2-carboxylate (Example 458, Step 4, 0.048 g, 0.16 mmol) converted to the lithium salt of 4-(2-azidoacetyl)morpholine-2-carboxylic acid (37 mg, 0.16 mmol) using the procedure described in Example 458, Step 6. MS m/z 215 (M+1).

Step 2: (2R)-4-(Azidoacetyl)-N-((1S,2R)-3-(((4S)-6-bromo-3,4-dihydrospiro[chromene-2,1'-cyclobutan]-4-yl)amino)-2-hydroxy-1-(phenylmethyl)propyl)-2-morpholinecarboxamide; and (2S)-4-(azidoacetyl)-N-((1S,2R)-3-(((4S)-6-bromo-3,4-dihydrospiro [chromene-2,1'-cyclobutan]-4-yl)amino)-2-hydroxy-1-(phenylmethyl)propyl)-2-morpholinecarboxamide (AMG 2027495)

In a 15-mL RBF, 4-(2-azidoacetyl)morpholine-2-carboxylic acid as the crude lithium salt (0.033 g, 0.15 mmol) was converted to the title compound using the procedure described in Example 458, Step 7. MS m/z 627/629 (M+1).

Example 460

(3,5)-N~3~-((1S,2R)-3-(((4S)-6-Ethyl-3,4-dihydrospiro[chromene-2,1'-cyclobutan]-4-yl)amino)-2-hydroxy-1-(phenylmethyl)propyl)-5-phenyl-N~1~-((1R)-1-phenylethyl)-1,3-piperidinedicarboxamide

Step 1. Methyl 1-(((R)-1-phenylethyl)carbamoyl)-5-phenylpiperidine-3-carboxylate To a 150 mL RBF was added methyl 5-phenylpiperidine-3-carboxylate (0.10 g, 0.46 mmol), toluene (15 mL), and (R)-(+)-1-phenylethyl isocyanate (0.065 ml, 0.46 mmol), and the mixture was stirred at RT. After 16 hours, the crude reaction was adsorbed onto a plug of silica gel and chromatographed through a Redi-Sep® pre-packed silica gel column (12 g), eluting with 0% to 100% EtOAc in hexane, to provide a mixture of methyl 1-(((R)-1-phenylethyl)carbamoyl)-5-phenylpiperidine-3-carboxylate and 1,3-bis((R)-1-phenylethyl)urea as a colorless solid MS m/z: 367.1 (M+1).

Step 2: 1-(((R)-1-phenylethyl)carbamoyl)-5-phenylpiperidine-3-carboxylic acid To a 150 mL RBF was added the mixture from step 1 (150 mg), THF:MeOH (3:1, 15 mL), and LiOH, 1M (1.00 ml, 1.0 mmol) and the mixture was stirred at RT. After 2 hours, the reaction was neutralized and extracted with EtOAc (3×20 mL). The combined organic layers were concentrated in vacuo to give a white solid. The material was carried forward without further purification.

Step 3: (3,5)-N~3~-((1S,2R)-3-(((4S)-6-ethyl-3,4-dihydrospiro[chromene-2,1'-cyclobutan]-4-yl) amino)-2-hydroxy-1-(phenylmethyl)propyl)-5-phenyl-N~1~-((1R)-1-phenylethyl)-1,3-piperidinedicarboxamide The crude material (79 mg) from step 2 was coupled using HATU and purified by reverse-phase preparative HPLC (Shimadzu) on a Phenomenex Gemini column (5 micron, C18, 110 Å, 150×30 mm) eluting at 45 mL/min with a linear gradient of 10% (v/v) to 100% MeCN (0.1% v/v TFA) in water (0.1% TFA) over 20 minutes to give (3,5)-N~3~-((1S,2R)-3-(((4S)-6-ethyl-3,4-dihydrospiro[chromene-2,1'-cyclobutan]-4-yl)amino)-2-hydroxy-1-(phenylmethyl)propyl)-5-phenyl-N~1~-((1R)-1-phenylethyl)-1,3-piperidinedicarboxamide as a colorless solid. MS m/z: 715.3 (M+1).

Example 461

(2R)-4-((3,3-dimethyl-1-piperidinyl)carbonyl)-N-((1S,2R) -3-(((4S)-6-ethyl-3,4-dihydrospiro [chromene-2,1'-cyclobutan]-4-yl)amino)-2-hydroxy-1-(phenylmethyl)propyl)-2-morpholinecarboxamide; and (2S)-4-((3,3-dimethyl-1-piperidinyl)carbonyl)-N-((1S,2R) -3-(((4S)-6-ethyl-3,4-dihydrospiro [chromene-2,1'-cyclobutan]-4-yl)amino)-2-hydroxy-1-(phenylmethyl)propyl)-2-morpholinecarboxamide

Step 1: Benzyl 4-(3,3-dimethylpiperidine-1-carbonyl)morpholine-2-carboxylate In a dry 25-mL RBF, phosgene (0.25 ml, 0.47 mmol) was dissolved in DCM (2 mL) and the solution was cooled to 0° C. A solution of benzyl morpholine-2-carboxylate (50%, 0.070 g, 0.16 mmol, Example 458, Step 2) and N-ethyl-N-isopropylpropan-2-amine (0.041 ml, 0.24 mmol) in DCM (2 mL) was added. The solution was stirred at 0° C. for 4 h, and the ice bath was removed, and the mixture stirred at RT for 1 hour. The reaction mixture was concentrated, and the residue dissolved in DCM (2 mL), and N-ethyl-N-isopropylpropan-2-amine (0.041 ml, 0.24 mmol) and 3,3-dimethylpiperidine (0.022 g, 0.20 mmol) were added by syringe. After 14 h, the reaction mixture was concentrated. The residue was purified through silica gel (20 mL) using 50% EtOAc-hexane to afford the title compound. MS m/z 361 (M+1).

Step 2: 4-(3,3-Dimethylpiperidine-1-carbonyl)morpholine-2-carboxylic acid

In a 15-mL RBF, the benzyl 4-(3,3-dimethylpiperidine-1-carbonyl)morpholine-2-carboxylate (0.036 g, 0.100 mmol) was converted to 4-(3,3-Dimethylpiperidine-1-carbonyl) morpholine-2-carboxylic acid using the procedure described in Example 458, Step 6, to afford the title compound as the crude lithium salt.

Step 3: (2R)-4-((3,3-Dimethyl-1-piperidinyl)carbonyl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-2-morpholinecarboxamide; and (2S)-4-((3,3-dimethyl-1-piperidinyl)carbonyl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-2-morpholinecarboxamide In a 25-mL RBF, the 4-(3,3-dimethylpiperidine-1-carbonyl)morpholine-2-carboxylic acid as the crude lithium salt (0.039 g, 0.099 mmol) was coupled with (S)-6-ethyl-2,2-spirocyclobutyl-4-amine (0.038 g, 0.099 mmol) according to the procedure described in Example 458, Step 7 to afford the title compound. MS m/z 633 (M+1).

Example 462

1-cyclopentyl-N-((1S,2R)-3-(((1R)-3,3-dimethyl-7-(methyloxy)-4-oxo-1,2,3,4-tetrahydro-1-naphthalenyl)amino)-2-hydroxy-1-(phenylmethyl)propyl)-2'-oxo-1',2'-dihydro-2,3'-bipyridine-5'-carboxamide Step 1: 6-methoxy-2,2-dimethyl-3,4-dihydronaphthalen-1(2H)-one 6-methoxy-1-tetralone (3.00 g, 17 mmol) was added to RBF followed by THF (20 mL). Sodium hydride (1.1 ml, 43 mmol) was added and the reaction was stirred at RT under nitrogen for 20 minutes. Gas evolution was observed. Iodomethane (2.7 ml, 43 mmol) was added via syringe and the reaction was stirred at RT overnight. The reaction was quenched with water (25 mL) and extracted with EtOAc (3×100 mL). The combined organic layers were washed with brine, dried over $MgSO_4$ and filtered. The solvent was evaporated and the residue was purified by column chromatography (0-10% EtOAc/Hexane to provide the title compound as a white solid (2.77 g, 80% yield). MS m/z: 205.2 (M+1).

Step 2: 4-bromo-6-methoxy-2,2-dimethyl-3,4-dihydronaphthalen-1(2H)-one

To a mixture of 6-methoxy-2,2-dimethyl-3,4-dihydronaphthalen-1(2H)-one (3.30 g, 16.2 mmol) and 1-bromopyrrolidine-2,5-dione (2.88 g, 16.2 mmol) in 50 mL of $CCl_4$, was added AIBN (0.265 g, 1.62 mmol). The mixture was heated to reflux for three hours. The reaction was cooled to RT and the reaction was quenched with water (25 mL) and extracted with EtOAc (3×100 mL). The combined organic layers were washed with brine, dried over $MgSO_4$ and filtered. The solvent was evaporated and the residue was purified by column chromatography (0-50% EtOAc/Hexane to provide the title compound as a white solid (3.92 g, 86% yield). MS m/z: 284.2 (M+1).

Step 3: 4-azido-6-methoxy-2,2-dimethyl-3,4-dihydronaphthalen-1(2H)-one

4-Bromo-6-methoxy-2,2-dimethyl-3,4-dihydronaphthalen-1(2H)-one (3.9 g, 14 mmol) was added to DMF (10 mL) followed by azidosodium (3.6 g, 55 mmol). The mixture was heated to 60° C. overnight. The reaction was cooled to RT and quenched with water (25 mL). The aqueous layer was extracted with $Et_2O$ (3×100 mL). The combined organic layers were washed with brine, dried over $MgSO_4$ and filtered. The solvent was evaporated and the residue was purified by column chromatography (0-50% EtOAc/Hexane to provide the title compound as a white solid (3.05 g, 90% yield). MS m/z: 268.2 (M+Na).

Step 4: 4-amino-6-methoxy-2,2-dimethyl-3,4-dihydronaphthalen-1(2H)-one

To a solution of 4-azido-6-methoxy-2,2-dimethyl-3,4-dihydronaphthalen-1(2H)-one (2.50 g, 10.2 mmol) in EtOH (100 mL) at RT was added palladium on carbon (1.08 g, 10.2 mmol) in two portions. A hydrogen balloon was affixed to the reaction flask and the head space above the solvent was purged with $H_2$. After 5 hours, the solution was filtered through a plug of celite and concentrated to provide the crude product as an oil. The residue was purified by column chromatography 100% DCM to 50% (10% MeOH/DCM/1% $NH_4OH$) to provide the title compound as a yellow oil (2.04 g, 91% yield). MS m/z: 220.2 (M+1).

Step 5: 4-((2R,3S)-3-amino-2-hydroxy-4-phenylbutylamino)-6-methoxy-2,2-dimethyl-3,4-dihydronaphthalen-1(2H)-one Tert-butyl(S)-1-((S)-oxiran-2-yl)-2-phenylethylcarbamate (2.4 g, 9.1 mmol) and 4-amino-6-methoxy-2,2-dimethyl-3,4-dihydronaphthalen-1(2H)-one (2.00 g, 9.1 mmol) were added to IPA (30 mL) and heated to 80° C. After 16 hours, the reaction was cooled to RT and concentrated in vaccuo. The residue was purified by column chromatography using 0-10% MeOH/DCM. The protected amine was take up in 14 mL of 4N HCl in MeOH and stirred at RT. After 3 hours, the reaction mixture was concentrated to afford the desired product as the HCl salt (0.95 g 55% yield). MS m/z: 283.2 (M+1).

Step 6: 1'-cyclopentyl-N-((1S,2R)-3-(((1R)-3,3-dimethyl-7-(methyloxy)-4-oxo-1,2,3,4-tetrahydro-1-naphthalenyl)amino)-2-hydroxy-1-(phenylmethyl)propyl)-2'-oxo-1',2'-dihydro-2,3'-bipyridine-5'-carboxamide 1-Cyclopentyl-6-oxo-5-(2-oxopyrrolidin-1-yl)-1,6-dihydropyridine-3-carboxylic acid (0.076 g, 0.26 mmol) was added to a vial followed by DMF (1 mL). HATU (0.15 g, 0.39 mmol) was added and the mixture was stirred for 5 minutes. 4-((2R,3S)-3-amino-2-hydroxy-4-phenylbutylamino)-6-methoxy-2,2-dimethyl-3,4-dihydronaphthalen-1(2H)-one (0.100 g, 0.26 mmol) was added followed by the addition of diisopropylethylamine (0.18 ml, 1.0 mmol). Reaction was allowed to stir at RT. After 2 hours, reaction the crude reaction mixture was purified using the Gilson. The solvent was evaporated to provide the title compound as a white solid. MS m/z: 655.6 (M+1).

Example 463

1-cyclopentyl-N-((1S,2R)-3-(((1R)-3,3-dimethyl-7-(methyloxy)-4-oxo-1,2,3,4-tetrahydro-1-naphthalenyl)amino)-2-hydroxy-1-(phenylmethyl)propyl)-6-oxo-5-(2-oxo-1-pyrrolidinyl)-1,6-dihydro-3-pyridinecarboxamide 1-cyclopentyl-6-oxo-5-(pyridin-2-yl)-1,6-dihydropyridine-3-carboxylic acid (0.0743 g, 0.261 mmol) was added to a vial followed by DMF (1 mL). HATU (0.15 g, 0.39 mmol) was added and the mixture was stirred for 5 minutes. 4-((2R,3S)-3-amino-2-hydroxy-4-phenylbutylamino)-6-methoxy-2,2-dimethyl-3,4-dihydronaphthalen-1(2H)-one (0.100 g, 0.26 mmol) was added followed by the addition of diisopropylethylamine (0.18 ml, 1.0 mmol). Reaction was allowed to stir at RT. After 2 hours, reaction the crude reaction mixture was purified using the Gilson. The solvent was evaporated to provide the title compound as a white solid. MS m/z: 649.6 (M+1).

| Ex. No. | Compound Name | Mass Found |
|---|---|---|
| 464 | (2S)—N—((1S,2R)-3-(((4S)-6-ethyl-3,4-dihydrospiro[chromene-2,1'-cyclobutan]-4-yl)amino)-2-hydroxy-1-(phenylmethyl)propyl)-4-((3-methylphenyl)carbonyl)-2-morpholinecarboxamide | 612 |
| 465 | (2R)—N—((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)tetrahydro-2-furancarboxamide | 540 |
| 466 | (2S)—N—((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)tetrahydro-2-furancarboxamide | 540 |
| 467 | N—((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)tetrahydro-3-furancarboxamide | 540 |
| 468 | (2S)—N—((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)tetrahydro-2-furancarboxamide | 540 |
| 469 | (3S)-3-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3,4-dihydro-1(2H)-isoquinolinone | 450.3 |
| 470 | N—((1S,2R)-3-(((4'R)-6'-bromo-3',4'-dihydro-1'H-spiro[cyclobutane-1,2'-quinolin]-4'-yl)amino)-2-hydroxy-1-(phenylmethyl)propyl)-1'-cyclopentyl-2'-oxo-1',2'-dihydro-2,3'-bipyridine-5'-carboxamide | 697 |
| 471 | N—((1S,2R)-3-(((4'S)-6'-bromo-3',4'-dihydro-1'H-spiro[cyclobutane-1,2'-quinolin]-4'-yl)amino)-2-hydroxy-1-(phenylmethyl)propyl)-1'-cyclopentyl-2'-oxo-1',2'-dihydro-2,3'-bipyridine-5'-carboxamide | 697 |
| 472 | N—((1S,2R)-1-((4-fluorophenyl)methyl)-3-(((4S)-7-fluoro-6-(1H-pyrazol-1-yl)-3,4-dihydrospiro[chromene-2,1'-cyclobutan]-4-yl)amino)-2-hydroxypropyl)cyclopropanecarboxamide | 523.2 |
| 473 | N—((1S,2R)-1-((4-fluorophenyl)methyl)-3-(((4S)-7-fluoro-6-(1H-pyrazol-1-yl)-3,4-dihydrospiro[chromene-2,1'-cyclobutan]-4-yl)amino)-2-hydroxypropyl)cyclobutanecarboxamide | 537 |
| 474 | (2R)—N—((1S)-3-(((4S)-6-ethyl-2,2-dimethyl-3,4-dihydro-2H-chromen-4-yl)amino)-2-oxo-1-(phenylmethyl)propyl)-4-(1-piperidinylcarbonyl)-2-morpholinecarboxamide | 591.2 |
| 475 | (2S)—N—((1S)-3-(((4S)-6-ethyl-2,2-dimethyl-3,4-dihydro-2H-chromen-4-yl)amino)-2-oxo-1-(phenylmethyl)propyl)-4-(1-piperidinylcarbonyl)-2-morpholinecarboxamide | 591.2 |
| 476 | 1'-cyclopentyl-N—((1S,2R)-3-((4S)-3,4-dihydrospiro[chromene-2,1'-cyclobutan]-4-ylamino)-2-hydroxy-1-(phenylmethyl)propyl)-2'-oxo-1',2'-dihydro-2,3'-bipyridine-5'-carboxamide | 619 |
| 477 | 1'-cyclopentyl-N—((1S)-1-((1R)-2-(((4S)-6-ethyl-3,4-dihydrospiro[chromene-2,1'-cyclobutan]-4-yl)amino)-1-hydroxyethyl)-3-pentyn-1-yl)-2'-oxo-1',2'-dihydro-2,3'-bipyridine-5'-carboxamide | 609.3 |
| 478 | N—((1S,2S,3S)-3-(((4S)-6-bromo-2,2-dimethyl-3,4-dihydro-2H-chromen-4-yl)amino)-2-hydroxy-1-(phenylmethyl)butyl)-1'-cyclopentyl-2'-oxo-1',2'-dihydro-2,3'-bipyridine-5'-carboxamide | 699.1 |
| 479 | N—((1S,2R,3S)-3-(((4S)-6-bromo-2,2-dimethyl-3,4-dihydro-2H-chromen-4-yl)amino)-2-hydroxy-1-(phenylmethyl)butyl)-1'-cyclopentyl-2'-oxo-1',2'-dihydro-2,3'-bipyridine-5'-carboxamide | 699.1 |
| 480 | N—((1S,2S,3R)-3-(((4S)-6-bromo-2,2-dimethyl-3,4-dihydro-2H-chromen-4-yl)amino)-2-hydroxy-1-(phenylmethyl)butyl)-1'-cyclopentyl-2'-oxo-1',2'-dihydro-2,3'-bipyridine-5'-carboxamide | 699.1 |
| 481 | N—((1S,2R)-3-(((4R)-6-bromo-2,2-dimethyl-1,2,3,4-tetrahydro-4-quinolinyl)amino)-2-hydroxy-1-(phenylmethyl)propyl)-1'-cyclopentyl-2'-oxo-1',2'-dihydro-2,3'-bipyridine-5'-carboxamide | 686 |
| 482 | N—((1S,2R)-3-(((4S)-6-bromo-2,2-dimethyl-1,2,3,4-tetrahydro-4-quinolinyl)amino)-2-hydroxy-1-(phenylmethyl)propyl)-1'-cyclopentyl-2'-oxo-1',2'-dihydro-2,3'-bipyridine-5'-carboxamide | 685 |

-continued

| Ex. No. | Compound Name | Mass Found |
|---|---|---|
| 483 | 1'-cyclopentyl-N—((1S,2R)-3-(((4S)-6-ethyl-3,4-dihydrospiro[chromene-2,1'-cyclobutan]-4-yl)amino)-2-hydroxy-1-((propyloxy)methyl)propyl)-2'-oxo-1',2'-dihydro-2,3'-bipyridine-5'-carboxamide | 629.3 |
| 484 | (2R)—N—((1S,2R)-3-(((4S)-6-ethyl-2,2-dimethyl-3,4-dihydro-2H-chromen-4-yl)amino)-2-hydroxy-1-(phenylmethyl)propyl)-4-(1-piperidinylcarbonyl)-2-morpholinecarboxamide | 593 |
| 485 | (2S)—N—((1S,2R)-3-(((4S)-6-ethyl-2,2-dimethyl-3,4-dihydro-2H-chromen-4-yl)amino)-2-hydroxy-1-(phenylmethyl)propyl)-4-(1-piperidinylcarbonyl)-2-morpholinecarboxamide | 593 |
| 486 | N—((1S,2R)-3-(((4R)-6-bromo-2,2-dimethyl-1,2,3,4-tetrahydro-4-quinolinyl)amino)-2-hydroxy-1-(phenylmethyl)propyl)-1'-cyclopentyl-2'-oxo-1',2'-dihydro-2,3'-bipyridine-5'-carboxamide | 686 |
| 487 | N—((1S,2R)-3-(((4S)-6-bromo-2,2-dimethyl-1,2,3,4-tetrahydro-4-quinolinyl)amino)-2-hydroxy-1-(phenylmethyl)propyl)-1'-cyclopentyl-2'-oxo-1',2'-dihydro-2,3'-bipyridine-5'-carboxamide | 686 |
| 488 | 1'-cyclopentyl-N—((1S,2R)-3-(((4R)-6-(2,2-dimethylpropyl)-2,2-dimethyl-1,2,3,4-tetrahydro-4-quinolinyl)amino)-2-hydroxy-1-(phenylmethyl)propyl)-2'-oxo-1',2'-dihydro-2,3'-bipyridine-5'-carboxamide | 676 |
| 489 | 1'-cyclopentyl-N—((1S,2R)-3-(((4S)-6-(2,2-dimethylpropyl)-2,2-dimethyl-1,2,3,4-tetrahydro-4-quinolinyl)amino)-2-hydroxy-1-(phenylmethyl)propyl)-2'-oxo-1',2'-dihydro-2,3'-bipyridine-5'-carboxamide | 676 |
| 490 | (2S)—N—((1S,2R)-1-((3-cyanophenyl)methyl)-2-hydroxy-3-(((5'S)-3'-methyl-5',8'-dihydro-6'H-spiro[cyclobutane-1,7'-quinolin]-5'-yl)amino)propyl)-4-((3-methylphenyl)carbonyl)-2-morpholinecarboxamide | 622.2 |
| 491 | (2R)—N—((1S,2R)-1-((3-cyanophenyl)methyl)-2-hydroxy-3-(((5'S)-3'-methyl-5',8'-dihydro-6'H-spiro[cyclobutane-1,7'-quinolin]-5'-yl)amino)propyl)-4-((3-methylphenyl)carbonyl)-2-morpholinecarboxamide | 622.2 |
| 492 | (2S)—N—((1S,2R)-1-((3,5-difluorophenyl)methyl)-2-hydroxy-3-(((5'S)-3'-methyl-5',8'dihydro-6'H-spiro[cyclobutane-1,7'-quinolin]-5'-yl)amino)propyl)-4-((3-methylphenyl)carbonyl)-2-morpholinecarboxamide | 633.2 |
| 493 | (2R)—N—((1S,2R)-1-((3,5-difluorophenyl)methyl)-2-hydroxy-3-(((5'S)-3'-methyl-5',8'-dihydro-6'H-spiro[cyclobutane-1,7'-quinolin]-5'-yl)amino)propyl)-4-((3-methylphenyl)carbonyl)-2-morpholinecarboxamide | 633.2 |
| 494 | (2S)—N—((1S,2R)-2-hydroxy-3-(((5'S)-3'-methyl-5',8'-dihydro-6'H-spiro[cyclobutane-1,7'-quinolin]-5'-yl)amino)-1-(phenylmethyl)propyl)-4-((3-methylphenyl)carbonyl)-2-morpholinecarboxamide | 597.2 |
| 495 | (2R)—N—((1S,2R)-2-hydroxy-3-(((5'S)-3'-methyl-5',8'-dihydro-6'H-spiro[cyclobutane-1,7'-quinolin]-5'-yl)amino)-1-(phenylmethyl)propyl)-4-((3-methylphenyl)carbonyl)-2-morpholinecarboxamide | 597.2 |
| 496 | (2S)—N—((1S,2R)-1-((3-cyanophenyl)methyl)-2-hydroxy-3-(((5S)-3,7,7-trimethyl-5,6,7,8-tetrahydro-5-quinolinyl)amino)propyl)-4-((3-methylphenyl)carbonyl)-2-morpholinecarboxamide | 610.2 |
| 497 | (2R)—N—((1S,2R)-1-((3-cyanophenyl)methyl)-2-hydroxy-3-(((5S)-3,7,7-trimethyl-5,6,7,8-tetrahydro-5-quinolinyl)amino)propyl)-4-((3-methylphenyl)carbonyl)-2-morpholinecarboxamide | 610.2 |
| 498 | (2S)—N—((1S,2R)-2-hydroxy-1-(phenylmethyl)-3-(((5S)-3,7,7-trimethyl-5,6,7,8-tetrahydro-5-quinolinyl)amino)propyl)-4-((3-methylphenyl)carbonyl)-2-morpholinecarboxamide | 585.2 |
| 499 | (2R)—N—((1S,2R)-2-hydroxy-1-(phenylmethyl)-3-(((5S)-3,7,7-trimethyl-5,6,7,8-tetrahydro-5-quinolinyl)amino)propyl)-4-((3-methylphenyl)carbonyl)-2-morpholinecarboxamide | 585.2 |
| 500 | 1'-cyclopentyl-N—((1S,2R)-3-(((4S)-6-ethyl-3,4-dihydrospiro[chromene-2,1'-cyclobutan]-4-yl)amino)-2-hydroxy-1-((2-methyl-1,3-thiazol-4-yl)methyl)propyl)-2'-oxo-1',2'-dihydro-2,3'-bipyridine-5'-carboxamide | 668.3 |
| 501 | N—((1S,2R)-3-(((4S)-2-(2,2-dimethylpropyl)-6,6-dimethyl-4,5,6,7-tetrahydro-1-benzothien-4-yl)amino)-2-hydroxy-1-(phenylmethyl)propyl)-1'-(1-methylethyl)-2'-oxo-1',2'-dihydro-2,3'-bipyridine-5'-carboxamide | 655.3 |

-continued

| Ex. No. | Compound Name | Mass Found |
|---|---|---|
| 502 | N—((1S,2R)-2-hydroxy-3-(((5'S)-3'-methyl-5',8'-dihydro-6'H-spiro[cyclobutane-1,7'-quinolin]-5'-yl)amino)-1-(phenylmethyl)propyl)tetrahydro-2H-pyran-4-carboxamide | 478.2 |
| 503 | N—((1S,2R)-1-((3,5-difluorophenyl)methyl)-2-hydroxy-3-(((5S)-3,7,7-trimethyl-5,6,7,8-tetrahydro-5-quinolinyl)amino)propyl)tetrahydro-2H-pyran-4-carboxamide | 502.2 |
| 504 | N—((1S,2R)-2-hydroxy-1-(phenylmethyl)-3-(((5S)-3,7,7-trimethyl-5,6,7,8-tetrahydro-5-quinolinyl)amino)propyl)tetrahydro-2H-pyran-4-carboxamide | 466.2 |
| 505 | 1'-cyclopentyl-N—((1S,2R)-3-(((1S)-3,3-dimethyl-7-((2-(methyloxy)ethyl)amino)-4-oxo-1,2,3,4-tetrahydro-1-naphthalenyl)amino)-2-hydroxy-1-(phenylmethyl)propyl)-2'-oxo-1',2'-dihydro-2,3'-bipyridine-5'-carboxamide | 692.6 |
| 507 | 1'-cyclopentyl-N—((1R,2R)-3-(((1S)-3,3-dimethyl-7-((2-(methyloxy)ethyl)amino)-4-oxo-1,2,3,4-tetrahydro-1-naphthalenyl)amino)-2-hydroxy-1-(phenylmethyl)propyl)-2'-oxo-1',2'-dihydro-2,3'-bipyridine-5'-carboxamide | 692.6 |
| 508 | N—((1S,2R)-3-(((4S)-2-ethyl-4,7-dihydro-5H-spiro[1-benzothiophene-6,1'-cyclobutan]-4-yl)amino)-2-hydroxy-1-(phenylmethyl)propyl)-1'-(1-methylethyl)-2'-oxo-1',2'-dihydro-2,3'-bipyridine-5'-carboxamide | 625.2 |
| 509 | (3R)—N—((1S,2R)-1-((3,5-difluorophenyl)methyl)-2-hydroxy-3-(((5'S)-3'-methyl-5',8'-dihydro-6'H-spiro[cyclobutane-1,7'-quinolin]-5'-yl)amino)propyl)tetrahydro-3-furancarboxamide | 500.2 |
| 510 | N—((1S,2R)-1-((3,5-difluorophenyl)methyl)-2-hydroxy-3-(((5'S)-3'-methyl-5',8'-dihydro-6'H-spiro[cyclobutane-1,7'-quinolin]-5'-yl)amino)propyl)tetrahydro-2H-pyran-4-carboxamide | 514.2 |
| 511 | (2R)—N—((1S,2R)-3-(((4S)-6-ethyl-3,4-dihydrospiro[chromene-2,1'-cyclobutan]-4-yl)amino)-2-hydroxy-1-(phenylmethyl)propyl)-4-((3-methylphenyl)carbonyl)-2-morpholinecarboxamide | 612 |
| 512 | 1'-cyclopentyl—N—((1S,2R)-3-(((3R)-2,2-dimethyl-2,3-dihydrofuro[2,3-b]pyridin-3-yl)amino)-2-hydroxy-1-(phenylmethyl)propyl)-2'-oxo-1',2'-dihydro-2,3'-bipyridine-5'-carboxamide | 594.2 |
| 513 | 1'-cyclopentyl-N—((1S,2R)-3-(((3S)-2,2-dimethyl-2,3-dihydrofuro[2,3-b]pyridin-3-yl)amino)-2-hydroxy-1-(phenylmethyl)propyl)-2'-oxo-1',2'-dihydro-2,3'-bipyridine-5'-carboxamide | 594.2 |
| 514 | (2S)—N—((1S,2R)-3-(((4S)-2-ethyl-6,6-dimethyl-4,5,6,7-tetrahydro-1-benzothien-4-yl)amino)-2-hydroxy-1-(phenylmethyl)propyl)-4-((3-methylphenyl)carbonyl)-2-morpholinecarboxamide | 604.2 |
| 515 | (2R)—N—((1S,2R)-3-(((4S)-2-ethyl-6,6-dimethyl-4,5,6,7-tetrahydro-1-benzothien-4-yl)amino)-2-hydroxy-1-(phenylmethyl)propyl)-4-((3-methylphenyl)carbonyl)-2-morpholinecarboxamide | 604.2 |
| 516 | (2R)—N—((1S,2R)-3-(((1S)-3,3-dimethyl-7-((3S)-tetrahydro-3-furanyloxy)-1,2,3,4-tetrahydro-1-naphthalenyl)amino)-2-hydroxy-1-(phenylmethyl)propyl)-5-oxotetrahydro-2-furancarboxamide | 537.3 |
| 517 | (2S)—N—((1S,2R)-3-(((1S)-3,3-dimethyl-7-((3S)-tetrahydro-3-furanyloxy)-1,2,3,4-tetrahydro-1-naphthalenyl)amino)-2-hydroxy-1-(phenylmethyl)propyl)-5-oxotetrahydro-2-furancarboxamide | 537.3 |
| 518 | 1-cyclopentyl-N—((1S,2R)-3-(((1S)-3,3-dimethyl-7-((3S)-tetrahydro-3-furanyloxy)-1,2,3,4-tetrahydro-1-naphthalenyl)amino)-2-hydroxy-1-(phenylmethyl)propyl)-6-oxo-1,6-dihydro-3-pyridinecarboxamide | 614.3 |
| 519 | 1'-cyclopentyl-N—((1S,2R)-3-(((1S)-3,3-dimethyl-7-((3S)-tetrahydro-3-furanyloxy)-1,2,3,4-tetrahydro-1-naphthalenyl)amino)-2-hydroxy-1-(phenylmethyl)propyl)-2'-oxo-1',2'-dihydro-2,3'-bipyridine-5'-carboxamide | 691.3 |
| 520 | 1'-cyclopentyl-N—((1S,2R)-2-hydroxy-1-(phenylmethyl)-3-(((4'S)-6'-((2S)-tetrahydro-2-furanylmethyl)-3',4'-dihydrospiro[cyclobutane-1,2'-pyrano[2,3-b]pyridin]-4'-yl)amino)propyl)-2'-oxo-1',2'-dihydro-2,3'-bipyridine-5'-carboxamide | 704 |
| 521 | (2S)—N—((1S,2R)-3-(((4S)-6-ethyl-3,4-dihydrospiro[chromene-2,1'-cyclobutan]-4-yl)amino)-2-hydroxy-1-(phenylmethyl)propyl)-4-(((2S)-2-methyl-4-morpholinyl)carbonyl)-2-morpholinecarboxamide | 621 |

-continued

| Ex. No. | Compound Name | Mass Found |
|---|---|---|
| 522 | 1-cyclopentyl-N—((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-6-oxo-5-(tetrahydro-2H-pyran-2-yl)-1,6-dihydro-3-pyridinecarboxamide | 669.3 (M − 28 + H) |
| 523 | (3S)-1-cyclobutyl-N—((1S,2R)-3-(((4S)-2-ethyl-6,6-dimethyl-4,5,6,7-tetrahydro-1-benzothien-4-yl)amino)-2-hydroxy-1-(phenylmethyl)propyl)-5-oxo-3-pyrrolidinecarboxamide | 538.2 |
| 524 | (3S)-1-cyclobutyl-N—((1S,2R)-2-hydroxy-3-(((4S)-6-(4-morpholinyl)-3,4-dihydrospiro[chromene-2,1'-cyclobutan]-4-yl)amino)-1-(phenylmethyl)propyl)-5-oxo-3-pyrrolidinecarboxamide | 602.9 |
| 525 | 1'-cyclopentyl-N—((1S,2R)-3-(((4S)-6-ethyl-3,4-dihydrospiro[chromene-2,1'-cyclobutan]-4-yl)amino)-2-hydroxy-1-(1,3-thiazol-4-ylmethyl)propyl)-2'-oxo-1',2'-dihydro-2,3'-bipyridine-5'-carboxamide | 654.3 |
| 526 | (2S)—N—((1S,2R)-2-hydroxy-3-(((4S)-6-(4-morpholinyl)-3,4-dihydrospiro[chromene-2,1'-cyclobutan]-4-yl)amino)-1-(phenylmethyl)propyl)-4-(tetrahydro-2H-pyran-4-ylcarbonyl)-2-morpholinecarboxamide | 663.4 |
| 527 | (3R,5S)—N—((1S,2R)-3-(((4S)-6-ethyl-3,4-dihydrospiro[chromene-2,1'-cyclobutan]-4-yl)amino)-2-hydroxy-1-(phenylmethyl)propyl)-1-((3-methylphenyl)carbonyl)-5-phenyl-3-piperidinecarboxamide | 686.3 |
| 528 | (2S)—N—((1S,2R)-2-hydroxy-3-(((4S)-6-(4-morpholinyl)-3,4-dihydrospiro[chromene-2,1'-cyclobutan]-4-yl)amino)-1-(phenylmethyl)propyl)-5-oxotetrahydro-2-furancarboxamide | 550.3 |
| 529 | (2R)—N—((1S,2R)-2-hydroxy-3-(((4S)-6-(4-morpholinyl)-3,4-dihydrospiro[chromene-2,1'-cyclobutan]-4-yl)amino)-1-(phenylmethyl)propyl)-5-oxotetrahydro-2-furancarboxamide | 550.3 |
| 520 | (2R)—N—((1S,2R)-3-(((4S)-6-ethyl-3,4-dihydrospiro[chromene-2,1'-cyclobutan]-4-yl)amino)-2-hydroxy-1-(phenylmethyl)propyl)-4-((3R)-tetrahydro-3-furanylcarbonyl)-2-morpholinecarboxamide | 592 |
| 531 | (2S)—N—((1S,2R)-3-(((4S)-6-ethyl-3,4-dihydrospiro[chromene-2,1'-cyclobutan]-4-yl)amino)-2-hydroxy-1-(phenylmethyl)propyl)-4-(1-piperidinylcarbonyl)-2-morpholinecarboxamide | 605 |
| 532 | (2R)—N—((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)-5-oxotetrahydro-2-furancarboxamide | 494 |
| 533 | (2S)—N—((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)-5-oxotetrahydro-2-furancarboxamide | 494 |
| 534 | (2R)—N—((1S,2R)-3-(((4'S)-6'-chloro-3',4'-dihydrospiro[cyclobutane-1,2'-pyrano[2,3-b]pyridin]-4'-yl)amino)-2-hydroxy-1-(phenylmethyl)propyl)-5-oxotetrahydro-2-furancarboxamide | 500, 502 |
| 535 | (2S)—N—((1S,2R)-3-(((4'S)-6'-chloro-3',4'-dihydrospiro[cyclobutane-1,2'-pyrano[2,3-b]pyridin]-4'-yl)amino)-2-hydroxy-1-(phenylmethyl)propyl)-5-oxotetrahydro-2-furancarboxamide | 500, 502 |
| 536 | N—((1S,2R)-1-((3-cyano-5-fluorophenyl)methyl)-3-(((4S)-6-ethyl-3,4-dihydrospiro[chromene-2,1'-cyclobutan]-4-yl)amino)-2-hydroxypropyl)-1'-cyclopentyl-2'-oxo-1',2'-dihydro-2,3'-bipyridine-5'-carboxamide | 690.3 |
| 537 | (2S)—N—((1S,2R)-2-hydroxy-3-(((4S)-6-(4-morpholinyl)-3,4-dihydrospiro[chromene-2,1'-cyclobutan]-4-yl)amino)-1-(phenylmethyl)propyl)-4-(4-morpholinylcarbonyl)-2-morpholinecarboxamide | 664.4 |
| 538 | N—((1S,2R)-2-hydroxy-1-(phenylmethyl)-3-((2S,4S)-3,4,4',5'-tetrahydrospiro[chromene-2,3'-furan]-4-ylamino)propyl)-1'-(1-methylethyl)-2'-oxo-1',2'-dihydro-2,3'-bipyridine-5'-carboxamide | 609.3 |
| 539 | N—((1S,2R)-2-hydroxy-3-(((4S)-6-(4-morpholinyl)-3,4-dihydrospiro[chromene-2,1'-cyclobutan]-4-yl)amino)-1-(phenylmethyl)propyl)-1'-(1-methylethyl)-2'-oxo-1',2'-dihydro-2,3'-bipyridine-5'-carboxamide | 678.2 |
| 540 | (2S)—N—((1S,2R)-3-(((4S)-6-ethyl-3,4-dihydrospiro[chromene-2,1'-cyclobutan]-4-yl)amino)-2-hydroxy-1-(phenylmethyl)propyl)-4-((3-(methyloxy)phenyl)carbonyl)-2-morpholinecarboxamide | 628 |
| 541 | (2S)-4-((3-cyanophenyl)carbonyl)-N—((1S,2R)-3-(((4S)-6-ethyl-3,4-dihydrospiro[chromene-2,1'-cyclobutan]-4- | 623 |

-continued

| Ex. No. | Compound Name | Mass Found |
|---|---|---|
| | yl)amino)-2-hydroxy-1-(phenylmethyl)propyl)-2-morpholinecarboxamide | |
| 542 | (2R)—N—((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-5-oxotetrahydro-2-furancarboxamide | 536.2 |

While the examples described above provide processes for synthesizing compounds of Formulas I-III, other methods may be utilized to prepare such compounds. Methods involving the use of protecting groups may be used. Particularly, if one or more functional groups, for example, carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products, unless present as part of a pro-drug. The specialist knows, or can easily establish, which protecting groups are suitable with the reactions described herein.

The protection of functional groups by protecting groups, the protecting groups themselves, and their removal reactions (commonly referred to as "deprotection") are described herein, as well as in various publications or in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, $4^{th}$ edition, Volume 15/1, Georg Thieme Verlag, Stuttgart (1974), in H.-D. Jakubke and H. Jescheit, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

Synthetic procedures may also be carried out where functional groups of starting compounds, which are not intended to take part in the reaction, may be present in unprotected form without the added step of protecting that group by, for example, one or more of the protecting groups mentioned above or taught in the references above.

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent (s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures, scalemic mixtures, single enantiomers, individual diastereomers and diastereomeric mixtures thereof. Thus, the compounds may possess cis- or trans- or E- or Z-double bond isomeric forms. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

All such isomeric forms of these compounds are expressly included in the present invention. As shown in the examples, many exemplary compounds of the present invention have multiple stereocenters, with both cis- and trans-orientation about the B group-hydroxy substituted carbon-carbon bond. This bond is part of the "Pr" core, as shown in the general synthetic schemes. In addition, many compounds of the invention have specific stereo chemistry about the N—$R^5$ bond as well.

The compounds of this invention may also be represented in multiple tautomeric forms. The invention expressly includes all tautomeric forms of the compounds described herein.

All crystal forms of the compounds described herein are expressly included in the present invention.

A compound of any of Formulas I-III described herein may be synthesized according to any of the procedures described herein. In the procedures described herein, the steps may be performed in an alternate order and may be preceded, or followed, by additional protection/deprotection steps as necessary. The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

In another embodiment of the invention, there is provided a method of making a compound of Formula I-III, the method comprising the step of reacting a compound 20

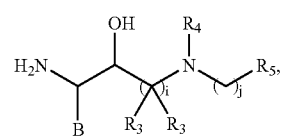

wherein i, j, A, B, $R^3$, $R^4$ and $R^5$ are as defined herein, with a compound having the structure $R^1$—W—X, wherein $R^1$ and W are as defined herein and X is a leaving group, to make a compound of claim 1.

As appreciated by one or ordinary skill in the art, compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

The pharmacological properties and biological activity of the compounds of the invention (Formulas I-III) are shown by the following biological evaluations.

Biological Evaluation

The following enzyme and cell-based assays were used to characterize the ability of compounds of the invention to generally regulate the cleavage of amyloid beta precursor protein, and to inhibit the production of amyloid beta.

In Vitro Enzymatic BACE FRET (Fluorescence Resonance Energy Transfer) Assay

Assay buffer is 0.05 M acetate, pH 4.2, 10% DMSO final, 100 uM genapol (which is a nonionic detergent, below it's Critical Micelle Concentration). Enzyme (0.2 nM) is pre-incubated for one hour with inhibitors added in 1 uL of DMSO. Then the assay is started by the addition of FRET substrate (50 nM) and incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

The compounds of Examples 1-3, 5-10, 12, 14-30, 35, 42-50, 52-54, 105-113, 115-138, 140, 142-169, 172-179, 182-190, 192, 194-240, 242-252, 254-277, 280-291, 293-294, 296-305, 307-364, 366, 373, 375-388, 390-406, 408-418, 420-446, 448-469, 471, 472, 475-477, 480-492, 496-500, 501-503, 505-511 and 513-529 exhibited $IC_{50}$ values of 5 µM or less in the FRET in-vitro enzyme assay.

BACE Cell-based Assay:

The cell-based assay measures inhibition or reduction of Aβ40 in conditioned medium of test compound treated cells, which express amyloid precursor protein.

Cells stably expressing Amyloid Precursor Protein (APP) were plated at a density of 40K cells/well in 96 well plates (Costar). The cells were cultivated for 24 h at 37° C. and 5% $CO_2$ in DMEM supplemented with 10% FBS. The test compounds were then added to cells in 10-point dose response concentrations with the starting concentration being either 100 µM or 10 µM. The compounds were diluted from stock solutions in DMSO and the final DMSO concentration of the test compounds on cells was 0.1%.

After 24 hours of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 µg/ml in Superblock/TBS (Pierce) that was supplemented with 0.05% Tween 20 (Sigma). Optimal concentration for the detection antibody 6E10-biotinylated was 0.5 µg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

The compounds of Examples 1-3, 5-10, 12, 14-19, 22-24, 29-30, 32, 43, 47-52, 105, 107-108, 110-111, 116-126, 128-138, 140-142, 144, 146-153, 158-165, 172-179, 181-189, 191-192, 195-206, 208-215, 218-223, 225-252, 254-277, 280-281, 283-291, 293-294, 296-305, 308, 310-313, 318-332, 335-344, 348-353, 357-364, 366-375, 378-388, 392-428, 432-436, 438-469, 471, 472, 473 and 475-477, 480-529 exhibited activities with $IC_{50}$ values of 5 µM or less in the cell-based assay.

Indications

Accordingly, compounds of the invention are useful for, but not limited to, the prevention or treatment of beta-secretase related diseases, including Alzheimer's disease. The compounds of the invention have the ability to modulate the formation of amyloid beta peptide (A-beta), and reduce the formation and deposition of plaque on the brain. In one embodiment of the invention, there is provided a method of treating a disorder related to a beta-secretase enzyme in a subject, the method comprising administering to the subject an effective dosage amount of a compound of Formulas I, II or III. In another embodiment, there is provided a method of reducing production of amyloid beta, and of reducing plaque formation. In yet another embodiment, there is provided a method of treating Alzheimer's disease.

Accordingly, the compounds of the invention would be useful in therapy as CNS agents in treating neurological disorders and related conditions.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment of the present invention, there is provided a method of manufacturing a medicament, the method comprising combining an amount of a compound according to Formulas I, II or III with a pharmaceutically acceptable carrier to manufacture the medicament.

In yet another embodiment, there is provided a method of manufacturing a medicament for the treatment of Alzheimer's disease, the method comprising combining an amount of a compound according to Formulas I, II or III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I:

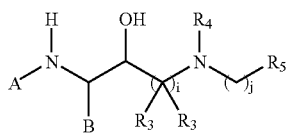

I or a stereoisomer, tautomer, or pharmaceutically acceptable salt thereof, wherein A is $R^1$—C(=O)—, $R^1$—OC(=O)—, $R^1$—NHC(=O)—, $R^1$—S(=O)$_b$— or $R^1$—NHS(=O)$_b$—, wherein
b is 1 or 2; and
$R^1$ is a partially or fully saturated 3-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substituents of oxo, $R^7$, $R^8$, $R^9$, -$NR^7R^7$, -$NR^7R^8$, —$OR^7$, —$SR^7$, —$OR^8$, —$SR^8$, —C(O)$R^7$, —OC(O)$R^7$, —COOR$^7$, —C(O)$R^8$, —OC(O)$R^8$, —COOR$^8$, —C(O)$NR^7R^7$, —C(S)$NR^7R^7$, —$NR^7$C(O)$R^7$, —$NR^7$C(S)$R^7$, —$NR^7$C(O)$NR^7R^7$, —$NR^7$C(S)$NR^7R^7$, —$NR^7$(COOR$^7$), —OC(O)$NR^7R^7$, —C(O)$NR^7R^8$, —C(S)$NR^7R^8$, —$NR^7$C(O)$R^8$, —$NR^7$C(S)$R^8$, —$NR^7$C(O)$NR^7R^8$, —$NR^7$C(S)$NR^7R^8$, —$NR^7$(COOR$^8$), —OC(O)$NR^7R^8$, —S(O)$_2NR^7R^7$ —$NR^7$S(O)$_2NR^7R^7$, —$NR^7$S(O)$_2R^7$, —S(O)$_2R^8$, —S(O)$_2NR^7R^8$, —$NR^7$S(O)$_2NR^7R^8$ or —$NR^7$S(O)$_2R^8$;

B is $R^2$—(CR$^{2a}R^{2a}$)$_h$—, $R^2$—O—(CR$^{2a}R^{2a}$)$_h$—, $R^2$—S—(CR$^{2a}R^{2a}$)$_h$—or $R^2$—N(R$^{2a}$)—(CR$^{2a}R^{2a}$)$_h$—, wherein
$R^2$ is —$C_1$-$C_{10}$ alkyl, —$C_1$-$C_{10}$ haloalkyl, $C_2$-$C_{10}$ alkenyl, $C_2$-$C_{10}$ alkynyl, or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of said $C_1$-$C_{10}$ alkyl, $C_2$-$C_{10}$ alkenyl and $C_2$-$C_{10}$ alkynyl, is optionally substituted independently with 1-5 substituents of $R^9$, and said ring system is optionally substituted independently with 1-5 substituents of oxo, $R^7$, $R^8$, $R^9$, —$NR^7R^7$, —$NR^7R^8$, —$OR^7$, —$SR^7$, —$OR^8$, —$SR^8$, —C(O)$R^7$, —OC(O)$R^7$, —COOR$^7$, —C(O)$R^8$, —OC(O)$R^8$, —COOR$^8$, —C(O)$NR^7R^7$, —C(S)$NR^7R^7$, —$NR^7$C(O)$R^7$, —$NR^7$C(S)$R^7$, —$NR^7$C(O)$NR^7R^7$, —$NR^7$C(S)$NR^7R^7$, —$NR^7$(COOR$^7$), —OC(O)$NR^7R^7$, —C(O)$NR^7R^8$, —C(S)$NR^7R^8$, —$NR^7$C(O)$R^8$, —$NR^7$C(S)$R^8$, —$NR^7$C(O)$NR^7R^8$, —$NR^7$C(S)$NR^7R^8$, —$NR^7$(COOR$^8$), —OC(O)$NR^7R^8$, —S(O)$_2NR^7R^7$, —$NR^7$S(O)$_2NR^7R^7$, —$NR^7$S(O)$_2R^7$, —S(O)$_2R^8$, —S(O)$_2NR^7R^8$, —$NR^7$S(O)$_2NR^7R^8$ or —$NR^7$S(O)$_2R^8$;
each $R^{2a}$, independently, is H, —OH, —$NO_2$, —CN, —$NH_2$, $C_1$-$C_{10}$ alkyl, $C_1$-$C_{10}$ alkoxyl or haloalkyl; and
h is 0, 1, 2 or 3;
i is 1, 2 or 3;
j is 0, 1 or 2;
each $R^3$, independently, is H, haloalkyl, —CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;
$R^4$ is H, haloalkyl, —CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;
$R^5$ is

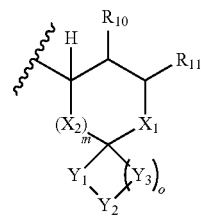

wherein $X^1$ is O;
each $X^2$, independently, is $CH_2$;
each of $Y^1$, $Y^2$ and $Y^3$, independently, is $CH_2$;
m is 1; and
o is 1 or 2;
$R^7$ is H, $C_{1-10}$-alkyl, $C_{2-10}$-alkenyl, $C_{2-10}$-alkynyl $C_{3-10}$-cycloalkyl, or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of —NR$^8$R$^9$, —NR$^9$R$^9$, —OR$^8$, —SR$^8$, —OR$^9$, —SR$^9$, —C(O)R$^8$, —OC(O)R$^8$, —COOR$^8$, —C(O)R$^9$, —OC(O)R$^9$, —COOR$^9$, —C(O)NR$^8$R$^9$, —C(O)NR$^9$R$^9$, —NR$^9$C(O)R$^8$, —NR$^9$C(O)R$^9$, —NR$^9$C(O)NR$^8$R$^9$, —NR$^9$C(O)NR$^9$R$^9$, —NR$^9$(COOR$^8$)—NR$^9$(COOR$^9$)—OC(O)NR$^8$R$^9$,—OC(O)NR$^9$R$^9$, —S(O)$_2$R$^8$, —S(O)$_2$NR$^8$R$^9$, —S(O)$_2$R$^9$, —S(O)$_2$NR$^9$R$^9$, —NR$^9$S(O)$_2$NR$^8$R$^9$, —NR$^9$S(O)$_2$NR$^9$R$^9$, —NR$^9$S(O)$_2$R$^8$, —NR$^9$S(O)$_2$R$^9$, R$^8$ or R$^9$;

R$^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R$^9$, oxo, —NR$^9$R$^9$, —OR$^9$; —SR$^9$, —C(O)R$^9$ or a partially or fully saturated or unsaturated 5-6 membered ring of carbon atoms optionally including 1-3 heteroatoms selected from O, N, or S, and optionally substituted independently with 1-5 substituents of R$^9$;

R$^9$ is H, halo, haloalkyl, —CN, —OH, —NO$_2$, —NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, —CN, —NO$_2$, —NH$_2$, —OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl,cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;

R$^{10}$ and R$^{11}$ taken together with the carbon atoms to which they are attached form a second phenyl ring optionally substituted independently with 1-5 substitutents of R$^{12}$, R$^{13}$, R$^{14}$ or R$^{15}$;

R$^{12}$ is H, halo, haloalkyl, —CN, —OH, —NO$_2$, —NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, —CN, —NO$_2$, —NH$_2$, —OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl, phenyl or R$^{14}$;

R$^{13}$ is —NR$^{14}$R$^{15}$, —NR$^{15}$R$^{15}$, —OR$^{14}$, —SR$^{14}$, —OR$^{15}$; —SR$^{15}$, —C(O)R$^{14}$, —OC(O)R$^{14}$, —COOR$^{14}$, —C(O)R$^{15}$, —OC(O)R$^{15}$, —COOR$^{15}$, —C(O)NR$^{14}$R$^{15}$, —C(O)NR$^{15}$R$^{15}$, —NR$^{14}$C(O)R$^{14}$, —NR$^{15}$C(O)R$^{14}$, —NR$^{14}$C(O)R$^{15}$, —NR$^{15}$C(O)R$^{15}$, —NR$^{15}$C(O)NR$^{14}$R$^{15}$, —NR$^{15}$C(O)NR$^{15}$R$^{15}$, —NR$^{15}$(COOR$^{14}$), —NR$^{15}$(COOR$^{15}$), —OC(O)NR$^{14}$R$^{15}$, —OC(O)NR$^{15}$R$^{15}$, —S(O)$_2$R$^{14}$, —S(O)$_2$R$^{15}$, —S(O)$_2$NR$^{14}$R$^{15}$, —S(O)$_2$NR$^{15}$R$^{15}$, —NR$^{14}$S(O)$_2$NR$^{14}$R$^{15}$, —NR$^{15}$S(O)$_2$NR$^{15}$R$^{15}$, —NR$^{14}$S(O)$_2$R$^{14}$ or —NR$^{15}$S(O)$_2$R$^{15}$;

R$^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R$^{15}$; and R$^{15}$ is H, halo, haloalkyl, —CN, —OH, —NO$_2$, —NH$_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, C$_{1-10}$-alkylamino-, C$_{1-10}$-dialkylamino-, C$_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, —CN, —NO$_2$, —NH$_2$, —OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

2. The compound of claim 1 wherein R$^1$ is

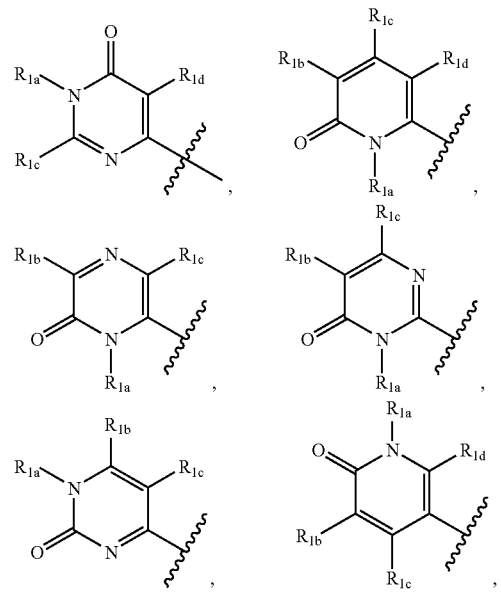

-continued

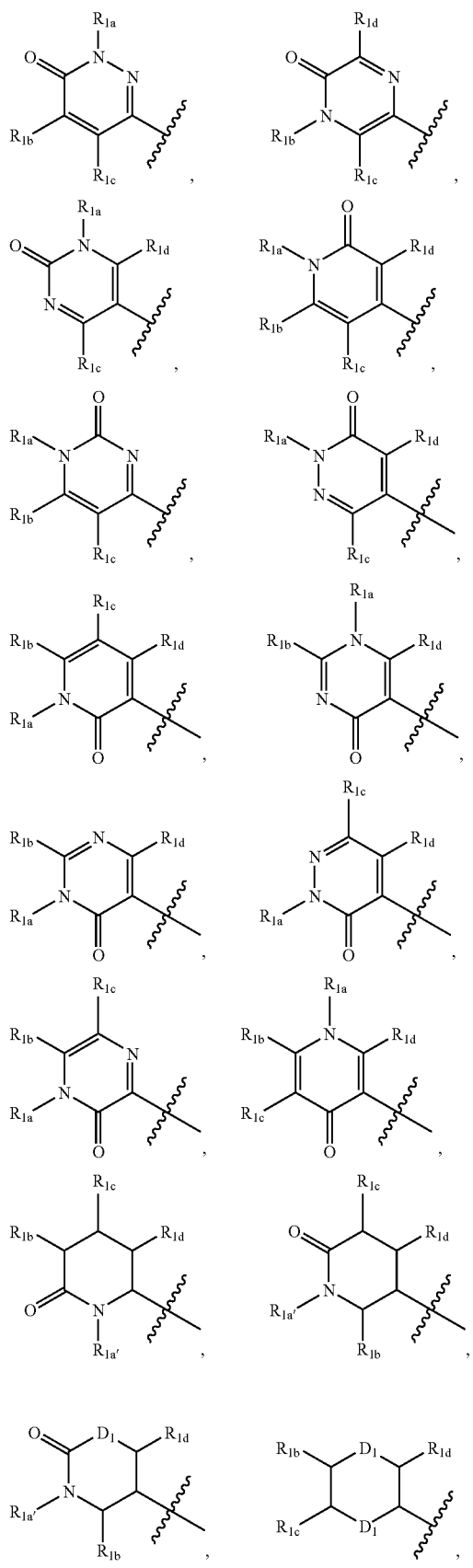

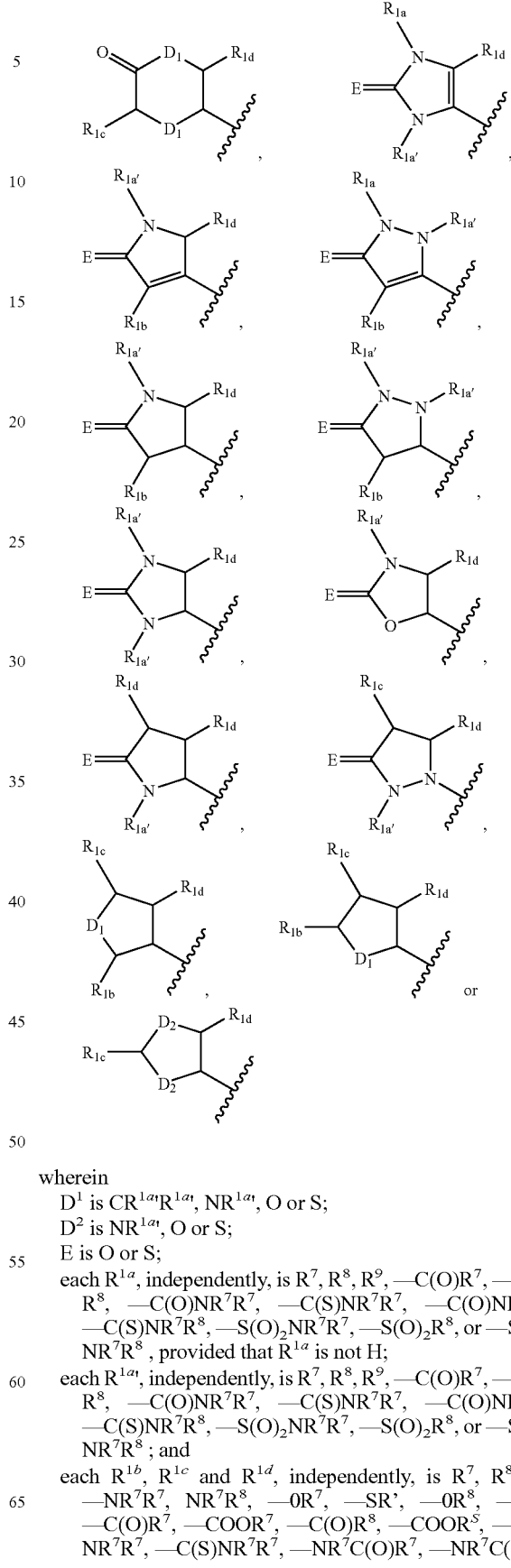

wherein
D¹ is $CR^{1a\prime}R^{1a\prime}$, $NR^{1a\prime}$, O or S;
D² is $NR^{1a\prime}$, O or S;
E is O or S;
each $R^{1a}$, independently, is $R^7$, $R^8$, $R^9$, —C(O)$R^7$, —C(O)$R^8$, —C(O)$NR^7R^7$, —C(S)$NR^7R^7$, —C(O)$NR^7R^8$, —C(S)$NR^7R^8$, —S(O)$_2NR^7R^7$, —S(O)$_2R^8$, or —S(O)$_2NR^7R^8$, provided that $R^{1a}$ is not H;
each $R^{1a\prime}$, independently, is $R^7$, $R^8$, $R^9$, —C(O)$R^7$, —C(O)$R^8$, —C(O)$NR^7R^7$, —C(S)$NR^7R^7$, —C(O)$NR^7R^8$, —C(S)$NR^7R^8$, —S(O)$_2NR^7R^7$, —S(O)$_2R^8$, or —S(O)$_2NR^7R^8$; and
each $R^{1b}$, $R^{1c}$ and $R^{1d}$, independently, is $R^7$, $R^8$, $R^9$, —$NR^7R^7$, $NR^7R^8$, —$OR^7$, —SR', —$OR^8$, —$SR^8$, —C(O)$R^7$, —COO$R^7$, —C(O)$R^8$, —COO$R^8$, —C(O)$NR^7R^7$, —C(S)$NR^7R^7$, —$NR^7C(O)R^7$, —$NR^7C(S)R^7$, —NR⁷C(O)NR⁷R⁷, —NR⁷C(S)NR⁷R⁷, —NR⁷(COOR⁷), —OC(O)NR⁷R⁷, —C(O)NR⁷R⁸, —C(S)NR⁷R⁸, —NR⁷C(O)R⁸, —NR⁷C(S)R⁸, —NR⁷C(O)NR⁷R⁸, —NR⁷C(S)NR⁷R⁸, —NR⁷(COOR⁸), —OC(O)NR⁷R⁸, —S(O)2NR⁷R⁷, —NR⁷S(O)₂NR⁷R⁷, —NR⁷S(O)₂R⁷, —S(O)₂R⁸, —S(O)₂NR⁷R⁸, —NR⁷S(O)₂NR⁷R⁸ or —NR⁷S(O)₂R⁸.

3. The compound of claim 1 wherein R² is an optionally substituted ring selected from phenyl, naphthyl, pyridyl, pyrimidyl, pyridazinyl, pyrazinyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl.

4. The compound of claim 1 wherein
each R³, independently, is H, haloalkyl, —CN, $C_{1-10}$-alkyl, $C_{2-10}$-alkenyl or $C_{2-10}$-alkynyl; and
R⁴ is H or $C_{1-10}$-alkyl.

5. The compound of claim 1 wherein
h is 1;
i is 1; and
j is 0.

6. A pharmaceutical composition comprising a pharmaceutically acceptable carrier and a compound according to claim 1.

7. A method of making a compound of claim 1, the method comprising the step of reacting a compound 20

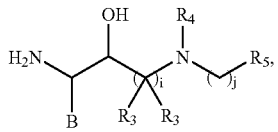

wherein i, j, A, B, R³, R⁴ and R⁵ are as defined in claim 1, with a compound having the structure A-X,
wherein A is as defined in claim 1 and X is a leaving group, to make a compound of claim 1.

8. The compound of claim 1, or a pharmaceutically acceptable salt thereof, selected from:
1-cyclopentyl-N-((2S,3R)-4-((S)-6-ethyl-2,2-spirocyclobutylchroman-4-ylamino)-3-hydroxy-1-(thiophen-3-yl)butan-2-yl)-6-oxo-5-(2-oxopyrrolidin-1-yl)-1,6-dihydropyridine-3-carboxamide;
N-((2S,3R)-1-(3-cyanophenyl)-4-((S)-6-ethyl-2,2-spirocyclobutylchroman-4-ylamino)-3-hydroxybutan-2-yl)-tetrahydrofuran-2-carboxamide;
(RS)-1-cyclopropyl-N-((2S,3R)-4-((S)-6-ethyl-2,2-spirocyclobutylchroman-4-ylamino)-3-hydroxy-1-phenylbutan-2-yl)-5-oxopyrrolidine-3-carboxamide;
N-((2S,3R)-4-((S)-6-ethyl-2,2spirocyclobutylchroman-4-ylamino)-3-hydroxy-1-phenylbutan-2-yl)-1,3-diisopropyl-2-oxo-hexahydropyrimidine-5-carboxamide;
N-((2S,3R)-4-((S)-6-ethyl-2,2-spirocyclobutylchroman-4-ylamino)-3-hydroxy-1-phenylbutan-2-yl)cyclopropanecarboxamide;
N-((2S,3R)-4-((S)-6-ethyl-2,2-spirocyclobutylchroman-4-ylamino)-3-hydroxy-1-phenylbutan-2-yl)cyclohexanecarboxamide;
(R)-4-benzoyl-N-((2S,3R)-4-((S)-6-ethyl-2,2-spirocyclopentylchroman-4-ylamino)-3-hydroxy-1-phenylbutan-2-yl)-7-fluoro-3,4-dihydro-2H-benzo[b][1,4]oxazine-2-carboxamide;
(S)-N-((2S,3R)-4-((S)-6-ethyl-2,2-spirocyclopentylchroman-4-ylamino)-3-hydroxy-1-phenylbutan-2-yl)-4-methylmorpholine-2-carboxamide;
N-((2S,3R)-4-((S)-6-ethyl-2,2-spirocyclobutylchroman-4-ylamino)-3-hydroxy-1-phenylbutan-2-yl)-4-(tetrahydro-2H-pyran-4-carbonyl)morpholine-2-carboxamide;
N²-((2S,3R)-4-((S)-6-ethyl-2,2-spirocyclobutylchroman-4-ylamino)-3-hydroxy-1-phenylbutan-2-yl)-N⁴-((R)-1-phenylethyl)morpholine-2,4-dicarboxamide;

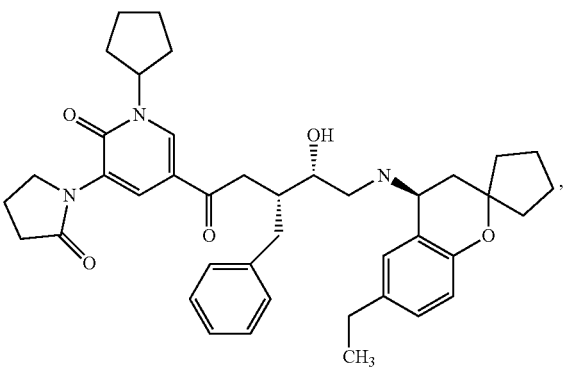

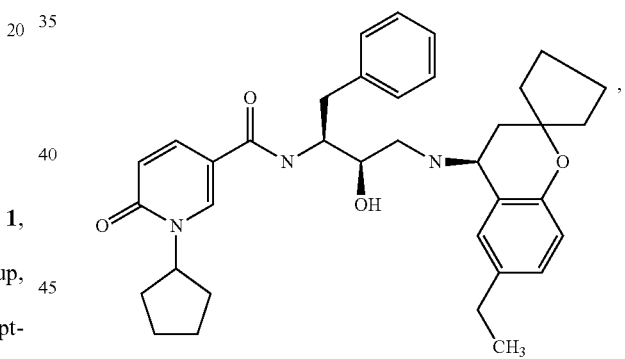

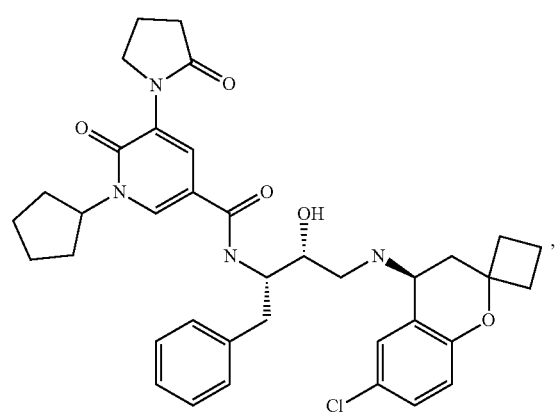

207
-continued
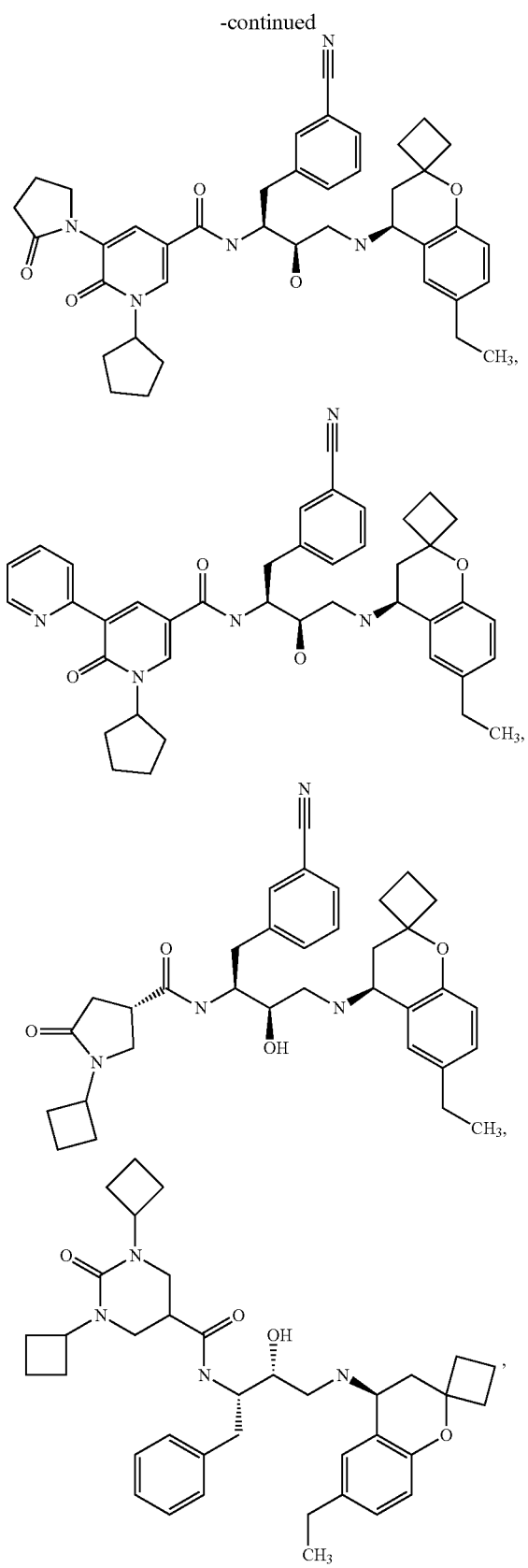
208
-continued
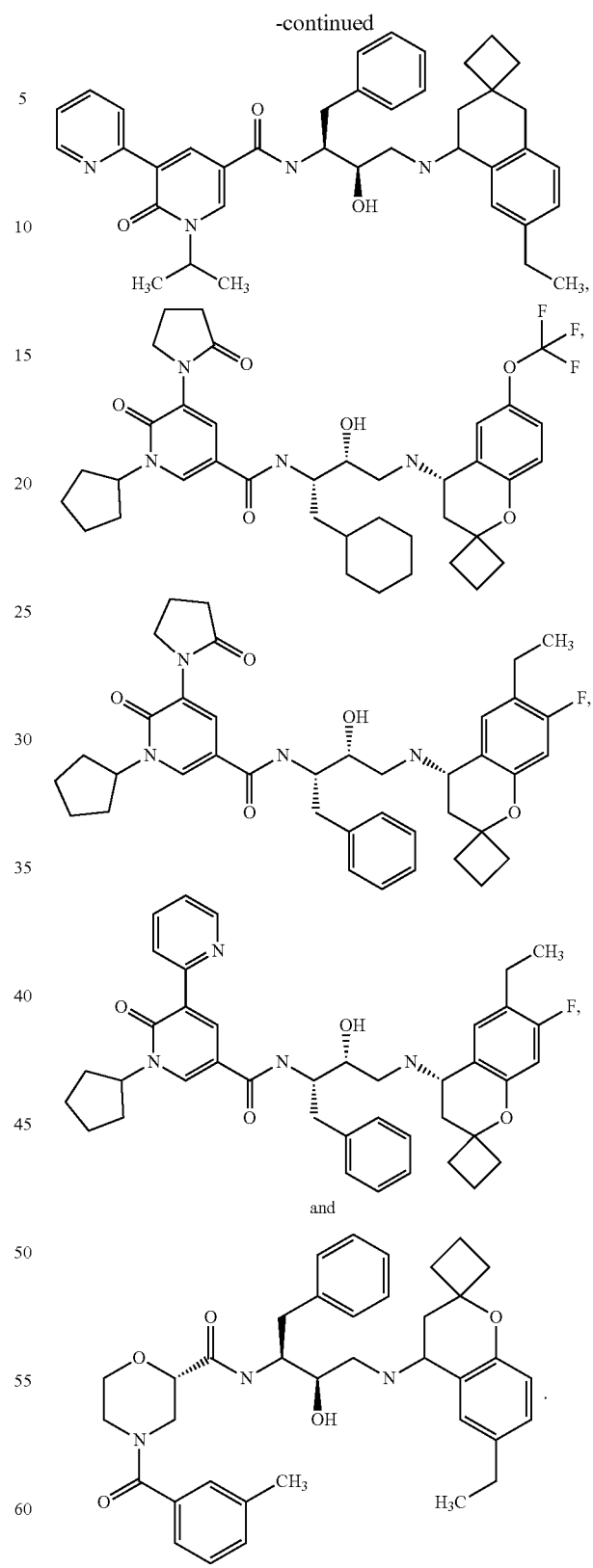
and
* * * * *